US012779152B2

(12) United States Patent
Lyman et al.

(10) Patent No.: US 12,779,152 B2
(45) **Date of Patent: *Nov. 3, 2026**

(54) DRY POWDER FORMULATIONS OF EPINEPHRINE AND ASSOCIATED METHODS

(71) Applicant: Belhaven BioPharma Inc., Raleigh, NC (US)

(72) Inventors: Scott Lyman, Raleigh, NC (US); Brian Taubenheim, Elkhart Lake, WI (US); Anthony Hickey, Chapel Hill, NC (US)

(73) Assignee: Belhaven BioPharma Inc., Raleigh, NC (US)

( * ) Notice: Subject to any disclaimer, the term of this patent is extended or adjusted under 35 U.S.C. 154(b) by 399 days.

This patent is subject to a terminal disclaimer.

(21) Appl. No.: 18/417,683

(22) Filed: Jan. 19, 2024

(65) Prior Publication Data

US 2024/0148990 A1 May 9, 2024

Related U.S. Application Data

(63) Continuation-in-part of application No. 18/514,634, filed on Nov. 20, 2023, which is a continuation-in-part of application No. 18/192,404, filed on Mar. 29, 2023, now Pat. No. 12,414,916, which is a continuation-in-part of application No. 17/836,588, filed on Jun. 9, 2022, now Pat. No. 11,617,716.

(60) Provisional application No. 63/209,221, filed on Jun. 10, 2021.

(51) Int. Cl.

| | |
|---|---|
| ***A61M 15/08*** | (2006.01) |
| ***A61K 31/137*** | (2006.01) |
| ***A61K 47/36*** | (2006.01) |
| ***A61M 15/00*** | (2006.01) |

(52) U.S. Cl.

CPC ........... *A61M 15/08* (2013.01); *A61K 31/137* (2013.01); *A61K 47/36* (2013.01); *A61M 15/008* (2014.02); *A61M 2202/064* (2013.01); *A61M 2205/3553* (2013.01); *A61M 2205/3584* (2013.01); *A61M 2205/502* (2013.01); *A61M 2209/06* (2013.01); *A61M 2210/0618* (2013.01)

(58) Field of Classification Search

None

See application file for complete search history.

(56) References Cited

U.S. PATENT DOCUMENTS

| | | | |
|---|---|---|---|
| 4,548,922 | A | 10/1985 | Carey et al. |
| 4,746,508 | A | 5/1988 | Carey et al. |
| 5,023,252 | A | 6/1991 | Hseih |
| 5,240,149 | A | 8/1993 | Schmidt |
| 5,328,099 | A | 7/1994 | Petit et al. |
| 5,568,884 | A | 10/1996 | Bruna |
| 5,731,303 | A | 3/1998 | Hsieh |
| 5,901,883 | A | 5/1999 | Ritsche |
| 5,911,937 | A | 6/1999 | Hekal |
| 6,029,663 | A | 2/2000 | Eisele et al. |
| 6,080,350 | A | 6/2000 | Hekal |
| 6,124,006 | A | 9/2000 | Hekal |
| 6,130,263 | A | 10/2000 | Hekal |
| 6,174,952 | B1 | 1/2001 | Hekal et al. |
| 6,179,164 | B1 | 1/2001 | Fuchs |
| 6,194,079 | B1 | 2/2001 | Hekal |
| 6,209,760 | B1 | 4/2001 | Fuchs |
| 6,214,255 | B1 | 4/2001 | Hekal |
| 6,221,446 | B1 | 4/2001 | Hekal |
| 6,234,366 | B1 | 5/2001 | Fuchs |
| 6,264,065 | B1 | 7/2001 | Jouillat |
| 6,367,473 | B1 | 4/2002 | Käfer |
| 6,398,074 | B1 | 6/2002 | Bruna et al. |
| 6,425,499 | B1 | 7/2002 | Guiffray |
| 6,427,680 | B1 | 8/2002 | Oechsel |
| 6,450,216 | B1 | 9/2002 | Stradella |
| 6,461,322 | B1 | 10/2002 | Ritsche |
| 6,484,715 | B1 | 11/2002 | Ritsche et al. |
| 6,486,231 | B1 | 11/2002 | Hekal |
| 6,626,379 | B1 | 9/2003 | Ritsche et al. |
| 6,679,248 | B2 | 1/2004 | Stadelhofer |
| 6,708,846 | B1 | 3/2004 | Fuchs et al. |
| 6,725,857 | B2 | 4/2004 | Ritsche |
| 6,877,672 | B2 | 4/2005 | Stihl |
| 6,886,556 | B2 | 5/2005 | Fuchs |

(Continued)

FOREIGN PATENT DOCUMENTS

| | | | |
|---|---|---|---|
| CA | 3238850 | A1 | 6/2023 |
| GB | 2400565 | A | 10/2004 |

(Continued)

OTHER PUBLICATIONS

Lapidot Intranasal Epinephrine Spray, p. 3047, Jun. 19, 2023.

Nutrition, What is Lactose Monohydrate, and how is it used? Accessed online Dec. 11, 2025 (Year: 2025).

Casale, Thomas B. et al., Pharmacokinetics/pharmacodynamics of epinephrine after single and repeat administration of neffy, EpiPen, and manual intramuscular injection, Journal of Allergy and Clinical Immunology, Dec. 2023, pp. 1587-1596, vol. 152, No. 6.

Bebarta VS, Pitotti RL, Dixon PS, Valtier S, Esquivel L, Bush A, Little CM. Hydroxocobalamin and epinephrine both improve survival in a swine model of cyanide-induced cardiac arrest. Ann Emerg Med. Oct. 2012;60(4):415-22. doi: 10.1016/j.annemergmed.2012.02.002. Epub Mar. 15, 2012. PMID: 22424656.

(Continued)

*Primary Examiner* — Melissa S Mercier

(74) *Attorney, Agent, or Firm* — Neo IP

(57) ABSTRACT

Provided herein are dry powder formulations comprising epinephrine alone or in combination with at least one enabling agent suitable for nasal application. Also provided are unit dose forms and devices comprising such formulations and methods of using such formulations for the treatment of various conditions including anaphylaxis, anaphylactoid reaction, respiratory conditions, hemodynamic collapse, and for administration during cardiopulmonary arrest and other life-threatening conditions.

20 Claims, 94 Drawing Sheets

(56) References Cited

U.S. PATENT DOCUMENTS 6,887,475 B1 5/2005 Lamb et al.
7,005,459 B2 2/2006 Hekal
7,011,234 B2 3/2006 Stradella
7,216,781 B2 5/2007 Duquet et al.
7,353,971 B2 4/2008 Stradella
7,387,265 B2 6/2008 Hess et al.
7,389,946 B2 6/2008 Bruna et al.
7,861,943 B2 1/2011 Feriani et al.
7,878,352 B2 2/2011 Spreckelsen et al.
7,946,455 B2 5/2011 Ritsche et al.
7,947,742 B2 5/2011 Batycky et al.
7,950,391 B2 5/2011 Fuchs
7,954,491 B2 6/2011 Hrkach
8,016,209 B2 9/2011 Hess et al.
8,263,581 B2 9/2012 Du
8,337,817 B2 12/2012 Nagata et al.
8,415,397 B2 4/2013 Batycky et al.
8,481,043 B2 7/2013 Bergenhem et al.
8,734,392 B2 5/2014 Stadelhofer
8,747,813 B2 6/2014 Batycky et al.
9,156,048 B2 10/2015 Maner
9,789,071 B2 10/2017 Fleming
9,808,818 B2 11/2017 Maner
9,834,341 B2 12/2017 Giraud et al.
9,902,788 B2 2/2018 Klein et al.
10,472,136 B2 11/2019 Giraud et al.
10,576,156 B2 3/2020 Maggio
10,653,690 B1 5/2020 Sävmarker et al.
10,668,228 B2 6/2020 Maner
10,682,414 B2 6/2020 Lowenthal et al.
10,688,044 B2 6/2020 Hartman et al.
10,765,602 B1 9/2020 Arnett et al.
10,806,709 B2 10/2020 Fleming et al.
10,806,870 B2 10/2020 Maner
10,814,079 B2 10/2020 Francis et al.
10,967,140 B2 4/2021 Petit
10,974,887 B2 4/2021 Freedman et al.
11,013,691 B2 5/2021 Fabio et al.
11,173,209 B2 11/2021 Maggio
11,191,838 B2 12/2021 Lowenthal et al.
11,400,045 B2 8/2022 Temtsin-Krayz et al.
11,717,571 B2 8/2023 Lowenthal et al.
11,744,895 B2 9/2023 Lowenthal et al.
11,865,252 B2 1/2024 Norrant et al.
12,037,336 B2 7/2024 McCarthy et al.
12,042,472 B2 7/2024 Howard et al.
12,090,139 B2 9/2024 Gandhi et al.
12,102,754 B2 10/2024 Haruta
12,133,837 B2 11/2024 Akasapu et al.
12,134,588 B2 11/2024 Sommadossi et al.
12,138,348 B2 11/2024 Eber et al.
12,150,921 B2 11/2024 Hartman et al.
12,186,426 B2 1/2025 Lim et al.
12,214,121 B2 2/2025 Meliniotis et al.
12,214,122 B2 2/2025 Clarke et al.
12,239,823 B2 3/2025 Buchine et al.
12,245,995 B2 3/2025 Hartman et al.
12,268,684 B2 4/2025 Sävmarker et al.
12,295,921 B2 5/2025 Hartman et al.
12,303,472 B2 5/2025 Sävmarker et al.
12,318,486 B2 6/2025 Eber et al.
12,324,838 B2 6/2025 Lowenthal et al.
2002/0079326 A1 6/2002 Fuchs
2002/0170928 A1 11/2002 Grychowski et al.
2004/0084554 A1 5/2004 Milian
2007/0272764 A1 11/2007 Poulard
2008/0269347 A1 10/2008 Bruss et al.
2009/0220435 A1 9/2009 Quay et al.
2010/0055152 A1 3/2010 Wahi
2010/0078447 A1 4/2010 Sauzade et al.
2010/0258118 A1 10/2010 Morton
2011/0194110 A1 8/2011 Langeard et al.
2011/0233232 A1 9/2011 Greiner-Perth et al.
2012/0318677 A1 12/2012 Bruna et al.
2013/0022750 A1 1/2013 Bruna et al.
2013/0081953 A1 4/2013 Bruna et al.
2013/0149459 A1 6/2013 Bruna et al.
2013/0171330 A1 7/2013 Sallak et al.
2013/0171334 A1 7/2013 Bruna et al.
2013/0312740 A1 11/2013 Pardonge
2014/0000588 A1 1/2014 Maner
2014/0034663 A1 2/2014 Königseder et al.
2014/0103064 A1 4/2014 Bruna et al.
2015/0299846 A1 10/2015 Bruna et al.
2016/0318051 A1 11/2016 Petit et al.
2016/0367017 A1 12/2016 Adams et al.
2017/0304459 A1 10/2017 Jadhav et al.
2018/0056022 A1 3/2018 Liu et al.
2019/0134322 A1 5/2019 Fabien
2019/0269781 A1 9/2019 Lowenthal et al.
2019/0269782 A1 9/2019 Lowenthal et al.
2019/0358417 A1 11/2019 Brouet et al.
2020/0155775 A1 5/2020 Keppner et al.
2020/0164164 A1 5/2020 Helmlinger et al.
2020/0246562 A1 8/2020 Fabien
2020/0375845 A1 12/2020 Arnett et al.
2021/0069126 A1 3/2021 Fleming
2021/0205238 A1 7/2021 Augustin et al.
2021/0264716 A1 8/2021 Norbeck et al.
2021/0361770 A1 11/2021 Lowenthal et al.
2021/0401825 A1 12/2021 Sävmarker et al.
2022/0218629 A1 7/2022 Rawas-Qalaji et al.
2022/0257884 A1 8/2022 Poullain et al.
2022/0362491 A1 11/2022 Petit et al.
2022/0395457 A1 12/2022 Lyman et al.
2023/0144040 A1 5/2023 Brouet et al.
2023/0225994 A1 7/2023 Howard et al.
2023/0233460 A1 7/2023 Lyman et al.
2023/0240983 A1 8/2023 Lyman et al.
2023/0302137 A1 9/2023 Lowenthal et al.
2024/0197653 A1 6/2024 Akasapu et al.
2024/0245856 A1 7/2024 Krishnan et al.
2024/0252489 A1 8/2024 Hoekman et al.
2024/0261227 A1 8/2024 Ogburn et al.
2024/0342117 A1 10/2024 Fraser et al.
2024/0366533 A1 11/2024 Howard et al.
2025/0000821 A1 1/2025 Zhang
2025/0009995 A1 1/2025 Walsh et al.
2025/0041544 A1 2/2025 Haruta
2025/0049862 A1 2/2025 O'Connor
2025/0099374 A1 3/2025 Boyer et al.
2025/0108017 A1 4/2025 Schobel et al.
2025/0114307 A1 4/2025 Eber et al.
2025/0120923 A1 4/2025 Akasapu et al.
2025/0195436 A1 6/2025 Eber et al.
2025/0195470 A1 6/2025 Gandhi et al.
2025/0205224 A1 6/2025 Sävmarker et al.

FOREIGN PATENT DOCUMENTS

WO 9732663 A1 9/1997
WO 2003037355 A1 5/2003
WO 2015035822 3/2015
WO WO-2015034822 A1 * 3/2015 ............. A61K 45/06
WO 2019182908 A1 9/2019
WO 2019241401 A1 12/2019

OTHER PUBLICATIONS

Bleske BE, Warren EW, Rice TL, Shea MJ, Amidon G, Knight P. Comparison of intravenous and intranasal administration of epinephrine during CPR in a canine model. Ann Emerg Med. Sep. 1992;21(9):1125-30. doi: 10.1016/s0196-0644(05)80657-2. PMID: 1514727. Abstract.

Bourganis V, Kammona O, Alexopoulos A, Kiparissides C. Recent advances in carrier mediated nose-to-brain delivery of pharmaceutics. Eur J Pharm Biopharm. Jul. 2018;128:337-362. doi: 10.1016/j.ejpb.2018.05.009. Epub May 4, 2018. PMID: 29733950.

Brown JC, Tuuri RE, Akhter S, Guerra LD, Goodman IS, Myers SR, Nozicka C, Manzi S, Long K, Turner T, Conners GP, Thompson RW, Park E. Lacerations and Embedded Needles Caused by Epinephrine Autoinjector Use in Children. Ann Emerg Med. Mar.

(56) References Cited

OTHER PUBLICATIONS

2016;67(3):307-315.e8. doi: 10.1016/j.annemergmed.2015.07.011. Epub Oct. 9, 2015. PMID: 26452720.
Casematrix, Cases for Inhalers, insulin, medical devices and more, available online Jan. 24, 2021). (Year: 2021).
Chooniedass R, Temple B, Becker A. Epinephrine use for anaphylaxis: Too seldom, too late: Current practices and guidelines in health care. Ann Allergy Asthma Immunol. Aug. 2017;119(2):108-110. doi: 10.1016/j.anai.2017.06.004. Epub Jul. 1, 2017. PMID: 28676208.
Chowdhury BA, Meyer RJ. Intramuscular versus subcutaneous injection of epinephrine in the treatment of anaphylaxis. J Allergy Clin Immunol. Apr. 2002;109(4):720; author reply 720-1. doi: 10.1067/mai.2002.123252. PMID: 11941328.
Clutter WE, Bier DM, Shah SD, Cryer PE. Epinephrine plasma metabolic clearance rates and physiologic thresholds for metabolic and hemodynamic actions in man. J Clin Invest. Jul. 1980;66(1):94-101. doi: 10.1172/JCI109840. PMID: 6995479; PMCID: PMC371510.
Costantino HR, Illum L, Brandt G, Johnson PH, Quay SC. Intranasal delivery: physicochemical and therapeutic aspects. Int J Pharm. Jun. 7, 2007;337(1-2):1-24. doi: 10.1016/j.ijpharm.2007.03.025. Epub Mar. 25, 2007. PMID: 17475423.
D Tabor, Surface forces and surface interactions, J. Colloid Interface Sci., vol. 58, Issue 1, 1977, pp. 2-13, https://doi.org/10.1016/0021-9797(77)90366-6.
Davis SS, Illum L. Absorption enhancers for nasal drug delivery. Clin Pharmacokinet. 2003;42(13): 1107-28. doi: 10.2165/00003088-200342130-00003. PMID: 14531723.
Dodd A, Hughes A, Turner PJ, 2021, Anaphylaxis management—Why are guidelines inconsistent?: A rapid review of advanced life support guidelines for cardiac arrest associated with anaphylaxis., Resuscitation, vol. 159, pp. 165-167.
Dreborg S, Kim H. The pharmacokinetics of epinephrine/adrenaline autoinjectors. Allergy Asthma Clin Immunol. Mar. 8, 2021;17(1):25. doi: 10.1186/s13223-021-00511-y. PMID: 33685510; PMCID: PMC7938517.
Dvauchelle T, Robert P, Donazzolo Y, Loyau S, Orlandini B, Lehert P, Lecomte JM, Schwartz JC. Bioavailability and Cardiovascular Effects of Adrenaline Administered by Anapen Autoinjector in Healthy Volunteers. J Allergy Clin Immunol Pract. Jul.-Aug. 2018;6(4):1257-1263. doi: 10.1016/j.jaip.2017.09.021. Epub Nov. 3, 2017. PMID: 29109047.
Fleming, J.T., et al., "Early Treatment of Food-Induced Anaphylaxis with Epinephrine Is Associated with a Lower Risk of Hospitalization," J. Allergy Clin Immunol Pract., Jan-Feb. 2015; 3(1):57-62; doi: 10.1016/j.jaip.2014.07.004 (published online Sep. 8, 2014).
Gabrielli, S., et al., "Teenagers and those with severe reactions are more likely to use their epinephrine autoinjectors in cases of anaphylaxis in Canada," J. Allergy & Clin. Immunology: In Practice, Clinical Communications, Mar. 1, 2019, 7(3): p. 1073-1075. E3, doi.org/10/1016/j.jaip.2018.07.044.
Gänger S, Schindowski K. Tailoring Compositions for Intranasal Nose-to-Brain Delivery: A Review on Architecture, Physico-Chemical Characteristics and Mucociliary Clearance of the Nasal Olfactory Mucosa. Pharmaceutics. Aug. 3, 2018;10(3):116. doi: 10.3390/pharmaceutics 10030116. PMID: 30081536; PMCID: PMC6161189.
Gill MA, Kislik AZ, Gore L, Chandna A. Stability of advanced life support drugs in the field. Am J Health Syst Pharm. Mar. 15, 2004;61(6):597-602. doi: 10.1093/ajhp/61.6.597. PMID: 15061431.
Greenberger PA, Wallace DV, Lieberman PL, Gregory SM. Contemporary issues in anaphylaxis and the evolution of epinephrine autoinjectors: What will the future bring? Ann Allergy Asthma Immunol. Oct. 2017;119(4):333-338. doi: 10.1016/j.anai.2017.07.030. PMID: 28958374.
Haidar SH, Makhlouf F, Schuirmann DJ, Hyslop T, Davit B, Conner D, Yu LX. Evaluation of a scaling approach for the bioequivalence of highly variable drugs. AAPS J. Sep. 2008;10(3):450-4. doi: 10.1208/s12248-008-9053-4. Epub Aug. 26, 2008. Erratum in: AAPS J. Sep. 2008;10(3):480. PMID: 18726698; PMCID: PMC2761698.
Hill RL, Wilmot JG, Belluscio BA, Cleary K, Lindisch D, Tucker R, Wilson E, Shukla RB. Comparison of drug delivery with autoinjector versus manual prefilled syringe and between three different autoinjector devices administered in pig thigh. Med Devices (Auckl). Aug. 2, 2016;9:257-66. doi: 10.2147/MDER.S83406. PMID: 27536164; PMCID: PMC4976900.
Ilium L and Fisher AN (1997) Intranasal delivery of peptides and proteins, in Inhalation Delivery of Therapeutic Peptides and Proteins (Adjei AL and Gupta PK eds), Marcel Dekker, New York.
Internet webpages, "2 Pack Molle Pouches—Tactical Compact Water-Resistant EDC Pouch", Mar. 5, 2019, pp. 1-5, https://www.amazon.com/Pack-Molle-Pouches-Tactical-Water-Resistant/dp/B07PFF47DX?th=1.
Johnstone J, Hobbins S, Parekh D, O'Hickey S. Excess subcutaneous tissue may preclude intramuscular delivery when using adrenaline autoinjectors in patients with anaphylaxis. Allergy. Jun. 2015;70(6):703-6. doi: 10.1111/all.12595. Epub Mar. 29, 2015. PMID: 25676800.
Judenherc-Haouzl A, Sonobe T, Bebarta VS, Haouzi P. On the Efficacy of Cardio-Pulmonary Resuscitation and Epinephrine Following Cyanide- and H2S Intoxication-Induced Cardiac Asystole. Cardiovasc Toxicol. Oct. 2018; 18 (5):436-449. doi: 10.1007/s12012-018-9454-2. PMID: 29644580; PMCID: PMC6126935.
Karalis V, Symillides M, Macheras P. Comparison of the reference scaled bioequivalence semi-replicate method with other approaches: focus on human exposure to drugs. Eur J Pharm Sci. Aug. 12, 2009;38(1):55-63. doi: 10.1016/j.ejps.2009.05.013. Epub Jun. 11, 2009. PMID: 19524039.
Kassel L, Jones C, Mengesha A. Epinephrine drug degradation in autoinjector products. J Allergy Clin Immunol Pract. Sep.-Oct. 2019;7(7):2491-2493. doi: 10.1016/j.jaip.2019.04.028. Epub May 28, 2019. PMID: 31151888.
Kemp SF, Lockey RF, Simons FE; World Allergy Organization ad hoc Committee on Epinephrine in Anaphylaxis. Epinephrine: the drug of choice for anaphylaxis. A statement of the World Allergy Organization. Allergy. Aug. 2008;63 (8):1061-70. doi: 10.1111/j.1398-9995.2008.01733.x. PMID: 18691308.
Kuehl PJ, Barrett EG, Cox J, Hammond B, Rudolph K, Suman JD, Williams G, Vermillion M., Nasal Sumatriptan: Deposition and Pharmacokinetic Effect of an Absorption Enhancer in Non-Human Primates, Respiratory Drug Delivery 2020. vol. 1, 2020: 165-174.
Lacwik, P., et. at., "Single, short-time exposure to heat in a car during sunny day can decrease epinephrine concentration in autoinjectors: a real-life pilot study," J. Allergy & Clin. Immunology, Apr. 1, 2019, 7(4): p. 1362-1364, published Nov. 28, 2018, doi.org/10.1016/j.jaip.2018.10.027.
Lam C, Turner P. Hemming D, et al., 2021, Seasonality of food related anaphylaxis admissions and associations with temperature and pollen levels, Journal of Allergy and Clinical Immunology: in Practice, vol. 9, ISSN:2213-2198, pp. 518-520.
Miles LM, Ratnarajah K, Gabrielli S, Abrams EM, Protudjer JLP, Bégin P, Chan ES, Upton J, Waserman S, Watson W, Gerdts J, Ben-Shoshan M. Community Use of Epinephrine for the Treatment of Anaphylaxis: A Review and Meta-Analysis. J Allergy Clin Immunol Pract. Jun. 2021;9(6):2321-2333. doi: 10.1016/j.jaip.2021.01.038. Epub Feb. 4, 2021. PMID: 33549844.
Moss, J, Jani, Y, Edwards, B, Tomlin, S, Rashed, AN. Pharmacokinetic and pharmacodynamic evidence of adrenaline administered via auto-injector for anaphylactic reactions: A review of literature. Br J Clin Pharmacol. 2021; 87: 816-824. https://doi.org/10.1111/bcp.14438.
Muraro A, Worm M, Alviani C, Cardona V, DunnGalvin A, Garvey LH, Riggioni C, de Silva D, Angier E, Arasi S, Bellou A, Beyer K, Bijlhout D, Bilò MB, Bindslev-Jensen C, Brockow K, Fernandez-Rivas M, Halken S, Jensen B, Khaleva E, Michaelis LJ, Oude Elberink HNG, Regent L, Sanchez A, Vlieg-Boerstra BJ, Roberts G; European Academy of Allergy and Clinical Immunology, Food Allergy, Anaphylaxis Guidelines Group. EAACI guidelines: Anaphylaxis (2021 update). Allergy. Feb. 2022;77(2):357-377. doi: 10.1111/all.15032. Epub Sep. 1, 2021. PMID: 34343358.

(56) References Cited

OTHER PUBLICATIONS

Okubo M, Komukai S, Callaway CW, Izawa J. Association of Timing of Epinephrine Administration With Outcomes in Adults With Out-of-Hospital Cardiac Arrest. JAMA Netw Open. Aug. 2, 2021;4(8):e2120176. doi: 10.1001/jamanetworkopen.2021.20176. PMID: 34374770; PMCID: PMC8356068.
Parish HG, Bowser CS, Morton JR, Brown JC. A systematic review of epinephrine degradation with exposure to excessive heat or cold. Ann Allergy Asthma Immunol. Jul. 2016;117(1):79-87. doi: 10.1016/j.anai.2016.04.006. Epub May 21, 2016. PMID: 27221065.
Patel N, Chong KW, Yip AYG, Ierodiakonou D, Bartra J, Boyle RJ, Turner PJ. Use of multiple epinephrine doses in anaphylaxis: A systematic review and meta-analysis. J Allergy Clin Immunol. Nov. 2021;148(5):1307-1315. doi: 10.1016/j.jaci.2021.03.042. Epub Apr. 20, 2021. PMID: 33862009; PMCID: PMC8588837.
Patil Armenian, Danielle Campagne, Geoff Stroh, Crystal Ives Tallman, William Z. D. Zeng, Thomas Lin & Roy R. Gerona (2017) Hot and Cold Drugs: National Park Service Medication Stability at the Extremes of Temperature, Prehospital Emergency Care, 21:3, 378-385, DOI: 10.1080/10903127.2016.1258098.
Paul Turner, Imperial College London. Pharmacokinetics of Intramuscular Adrenaline in Food-Allergic Teenagers: Does Dose Matter? The PIMAT Study. Version 1.2, Sep. 29, 2017.
Ponda P, Russell AF, Yu JE, Land MH, Crain MG, Patel K, Shroba JA, Sriaroon P. Access barriers to epinephrine autoinjectors for the treatment of anaphylaxis: A survey of practitioners. J Allergy Clin Immunol Pract. Oct. 2021;9(10):3814-3815.e4. doi: 10.1016/j.jaip.2021.05.028. Epub Jun. 11, 2021. PMID: 34126272.
Prince BT, Mikhail I, Stukus DR. Underuse of epinephrine for the treatment of anaphylaxis: missed opportunities. J Asthma Allergy. Jun. 20, 2018;11:143-151. doi: 10.2147/JAA.S159400. PMID: 29950873; PMCID: PMC6016581.
Proxim/Proximed, Directions for use: Nasal Turbuhaler, available online Sep. 30, 2020). (Year: 2020).
Rachid O, Simons FE, Rawas-Qalaji M, Lewis S, Simons KJ. Epinephrine doses delivered from auto-injectors stored at excessively high temperatures. Drug Dev Ind Pharm. Jan. 2016;42(1):131-135. doi: 10.3109/03639045.2015.1035283. Epub May 22, 2015. PMID: 25997362.
Rawas-Qalaji M, Simons FE, Collins D, Simons KJ. Long-term stability of epinephrine dispensed in unsealed syringes for the first-aid treatment of anaphylaxis. Ann Allergy Asthma Immunol. Jun. 2009;102(6):500-3. doi: 10.1016/S1081-1206(10)60124-X. PMID: 19558009.
Robert J Good, Surface free energy of solids and liquids: Thermodynamics, molecular forces, and structure, J. Colloid Interface Sci., vol. 59, Issue 3, 1977, pp. 398-419, https://doi.org/10.1016/0021-9797(77)90034-0.
Roth JV, Shields A. A dilemma: How does one treat anaphylaxis in the sulfite allergic patient since epinephrine contains sodium metabisulfite? Anesth Analg. May 2004;98(5):1499; author reply 1500. doi: 10.1213/01.ane.0000120092.39021.f2. PMID: 15105239.
Rygg A, Hindle M, Longest PW. Linking Suspension Nasal Spray Drug Deposition Patterns to Pharmacokinetic Profiles: A Proof-of-Concept Study Using Computational Fluid Dynamics. J Pharm Sci. Jun. 2016;105(6):1995-2004. doi: 10.1016/j.xphs.2016.03.033. PMID: 27238495; PMCID: PMC4886237.
Satish Balakrishna Bhise, Adhikrao Vyankatrao Yadav, Amelia Makrand Avachat, Rajkumar Malayandi, Bioavailability of intranasal drug delivery system, Biopharmaceutical Research Group, Department of Biopharmaceutics, Government College of Pharmacy, Karad, India, Asian Journal of Pharmaceutics, vol. 2, No. 4 (2008).
Sclar DA. Bioequivalence evaluation of epinephrine autoinjectors with attention to rapid delivery. Ther Clin Risk Manag. 2013;9:149-51. doi: 10.2147/TCRM.S43774. Epub Apr. 12, 2013. PMID: 23610523; PMCID: PMC3629870.
Simons FE, Gu X, Simons KJ. Epinephrine absorption in adults: intramuscular versus subcutaneous injection. J Allergy Clin Immunol. Nov. 2001;108(5):871-3. doi: 10.1067/mai.2001.119409. PMID: 11692118.
Simons FE, Lieberman PL, Read EJ Jr, Edwards ES. Hazards of unintentional injection of epinephrine from autoinjectors: a systematic review. Ann Allergy Asthma Immunol. Apr. 2009;102(4):282-7. doi: 10.1016/S1081-1206(10)60332-8. PMID: 19441598.
Simons FE, Roberts JR, Gu X, Simons KJ. Epinephrine absorption in children with a history of anaphylaxis. J Allergy Clin Immunol. Jan. 1998;101(1 Pt 1): 33-7. doi: 10.1016/S0091-6749(98)70190-3. PMID: 9449498.
Song TT, Nelson MR, Chang JH, Engler RJ, Chowdhury BA. Adequacy of the epinephrine autoinjector needle length in delivering epinephrine to the intramuscular tissues. Ann Allergy Asthma Immunol. May 2005;94(5):539-42. doi: 10.1016/S1081-1206(10)61130-1. PMID: 15945556.
Stetcher, D., et.al., "Epinephrine Auto-injectors: Is Needle Length Adequate for Delivery of Epinephrine Intramuscularly?" Pediatrics, Jul. 2009, 124(1): 65-70, doi:10.1542/peds.2008-3388.
Susan C. Smolinske (1992) Review of Parenteral Sulfite Reactions, Journal of Toxicology: Clinical Toxicology, 30:4, 597-606, DOI: 10.3109/15563659209017945.
Takeuchi H, Thongborisute J, Matsui Y, Sugihara H, Yamamoto H, Kawashima Y. Novel mucoadhesion tests for polymers and polymer-coated particles to design optimal mucoadhesive drug delivery systems. Adv Drug Deliv Rev. Nov. 3, 2005;57(11):1583-94. doi: 10.1016/j.addr.2005.07.008. Epub Sep. 16, 2005. PMID: 16169120.
Tiozzo Fasiolo L, Manniello MD, Tratta E, Buttini F, Rossi A, Sonvico F, Bortolotti F, Russo P, Colombo G. Opportunity and challenges of nasal powders: Drug composition and delivery. Eur J Pharm Sci. Feb. 15, 2018;113:2-17. doi: 10.1016/j.ejps.2017.09.027. Epub Sep. 20, 2017. PMID: 28942007.
Turner P, 2021, A Cost-effectiveness Analysis of Epinephrine Autoinjector Risk Stratification for Patients with Food Allergy—One Epinephrine Autoinjector or Two?, Journal of Allergy and Clinical Immunology: in Practice, ISSN:2213-2201.
Turner P, Boyle R, Durham S, 2021, Limited effect of intramuscular epinephrine on cardiovascular parameters during peanut-induced anaphylaxis: an observational cohort study, Journal of Allergy and Clinical Immunology: in Practice, vol. 9, ISSN:2213-2198, pp. 527-530.
Turner P, Patel N, 2021, Using data from food challenges to inform management of food-allergic consumers: a systematic review with individual participant data meta-analysis, Journal of Allergy and Clinical Immunology, ISSN:0091-6749.
Turner PJ, Ruiz-Garcia M, Durham SR, Boyle RJ. Limited effect of intramuscular epinephrine on cardiovascular parameters during peanut-induced anaphylaxis: An observational cohort study. J Allergy Clin Immunol Pract. Jan. 2021;9(1):527-530. doi: 10.1016/j.jaip.2020.08.041. Epub Sep. 2, 2020. PMID: 32889224; PMCID: PMC7794658.
U.S. Food & Drug Administration. Multidisciplinary Review. NDA 201-739, S-008 and S-009. Auvi-Q (epinephrine injection, USP) Auto-Injector. Sep. 2017, available at www.fda.gov/media/109468/download.
US FDA, FY2018 Regulatory Science Report: Physiologically-Based Absorption and Pharmacokinetic Models for Non-Oral Routes, https://www.fda.gov/media/130623/download (last accessed Jun. 10, 2021).
Wasserman, S., et al. "Epinephrine Autoinjectors: New Data, New Problems," J Allergy Clin Immunol Pract., Sep.-Oct. 2017; 5(5):1180-1191, doi: 10.1016/j.jaip.2017.06.027.
Worm, M., Nguyen, D., Rackley, R. et al. Epinephrine delivery via EpiPen® Auto-Injector or manual syringe across participants with a wide range of skin-to-muscle distances. Clin Transl Allergy 10, 21 (2020). https://doi.org/10.1186/s13601-020-00326-x.

* cited by examiner

| Formulation | | | Spray Dryer Parameters | | | | Particle Size Distribution Results | | |
|---|---|---|---|---|---|---|---|---|---|
| Formulation feed strength, (% w/v) | Composition (% w/w) | Solvent mix | Inlet temp (°C) | Aspirator Power (%) | Pump Rate (%) | Nozzle power (%) | | d(4,3) µm | d(0.9) µm |
| 2.5% | Lactose/API 90/10 | EtOH/$H_2O$, 20/80 v/v | 110 | 100 | 10 | 40 | non-sonicated | 18.060 | 36.741 |
| | | | | | | | sonicated | 13.144 | 26.649 |
| 2.5% | Lactose/API/Leucine 80/10/10 | EtOH/$H_2O$, 20/80 v/v | 110 | 100 | 10 | 40 | non-sonicated | 9.956 | 18.007 |
| | | | | | | | sonicated | 9.700 | 17.798 |
| 2.5% | Trehalose/API/Leucine 80/10/10 | EtOH/$H_2O$, 20/80 v/v | 110 | 100 | 10 | 40 | non-sonicated | 12.135 | 18.829 |
| | | | | | | | sonicated | 12.075 | 18.793 |
| 2.5% | Lactose/API/Leucine 80/10/10 | EtOH/$H_2O$, 20/80 v/v | 110 | 100 | 10 | 35 | non-sonicated | 11.237 | 19.006 |
| | | | | | | | sonicated | 10.201 | 19.473 |
| 2.5% | Trehalose/API/Leucine 80/10/10 | EtOH/$H_2O$, 20/80 v/v | 110 | 100 | 15 | 30 | non-sonicated | 11.820 | 18.417 |
| | | | | | | | sonicated | 34.783 | 24.682 |
| 1% | Na-CMC/API/Leucine 80/10/10 | EtOH/$H_2O$, 20/80 v/v | 130 | 100 | 15 | 30 | non-sonicated | 31.638 | 64.248 |
| | | | | | | | sonicated | 17.281 | 33.140 |
| 5% | Lactose/API/Leucine 80/10/10 | EtOH/$H_2O$, 20/80 v/v | 110 | 100 | 10 | 35 | non-sonicated | 13.809 | 23.552 |
| | | | | | | | sonicated | 12.729 | 23.591 |
| 2.5% | Lactose/API/Leucine/NaCl 78/10/10/ | EtOH/$H_2O$, 20/80 v/v | 120 | 100 | 10 | 35 | non-sonicated | 9.819 | 18.285 |
| | | | | | | | sonicated | - | - |
| 2.5% | Lactose/API/chitosan 70/10/20 | EtOH/$H_2O$, 20/80 v/v | - | - | - | - | Insoluble in the solvent mix | | |
| 2.5% | Lactose/API/chitosan 70/10/20 | EtOH/$H_2O$, 10/90 v/v | - | - | - | - | Insoluble in the solvent mix | | |
| 2.5% | Lactose/API/chitosan 70/10/20 | EtOH/$H_2O$, 10/90 v/v (acidified) | - | - | - | - | Viscosity too high to spray dry | | |
| 2.5% | Lactose/API/chitosan 80/10/10 | EtOH/$H_2O$, 10/90 v/v (acidified) | - | - | - | - | Insoluble in the solvent mix | | |
| 1% | Lactose/API/Carbomer 934 85/10/5 | EtOH/$H_2O$, 20/80 v/v | 130 | 100 | 15 | 45 | non-sonicated | 26.103 | 60.283 |
| | | | | | | | sonicated | 14.574 | 31.981 |
| 2.5% | Lactose/API/Tween 80 89.9/10/0.1/ | EtOH/$H_2O$, 20/80 v/v | 130 | 100 | 10 | 40 | non-sonicated | 19.191 | 42.749 |
| | | | | | | | sonicated | 13.824 | 28.463 |

FIG. 1

| Formulation | | Spray Dryer Parameters | | | | | Particle Size Distribution Results | | |
|---|---|---|---|---|---|---|---|---|---|
| Formulation feed strength, (% w/v) | Composition (% w/w) | Solvent mix | Inlet temp (°C) | Aspirator Power (%) | Pump Rate (%) | Nozzle power (%) | | d(4,3) µm | d(0.9) µm |
| 1% | Na-CMC/API 90/10 | EtOH/$H_2O$, 20/80 v/v | 130 | 100 | 15 | 40 | non-sonicated | 14.471 | 24.979 |
| | | | | | | | sonicated | 12.324 | 21.007 |
| 2.5% | Lactose/API/NaCl 88/10/2 | EtOH/$H_2O$, 20/80 v/v | 130 | 100 | 15 | 35 | non-sonicated | 18.727 | 37.747 |
| | | | | | | | sonicated | 20.220 | 41.416 |
| 1% | Na-CMC/API/NaCl 88/10/2 | EtOH/$H_2O$, 20/80 v/v | 130 | 100 | 15 | 37 | non-sonicated | 13.084 | 21.962 |
| | | | | | | | sonicated | 11.605 | 18.723 |
| 2.5% | Lactose/API/Tween 80 89.5/10/0.5 | EtOH/$H_2O$, 20/80 v/v | 130 | 100 | 23 | 35 | non-sonicated | 42.106 | 83.484 |
| | | | | | | | sonicated | 32.413 | 61.869 |
| 1% | Na-CMC/API/Tween 80 89.5/10/0.5 | EtOH/$H_2O$, 20/80 v/v | 130 | 100 | 25 | 40 | non-sonicated | 14.769 | 25.036 |
| | | | | | | | sonicated | 12.622 | 21.299 |
| 1% | Na-CMC/API/Leucine/NaCl 78/10/10/2 | EtOH/$H_2O$, 20/80 v/v | 130 | 100 | 15 | 45 | non-sonicated | 17.229 | 34.355 |
| | | | | | | | sonicated | 12.139 | 20.724 |
| 1% | Na-CMC/API/Carbomer 934 85/10/5 | EtOH/$H_2O$, 20/80 v/v | 130 | 100 | 20 | 45 | non-sonicated | 11.714 | 18.123 |
| | | | | | | | sonicated | 9.423 | 14.518 |
| 5% | Lactose/API/Nicotinic acid 88/10/2 | EtOH/$H_2O$, 20/80 v/v | 130 | 100 | 23 | 35 | non-sonicated | 17.376 | 34.458 |
| | | | | | | | sonicated | 18.476 | 35.815 |
| 1.5% | Na-CMC/API/Nicotinic acid 88/10/2 | EtOH/$H_2O$, 20/80 v/v | 130 | 100 | 25 | 47 | non-sonicated | 17.436 | 30.728 |
| | | | | | | | sonicated | 13.701 | 23.134 |
| 5% | Lactose/API/Hyaluronate 89.5/10/0.5 | EtOH/$H_2O$, 20/80 v/v | 130 | 100 | 15 | 45 | non-sonicated | 20.479 | 46.885 |
| | | | | | | | sonicated | 18.419 | 41.286 |
| 2% | Na-CMC/API/Hyaluronate 89.5/10/0.5 | EtOH/$H_2O$, 20/80 v/v | 130 | 100 | 25 | 55 | non-sonicated | 18.111 | 32.800 |
| | | | | | | | sonicated | 14.827 | 25.977 |
| 5% | Lactose/API/Caffeine 85/10/5 | EtOH/$H_2O$, 20/80 v/v | 130 | 100 | 22 | 34 | non-sonicated | 74.973 | 190.149 |
| | | | | | | | sonicated | 53.744 | 118.603 |
| 5% | Lactose/API/Caffeine 85/10/5 | EtOH/$H_2O$, 20/80 v/v | 130 | 100 | 15 | 45 | non-sonicated | 26.829 | 52.352 |
| | | | | | | | sonicated | 24.960 | 48.269 |
| 5% | Lactose/API/Caffeine 85/10/5 | EtOH/$H_2O$, 20/80 v/v | 140 | 100 | 15 | 48 | non-sonicated | 28.430 | 55.336 |
| | | | | | | | sonicated | 25.269 | 50.206 |
| 2% | Na-CMC/API/Caffeine 85/10/5 | EtOH/$H_2O$, 20/80 v/v | 130 | 100 | 20 | 50 | non-sonicated | 12.995 | 212.626 |
| | | | | | | | sonicated | 11.206 | 18.457 |

FIG. 2

| Formulation | | | Spray Dryer Parameters | | | | Particle Size Distribution Results | | |
|---|---|---|---|---|---|---|---|---|---|
| Formulation feed strength, (% w/v) | Composition (% w/w) | Solvent mix | Inlet temp (°C) | Aspirator Power (%) | Pump Rate (%) | Nozzle power (%) | | d(4,3) µm | d(0.9) µm |
| 2.5% | Lactose/API 90/10 | EtOH/$H_2O$, 20/80 v/v | 110 | 100 | 10 | 40 | non-sonicated | 19.721 | 40.427 |
| | | | | | | | sonicated | 14.486 | 30.101 |
| 2.5% | Lactose/API 90/10 | EtOH/$H_2O$, 20/80 v/v | 110 | 100 | 10 | 40 | non-sonicated | 16.648 | 34.541 |
| | | | | | | | sonicated | 46.161 | 152.013 |
| 2.5% | Lactose/API/NaCl 88/10/2 | EtOH/$H_2O$, 20/80 v/v | 140 | 100 | 20 | 35 | n/a | | |
| | | | | | | | sonicated | 24.604 | 49.635 |
| 5% | Lactose/API/Nicotinic acid 88/10/2 | EtOH/$H_2O$, 20/80 v/v | 130 | 100 | 23 | 35 | n/a | | |
| | | | | | | | sonicated | 38.188 | 76.434 |
| 2% | Na-CMC/API/Nicotinic acid 88/10/2 | EtOH/$H_2O$, 20/80 v/v | 130 | 100 | 16 | 46 | n/a | | |
| | | | | | | | sonicated | 14.624 | 24.057 |
| 1% | Na-CMC/API/Leucine 80/10/10 | EtOH/$H_2O$, 20/80 v/v | 130 | 100 | 15 | 45 | n/a | | |
| | | | | | | | sonicated | 14.624 | 24.057 |
| 2% | Na-CMC/API 90/10 | EtOH/$H_2O$, 20/80 v/v | 130 | 100 | 15 | 47 | n/a | | |
| | | | | | | | sonicated | 14.757 | 24.665 |
| 2.5% | Lactose/API/Tween 80 89.5/10/0.5 | EtOH/$H_2O$, 20/80 v/v | 130 | 100 | 18 | 45 | n/a | | |
| | | | | | | | sonicated | 22.480 | 41.142 |
| 5% | Lactose/API/Nicotinic acid 88/10/2 | EtOH/$H_2O$, 20/80 v/v | 130 | 100 | 20 | 36 | n/a | | |
| | | | | | | | sonicated | 24.589 | 48.277 |

FIG. 3

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | Epinephrine (ng/mL) | | | | | | | |
| Epinephrine | Lactose | 1 | 0.00 | 32.2 | 46.3 | 64.7 | 41.8 | 38.5 | 9.87 | 0.00 |
| | | 2 | 0.00 | 0.00 | 28.0 | 18.5 | 16.4 | 10.1 | 0.00 | 0.00 |
| | | 3 | 0.00 | 111 | 153 | 67.6 | 38.3 | 14.8 | 0.00 | 0.00 |
| | | **N** | **3** | **3** | **3** | **3** | **3** | **3** | **3** | **3** |
| | | **Mean** | **0.00** | **47.7** | **75.8** | **50.3** | **32.2** | **21.1** | **3.29** | **0.00** |
| | | **CV%** | **NC** | **119.6** | **89.1** | **54.8** | **42.8** | **72.0** | **173.2** | **NC** |

FIG. 10

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | Epinephrine (ng/mL) | | | | | | | |
| Epinephrine | Sodium CMC | 22 | 0.00 | 0.00 | 2.90 | 0.00 | 5.28 | 13.3 | 6.17 | 4.36 |
| | | 23 | 0.00 | 0.00 | 2.95 | 14.6 | 19.6 | 19.6 | 10.1 | 7.65 |
| | | 24 | 0.00 | 11.1 | 5.71 | 9.25 | 22.5 | 23.6 | 39.2 | 5.59 |
| | | **N** | **3** | **3** | **3** | **3** | **3** | **3** | **3** | **3** |
| | | **Mean** | **0.00** | **3.70** | **3.85** | **7.95** | **15.8** | **18.8** | **18.5** | **5.87** |
| | | **CV%** | **NC** | **173.2** | **41.7** | **92.9** | **58.4** | **27.6** | **97.6** | **28.3** |

FIG. 11

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Caffeine (5% w/w) | Lactose | 19 | 0.00 | 87.3 | 62.3 | 23.6 | 16.0 | 4.15 | 2.69 | 0.00 |
| | | 20 | 0.00 | 106 | 95.8 | 86.2 | 36.0 | 13.1 | 7.85 | 6.20 |
| | | 21 | 0.00 | 43.2 | 88.4 | 71.8 | 23.3 | 19.3 | 10.4 | 3.53 |
| | | **N** | **3** | **3** | **3** | **3** | **3** | **3** | **3** | **3** |
| | | **Mean** | **0.00** | **78.8** | **82.2** | **60.5** | **25.1** | **12.2** | **6.98** | **3.24** |
| | | **CV%** | **NC** | **40.9** | **21.4** | **54.2** | **40.3** | **62.5** | **56.3** | **95.9** |

FIG. 12

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Caffeine (5% w/w) | Sodium CMC | 40 | 0.00 | 7.80 | 18.9 | 16.0 | 15.2 | 16.3 | 20.6 | 14.4 |
| | | 41 | 0.00 | 18.4 | 23.1 | 27.7 | 29.0 | 36.3 | 43.8 | 0.00 |
| | | 42 | 0.00 | 16.3 | 16.1 | 24.0 | 16.3 | 20.9 | 10.1 | 4.36 |
| | | **N** | **3** | **3** | **3** | **3** | **3** | **3** | **3** | **3** |
| | | **Mean** | **0.00** | **14.2** | **19.4** | **22.6** | **20.2** | **24.5** | **24.8** | **6.25** |
| | | **CV%** | **NC** | **39.6** | **18.2** | **26.5** | **38.0** | **42.8** | **69.4** | **118.1** |

FIG. 13

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Hyaluronate (0.5% w/w) | Lactose | 16 | 0.00 | 3.57 | 3.45 | 4.45 | 3.50 | 0.00 | 0.00 | 0.00 |
| | | 17 | 0.00 | 43.7 | 13.7 | 11.3 | 2.88 | 0.00 | 2.72 | 0.00 |
| | | 18 | 0.00 | 11.9 | 5.29 | 0.00 | 2.92 | 0.00 | 0.00 | 0.00 |
| | | **N** | **3** | **3** | **3** | **3** | **3** | **3** | **3** | **3** |
| | | **Mean** | **0.00** | **19.7** | **7.48** | **5.25** | **3.10** | **0.00** | **0.907** | **0.00** |
| | | **CV%** | **NC** | **107.4** | **73.1** | **108.4** | **11.2** | **NC** | **173.2** | **NC** |

FIG. 14

| | | | Time (h) | | | | | | | |
|---|---|---|---|---|---|---|---|---|---|---|
| | | | **0.0** | **1.0** | **3.0** | **5.0** | **10.0** | **15.0** | **30.0** | **60.0** |
| **Test Article** | **Carrier** | **Animal** | **Epinephrine (ng/mL)** | | | | | | | |
| Epinephrine + Hyaluronate (0.5% w/w) | Sodium CMC | 37 | 0.00 | 4.78 | 14.3 | 16.7 | 31.8 | 26.1 | 28.9 | 46.1 |
| | | 38 | 0.00 | 3.47 | 10.2 | 20.2 | ISV | 28.2 | 15.9 | 14.3 |
| | | 39 | 0.00 | 4.53 | 13.4 | 14.6 | 16.8 | 20.1 | 19.8 | 12.6 |
| | | **N** | **3** | **3** | **3** | **3** | **2** | **3** | **3** | **3** |
| | | **Mean** | **0.00** | **4.26** | **12.6** | **17.2** | **24.3** | **24.8** | **21.5** | **24.3** |
| | | **CV%** | **NC** | **16.3** | **17.1** | **16.5** | **43.6** | **16.9** | **31.0** | **77.5** |

FIG. 15

| | | | Time (h) | | | | | | | |
|---|---|---|---|---|---|---|---|---|---|---|
| | | | **0.0** | **1.0** | **3.0** | **5.0** | **10.0** | **15.0** | **30.0** | **60.0** |
| **Test Article** | **Carrier** | **Animal** | **Epinephrine (ng/mL)** | | | | | | | |
| Epinephrine + Leucine (10% w/w) | Lactose | 4 | 0.00 | 0.00 | 0.00 | 0.00 | 0.00 | 0.00 | 0.00 | 0.00 |
| | | 5 | 0.00 | 0.00 | 0.00 | 0.00 | 0.00 | 0.00 | 0.00 | 0.00 |
| | | 6 | 0.00 | 0.00 | 0.00 | 0.00 | 0.00 | 0.00 | 0.00 | 0.00 |
| | | **N** | **3** | **3** | **3** | **3** | **3** | **3** | **3** | **3** |
| | | **Mean** | **0.00** | **0.00** | **0.00** | **0.00** | **0.00** | **0.00** | **0.00** | **0.00** |

FIG. 16

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Leucine (10% w/w) | Sodium CMC | 25 | 0.00 | 0.00 | 6.00 | 4.08 | 7.56 | 6.80 | 8.47 | 7.98 |
| | | 26 | 0.00 | 3.43 | 7.58 | 14.2 | 36.1 | 18.8 | 8.61 | 7.12 |
| | | 27 | 0.00 | 0.00 | 4.62 | 10.6 | 14.9 | 11.6 | 8.65 | 9.92 |
| | | **N** | **3** | **3** | **3** | **3** | **3** | **3** | **3** | **3** |
| | | **Mean** | **0.00** | **1.14** | **6.07** | **9.63** | **19.5** | **12.4** | **8.58** | **8.34** |
| | | **CV%** | **NC** | **173.2** | **24.4** | **53.3** | **75.9** | **48.7** | **1.1** | **17.2** |

FIG. 17

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + NaCl (2% w/w) | Lactose | 10 | 0.00 | 6.57 | 26.4 | 27.6 | 26.7 | 21.0 | 12.3 | 11.2 |
| | | 11 | 0.00 | 22.9 | 21.7 | 22.4 | 91.1 | 16.3 | 16.2 | 6.31 |
| | | 12 | 0.00 | 42.1 | 61.5 | 46.6 | 20.1 | 7.31 | 7.68 | 0.00 |
| | | **N** | **3** | **3** | **3** | **3** | **3** | **3** | **3** | **3** |
| | | **Mean** | **0.00** | **23.9** | **36.5** | **32.2** | **46.0** | **14.9** | **12.1** | **5.84** |
| | | **CV%** | **NC** | **74.5** | **59.5** | **39.6** | **85.3** | **46.8** | **35.4** | **96.2** |

FIG. 18

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + NaCl (2% w/w) | Sodium CMC | 31 | 0.00 | 0.00 | 4.49 | 7.32 | 13.8 | 9.65 | 10.2 | 7.32 |
| | | 32 | 0.00 | 3.40 | 7.33 | 15.3 | 14.0 | 15.4 | 15.8 | 8.10 |
| | | 33 | 0.00 | 4.57 | 19.8 | 54.2 | 177 | 117 | 74.6 | 39.9 |
| | | **N** | **3** | **3** | **3** | **3** | **3** | **3** | **3** | **3** |
| | | **Mean** | **0.00** | **2.66** | **10.5** | **25.6** | **68.3** | **47.4** | **33.5** | **18.4** |
| | | **CV%** | **NC** | **89.4** | **77.3** | **98.0** | **137.9** | **127.5** | **106.4** | **100.8** |

FIG. 19

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Niacin (2% w/w) | Lactose | 7 | 0.00 | 82.8 | 78.1 | 47.1 | 32.3 | 55.1 | Not received | NC |
| | | 8 | 0.00 | 97.4 | 135 | 107 | 28.2 | 21.0 | 0.00 | 0.00 |
| | | 9 | 0.00 | 575 | 683 | NC | NC | NC | NC | NC |
| | | 46 | 0.00 | 61.2 | 83.8 | 35.2 | 24.9 | 16.1 | 7.90 | 0.00 |
| | | 47 | 0.00 | 116 | 180 | 43.6 | 13.4 | 10.2 | 0.00 | 0.00 |
| | | **N** | **5** | **5** | **5** | **4** | **4** | **4** | **3** | **3** |
| | | **Mean** | **0.00** | **186** | **232** | **58.2** | **24.7** | **25.6** | **2.63** | **0.00** |
| | | **CV%** | | **117.0** | **110.1** | **56.5** | **32.9** | **78.7** | **173.2** | |

FIG. 20

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | Epinephrine (ng/mL) | | | | | | | |
| Epinephrine + Niacin (2% w/w) | Sodium CMC | 28 | 0.00 | 5.96 | 7.30 | 12.8 | 21.0 | 15.4 | 11.3 | 2.90 |
| | | 29 | 0.00 | 4.25 | 13.8 | 18.9 | 17.0 | 16.1 | 13.7 | 11.7 |
| | | 30 | 0.00 | 5.24 | 10.8 | 11.3 | 23.1 | 27.6 | 28.7 | 18.0 |
| | | **N** | **3** | **3** | **3** | **3** | **3** | **3** | **3** | **3** |
| | | **Mean** | **0.00** | **5.15** | **10.6** | **14.3** | **20.4** | **19.7** | **17.9** | **10.9** |
| | | **CV%** | **NC** | **16.7** | **30.6** | **28.1** | **15.2** | **34.8** | **52.7** | **69.8** |

FIG. 21

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | Epinephrine (ng/mL) | | | | | | | |
| Epinephrine + Polysorbate (0.5% w/w) | Lactose | 13 | 0.00 | 52.3 | 79.5 | 67.9 | 32.3 | 34.0 | 14.7 | 13.5 |
| | | 14 | 0.00 | 124 | 40.0 | 51.3 | 23.4 | 9.07 | 8.07 | 5.91 |
| | | 15 | 0.00 | 88.4 | 32.8 | 100 | 18.2 | 7.18 | 5.57 | 7.55 |
| | | **N** | **3** | **3** | **3** | **3** | **3** | **3** | **3** | **3** |
| | | **Mean** | **0.00** | **88.2** | **50.8** | **73.1** | **24.6** | **16.8** | **9.45** | **8.99** |
| | | **CV%** | **NC** | **40.6** | **49.5** | **33.9** | **28.9** | **89.4** | **49.9** | **44.4** |

FIG. 22

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine + Polysorbate (0.5% w/w) | Sodium CMC | 34 | 0.00 | 0.00 | 15.2 | 16.2 | 18.5 | 12.0 | 12.9 | 9.70 |
| | | 35 | 0.00 | 0.00 | 7.28 | 8.05 | 10.7 | 12.1 | 11.3 | 10.8 |
| | | 36 | 0.00 | 2.57 | 7.72 | 34.0 | 13.7 | 14.2 | 24.4 | 15.1 |
| | | **N** | **3** | **3** | **3** | **3** | **3** | **3** | **3** | **3** |
| | | **Mean** | **0.00** | **0.857** | **10.1** | **19.4** | **14.3** | **12.8** | **16.2** | **11.9** |
| | | **CV%** | **NC** | **173.2** | **44.2** | **68.3** | **27.5** | **9.7** | **44.1** | **24.0** |

FIG. 23

| | | | Time (h) | | | | | | | |
|---|---|---|---|---|---|---|---|---|---|---|
| | | | 0.0 | 1.0 | 3.0 | 5.0 | 10.0 | 15.0 | 30.0 | 60.0 |
| **Test Article** | **Carrier** | **Animal** | **Epinephrine (ng/mL)** | | | | | | | |
| Epinephrine intramuscular injection at 0.7 mg/kg | Liquid | 43 | 0.00 | 165 | 62.1 | 36.9 | 44.5 | 296 | - | - |
| | | 44 | 0.00 | 933 | 464 | - | - | - | - | - |
| | | 45 | 0.00 | 5.66 | 54.2 | 20.4 | 55.7 | 37.1 | 23.2 | 10.3 |
| | | **N** | **3** | **3** | **3** | **2** | **2** | **2** | **1** | **1** |
| | | **Mean** | **0.00** | **368** | **193** | **28.7** | **50.1** | **167** | **23.2** | **10.3** |
| | | **CV%** | **NC** | **134.8** | **121.2** | **40.7** | **15.8** | **109.9** | **NC** | **NC** |

FIG. 24

FIG. 25

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine | Lactose | 1 | 0.45 | 64.7 | 5.0 | 984 | 9.07 | 1110 |
| | | 2 | 0.48 | 28.0 | 3.0 | 226 | 11.5 | 393 |
| | | 3 | 0.45 | 153 | 3.0 | 910 | 4.56 | 1010 |
| | | | **N** | **3** | **3** | **3** | **3** | **3** |
| | | | **Mean** | **81.9** | **3.67** | **707** | **8.36** | **838** |
| | | | **CV%** | **78.4** | **31.5** | **59.1** | **41.8** | **46.4** |

FIG. 26

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine | Sodium CMC | 22 | 0.42 | 13.3 | 15.0 | 361 | - | - |
| | | 23 | 0.47 | 19.6 | 10.0 | 683 | 36.0 | 1080 |
| | | 24 | 0.60 | 39.2 | 30.0 | 1220 | - | - |
| | | | **N** | **3** | **3** | **3** | **1** | **1** |
| | | | **Mean** | **24.0** | **18.3** | **755** | **36.0** | **1080** |
| | | | **CV%** | **56.2** | **56.8** | **57.5** | **NC** | **NC** |

FIG. 27

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Caffeine (5% w/w) | Lactose | 19 | 0.46 | 87.3 | 1.0 | 464 | 6.41 | 489 |
| | | 20 | 0.51 | 106 | 1.0 | 1200 | 45.1 | 1600 |
| | | 21 | 0.48 | 88.4 | 3.0 | 1040 | 18.3 | 1130 |
| | | | **N** | **3** | **3** | **3** | **3** | **3** |
| | | | **Mean** | **93.9** | **1.67** | **902** | **23.3** | **1080** |
| | | | **CV%** | **11.2** | **69.3** | **43.0** | **85.1** | **52.1** |

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Caffeine (5% w/w) | Sodium CMC | 40 | 0.52 | 20.6 | 30.0 | 1020 | - | - |
| | | 41 | 0.51 | 43.8 | 30.0 | 1010 | - | - |
| | | 42 | 0.48 | 24.0 | 5.0 | 701 | 20.5 | 830 |
| | | | **N** | **3** | **3** | **3** | **1** | **1** |
| | | | **Mean** | **29.5** | **21.7** | **909** | **20.5** | **830** |
| | | | **CV%** | **42.5** | **66.6** | **19.8** | **NC** | **NC** |

FIG. 28

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Hyaluronate (0.5% w/w) | Lactose | 16 | 0.22 | 4.45 | 5.0 | 36.5 | - | - |
| | | 17 | 0.14 | 43.7 | 1.0 | 157 | 12.9 | 207 |
| | | 18 | 0.08 | 11.9 | 1.0 | 34.8 | - | - |
| | | | **N** | **3** | **3** | **3** | **1** | **1** |
| | | | **Mean** | **20.0** | **2.33** | **76.1** | **12.9** | **207** |
| | | | **CV%** | **104.1** | **99.0** | **92.0** | **NC** | **NC** |

FIG. 29

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Hyaluronate (0.5% w/w) | Sodium CMC | 37 | 0.65 | 46.1 | 60.0 | 1860 | - | - |
| | | 38 | 0.47 | 28.2 | 15.0 | 1060 | - | - |
| | | 39 | 0.48 | 20.1 | 15.0 | 996 | - | - |
| | | | **N** | **3** | **3** | **3** | **0** | **0** |
| | | | **Mean** | **31.5** | **30.0** | **1300** | **NC** | **NC** |
| | | | **CV%** | **42.3** | **86.6** | **36.7** | **NC** | **NC** |

FIG. 30

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Leucine (10% w/w) | Lactose | 4 | 0.37 | 0.00 | 0.0 | - | - | - |
| | | 5 | 0.33 | 0.00 | 0.0 | - | - | - |
| | | 6 | 0.16 | 0.00 | 0.0 | - | - | - |
| | | | **N** | **3** | **3** | **0** | **0** | **0** |
| | | | **Mean** | **0.00** | **0.00** | - | - | - |
| | | | **CV%** | **NC** | **NC** | - | - | - |

FIG. 31

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Leucine (10% w/w) | Sodium CMC | 25 | 0.52 | 8.47 | 30.0 | 442 | - | - |
| | | 26 | 0.48 | 36.1 | 10.0 | 724 | 35.7 | 1090 |
| | | 27 | 0.50 | 14.9 | 10.0 | 579 | 298 | 4840 |
| | | | **N** | **3** | **3** | **3** | **2** | **2** |
| | | | **Mean** | **19.8** | **16.7** | **582** | **167** | **2970** |
| | | | **CV%** | **72.9** | **69.3** | **24.2** | **111.1** | **89.4** |

FIG. 32

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + NaCl (2% w/w) | Lactose | 10 | 0.45 | 27.6 | 5.0 | 941 | 42.4 | 1630 |
| | | 11 | 0.43 | 91.1 | 10.0 | 1160 | 30.7 | 1440 |
| | | 12 | 0.44 | 61.5 | 3.0 | 565 | 10.6 | 683 |
| | | | **N** | **3** | **3** | **3** | **3** | **3** |
| | | | **Mean** | **60.1** | **6.00** | **889** | **27.9** | **1250** |
| | | | **CV%** | **52.9** | **60.1** | **33.8** | **57.6** | **40.0** |

FIG. 33

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + NaCl (2% w/w) | Sodium CMC | 31 | 0.40 | 13.8 | 10.0 | 536 | 101 | 1610 |
| | | 32 | 0.54 | 15.8 | 30.0 | 761 | - | - |
| | | 33 | 0.46 | 177 | 10.0 | 4480 | 29.5 | 6180 |
| | | | **N** | **3** | **3** | **3** | **2** | **2** |
| | | | **Mean** | **68.9** | **16.7** | **1930** | **65.4** | **3890** |
| | | | **CV%** | **136.0** | **69.3** | **115.0** | **77.6** | **83.1** |

FIG. 34

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Niacin (2% w/w) | Lactose | 7 | 9.61 | 82.8 | 1.0 | 740 | 26.7 | 2860 |
| | | 8 | 0.29 | 135 | 3.0 | 940 | 4.26 | 1070 |
| | | 9 | 0.50 | 683 | 3.0 | 1550 | - | - |
| | | 46 | 0.00 | 83.8 | 3.0 | 710 | 11.7 | 844 |
| | | 47 | 0.00 | 180 | 3.0 | 733 | 4.77 | 803 |
| | | | **N** | **5** | **5** | **5** | **4** | **4** |
| | | | **Mean** | **233** | **2.60** | **934** | **11.9** | **1390** |
| | | | **CV%** | **109.4** | **34.4** | **38.0** | **88.1** | **70.6** |

FIG. 35

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Niacin (2% w/w) | Sodium CMC | 28 | 0.50 | 21.0 | 10.0 | 595 | 18.1 | 671 |
| | | 29 | 0.45 | 18.9 | 5.0 | 828 | 94.0 | 2420 |
| | | 30 | 0.51 | 28.7 | 30.0 | 1360 | - | - |
| | | | **N** | **3** | **3** | **3** | **2** | **2** |
| | | | **Mean** | **22.9** | **15.0** | **929** | **56.1** | **1540** |
| | | | **CV%** | **22.6** | **88.2** | **42.4** | **95.7** | **79.9** |

FIG. 36

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Polysorbate (0.5% w/w) | Lactose | 13 | 0.54 | 79.5 | 3.0 | 1480 | 26.9 | 2000 |
| | | 14 | 0.47 | 124 | 1.0 | 892 | 71.9 | 1500 |
| | | 15 | 0.44 | 100 | 5.0 | 880 | 65.0 | 1590 |
| | | | **N** | **3** | **3** | **3** | **3** | **3** |
| | | | **Mean** | **101** | **3.00** | **1080** | **54.6** | **1700** |
| | | | **CV%** | **22.0** | **66.7** | **31.6** | **44.3** | **15.7** |

FIG. 37

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine + Polysorbate (0.5% w/w) | Sodium CMC | 34 | 0.42 | 18.5 | 10.0 | 732 | 128 | 2520 |
| | | 35 | 0.42 | 12.1 | 15.0 | 633 | - | - |
| | | 36 | 0.51 | 34.0 | 5.0 | 1110 | 622 | 14700 |
| | | | **N** | **3** | **3** | **3** | **2** | **2** |
| | | | **Mean** | **21.5** | **10.0** | **824** | **375** | **8590** |
| | | | **CV%** | **52.3** | **50.0** | **30.2** | **93.1** | **99.8** |

FIG. 38

| Test Article | Carrier | Animal | Dose (mg) | Cmax (ng/mL) | Tmax (min) | AUClast (min*ng/mL) | t½ (min) | AUCinf (min*ng/mL) |
|---|---|---|---|---|---|---|---|---|
| Epinephrine intramuscular injection at 0.7 mg/kg | Liquid | 43 | 0.00 | 296 | 15.0 | 1440 | - | - |
| | | 44 | 0.00 | 933 | 1.0 | 1810 | - | - |
| | | 45 | 0.00 | 55.7 | 10.0 | 1470 | 24.5 | 1840 |
| | | | **N** | **3** | **3** | **3** | **1** | **1** |
| | | | **Mean** | **428** | **8.67** | **1580** | **24.5** | **1840** |
| | | | **CV%** | **105.9** | **81.9** | **12.9** | **NC** | **NC** |

FIG. 39

Calibration Curve Data for Epinephrine in Rat $K_2EDTA$ Plasma

| Batch Number (Analysis Date) | Nominal Concentrations 5.00 (ng/mL) | 10.0 (ng/mL) | 25.0 (ng/mL) | 100 (ng/mL) | 300 (ng/mL) | 900 (ng/mL) | 1000 (ng/mL) | Calibration Curve Parameters A[a] | B[a] | C[a] | RSQ[b] |
|---|---|---|---|---|---|---|---|---|---|---|---|
| 1 | 5.21 | 8.61 | 36.1[c] | 113 | 405[c] | 946 | 1040 | 4.36E-06 | 1.78E-02 | 6.29E-02 | 9.925E-01 |
| (21 Oct 2021) | 5.11 | 10.3 | 23.1 | 95.5 | 316 | 834 | 961 | | | | |
| 2 | 5.17 | 7.52[c] | 25.9 | 103 | 335 | 1010 | 1010 | 5.77E-08 | 1.13E-03 | 2.06E-03 | 9.904E-01 |
| (22 Oct 2021) | 4.92 | 6.80[c] | 21.7 | 95.6 | 297 | 628[c] | 857 | | | | |
| 3 | 5.13 | 7.24[c] | 22.7 | 0.682[c] | 303 | 871 | 1040 | 1.83E-07 | 9.52E-03 | -6.49E-03 | 9.955E-01 |
| (21 Oct 2021) | 4.99 | 9.60 | 27.2 | 93.9 | 332 | 873 | 992 | | | | |
| 4 | 3.22[d] | 9.24 | 25.4 | 89.3 | 320 | 930 | 910 | 1.74E-06 | 9.72E-03 | 4.42E-03 | 9.916E-01 |
| (22 Oct 2021) | 5.19 | 10.5 | 21.4 | 106 | 337 | 920 | 999 | | | | |
| 5 | 4.91 | 9.97 | 23.5 | 96.4 | 309 | 868 | 1030 | 6.32E-07 | 7.81E-03 | -1.47E-02 | 9.971E-01 |
| (22 Oct 2021) | 6.79[d] | 10.7 | 19.8[c] | 95.8 | 327 | 908 | 967 | | | | |
| 6 | 5.45 | 9.42 | 17.1[c] | 100 | 317 | 881 | 1050 | 9.16E-07 | 8.00E-03 | -6.91E-03 | 9.960E-01 |
| (23 Oct 2021) | 4.70 | 7.52[c] | 18.9[c] | 94.8 | 316 | 841 | 998 | | | | |
| 7 | 5.03 | 11.9[c] | 21.8 | 111 | 361[c] | 897 | 1050 | 7.70E-08 | 9.04E-04 | -1.22E-03 | 9.900E-01 |
| (22 Oct 2021) | 5.44 | 8.69 | 23.2 | 108 | 320 | 917 | 903 | | | | |
| Mean | 5.10 | 9.67 | 23.6 | 100 | 319 | 900 | 986 | 1.14E-06 | 7.84E-03 | 5.72E-03 | 9.933E-01 |
| S.D. | 0.215 | 0.756 | 1.96 | 7.35 | 12.3 | 47.1 | 60.2 | | | | |
| %CV | 4.2 | 7.8 | 8.3 | 7.4 | 3.9 | 5.2 | 6.1 | | | | |
| %Bias | 2.0 | -3.3 | -5.6 | 0.0 | 6.3 | 0.0 | -1.4 | | | | |
| n | 12 | 9 | 10 | 13 | 12 | 13 | 14 | 7 | 7 | 7 | 7 |

[a] = Quadratic Regression: $y = Ax^2 + Bx + C$ where y is the peak area ratio of Epinephrine to Int. Std., x is the concentration of Epinephrine, and A, B, and C are regression constants. Regression weighted $1/x^2$.

[b] = RSQ = R-Squared

[c] = Value outside of acceptance criteria (± 15% theoretical). Value excluded from regression and summary statistics.

[d] = Value outside of acceptance criteria (± 20% theoretical). Value excluded from regression and summary statistics.

FIG. 79

Quality Control Evaluation Data for Epinephrine in Rat $K_2$EDTA Plasma

| Batch Number (Analysis Date) | Nominal Concentration LMQC (15.0 ng/mL) | MQC (50.0 ng/mL) | HQC (800 ng/mL) | DQC[a] (800 ng/mL) |
|---|---|---|---|---|
| 1 | 14.1 | 43.3 | 886 | |
| (21 Oct 2021) | 15.1 | 45.8 | 728 | |
| 2 | 14.8 | 37.7 [b] | 884 | |
| (22 Oct 2021) | 9.83 [b] | 42.9 | 751 | |
| 3 | 12.0 [b] | 44.5 | 815 | |
| (21 Oct 2021) | 13.4 | 102 [b] | 798 | |
| 4 | 13.6 | 46.8 | 793 | |
| (22 Oct 2021) | 11.6 [b] | 103 [b] | 793 | |
| 5 | 14.7 | 48.8 | 791 | |
| (22 Oct 2021) | 17.2 | 44.1 | 817 | |
| 6 | 16.5 | 50.6 | 764 | |
| (23 Oct 2021) | 12.5 [b] | 53.7 | 680 | |
| 7 | 14.1 | 49.9 | 695 | 799 |
| (22 Oct 2021) | 8.88 [b] | 49.0 | 763 | 649 [b] |
| | | | | 838 |
| Mean | 13.5 | 54.4 | 783 | 762 |
| S.D. | 2.33 | 20.7 | 59.9 | 99.8 |
| %CV | 17.3 | 38.1 | 7.7 | 13.1 |
| %Bias | -10.0 | 8.8 | -2.1 | -4.8 |
| n | 14 | 14 | 14 | 3 |

[a] = Dilution QCs undiluted concentration 800 ng/mL; a 5-fold dilution with blank matrix was performed prior to extraction and analysis.

[b] = Value outside of acceptance criteria (± 15% theoretical) but included in summary statistics.

FIG. 80

| | | Time (min) | | | | | | | | | | |
|---|---|---|---|---|---|---|---|---|---|---|---|---|
| | | 0.0 | 2.0 | 5.0 | 7.0 | 10.0 | 15.0 | 20.0 | 30.0 | 60.0 | 90.0 | 120.0 |
| **Treatment** | **Animal** | **Epinephrine (pg/mL)** | | | | | | | | | | |
| 10%/40 mg w Tween | 4428732 | 0.00 | 1090 | 642 | 550 | 541 | 499 | 490 | 673 | 725 | 861 | 1150 |
| | TPO9 | 0.00 | 2800 | 2070 | 1270 | 971 | 879 | 1030 | 956 | 366 | 606 | 623 |
| | TVO9 | 0.00 | 8680 | 4230 | 2680 | 2140 | 1810 | 1660 | 872 | 1100 | 1050 | 2040 |
| | TWO9 | 0.00 | 6840 | 4690 | 3940 | 3550 | 2360 | 2490 | 1420 | 1400 | 1700 | 1590 |
| | **N** | **4** | **4** | **4** | **4** | **4** | **4** | **4** | **4** | **4** | **4** | **4** |
| | **Mean** | **0.00** | **4850** | **2910** | **2110** | **1800** | **1390** | **1420** | **980** | **898** | **1050** | **1350** |
| | **SD** | **0.00** | **3510** | **1890** | **1510** | **1350** | **851** | **860** | **316** | **449** | **467** | **606** |
| | **CV%** | | **72.3** | **65.1** | **71.4** | **74.9** | **61.4** | **60.7** | **32.3** | **50.1** | **44.3** | **44.9** |
| | **Min** | **0.00** | **1090** | **642** | **550** | **541** | **499** | **490** | **673** | **366** | **606** | **623** |
| | **Median** | **0.00** | **4820** | **3150** | **1980** | **1560** | **1340** | **1350** | **914** | **913** | **956** | **1370** |
| | **Max** | **0.00** | **8680** | **4690** | **3940** | **3550** | **2360** | **2490** | **1420** | **1400** | **1700** | **2040** |

FIG. 81

| | | Time | | | | | | | | | | |
|---|---|---|---|---|---|---|---|---|---|---|---|---|
| | | 0.0 | 3.0 | 5.0 | 7.0 | 10.0 | 15.0 | 20.0 | 30.0 | 60.0 | 90.0 | 120.0 |
| **Treatment** | **Animal** | **Epinephrine** | | | | | | | | | | |
| 10%/60mg | IQK9 | 0.00 | 4460 | 6340 | 6340 | 5630 | 5830 | 3850 | 2140 | 1600 | 1470 | 1600 |
| | TPO9 | 0.00 | 3850 | 3450 | 3450 | 3110 | 1550 | 1020 | 1110 | 439 | 606 | 794 |
| | TV09 | 0.00 | 2320 | 1500 | 1500 | 1400 | 835 | 972 | 1130 | 1960 | 1020 | 1060 |
| | **N** | **3** | **3** | **3** | **3** | **3** | **3** | **3** | **3** | **3** | **3** | **3** |
| | **Mean** | **0.00** | **3540** | **3760** | **3760** | **3380** | **2740** | **1950** | **1460** | **1330** | **1030** | **1150** |
| | **SD** | **0.00** | **1100** | **2440** | **2440** | **2130** | **2700** | **1650** | **589** | **795** | **432** | **411** |
| | **CV%** | | **31.1** | **64.7** | **64.7** | **63.0** | **98.6** | **84.6** | **40.3** | **59.6** | **41.9** | **35.7** |
| | **Min** | **0.00** | **2320** | **1500** | **1500** | **1400** | **835** | **972** | **1110** | **439** | **606** | **794** |
| | **Median** | **0.00** | **3850** | **3450** | **3450** | **3110** | **1550** | **1020** | **1130** | **1600** | **1020** | **1060** |
| | **Max** | **0.00** | **4460** | **6340** | **6340** | **5630** | **5830** | **3850** | **2140** | **1960** | **1470** | **1600** |

FIG. 82

| | | Time | | | | | | | | | | |
|---|---|---|---|---|---|---|---|---|---|---|---|---|
| | | 0.0 | 2.0 | 5.0 | 7.0 | 10.0 | 15.0 | 20.0 | 30.0 | 60.0 | 90.0 | 120.0 |
| Treatment | Animal | Epinephrine | | | | | | | | | | |
| 10%/60mg w Tween | TV09 | 0.00 | 7480 | 7680 | 8550 | 7180 | 4250 | 3220 | 3490 | 3860 | 5100 | 6550 |
| | TWO9 | 0.00 | 5160 | 4650 | 3160 | 1760 | 1800 | 1940 | 1160 | 1110 | 1060 | 932 |
| | **N** | **2** | **2** | **2** | **2** | **2** | **2** | **2** | **2** | **2** | **2** | **2** |
| | **Mean** | **0.00** | **6320** | **6170** | **5860** | **4470** | **3030** | **2580** | **2330** | **2490** | **3080** | **3740** |
| | **SD** | **0.00** | **1640** | **2140** | **3810** | **3830** | **1730** | **905** | **1650** | **1940** | **2860** | **3970** |
| | **CV%** | | **26.0** | **34.8** | **65.1** | **85.7** | **57.3** | **35.1** | **70.9** | **78.3** | **92.8** | **106.2** |
| | **Min** | **0.00** | **5160** | **4650** | **3160** | **1760** | **1800** | **1940** | **1160** | **1110** | **1060** | **932** |
| | **Median** | **0.00** | **6320** | **6170** | **5860** | **4470** | **3030** | **2580** | **2330** | **2490** | **3080** | **3740** |
| | **Max** | **0.00** | **7480** | **7680** | **8550** | **7180** | **4250** | **3220** | **3490** | **3860** | **5100** | **6550** |

FIG. 83

| | | Time (min) | | | | | | | | | | | |
|---|---|---|---|---|---|---|---|---|---|---|---|---|---|
| | | 0.0 | 2.0 | 3.0 | 5.0 | 7.0 | 10.0 | 15.0 | 20.0 | 30.0 | 60.0 | 90.0 | 120.0 |
| Treatment | Animal | Epinephrine (pg/mL) | | | | | | | | | | | |
| 20%/30mg | 4428732 | 0.00 | | 6500 | 4640 | 3470 | 2240 | 1530 | 1390 | 1050 | 1010 | 743 | 1060 |
| | TPO9 | 0.00 | 9830 | | 5730 | 5280 | 4240 | 2690 | 1920 | 1130 | 2110 | 2940 | 1160 |
| | TVO9 | 0.00 | 12200 | | 6900 | 7400 | 4260 | 3930 | 2640 | 2050 | 1410 | 2150 | 1920 |
| | TWO9 | 0.00 | | 5550 | 6850 | 5640 | 5290 | 3120 | 2770 | 1390 | 1330 | 1730 | 1690 |
| | **N** | **4** | **2** | **2** | **4** | **4** | **4** | **4** | **4** | **4** | **4** | **4** | **4** |
| | **Mean** | **0.00** | **11000** | **6030** | **6030** | **5450** | **4010** | **2820** | **2180** | **1410** | **1470** | **1890** | **1460** |
| | **SD** | **0.00** | **1680** | **672** | **1070** | **1610** | **1280** | **1000** | **646** | **454** | **463** | **915** | **414** |
| | **CV%** | | **15.2** | **11.1** | **17.8** | **29.6** | **31.8** | **35.5** | **29.6** | **32.3** | **31.6** | **48.4** | **28.4** |
| | **Min** | **0.00** | **9830** | **5550** | **4640** | **3470** | **2240** | **1530** | **1390** | **1050** | **1010** | **743** | **1060** |
| | **Median** | **0.00** | **11000** | **6030** | **6290** | **5460** | **4250** | **2910** | **2280** | **1260** | **1370** | **1940** | **1430** |
| | **Max** | **0.00** | **12200** | **6500** | **6900** | **7400** | **5290** | **3930** | **2770** | **2050** | **2110** | **2940** | **1920** |

FIG. 84

| | | Time (min) | | | | | | | | | | |
|---|---|---|---|---|---|---|---|---|---|---|---|---|
| | | 0.0 | 2.0 | 5.0 | 7.0 | 10.0 | 15.0 | 20.0 | 30.0 | 60.0 | 90.0 | 120.0 |
| Treatment | Animal | Epinephrine (pg/mL) | | | | | | | | | | |
| 20%/30mg w Tween | IQK9 | 0.00 | 2060 | 2310 | 2450 | 2190 | 1750 | 1670 | 2420 | 4080 | 2890 | 2840 |
| | TPO9 | 0.00 | 535 | 900 | 1020 | 927 | 772 | 853 | 809 | 1260 | 1020 | 1160 |
| | TWO9 | 0.00 | 3170 | 1950 | 1160 | 871 | 744 | 686 | 751 | 779 | 716 | 717 |
| | **N** | **3** | **3** | **3** | **3** | **3** | **3** | **3** | **3** | **3** | **3** | **3** |
| | **Mean** | **0.00** | **1920** | **1720** | **1540** | **1330** | **1090** | **1070** | **1330** | **2040** | **1540** | **1570** |
| | **SD** | **0.00** | **1320** | **733** | **788** | **746** | **573** | **527** | **947** | **1780** | **1180** | **1120** |
| | **CV%** | | **68.8** | **42.6** | **51.1** | **56.1** | **52.6** | **49.2** | **71.4** | **87.4** | **76.3** | **71.2** |
| | **Min** | **0.00** | **535** | **900** | **1020** | **871** | **744** | **686** | **751** | **779** | **716** | **717** |
| | **Median** | **0.00** | **2060** | **1950** | **1160** | **927** | **772** | **853** | **809** | **1260** | **1020** | **1160** |
| | **Max** | **0.00** | **3170** | **2310** | **2450** | **2190** | **1750** | **1670** | **2420** | **4080** | **2890** | **2840** |

FIG. 85

| | | Time (min) | | | | | | | | | | |
|---|---|---|---|---|---|---|---|---|---|---|---|---|
| | | 0.0 | 3.0 | 5.0 | 7.0 | 10.0 | 15.0 | 20.0 | 30.0 | 60.0 | 90.0 | 120.0 |
| Treatment | Animal | Epinephrine (pg/mL) | | | | | | | | | | |
| Epi-Pen IM Injection | 4428732 | 0.00 | 272 | 401 | 355 | 305 | 319 | 596 | 316 | 372 | 840 | 862 |
| | IQK9 | 0.00 | 2590 | 1810 | 1200 | 762 | 473 | 742 | 739 | 1530 | 1800 | 1080 |
| | TPO9 | 0.00 | 417 | 724 | 541 | 564 | 1080 | 876 | 1200 | 1320 | NS | 1090 |
| | TV09 | 0.00 | 838 | 816 | 834 | 1290 | 995 | 833 | 1010 | 2050 | 1700 | 1360 |
| | **N** | **4** | **4** | **4** | **4** | **4** | **4** | **4** | **4** | **4** | **3** | **4** |
| | **Mean** | **0.00** | **1030** | **938** | **733** | **730** | **717** | **762** | **816** | **1320** | **1450** | **1100** |
| | **SD** | **0.00** | **1070** | **608** | **369** | **417** | **377** | **124** | **383** | **701** | **528** | **204** |
| | **CV%** | | **103.7** | **64.8** | **50.3** | **57.2** | **52.6** | **16.3** | **47.0** | **53.2** | **36.5** | **18.6** |
| | **Min** | **0.00** | **272** | **401** | **355** | **305** | **319** | **596** | **316** | **372** | **840** | **862** |
| | **Median** | **0.00** | **628** | **770** | **688** | **663** | **734** | **788** | **875** | **1430** | **1700** | **1090** |
| | **Max** | **0.00** | **2590** | **1810** | **1200** | **1290** | **1080** | **876** | **1200** | **2050** | **1800** | **1360** |

FIG. 86

| Treatment | Dose (mg) | Animal | Cmax (pg/mL) | Tmax (min) | AUClast (min*pg/mL) |
|---|---|---|---|---|---|
| 10%/40 mg w Tween | 4.0 | 4428732 | 1150 | 120.00 | 92300 |
| | | TPO9 | 2800 | 2.00 | 87400 |
| | | TVO9 | 8680 | 2.00 | 180000 |
| | | TWO9 | 6840 | 2.00 | 228000 |
| | | **N** | **4** | **4** | **4** |
| | | **Mean** | **4870** | **31.5** | **147000** |
| | | **CV%** | **71.7** | **187.3** | **46.8** |
| | | **Min** | **1150** | **2.00** | **87400** |
| | | **Median** | **4820** | **2.00** | **136000** |
| | | **Max** | **8680** | **120** | **228000** |
| | | **Geometric Mean** | **3720** | **5.57** | **135000** |
| | | **Geometric CV%** | **115.67** | **806.74** | **50.85** |

FIG. 87

| Treatment | Dose (mg) | Animal | Cmax (pg/mL) | Tmax (min) | AUClast (min*pg/mL) |
|---|---|---|---|---|---|
| 10%/60mg | 6.0 | IQK9 | 6340 | 5.00 | 278000 |
| | | TPO9 | 3850 | 3.00 | 116000 |
| | | TV09 | 2320 | 3.00 | 156000 |
| | | **N** | **3** | **3** | **3** |
| | | **Mean** | **4170** | **3.67** | **183000** |
| | | **CV%** | **48.7** | **31.5** | **45.8** |
| | | **Min** | **2320** | **3.00** | **116000** |
| | | **Median** | **3850** | **3.00** | **156000** |
| | | **Max** | **6340** | **5.00** | **278000** |
| | | **Geometric Mean** | **3840** | **3.56** | **171000** |
| | | **Geometric CV%** | **53.61** | **30.15** | **46.49** |

FIG. 88

| Treatment | Dose (mg) | Animal | Cmax (pg/mL) | Tmax (min) | AUClast (min*pg/mL) |
|---|---|---|---|---|---|
| 10%/60mg w Tween | 6.0 | TV09 | 8550 | 7.00 | 569000 |
| | | TWO9 | 5160 | 2.00 | 165000 |
| | | **N** | **2** | **2** | **2** |
| | | **Mean** | **6860** | **4.50** | **367000** |
| | | **CV%** | **35.0** | **78.6** | **78.0** |
| | | **Min** | **5160** | **2.00** | **165000** |
| | | **Median** | **6860** | **4.50** | **367000** |
| | | **Max** | **8550** | **7.00** | **569000** |
| | | **Geometric Mean** | **6640** | **3.74** | **306000** |
| | | **Geometric CV%** | **36.88** | **109.17** | **107.71** |

FIG. 89

| Treatment | Dose (mg) | Animal | Cmax (pg/mL) | Tmax (min) | AUClast (min*pg/mL) |
|---|---|---|---|---|---|
| 20%/30mg | 6.0 | 4428732 | 6500 | 3.00 | 150000 |
| | | TPO9 | 9830 | 2.00 | 283000 |
| | | TVO9 | 12200 | 2.00 | 297000 |
| | | TWO9 | 6850 | 5.00 | 243000 |
| | | **N** | **4** | **4** | **4** |
| | | **Mean** | **8850** | **3.00** | **243000** |
| | | **CV%** | **30.4** | **47.1** | **27.2** |
| | | **Min** | **6500** | **2.00** | **150000** |
| | | **Median** | **8340** | **2.50** | **263000** |
| | | **Max** | **12200** | **5.00** | **297000** |
| | | **Geometric Mean** | **8550** | **2.78** | **235000** |
| | | **Geometric CV%** | **30.70** | **45.62** | **31.97** |

FIG. 90

| Treatment | Dose (mg) | Animal | Cmax (pg/mL) | Tmax (min) | AUClast (min*pg/mL) |
|---|---|---|---|---|---|
| 20%/30mg w Tween | 6.0 | IQK9 | 4080 | 60.00 | 346000 |
| | | TPO9 | 1260 | 60.00 | 122000 |
| | | TWO9 | 3170 | 2.00 | 98400 |
| | | **N** | **3** | **3** | **3** |
| | | **Mean** | **2840** | **40.7** | **189000** |
| | | **CV%** | **50.7** | **82.3** | **72.4** |
| | | **Min** | **1260** | **2.00** | **98400** |
| | | **Median** | **3170** | **60.0** | **122000** |
| | | **Max** | **4080** | **60.0** | **346000** |
| | | **Geometric Mean** | **2540** | **19.3** | **161000** |
| | | **Geometric CV%** | **68.27** | **680.28** | **75.66** |

FIG. 91

| Treatment | Dose (mg) | Animal | Cmax (pg/mL) | Tmax (min) | AUClast (min*pg/mL) |
|---|---|---|---|---|---|
| Epi-Pen IM Injection | 0.3 | 4428732 | 862 | 120.00 | 65100 |
| | | IQK9 | 2590 | 3.00 | 154000 |
| | | TPO9 | 1320 | 60.00 | 134000 |
| | | TV09 | 2050 | 60.00 | 175000 |
| | | **N** | **4** | **4** | **4** |
| | | **Mean** | **1710** | **60.8** | **132000** |
| | | **CV%** | **44.9** | **78.6** | **36.1** |
| | | **Min** | **862** | **3.00** | **65100** |
| | | **Median** | **1690** | **60.0** | **144000** |
| | | **Max** | **2590** | **120** | **175000** |
| | | **Geometric Mean** | **1570** | **33.7** | **124000** |
| | | **Geometric CV%** | **51.73** | **374.52** | **46.43** |

FIG. 92

FIG. 93

| | | Animal | | | | | |
|---|---|---|---|---|---|---|---|
| | | 4428732 | IQK9 | TPO9 | TV09 | TVO9 | TWO9 |
| Treatment | Dose (mg) | AUClast (min*pg/mL) | | | | | |
| 10%/40 mg w Tween | 4 | 92300 | ND | 87400 | ND | 180000 | 228000 |
| 10%/60mg | 6 | ND | 278000 | 116000 | 156000 | ND | ND |
| 10%/60mg w Tween | 6 | ND | ND | ND | 569000 | ND | 165000 |
| 20%/30mg | 6 | 150000 | ND | 283000 | ND | 297000 | 243000 |
| 20%/30mg w Tween | 6 | ND | 346000 | 122000 | ND | ND | 98400 |
| Epi-Pen IM Injection | 0.3 | 65100 | 154000 | 134000 | 175000 | ND | ND |

ND =Not Done

| Treatment | Dose (mg) | Animal | | | | | |
|---|---|---|---|---|---|---|---|
| | | 4428732 | IQK9 | TPO9 | TV09 | TVO9 | TWO9 |
| | | Relative Bioavailability (AUClast) (Treatment/EpiPen)*(DoseEpiPen/DoseTreatment) | | | | | |
| 10%/40 mg w Tween | 4 | 10.6% | ND | 4.9% | ND | ND | ND |
| 10%/60mg | 6 | ND | 9.0% | 4.3% | 4.5% | ND | ND |
| 10%/60mg w Tween | 6 | ND | ND | ND | 16.3% | ND | ND |
| 20%/30mg | 6 | 11.5% | ND | 10.6% | ND | ND | ND |
| 20%/30mg w Tween | 6 | ND | 11.2% | 4.6% | ND | ND | ND |
| Epi-Pen IM Injection | 0.3 | Reference | Reference | Reference | Reference | ND | ND |

ND =Not Done

FIG. 94

| Treatment | Dose (mg) | Animal | | | | | |
|---|---|---|---|---|---|---|---|
| | | 4428732 | IQK9 | TPO9 | TV09 | TVO9 | TWO9 |
| | | Comparative Bioavailability (AUClast) (Treatment/EpiPen) | | | | | |
| 10%/40 mg w Tween | 4 | 142% | ND | 65.2% | ND | ND | ND |
| 10%/60mg | 6 | ND | 181% | 86.6% | 89.1% | ND | ND |
| 10%/60mg w Tween | 6 | ND | ND | ND | 325% | ND | ND |
| 20%/30mg | 6 | 230% | ND | 211% | ND | ND | ND |
| 20%/30mg w Tween | 6 | ND | 225% | 91.0% | ND | ND | ND |
| Epi-Pen IM Injection | 0.3 | Reference | Reference | Reference | Reference | ND | ND |

ND =Not Done

FIG. 95

Treatment = 10% epinephrine/40 mg with Tween, Dose Level = 4 mg

Treatment = 10% epinephrine/60 mg, Dose Level = 6 mg

Treatment = 10% epinephrine/60 mg with Tween, Dose Level = 6 mg

Treatment = 20% epinephrine/30 mg, Dose Level = 6 mg

Treatment = 20% epinephrine/30 mg with Tween, Dose Level = 6 mg

Treatment = EPIPEN IM Injection, Dose Level = 0.3 mg

Treatment = 10% epinephrine/40 mg with Tween, Dose Level = 4 mg

Treatment = 10% epinephrine/60 mg, Dose Level = 6 mg

Treatment = 10% epinephrine/60 mg with Tween, Dose Level = 6 mg

Treatment = 20% epinephrine/30 mg, Dose Level = 6 mg

Treatment = 20% epinephrine/30 mg with Tween, Dose Level = 6 mg

Treatment = EPIPEN IM Injection, Dose Level = 0.3 mg

| Independent Variables | TT Trial 1 | TT Trial 2 | TT Trial 3 | TT Trial 4 | TT Trial 5 | TT Trial 6 | TT Trial 7 | TT Trial 8 |
|---|---|---|---|---|---|---|---|---|
| Feed solution batch size (g) | 600 | 600 | 600 | 600 | 600 | 2400 | 2400 | 2000 |
| Nitrogen gas | Not used | Not used | N2 for atomisation | N2 for atomisation | yes | yes | yes | yes |
| Feed solution solid content (wt%) | 2.5 | 2.5 | 2.5 | 2.5 | 2.5 | 2.5 | 2.5 | 2.5 |
| Feed solution pH | 2.31 | 3.1 | 3.13 | ND | 3.07 | 2.94 | 2.96 | 3.07 |
| Nozzle diameter (mm) | Ultrasonic 1.0mm | Ultrasonic 1.0mm | Standard 1.2 | Standard 1.2 | Standard 1.2 | Standard 1.2 | Standard 1.2 | Standard 1.2 |
| Inlet temperature (°C) | 180 | 170 | 150 | 140 | 150 | 150 | 150 | 150 |
| Outlet temperature (°C) | 52 to 78 | 74 to 96 | 65 to 68 | 66 to 71 | 59 to 61 | 44 to63 | 52 to 62 | 52 to 64 |
| Cyclone temperature (°C) | 58 to 76 | 67 to 82 | 46 to 50 | 48 to 51 | 46 to 47 | 42 to 51 | 47 to 51 | 47 to 52 |
| Feed rate (g/min) | 2.6 to 3.1 | 2.4 | 5.1 to 7.1 | 3.7 to 5.3 | 6.5 | 6.3 | 6.3 to 5.9 | 5.9 |
| Air flow rate ($m^3$/min) | 0.30 to 0.35 | 0.35 | 0.3 | 0.3 | 0.25 | 0.25 | 0.25 | 0.25 |
| Nozzle gas pressure (bar) | 1.5 to 2 | 2 | 0.8 | 0.8 | 0.4 | 0.4 | 0.4 | 0.4 |
| Cyclone gas pressure (bar) | 0.2 to 0.5 | 0.2 to 0.5 | 0.8 | 0.8 | 0.4 to 0.6 | 0.4 | 0.4 to 0.6 | 0.4 to 0.6 |
| Dependent Variables | TT Trial 1 | TT Trial 2 | TT Trial 3 | TT Trial 4 | TT Trial 5 | TT Trial 6 | TT Trial 7 | TT Trial 8 |
| Reconstituted pH | 2.03 | 2.79 | 3.12 | 3.09 | 3.15 | 3.17 | 3.12 | 3.29 |
| XRPD (amorphous Y/N) | Y | Y | Y | Y | Y | Y | Y | Y |
| Assay (% claim label) | 42.7 | 79.4 | 95.4 | 96.4 | 94.1 | 93.9 | 94.2 | 96.0 |
| Related substances (%) | 61.3 | 25.2 | 1.5 | 1.6 | 2.2 | 2.2 | 2.5 | 1.1 |
| RRT 0.66 | 12.0 | 6.1 | 0.2 | 0.2 | 0.3 | 0.2 | 0.3 | 0.2 |
| RRT 0.69 | 16.6 | 5.8 | 0.3 | 0.4 | 0.5 | 0.4 | 0.2 | 0.3 |
| RRT 2.57 | 1.9 | 0.9 | 0.3 | 0.2 | 0.3 | 0.6 | 0.4 | 0.2 |
| Particle size | | | | | | | | |
| d10 (μm) | 4.96 | 5.73 | 2.15 | 1.90 | 5.33 | 4.17 | 3.46 | 3.48 |
| d50 (μm) | 21.57 | 22.29 | 8.35 | 7.46 | 20.74 | 14.25 | 12.8 | 12.8 |
| d90 (μm) | 35.16 | 35.33 | 24.17 | 22.67 | 121.23 | 42.31 | 37.07 | 55.16 |
| Enantiomeric purity (D-Epinephrine Peak) | Present | Not present | Not present | Not present | Not tested | Not present | Unacceptable chromatography | |
| Water content (%) (by STA includes water and residual solvents) | 12.66 | 8.70 | 5.13 | 5.14 | 6.754 | 8.04 | 6.176 | 5.955 |
| Appearance | Light brown | Light brown | White to off white | White to off white | White to off white | White to off white | White to off white | White to off white |
| % Yield | 30 | 62 | 63 | 61 | 49 | 54 | 38 | 32 |

FIG. 130A

| Independent Variables | TT Trial 10 (initial) | TT Trial 11 (initial) |
|---|---|---|
| Feed solution batch size (g) | 600 | 1000 |
| Spray drying time (min) | 270 | 440 |
| Nitorgen gas | yes | yes |
| Feed solution solid content (wt%) | 2.5 | 2.5 |
| Feed solution pH | ND | ND |
| Nozzle diameter (mm) | Standard 1.2 | Standard 1.2 |
| Inlet temperature (°C) | 125 | 125 |
| Outlet temperature (°C) | 62 to 66 | 62 to 64 |
| Cyclone temperature (°C) | 53 to 58 | 53 to 58 |
| Feed rate (g/min) | 2.2 to 2.4 | 2.2 to 2.4 |
| Air flow rate ($m^3$/min) | 0.25 | 0.25 |
| Nozzle gas pressure (bar) | 0.8 | 0.8 |
| Cyclone gas pressure (bar) | 0.2 | 0.2 to 0.3 |
| **Dependent Variables** | **TT Trial 10** | **TT Trial 11** |
| Reconstituted pH | 3.65 | 2.85 |
| XRPD (amorphous Y/N) | Y | Y |
| Assay (% claim label) | 98.5 | 98.1 |
| Related substances (%) | 0.1 | 2.1 |
| RRT 0.66 | <LOQ | 0.2 |
| RRT 0.69 | 0.1 | 0.5 |
| RRT 2.57 | <LOQ | 0.3 |
| Particle size | | |
| d10 (μm) | 6.45 | 2.4 |
| d50 (μm) | 16.01 | 10.83 |
| d90 (μm) | 35.44 | 33.46 |
| Enantiomeric purity (D-Epinephrine Peak) | | |
| Water content (%) (by STA includes water and residual solvents) | 4.01 | 3.98 |
| Water content (%) by Karl Fischer (water only) | 3.9 | 3.5 |
| Appearance | White to off white | White to off white |
| % Yield | 30 | 64 |
| Yield (g) | 4.5 | 16 |

FIG. 130B

| Independent Variables | TT Trial 12 (at reduced pH) | TT Trial 13 (Tween 80) | TT Trial 14 (Mannitol) |
|---|---|---|---|
| Feed solution batch size (g) | 1000 | 600 | 350 |
| Spray drying time (min) | 440 | 270 | 160 |
| Nitorgen gas | yes | yes | yes |
| Feed solution solid content (wt%) | 2.5 | 2.5 | 2.5 |
| Feed solution pH | 2.27 | 3.05 | 3.04 |
| Nozzle diameter (mm) | Standard 1.2 | Standard 1.2 | Standard 1.2 |
| Inlet temperature (°C) | 125 | 125 | 125 |
| Outlet temperature (°C) | 61 to 66 | 61 to 67 | 62 to 64 |
| Cyclone temperature (°C) | 50 to 53 | 47 to 53 | 50 to 54 |
| Feed rate (g/min) | 2.2 to 2.4 | 2.2 to 2.4 | 2.2 to 2.4 |
| Air flow rate ($m^3$/min) | 0.25 | 0.25 | 0.25 |
| Nozzle gas pressure (bar) | 0.8 | 0.8 | 0.8 |
| Cyclone gas pressure (bar) | 0.3 | 0.3 | 0.25 to 0.3 |
| Dependent Variables | TT Trial 12 | TT Trial 13 | TT Trial 14 |
| Reconstituted pH | 2.02 | TBC | |
| XRPD (amorphous Y/N) | Y | | |
| Assay (% claim label) | 80.7 | 96.6 | 86.5 |
| Related substances (%) | 15.8 | 3.7 | 16.6 |
| RRT 0.66 | | | |
| RRT 0.69 | | | |
| RRT 2.57 | | | |
| Particle size | | | |
| d10 (μm) | 1.86 | 1.88 | 2.61 |
| d50 (μm) | 8.03 | 8.15 | 11.18 |
| d90 (μm) | 24.75 | 24.11 | 29.39 |
| Enantiomeric purity (D-Epinephrine Peak) | | | 6.2 |
| Water content (%) (by STA includes water and residual solvents) | 6.22 | 3.75 | |
| Water content (%) by Karl Fischer (water only) | 4.0 | 3.6 | |
| Appearance | White to off white | White to off white | White to off white |
| % Yield | 74 | 65 | 67 |
| Yield (g) | 18.5 | 9.75 | 5.91 |

FIG. 130C

| | SD12 | SD13 |
|---|---|---|
| Date | 07-Apr-23 | 13-Apr-23 |
| System | SD30 | SD30 |
| Carrier | Lactose | Lactose |
| Carrier Mass (g) | 37.3049 | 74.6129 |
| Drug Mass (g) | 9.1011 | 18.1842 |
| Trisodium Citrate | 3.6007 | 7.2168 |
| Solvent System | 4:1 Water:Ethanol | 4:1 Water:Ethanol |
| pH Pre EpiBit | 4.95 | 4.75 |
| pH Post EpiBit | 3.6 | 3.56 |
| pH Post TSC | 4.61 | 4.48 |
| Concentration (mg/mL) | 80.66 | 80.72 |
| Feed Volume | 620 | 1239 |
| Drying Gas Rate (scfm) | 29-31 | 29-31 |
| Atomizing Gas Rate (psi) | 58-60 | 59-61 |
| Atomizing Gas Temp (°C) | 48-52 | 50-53 |
| Inlet Temperature (°C) | 125-126 | 125 |
| Outlet Temperature (°C) | 63-64 | 65-67 |
| Liquid Feed Rate (ml/min) | 12 | 12 |
| Nozzle (mm) | SU2 | Fluid Cap 2850 + Aircap 64 |
| Cyclone | Standard | Standard |
| Starting Mass (g) | 50.0067 | 100.0139 |
| Final Mass (g) | 32.1 | 70.4 |
| % Yield | 64.19% | 70.39% |
| SEM | Yes | Yes |
| Dv10 | 1.17 | 1.15 |
| Dv50 | 2.91 | 2.83 |
| Dv90 | 7 | 7.35 |
| KF | 3.16% | 3.22% |
| Bulk Density | | |
| Tapped Density | | |

FIG. 140A

| | SD15.1 | SD15.2 | SD15.3 |
|---|---|---|---|
| Date | 27-Apr-23 | 27-Apr-23 | 27-Apr-23 |
| System | SD30 | SD30 | SD30 |
| Carrier | Lactose | Lactose | Lactose |
| Carrier Mass (g) | 56.6098 | 56.6098 | 56.6098 |
| Drug Mass (g) | 13.2068 | 13.2068 | 13.2068 |
| Trisodium Citrate | 5.3026 | 5.3026 | 5.3026 |
| Solvent System | Water | Water | Water |
| pH Pre EpiBit | 4.24 | 4.24 | 4.24 |
| pH Post EpiBit | 3.37 | 3.37 | 3.37 |
| pH Post TSC | 4.42 | 4.42 | 4.42 |
| Concentration (mg/mL) | 110.15 | 110.15 | 110.15 |
| Feed Volume | 227.33 | 227.33 | 227.33 |
| Drying Gas Rate (scfm) | 30-31 | 40 | 44-45 |
| Atomizing Gas Rate (psi) | 20 | 19-20 | 40 |
| Atomizing Gas Temp (°C) | 30-31 | 32 | 49-51 |
| Inlet Temperature (°C) | 125 | 135 | 155 |
| Outlet Temperature (°C) | 64-65 | 64-66 | 63-65 |
| Liquid Feed Rate (ml/min) | 12 | 21 | 35 |
| Nozzle (mm) | Fluid Cap 2850 + Aircap 64 | Fluid Cap 2850 + Aircap 64 | SU4 |
| Cyclone | Standard | Standard | Standard |
| Starting Mass (g) | 75.1192 | 75.1192 | 75.1192 |
| Final Mass (g) | 12.5 | 16.2 | 2.97 |
| % Yield | 49.92% | 64.70% | 11.85% |
| SEM | Yes | Yes | No |
| Dv10 | 1.51 | 2.87 | 0 |
| Dv50 | 4.48 | 11.2 | 0 |
| Dv90 | 11.1 | 27.9 | 0 |
| KF | 2.51% | 2.60% | |
| Bulk Density | 0.191 | 0.192 | |
| Tapped Density | 0.264 | 0.271 | |

FIG. 140B

| | SD16 | SD17 |
|---|---|---|
| Date | 03-May-23 | 08-May-23 |
| System | SD30 | SD30 |
| Carrier | Lactose | Lactose |
| Carrier Mass (g) | 50.8838 | 50.8838 |
| Drug Mass (g) | 35.0954 | 35.0537 |
| Trisodium Citrate | 14.0389 | 14.0399 |
| Solvent System | Water | Water |
| pH Pre EpiBit | 4.72 | 4.69 |
| pH Post EpiBit | 3.4 | 3.34 |
| pH Post TSC | 4.33 | 4.28 |
| Concentration (mg/mL) | 149.95 | 149.89 |
| Feed Volume | 667 | 667 |
| Drying Gas Rate (scfm) | 30-31 | 34-35 |
| Atomizing Gas Rate (psi) | 19-20 | 19-20 |
| Atomizing Gas Temp (°C) | 31-32 | 29-32 |
| Inlet Temperature (°C) | 124-126 | 125 |
| Outlet Temperature (°C) | 54-55 | 62-63 |
| Liquid Feed Rate (ml/min) | 16 | 15 |
| Nozzle (mm) | Fluid Cap 2850 + Aircap 64 | Fluid Cap 2850 + Aircap 64 |
| Cyclone | Standard | Standard |
| Starting Mass (g) | 100.0181 | 99.9774 |
| Final Mass (g) | 22.1 | 43.5 |
| % Yield | 22.10% | 43.51% |
| SEM | No | Yes |
| Dv10 | 0 | 2.42 |
| Dv50 | 0 | 8.09 |
| Dv90 | 0 | 284 |
| KF | | 2.42 |
| Bulk Density | | |
| Tapped Density | | |

FIG. 140C

DRY POWDER FORMULATIONS OF EPINEPHRINE AND ASSOCIATED METHODS

CROSS REFERENCES TO RELATED APPLICATIONS

This application is related to and claims priority from the following U.S. patents and patent applications. This application is a continuation-in-part of U.S. patent application Ser. No. 18/514,634, filed Nov. 20, 2023, which is a continuation-in-part of U.S. patent application Ser. No. 18/192,404, filed Mar. 29, 2023, which is a continuation-in-part of U.S. patent application Ser. No. 17/836,588, filed Jun. 9, 2022, which claims priority to and the benefit of U.S. Provisional Patent Application No. 63/209,221, filed Jun. 10, 2021. Each of the above-listed applications is incorporated herein by reference in its entirety.

BACKGROUND OF THE INVENTION

1. Field of the Invention

The present invention relates to epinephrine, and more specifically to dry powder formulations of epinephrine and methods of treatment of various conditions using the dry power formulations.

2. Description of the Prior Art

It is generally known in the prior art to provide epinephrine for the treatment of anaphylactic reactions, which are commonly triggered by food allergies, insect bites or stings, vaccine injections, allergies to latex and other substances, allergic reactions to drugs, and other exposures. It is also generally known in the prior art to administer epinephrine for the treatment of other conditions, including anaphylactoid reaction, septic shock, respiratory conditions including bronchospasm, hemodynamic collapse including hypotension, and for administration during cardiopulmonary arrest and other life-threatening conditions. Epinephrine is delivered parenterally, either intravenously or by subcutaneous or intra-muscular needle and syringe injection. Increasingly, epinephrine is delivered by auto-injectors, which may be used within medical facilities by medical personnel or in ambulatory settings by non-medically trained bystanders, caregivers, and patients themselves. Self-administration via auto-injector has dramatically improved the availability of epinephrine treatment in anaphylactic emergency situations. Alternative epinephrine delivery routes that do not require a needle or syringe have been explored in the prior art.

Prior art patent documents include the following:

U.S. Pat. No. 9,789,071 for Intranasal formulation of epinephrine for the treatment of anaphylaxis by inventor Fleming, filed Jun. 27, 2013 and issued Oct. 17, 2017, is directed to pharmaceutical compositions of epinephrine for delivery to the nasal mucosa and methods of treating a subject in acute severe anaphylaxis, bronchospasm or during cardiopulmonary resuscitation (CPR). The composition further comprising agents, that either prevent localized degradation of epinephrine or enhance its absorption in the nasal mucosa to counter anaphylactic effects, symptoms or complications in a subject.

U.S. Pat. No. 8,747,813 for Inhalable epinephrine by inventors Batycky, et al., filed Mar. 6, 2013 and issued Jun. 10, 2014, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants. The patent discloses that the particles have aerodynamic characteristics that permit targeted delivery of epinephrine to the site(s) of action.

U.S. Pat. No. 8,415,397 for Inhalable epinephrine by inventors Batycky, et al., filed Apr. 8, 2011 and issued Apr. 9, 2013, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants. The patent discloses that the particles have aerodynamic characteristics that permit targeted delivery of epinephrine to the site(s) of action.

U.S. Pat. No. 7,954,491 for Low dose pharmaceutical powders for inhalations by inventor Hrkrach, filed Jun. 14, 2004 and issued Jun. 7, 2011, is directed to a method of delivering an agent to the pulmonary system of a compromised patient, in a single breath-activated step, comprising administering a particle mass comprising an agent from an inhaler containing less than 5 milligrams of the mass, wherein at least about 50% of the mass in the receptacle is delivered to the pulmonary system of a patient. The patent also discloses receptacles containing the particle mass and the inhaler for use therein.

U.S. Pat. No. 7,947,742 for Inhalable epinephrine by inventors Batycky, et al., filed Jun. 26, 2003 and issued May 24, 2011, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants. The patent discloses that the particles have aerodynamic characteristics that permit targeted delivery of epinephrine to the site(s) of action.

U.S. Pat. No. 10,688,044 for Epinephrine Spray Formulations by inventors Hartman et al., filed Mar. 15, 2019 and issued Jun. 23, 2020, is directed to epinephrine spray formulations. Also provided are methods of treating anaphylaxis by administering epinephrine spray formulations to subjects in need of such treatment.

U.S. Pat. No. 11,013,691 for Heat-Stable Dry Powder Pharmaceutical Compositions and Methods by inventors Fabio et al., filed Aug. 1, 2019 and issued May 25, 2021, is directed to heat-stable dry powders which include peptides or protein such as oxytocin for use as a pharmaceutical composition. The composition is highly stable at increased temperatures and relatively high humid environments, and are intended for storage at room temperature with an improved shelf-life. In particular, the dry powders are intended for inhalation, however, other routes of administration can be used when reconstituted in solution.

US Patent Pub. No. 2021/0205238 for Stabilized Injectable Pharmaceutical Composition of L-epinephrine by inventors Augustin et al., filed Apr. 10, 2020 and published July 8, 202, is directed to injectable pharmaceutical compositions comprising epinephrine, an antioxidant selected from the group consisting of sodium metabisulfite, sodium sulfite and sodium bisulfite, tartrate, a tonicity regulating agent, EDTA or Na2EDTA*2H2O and pH 3.0-4.5.

U.S. Pat. No. 10,806,709 for Intranasal Formulation of Epinephrine for the Treatment of Anaphylaxis by inventor Fleming, filed Jun. 27, 2013 and issued Oct. 17, 2017, is directed to pharmaceutical compositions of epinephrine for delivery to the nasal mucosa and methods of treating a subject in acute severe anaphylaxis, bronchospasm or during cardiopulmonary resuscitation (CPR). The composition further comprising agents, that either prevent localized degradation of epinephrine or enhance its absorption in the nasal mucosa to counter anaphylactic effects, symptoms or complications in a subject.

US Patent Pub. No. 2016/0220489 for Intranasal Formulation for the Treatment of Cardiopulmonary Resuscitation (CPR), Cardiac Life Support (CLS), Anaphylaxis and/or Anaphylactoid Reactions by inventors Fleming et al., filed Mar. 2, 2016 and published Aug. 4, 2016, is directed to dry powder compositions and unit doses that comprise vasoactive agents, and/or anti-anaphylactic and/or anti-anaphylactoid agents suitable for intranasal administration, methods of making the compositions, and methods of using the compositions to treat disorders, for example anaphylaxis, anaphylactoid reactions, bronchospasm, cardiac arrest, hypotensive shock, or other situations requiring the need to implement cardiopulmonary resuscitation (CPR) and/or basic or advanced cardiac life support (ACLS).

US Patent Pub. No. 2008/0269347 for Epinephrine Formulations by inventors Bruss et al., filed Sep. 28, 2007 and published Oct. 30, 2008, is directed to an epinephrine formulation that has enhanced stability. In particular embodiments, the formulation is an injectable formulation. In specific aspects, the formulation comprises epinephrine, EDTA, and one or more of an antioxidant such as cysteine, citric acid, acetylcysteine, or thioglycerol. The formulations are suitable for any medical condition that is in need of epinephrine, although in specific embodiments the medical condition is anaphylaxis, asthma, or cardiac arrest.

U.S. Pat. No. 11,400,045 for Treatment with Powdered Intranasal Epinephrine by inventors Temtsin-Krayz et al., filed Dec. 28, 2020 and issued Aug. 2, 2022, is directed to a pharmaceutical composition in dry powder form for intranasal administration, having an anti-anaphylactic adrenergic receptor agonist in the form of dry powder for intranasal administration, the composition having solid particles of the active agent in combination with at least one functional additive, and solid particles of an inert carrier.

US Patent Pub. No. 2017/0304459 for Methods and Compositions for Inhalation Delivery of Conjugated Oligonucleotide by inventors Jadhav et al., filed Apr. 7, 2017 and published Oct. 26, 2017, is directed to an inhalable formulation comprising a ligand conjugated oligonucleotide and particles of a physiologically acceptable pharmacologically-inert carrier.

SUMMARY OF THE INVENTION

The present invention relates to epinephrine, and more specifically to dry powder formulations of epinephrine and methods of treatment of various conditions using the dry power formulations.

It is an object of this invention to provide therapeutic formulations for enabling the absorption and bioavailability of epinephrine when sprayed into the human nasal passages. In all aspects of the present invention, epinephrine is the primary active ingredient to counteract the physiological changes that occur during anaphylaxis that lead to morbidity and mortality.

In one embodiment, the present invention provides an intranasal device for administration of a pharmaceutical composition including a reservoir and a means for discharging one or more doses of the pharmaceutical composition, wherein the reservoir contains a quantity of the pharmaceutical composition, wherein the pharmaceutical composition is a dry powder including, epinephrine or a pharmaceutically acceptable salt thereof, wherein the pharmaceutical composition provides a dose of about 0.01 mg to about 10 mg of the epinephrine or the pharmaceutically acceptable salt thereof, citric acid or a pharmaceutically acceptable salt thereof, and a carrier.

In another embodiment, the present invention provides a kit for intranasal administration of a pharmaceutical composition including at least one intranasal device, wherein each of the at least one intranasal device includes a reservoir and a means for discharging one or more doses of the pharmaceutical composition, wherein the reservoir contains a quantity of the pharmaceutical composition, and a pouch and/or a hard case, wherein the at least one intranasal device is enclosed in the pouch and/or the hard case, wherein the pharmaceutical composition is a dry powder including, epinephrine or a pharmaceutically acceptable salt thereof, wherein the pharmaceutical composition provides a dose of about 0.01 mg to about 10 mg of the epinephrine or the pharmaceutically acceptable salt thereof, citric acid or a pharmaceutically acceptable salt thereof, and a carrier.

In yet another embodiment, the present invention provides an intranasal device for administration of a pharmaceutical composition including a reservoir and a means for discharging one or more doses of the pharmaceutical composition, wherein the reservoir contains a quantity of the pharmaceutical composition, wherein the pharmaceutical composition is a spray-dried powder including, epinephrine or a pharmaceutically acceptable salt thereof, wherein the pharmaceutical composition provides a dose of about 0.01 mg to about 10 mg of the epinephrine or the pharmaceutically acceptable salt thereof, a pharmaceutically acceptable citrate salt, and a carrier, wherein the pharmaceutical composition does not include an additional vasodilator, and wherein the intranasal device further includes a nasal probe and an actuator.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 1 is a summary table for test formulations prepared according to the present invention.

FIG. 2 is another summary table for test formulations prepared according to the present invention.

FIG. 3 is yet another summary table for test formulations prepared according to the present invention.

FIG. 10 is a table of epinephrine concentration-time data in rats for epinephrine with a lactose carrier.

FIG. 11 is a table of epinephrine concentration-time data in rats for epinephrine with a sodium carboxymethylcellulose (CMC) carrier.

FIG. 12 is a table of epinephrine concentration-time data in rats for epinephrine and caffeine (5% w/w) with a lactose carrier.

FIG. 13 is a table of epinephrine concentration-time data in rats for epinephrine and caffeine (5% w/w) with a sodium CMC carrier.

FIG. 14 is a table of epinephrine concentration-time data in rats for epinephrine and hyaluronate (0.5% w/w) with a lactose carrier.

FIG. 15 is a table of epinephrine concentration-time data in rats for epinephrine and hyaluronate (0.5% w/w) with a sodium CMC carrier.

FIG. 16 is a table of epinephrine concentration-time data in rats for epinephrine and leucine (10% w/w) with a lactose carrier.

FIG. 17 is a table of epinephrine concentration-time data in rats for epinephrine and leucine (10% w/w) with a sodium CMC carrier.

FIG. 18 is a table of epinephrine concentration-time data in rats for epinephrine and sodium chloride (2% w/w) with a lactose carrier.

FIG. 19 is a table of epinephrine concentration-time data in rats for epinephrine and sodium chloride (2% w/w) with a sodium CMC carrier.

FIG. 20 is a table of epinephrine concentration-time data in rats for epinephrine and niacin (2% w/w) with a lactose carrier.

FIG. 21 is a table of epinephrine concentration-time data in rats for epinephrine and niacin (2% w/w) with a sodium CMC carrier.

FIG. 22 is a table of epinephrine concentration-time data in rats for epinephrine and polysorbate (0.5% w/w) with a lactose carrier.

FIG. 23 is a table of epinephrine concentration-time data in rats for epinephrine and polysorbate (0.5% w/w) with a sodium CMC carrier.

FIG. 24 is a table of epinephrine concentration-time data in rats for epinephrine intramuscular injection at 0.7 mg/kg.

FIG. 25 is a table of epinephrine pharmacokinetic parameters in rats for epinephrine with a lactose carrier.

FIG. 26 is a table of epinephrine pharmacokinetic parameters in rats for epinephrine with a sodium CMC carrier.

FIG. 27 is a table of epinephrine pharmacokinetic parameters in rats for epinephrine and caffeine (5% w/w) with a lactose carrier.

FIG. 28 is a table of epinephrine pharmacokinetic parameters in rats for epinephrine and caffeine (5% w/w) with a sodium CMC carrier.

FIG. 29 is a table of epinephrine pharmacokinetic parameters in rats for epinephrine and hyaluronate (0.5% w/w) with a lactose carrier.

FIG. 30 is a table of epinephrine pharmacokinetic parameters in rats for epinephrine and hyaluronate (0.5% w/w) with a sodium CMC carrier.

FIG. 31 is a table of epinephrine pharmacokinetic parameters in rats for epinephrine and leucine (10% w/w) with a lactose carrier.

FIG. 32 is a table of epinephrine pharmacokinetic parameters in rats for epinephrine and leucine (10% w/w) with a sodium CMC carrier.

FIG. 33 is a table of epinephrine pharmacokinetic parameters in rats for epinephrine and sodium chloride (2% w/w) with a lactose carrier.

FIG. 34 is a table of epinephrine pharmacokinetic parameters in rats for epinephrine and sodium chloride (2% w/w) with a sodium CMC carrier.

FIG. 35 is a table of epinephrine pharmacokinetic parameters in rats for epinephrine and niacin (2% w/w) with a lactose carrier.

FIG. 36 is a table of epinephrine pharmacokinetic parameters in rats for epinephrine and niacin (2% w/w) with a sodium CMC carrier.

FIG. 37 is a table of epinephrine pharmacokinetic parameters in rats for epinephrine and polysorbate (0.5% w/w) with a lactose.

FIG. 38 is a table of epinephrine pharmacokinetic parameters in rats for epinephrine and polysorbate (0.5% w/w) with a sodium CMC carrier.

FIG. 39 is a table of epinephrine pharmacokinetic parameters in rats for epinephrine intramuscular injection at 0.7 mg/kg.

FIG. 79 is a table of calibration curve data for epinephrine in rat potassium EDTA plasma.

FIG. 80 is a table of quality control evaluation data for epinephrine in rat potassium EDTA plasma.

FIG. 81 illustrates a table of plasma epinephrine concentration-time data in dogs following a 40 mg dosage of 10% w/w epinephrine, 2% NaCl, 0.1% w/v polysorbate (TWEEN 80), and lactose.

FIG. 82 illustrates a table of plasma epinephrine concentration-time data in dogs following a 60 mg dosage of 10% w/w epinephrine, 2% NaCl, and lactose.

FIG. 83 illustrates a table of plasma epinephrine concentration-time data in dogs following a 60 mg dosage of 10% w/w epinephrine, 2% NaCl, 0.1% w/v polysorbate (TWEEN 80), and lactose.

FIG. 84 illustrates a table of plasma epinephrine concentration-time data in dogs following a 30 mg dosage of 20% w/w epinephrine, 2% NaCl, and lactose.

FIG. 85 illustrates a table of plasma epinephrine concentration-time data in dogs following a 30 mg dosage of 20% w/w epinephrine, 2% NaCl, 0.1% w/v polysorbate (TWEEN 80), and lactose.

FIG. 86 illustrates a table of plasma epinephrine concentration-time data in dogs following a 0.3 mg IM dosage of epinephrine using an EPIPEN.

FIG. 87 illustrates a table of epinephrine pharmacokinetic parameters in dogs following a 40 mg dosage of 10% w/w epinephrine, 2% NaCl, 0.1% w/v polysorbate (TWEEN 80), and lactose.

FIG. 88 illustrates a table of epinephrine pharmacokinetic parameters in dogs following a 60 mg dosage of 10% w/w epinephrine, 2% NaCl, and lactose.

FIG. 89 illustrates a table of epinephrine pharmacokinetic parameters in dogs following a 60 mg dosage of 10% w/w epinephrine, 2% NaCl, 0.1% w/v polysorbate (TWEEN 80), and lactose.

FIG. 90 illustrates a table of epinephrine pharmacokinetic parameters in dogs following a 30 mg dosage of 20% w/w epinephrine, 2% NaCl, and lactose.

FIG. 91 illustrates a table of epinephrine pharmacokinetic parameters in dogs following a 30 mg dosage of 20% w/w epinephrine, 2% NaCl, 0.1% w/v polysorbate (TWEEN 80), and lactose.

FIG. 92 illustrates a table of epinephrine pharmacokinetic in dogs following a 0.3 mg IM dosage of epinephrine using an EPIPEN.

FIG. 93 illustrates a summary of epinephrine AUClast results.

FIG. 94 illustrates relative bioavailability calculations (AUClast).

FIG. 95 illustrates comparative bioavailability calculations (AUClast).

FIG. 117 illustrates a graph of partial AUC for 0-30 minutes by treatment.

FIG. 118 illustrates a graph of partial AUC for 0-60 minutes by treatment.

FIG. 119 illustrates a graph of individual animal plasma epinephrine concentration-time profiles for 0.3 mg IM administration for a pilot study and a main study.

FIG. 120 illustrates a graph of mean plasma epinephrine concentration-time profiles for 0.3 mg IM administration for a pilot study and a main study.

FIG. 121 illustrates a graph of shot weight data.

FIG. 122 illustrates a graph of actuation force.

FIG. 123 illustrates a force to actuate representative profile.

FIG. 124 illustrates a graph of particle size distribution.

FIG. 125 illustrates a graph of particle size distribution with outliers removed.

FIG. 126 illustrates a graph of water content.

FIG. 127 illustrates delivery angle for a nasal device.

FIG. 128 illustrates angle from the center wall for a nasal device.

Figure 129:
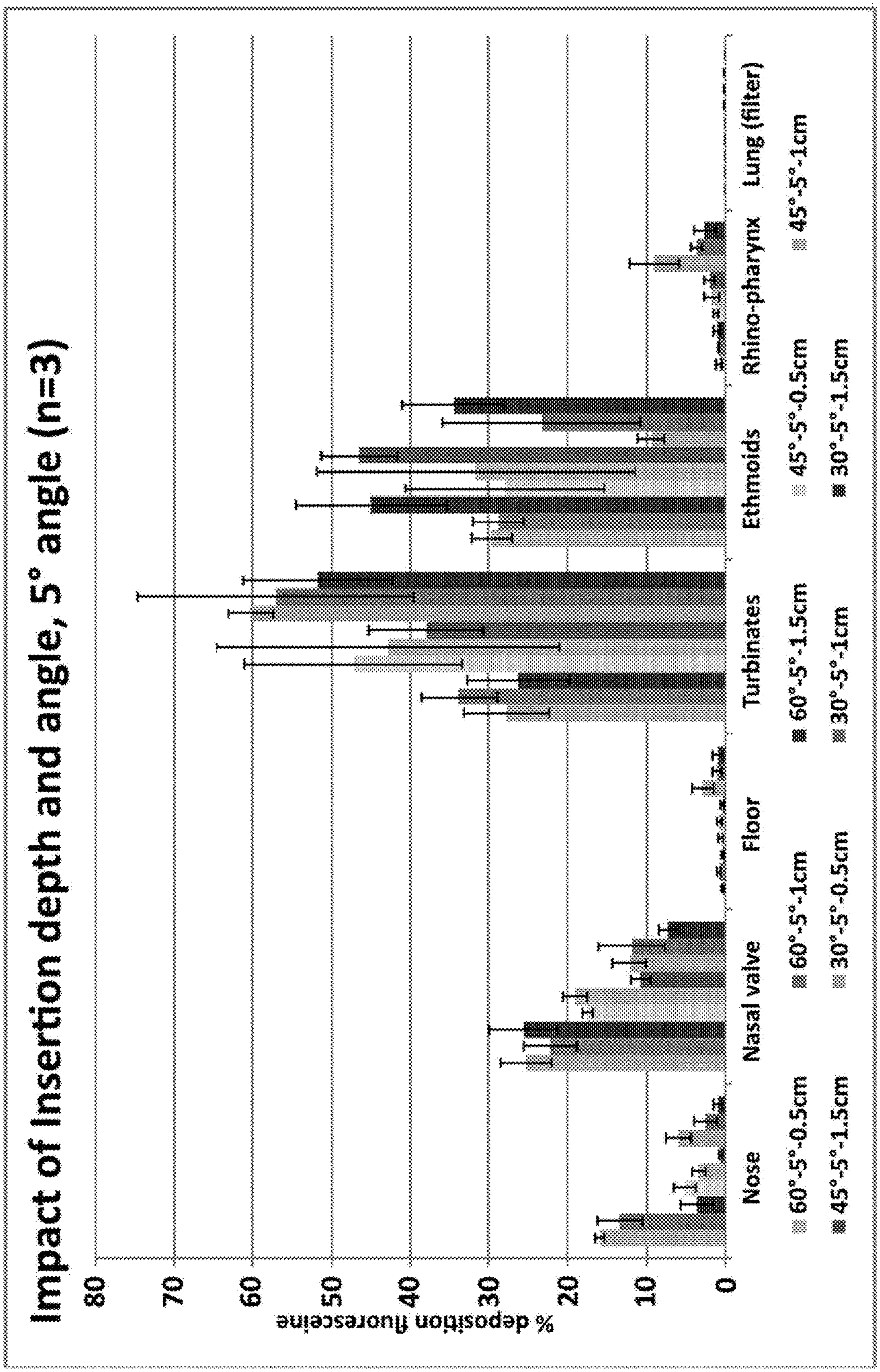

FIG. 129 illustrates impact of insertion depth and angle for a nasal device.

FIG. 130A illustrates a formulation table of technical batches used in experimental trials.

FIG. 130B illustrates a formulation table of technical batches used in experimental trials.

FIG. 130C illustrates a formulation table of technical batches used in experimental trials.

Figure 131:
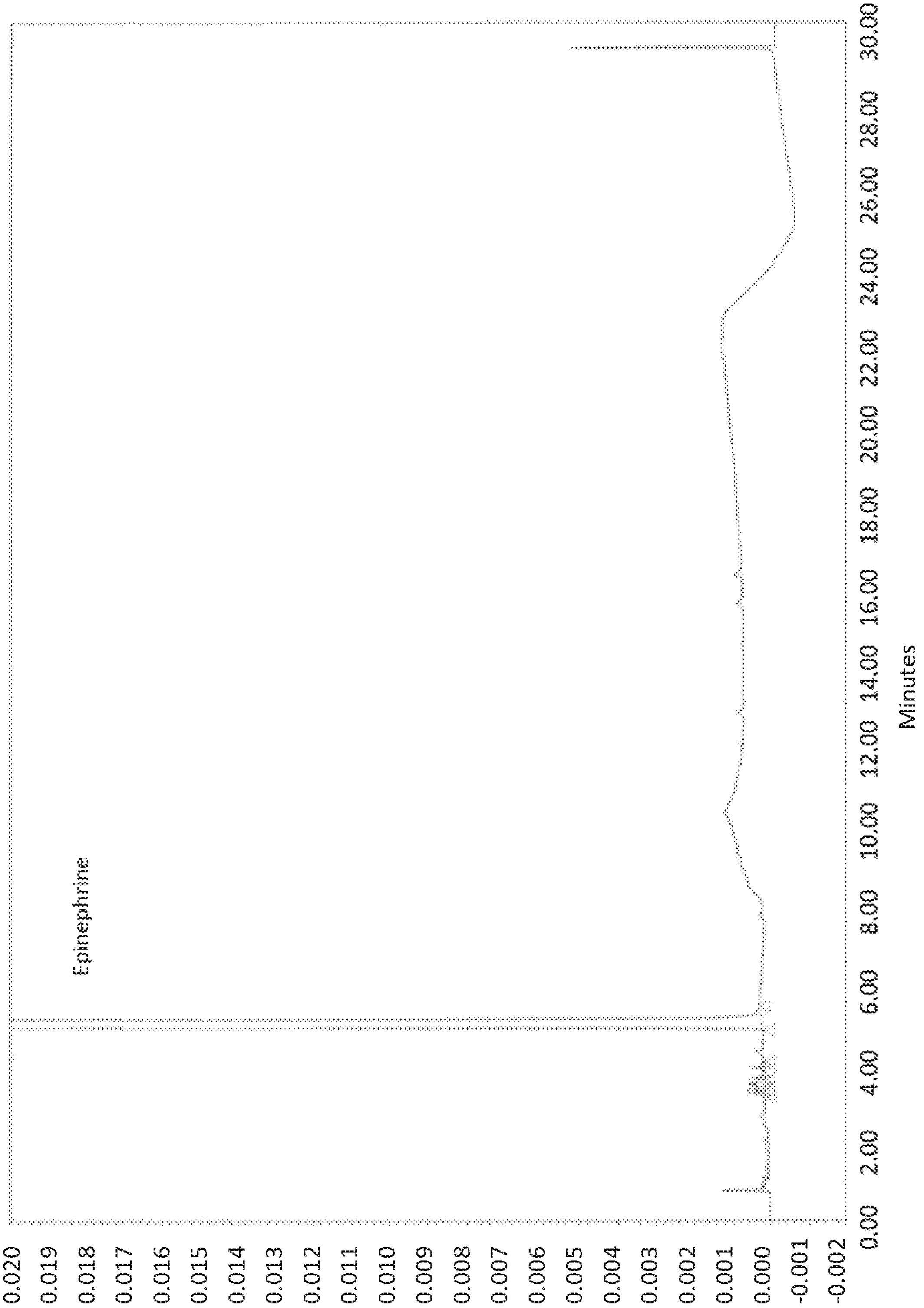

FIG. 131 illustrates the initial chromatogram of Trial 10.

Figure 132:
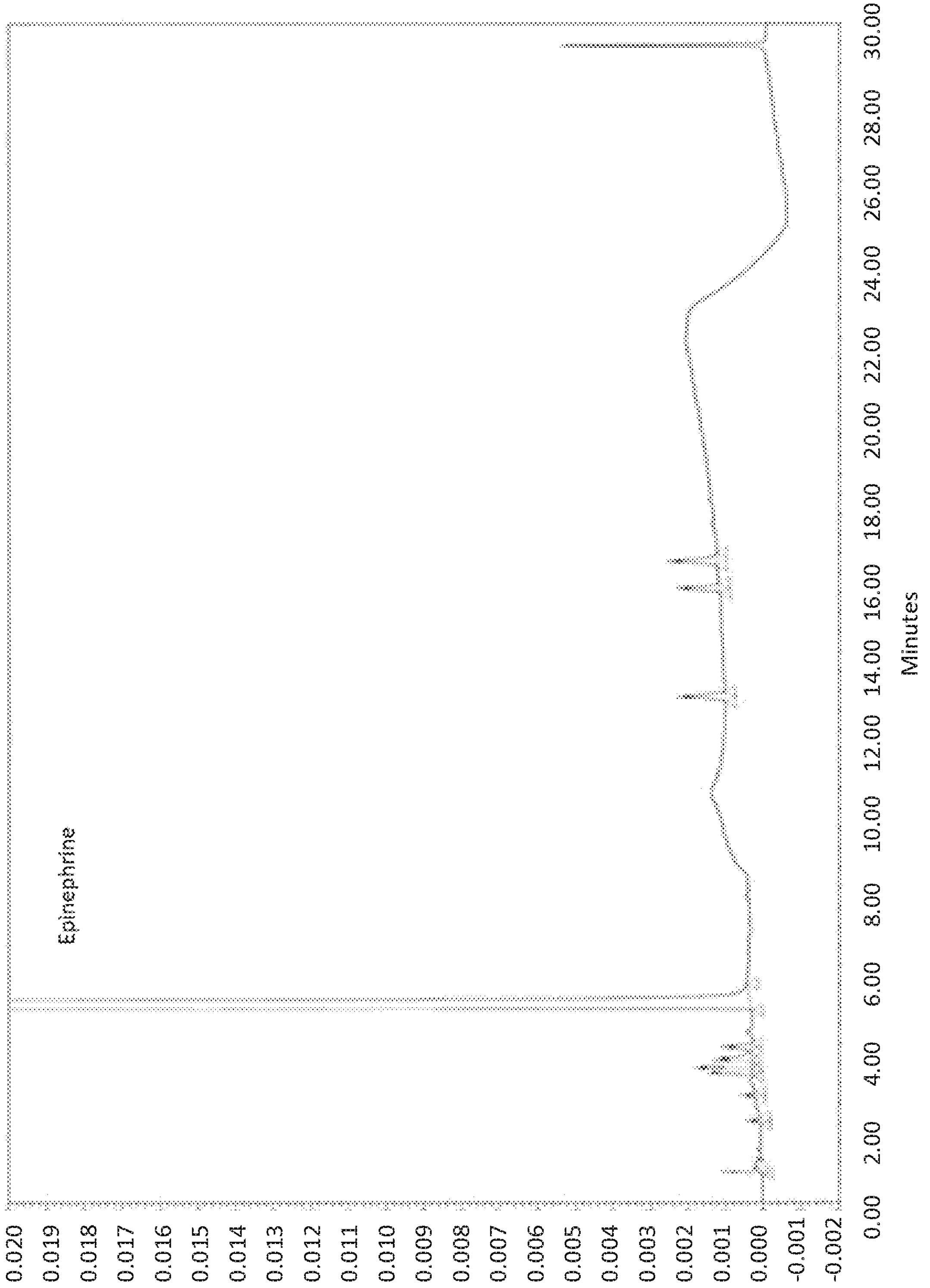

FIG. 132 illustrates the initial chromatogram of Trial 8.

Figure 133:
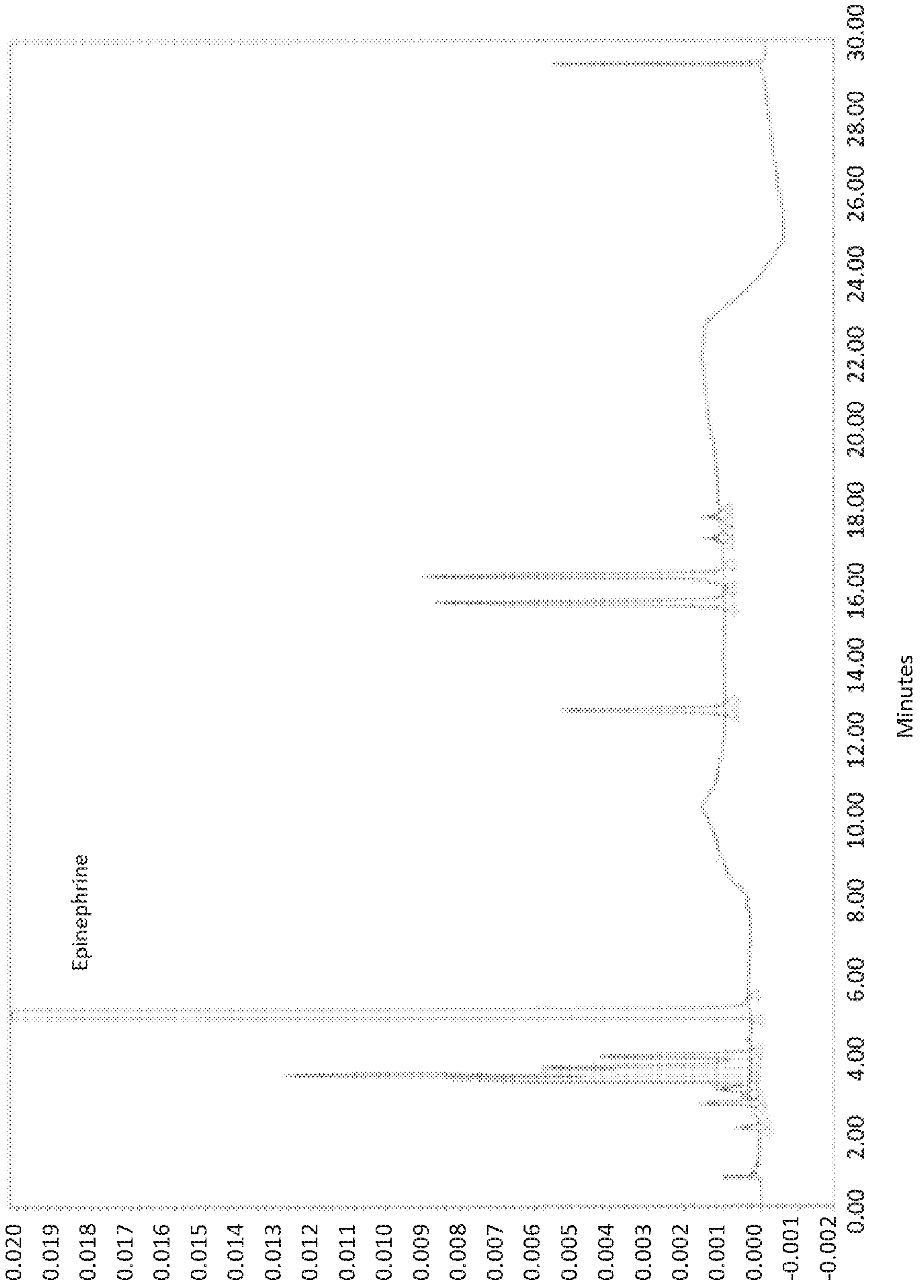

FIG. 133 illustrates the chromatogram of Trial 8 after 4 weeks.

Figure 134:
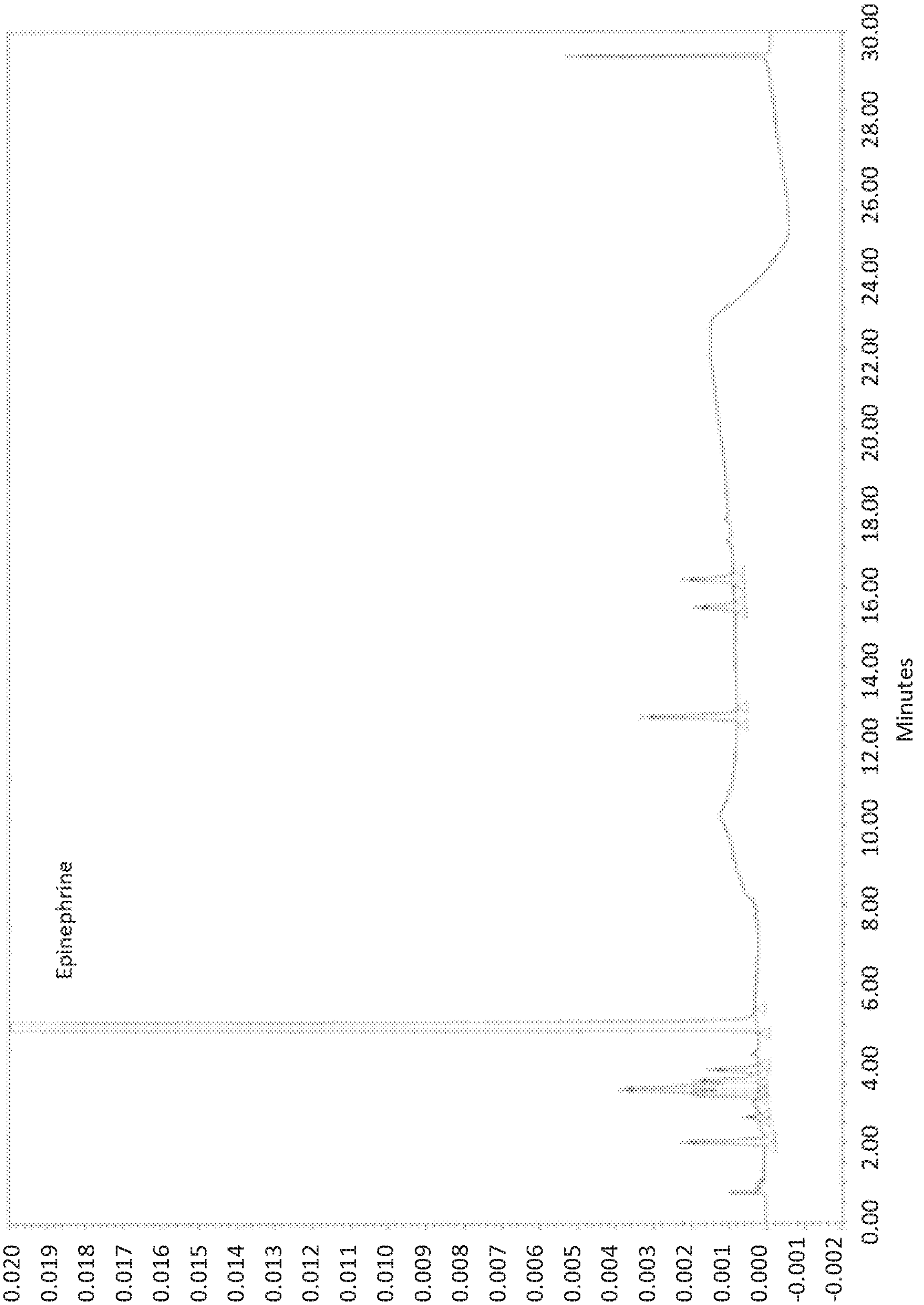

FIG. 134 illustrates the initial chromatogram of Trial 11.

Figure 135:
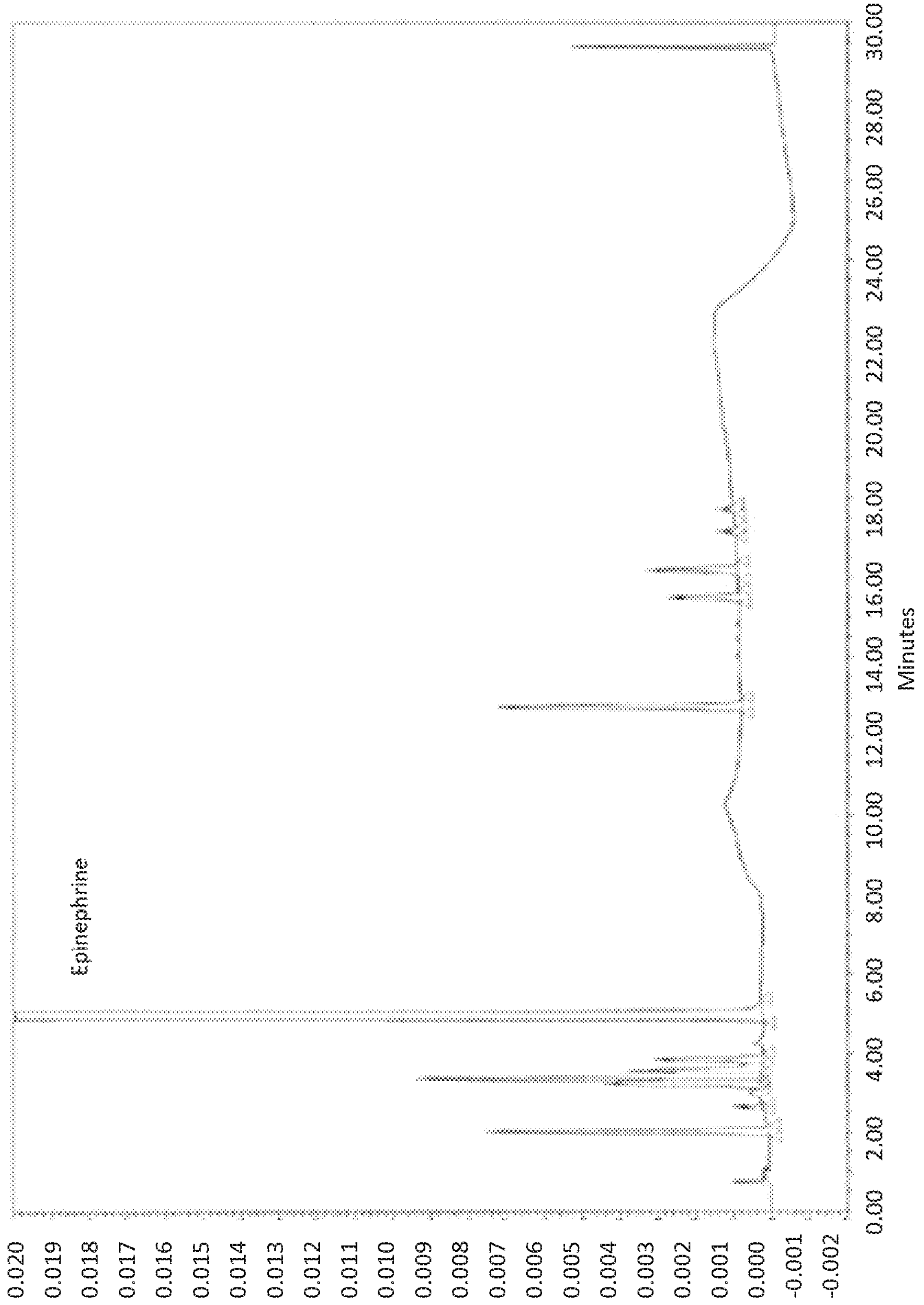

FIG. 135 illustrates the chromatogram of Trial 11 after the trial was maintained at 40° C. for 24 hours.

Figure 136:
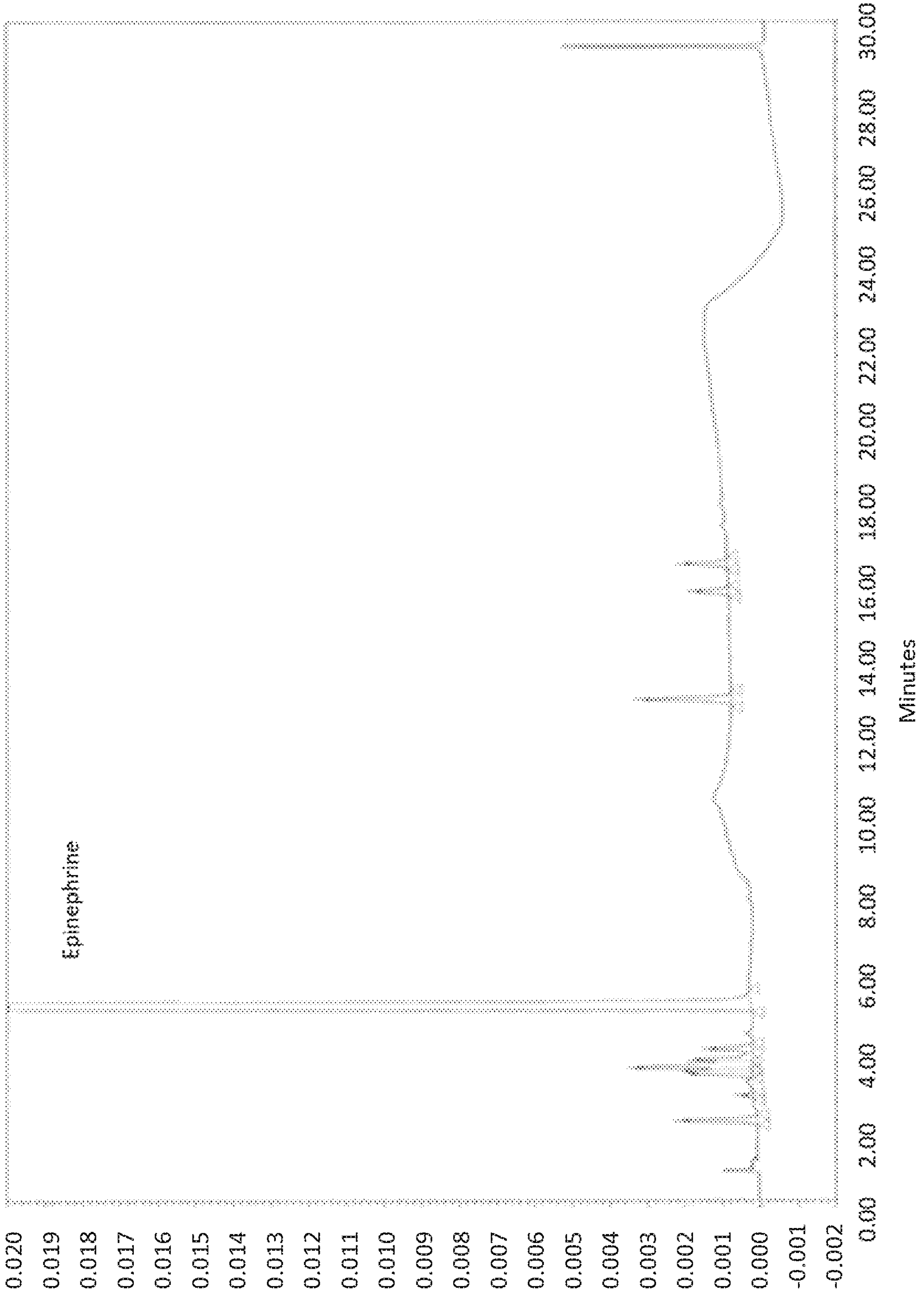

FIG. 136 illustrates the chromatogram of Trial 11 at a pH of 3.1.

Figure 137:
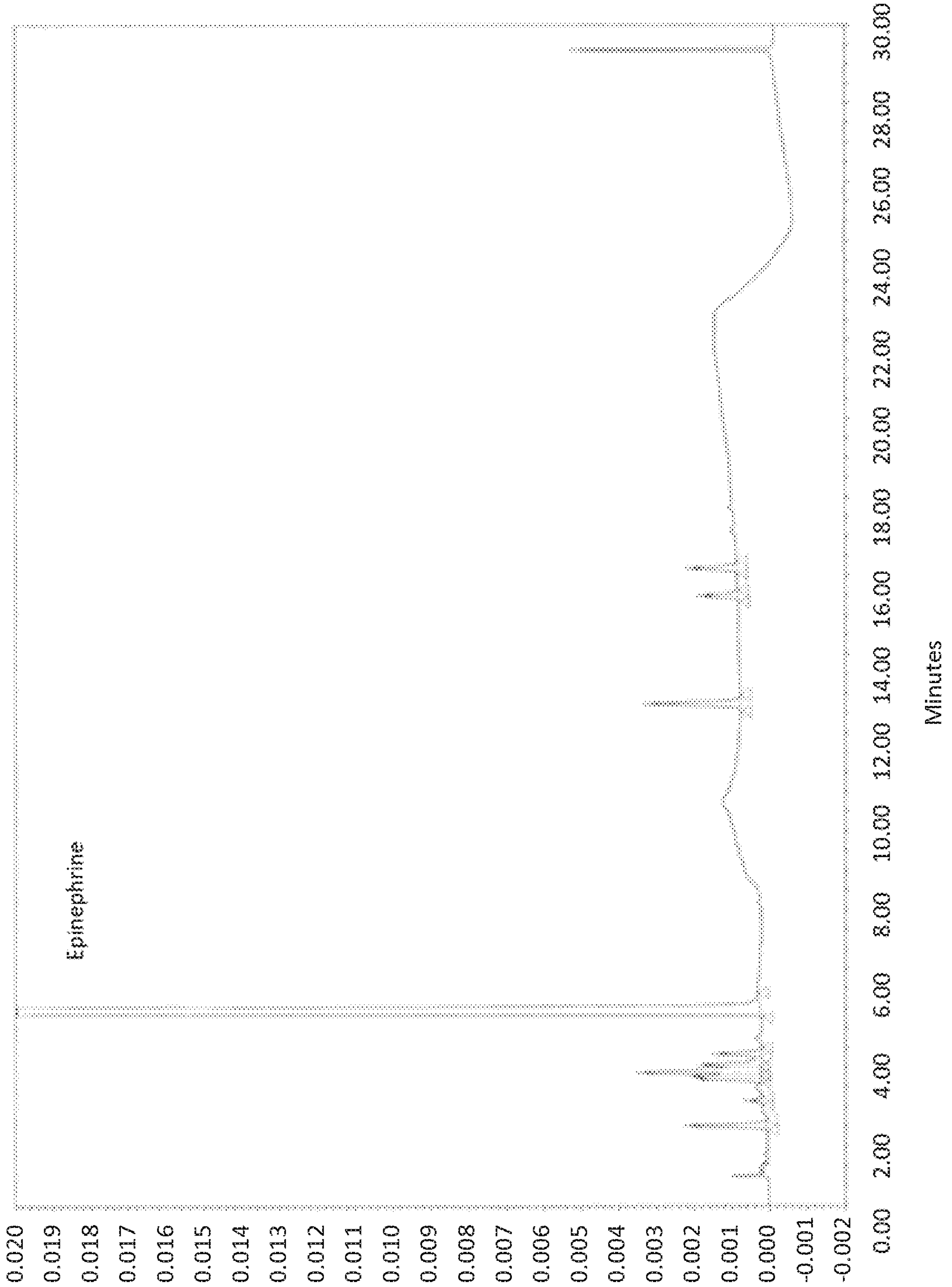

FIG. 137 illustrates the chromatogram of Trial 12 at a pH of 2.3.

Figure 138:
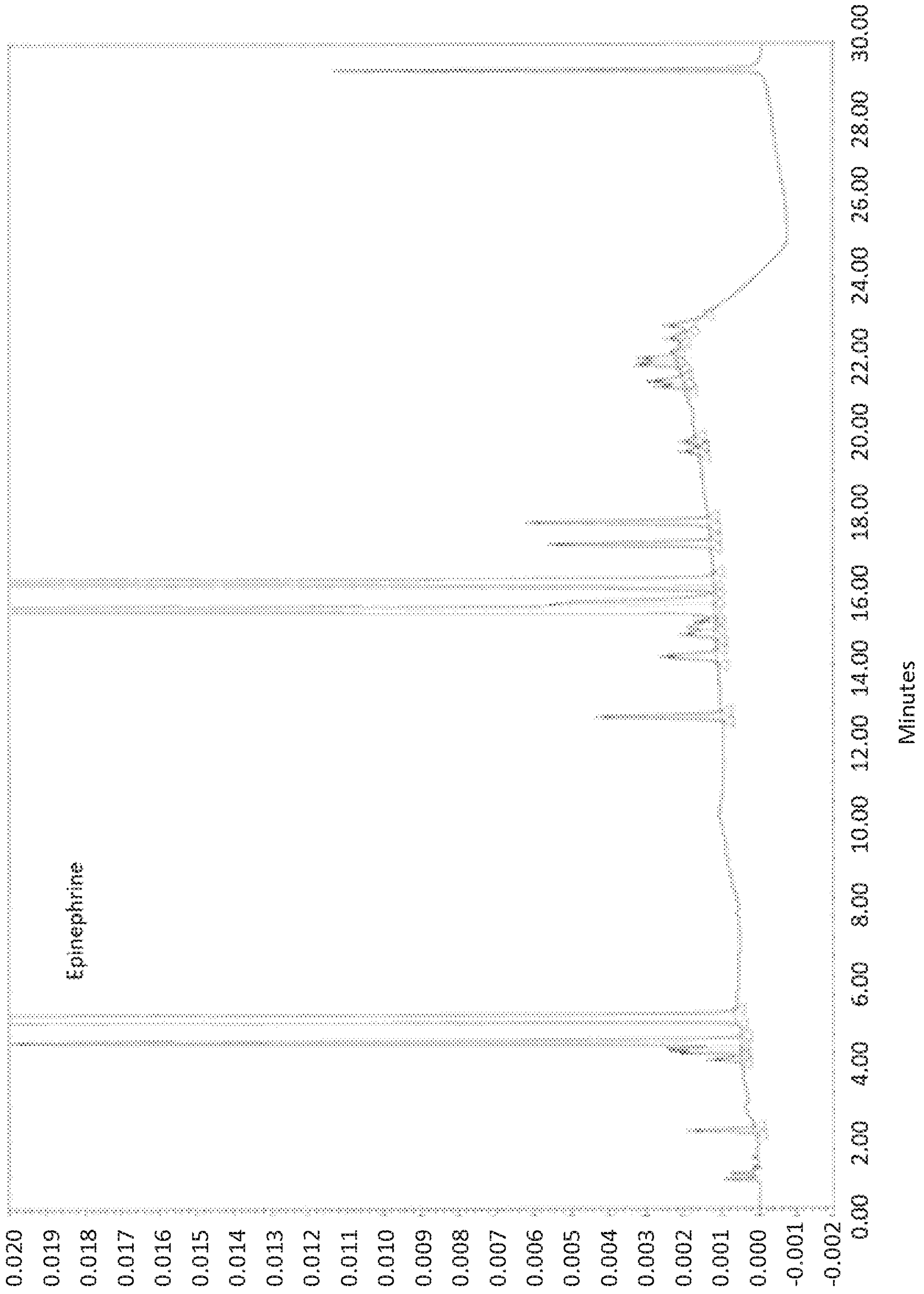

FIG. 138 illustrates the chromatogram of Trial 14.

Figure 139:
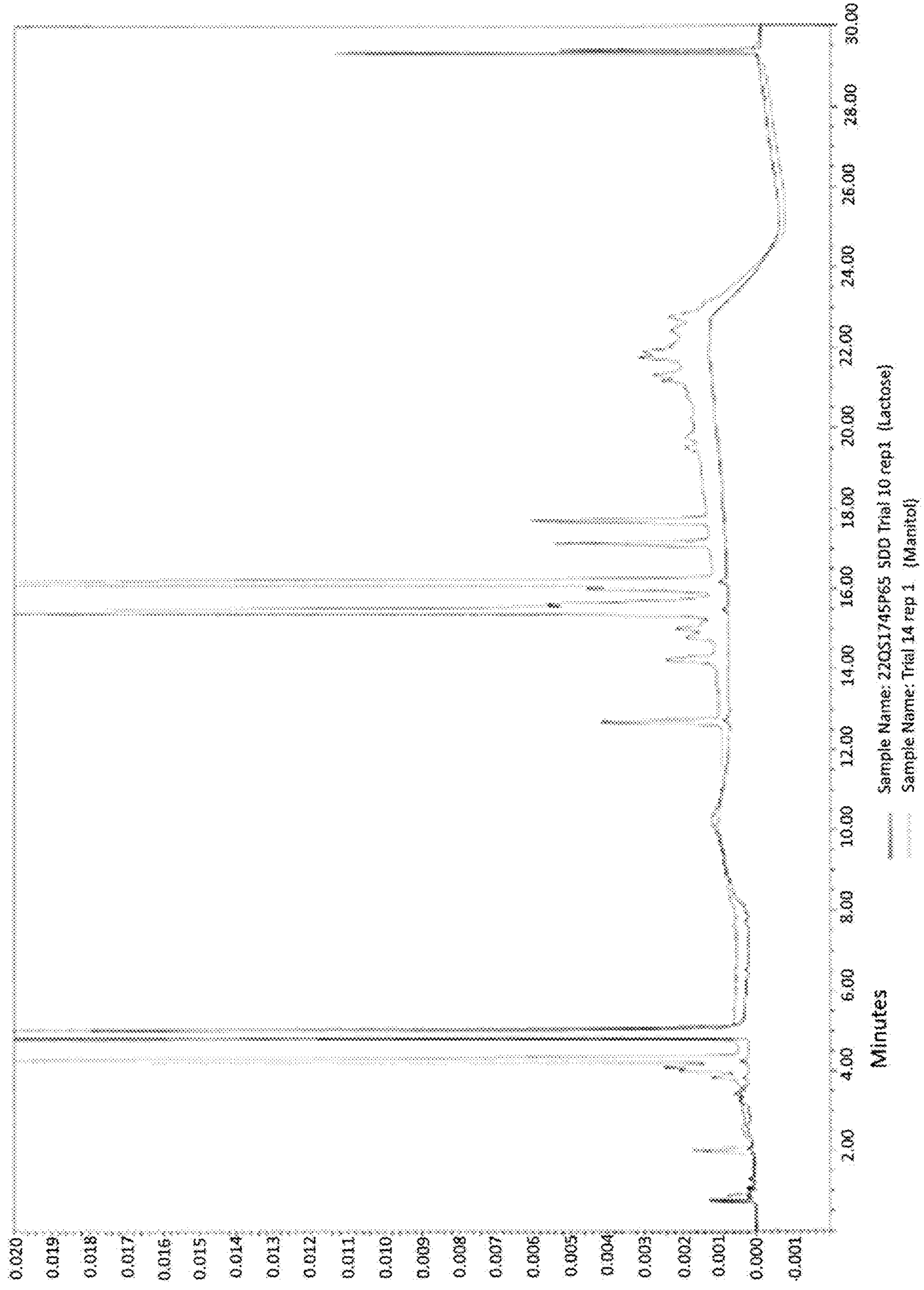

FIG. 139 illustrates the initial chromatogram of Trial 11 overlaid with the chromatogram of Trial 14.

FIG. 140A illustrates a formulation table of technical batches used in experimental trials.

FIG. 140B illustrates a formulation table of technical batches used in experimental trials.

FIG. 140C illustrates a formulation table of technical batches used in experimental trials.

Figure 141:
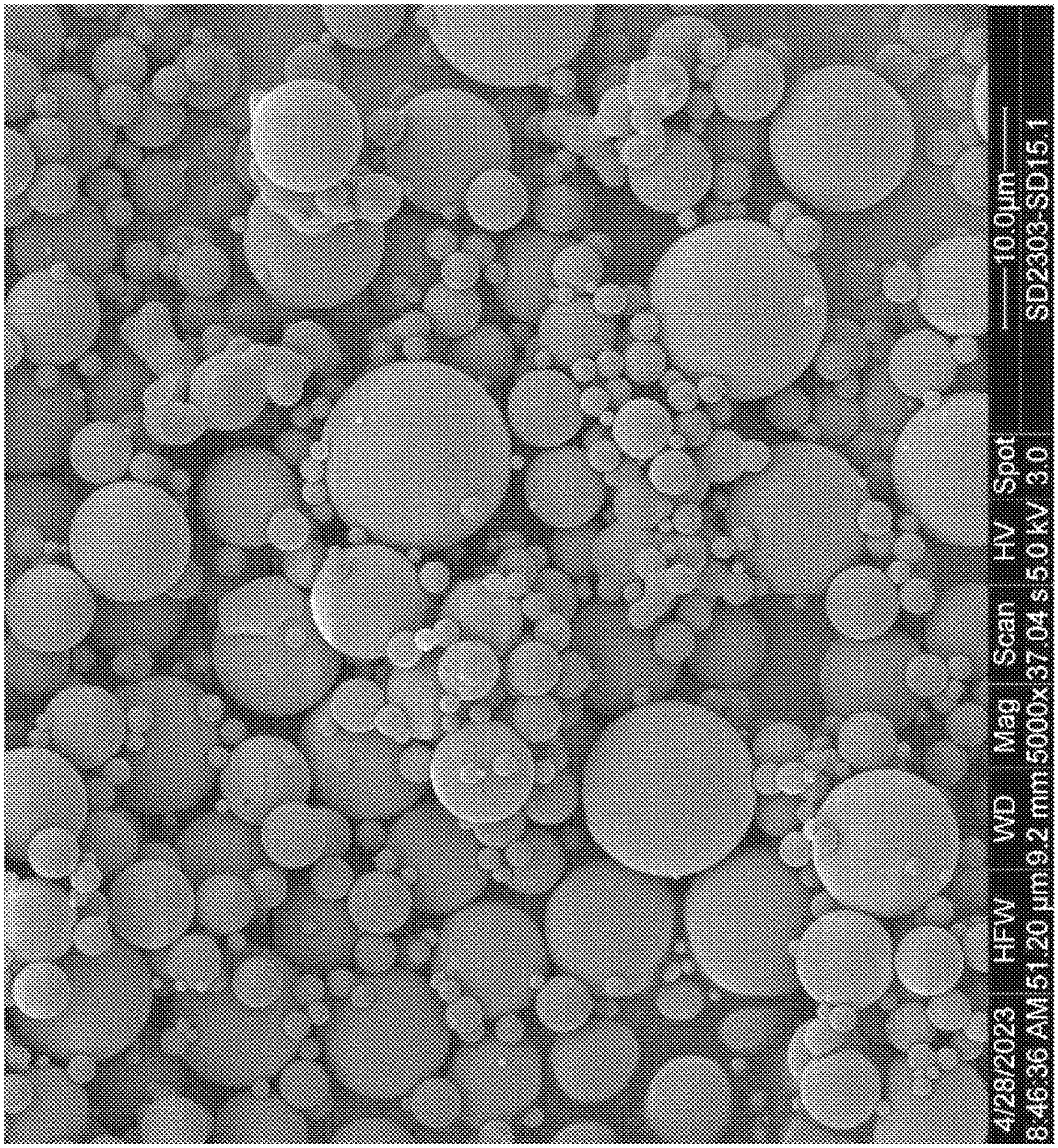

FIG. 141 illustrates the results of Scanning Electron Microscopy (SEM) of an acceptable homogenous powder composition according to one embodiment of the present invention.

Figure 142:
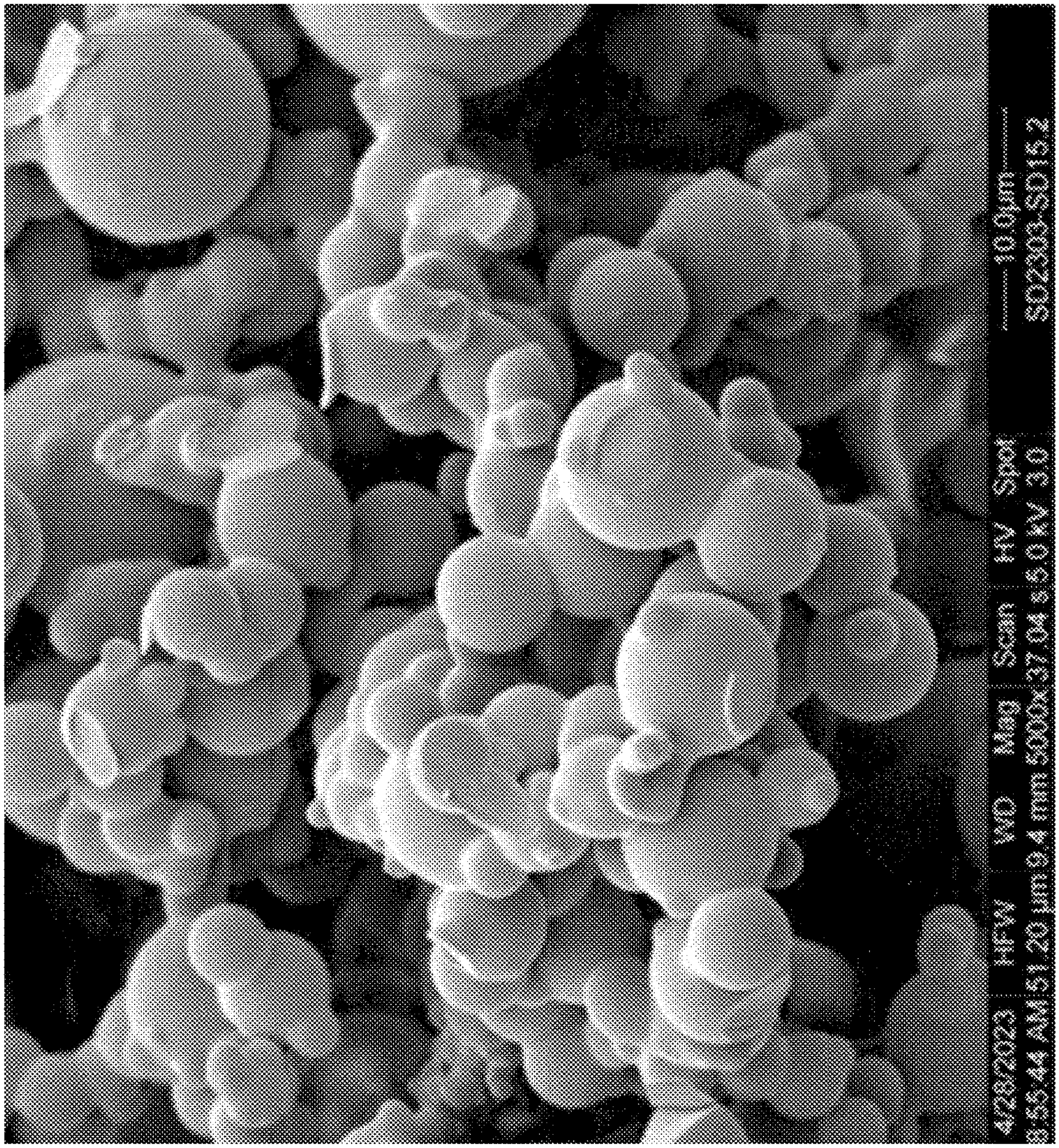

FIG. 142 illustrates the results of Scanning Electron Microscopy (SEM) of a powder composition which has agglomerated.

DETAILED DESCRIPTION

The present invention is generally directed to epinephrine, and more specifically to dry powder formulations of epinephrine and methods of treatment of various conditions using the dry power formulations.

In one embodiment, the present invention provides an intranasal device for administration of a pharmaceutical composition including a reservoir and a means for discharging one or more doses of the pharmaceutical composition, wherein the reservoir contains a quantity of the pharmaceutical composition, wherein the pharmaceutical composition is a dry powder including, epinephrine or a pharmaceutically acceptable salt thereof, wherein the pharmaceutical composition provides a dose of about 0.01 mg to about 10 mg of the epinephrine or the pharmaceutically acceptable salt thereof, citric acid or a pharmaceutically acceptable salt thereof, and a carrier. In one embodiment, a median particle diameter of the epinephrine or the pharmaceutically acceptable salt thereof is about 20 μm to about 75 μm. In one embodiment, the pharmaceutical composition further includes an anticaking agent. In one embodiment, the pharmaceutical composition further includes at least one antihistamine. In one embodiment, the pharmaceutical composition further includes at least one steroid. In one embodiment, the pharmaceutical composition further includes a catechol-o-methyl transferase (COMT) inhibitor. In one embodiment, the pharmaceutical composition further includes one or more agents selected from a group consisting of a mucosal permeation or penetration enhancer, a mucoadhesive, a mucosal transit slowing agent, a mucosal transport enhancer, or any combination thereof. In one embodiment, the intranasal device has 3600 functionality and is constructed and configured to dispense a dose from any position. In one embodiment, the intranasal device further includes an intranasal device global positioning system (GPS) device or is coupled to a GPS device, wherein the intranasal device GPS or the GPS device is constructed and configured to provide location data. In one embodiment, the intranasal device further includes a communications interface, wherein the communications interface is constructed and configured to transmit data wirelessly to at least one remote device. In one embodiment, the carrier includes mannitol, a cyclodextrin, citric acid, lactose, and/or sodium carboxymethylcellulose. In one embodiment, the pharmaceutical composition does not include a preservative. In one embodiment, the quantity of the pharmaceutical composition is between about 5 mg and about 75 mg. In one embodiment, the intranasal device further includes a sensor that is adapted to detect a displacement or a deformation of a portion of the intranasal device when the dry powder is dispensed from the reservoir. In one embodiment, the intranasal device further includes a display and a power supply, a timer, a clock, and/or a printed circuit board, wherein the display is constructed and configured to display a time of dose dispensation.

In another embodiment, the present invention provides a kit for intranasal administration of a pharmaceutical composition including at least one intranasal device, wherein each of the at least one intranasal device includes a reservoir and a means for discharging one or more doses of the pharmaceutical composition, wherein the reservoir contains a quantity of the pharmaceutical composition, and a pouch and/or a hard case, wherein the at least one intranasal device is enclosed in the pouch and/or the hard case, wherein the pharmaceutical composition is a dry powder including, epinephrine or a pharmaceutically acceptable salt thereof, wherein the pharmaceutical composition provides a dose of about 0.01 mg to about 10 mg of the epinephrine or the pharmaceutically acceptable salt thereof, citric acid or a pharmaceutically acceptable salt thereof, and a carrier. In one embodiment, the hard case includes a desiccant plastic. In one embodiment, the pouch and/or the hard case is water resistant or waterproof. In one embodiment, the pouch and/or the hard case is Modular Lightweight Load-carrying Equipment (MOLLE)-compatible.

In yet another embodiment, the present invention provides an intranasal device for administration of a pharmaceutical composition including a reservoir and a means for discharging one or more doses of the pharmaceutical composition, wherein the reservoir contains a quantity of the pharmaceutical composition, wherein the pharmaceutical composition is a spray-dried powder including, epinephrine or a pharmaceutically acceptable salt thereof, wherein the pharmaceutical composition provides a dose of about 0.01 mg to about 10 mg of the epinephrine or the pharmaceutically acceptable salt thereof, a pharmaceutically acceptable citrate salt, and a carrier, wherein the pharmaceutical composition does not include an additional vasodilator, and wherein the intranasal device further includes a nasal probe and an actuator. In one embodiment, the pharmaceutically acceptable citrate salt is trisodium citrate.

Epinephrine is the gold standard for treatment of anaphylactic reactions, which are commonly triggered by food allergies, insect bites or stings, vaccine injections, allergies to latex and other substances, allergic reactions to drugs, and other exposures. Epinephrine is delivered intravenously and by needle and syringe injection, which may be subcutaneous or intra-muscular. Increasingly, epinephrine is delivered by auto-injectors, which may be used within medical facilities or in ambulatory settings by medical and non-medical personnel, caregivers, and patients themselves. Self-administration via auto-injector has dramatically improved the availability of epinephrine treatment in emergency situations.

However, auto-injectors have a number of known disadvantages. These include widespread fear of needles and the size of the units themselves, which may be cumbersome to carry. Many patients and caregivers avoid carrying epinephrine auto-injectors during hot weather or leaving them in automobiles or other places where the aqueous epinephrine formulation is liable to degrade and lose potency. These factors lead many patients or caregivers to not have epinephrine available during emergency anaphylactic events, or if it is available, they may be reluctant to use the device. Delayed access and delayed use of epinephrine auto-injectors has been associated with increased morbidity and mortality. See, e.g., Fleming, J. T., et al., "Early Treatment of Food-Induced Anaphylaxis with Epinephrine Is Associated with a Lower Risk of Hospitalization," J. Allergy Clin Immunol Pract., January-February 2015; 3(1):57-62; doi: 10.1016/j.jaip.2014.07.004 (published online Sep. 8, 2014) and Gabrielli, S., et al., "Teenagers and those with severe reactions are more likely to use their epinephrine autoinjectors in cases of anaphylaxis in Canada," J. Allergy & Clin. Immunology: In Practice, Clinical Communications, Mar. 1, 2019, 7(3): P1073-1075.E3, doi.org/10/1016/j.jaip.2018.07.044, each of which is incorporated herein by reference in its entirety.

In addition, studies have shown that many patients do not use auto-injectors correctly. In one recent study of epinephrine auto-injector carriage and use practices among children, adolescents, and adults in the United States, the investigators reported that "*Of the* 242*patients,* 54% *were not able to recall all the steps for correct EAI use or completely failed to activate the device*." Wasserman, S., et. al. "Epinephrine Autoinjectors: New Data, New Problems," J Allergy Clin Immunol Pract., September-October 2017; 5(5):1180-1191, doi: 10.1016/j.jaip.2017.06.027, which is incorporated herein by reference in its entirety.

Further, studies have shown that due to obesity many patients using auto-injectors do not receive the recommended dose via an intramuscular (IM) injection. One US study estimated that some thirty percent (30%) of both adults and children would not receive an IM injection. When injected, subcutaneously (SQ), a substantially lower plasma drug level and delayed delivery has been found. See Stetcher, D., et.al., "Epinephrine Auto-injectors: Is Needle Length Adequate for Delivery of Epinephrine Intramuscularly?" Pediatrics, July 2009, 124(1): 65-70, doi:10.1542/peds.2008-3388 and Simons F E, Gu X, Simons K J. Epinephrine absorption in adults: intramuscular versus subcutaneous injection. J Allergy Clin Immunol. 2001 November; 108(5):871-3. doi: 10.1067/mai.2001.119409. PMID: 11692118, each of which is incorporated herein by reference in its entirety.

Similarly, needle length may be inappropriate in devices used to treat infants and toddlers. Infants and young children may be uncooperative and unable to hold still while an injection is given, which may cause injuries (e.g., lacerations, bent needles, embedded needles). Further, the needle may strike bone in smaller patients. See, e.g., Greenberger P A, Wallace D V, Lieberman P L, Gregory S M. Contemporary issues in anaphylaxis and the evolution of epinephrine autoinjectors: What will the future bring? Ann Allergy Asthma Immunol. 2017 October; 119(4):333-338. doi: 10.1016/j.anai.2017.07.030. PMID: 28958374, which is incorporated herein by reference in its entirety. For additional information about injuries caused by auto-injectors, see Brown J C, Tuuri R E, Akhter S, Guerra L D, Goodman I S, Myers S R, Nozicka C, Manzi S, Long K, Turner T, Conners G P, Thompson R W, Park E. Lacerations and Embedded Needles Caused by Epinephrine Autoinjector Use in Children. Ann Emerg Med. 2016 March; 67(3):307-315.e8. doi: 10.1016/j.annemergmed.2015.07.011. Epub 2015 October 9. PMID: 26452720, which is incorporated herein by reference in its entirety. Further, there are issues with unintentional epinephrine injections from auto-injectors, for example, while self-injecting epinephrine, injecting epinephrine into someone with anaphylaxis, or demonstrating use of the auto-injector. See, e.g., Simons F E, Lieberman P L, Read E J Jr, Edwards E S. Hazards of unintentional injection of epinephrine from autoinjectors: a systematic review. Ann Allergy Asthma Immunol. 2009 April; 102(4): 282-7. doi: 10.1016/S1081-1206(10)60332-8. PMID: 19441598, which is incorporated herein by reference in its entirety.

Delay or lack of usage of epinephrine in an anaphylactic event leads to increased morbidity and mortality. See, e.g., Chooniedass R, Temple B, Becker A. Epinephrine use for anaphylaxis: Too seldom, too late: Current practices and guidelines in health care. Ann Allergy Asthma Immunol. 2017 August; 119(2):108-110. doi: 10.1016/j.anai.2017.06.004. Epub 2017 Jul. 1. PMID: 28676208, which is incorporated herein by reference in its entirety. Delay in usage of epinephrine also leads to an increased risk for biphasic anaphylactic reactions. See, e.g., Miles L M, Ratnarajah K, Gabrielli S, Abrams E M, Protudjer J L P, Begin P, Chan E S, Upton J, Waserman S, Watson W, Gerdts J, Ben-Shoshan M. Community Use of Epinephrine for the Treatment of Anaphylaxis: A Review and Meta-Analysis. J Allergy Clin Immunol Pract. 2021 June; 9(6):2321-2333. doi: 10.1016/j.jaip.2021.01.038. Epub 2021 Feb. 4. PMID: 33549844, which is incorporated herein by reference in its entirety.

Further, auto-injector devices are used to deliver epinephrine either subcutaneously or via the intra-muscular route at a standard dosage of 0.3 mg (0.3 mL, 1:1000) for adults weighing more than 30 kg. However, the American Heart Association recommends a standard dose of 1 mg of epinephrine every 3-5 minutes for patients in cardiac arrest. Thus, auto-injectors are not viable methods for epinephrine delivery in the response to a cardiac event, at least because the epinephrine formulations contained within auto-injectors do not contain an effective dose of epinephrine for administration in such events. In order to deliver an effective dosage, epinephrine is traditionally administered intravenously in response to a cardiac event such as sudden cardiac arrest and/or hypotension and low mean arterial pressure due to septic shock. The intravenous route of epinephrine delivery requires administration by a medical professional, as non-medically trained bystanders are not capable nor equipped for such administration. However, there is an identified association between the increased time to administer epinephrine in response to a cardiac event and decreased probability of in-hospital survival. See, e.g., Donnino M W, Salcicciolі J D, Howell M D, Cocchi M N, Giberson B, Berg K et al. Time to administration of epinephrine and outcome after in-hospital cardiac arrest with non-shockable rhythms: retrospective analysis of large in-hospital data registry BMJ 2014; 348:g3028 doi:10.1136/bmj.g3028. PMID: 24846323; PMCID: PMC4027796, which is incorporated herein by reference in its entirety. There is a significant delay between the onset of a cardiac event such as sudden cardiac arrest (SCA) and epinephrine delivery in traditional epinephrine delivery systems (i.e., intravenous methods). This is due in large part to the time consuming process of alerting medical services and dispatching a response team. The average emergency response time is seven minutes, with rural response times increasing to an average of 14 minutes with some response times taking as long as 30 minutes. See, e.g., Mell H K, Mumma S N, Hiestand B, Carr B G, Holland T, Stopyra J. Emergency Medical Services Response Times in Rural, Suburban, and Urban Areas. JAMA Surg. 2017 Oct. 1; 152(10):983-984. doi: 10.1001/jamasurg.2017.2230. PMID: 28724118; PMCID: PMC5831456, which is incorporated herein by reference in its entirety. Further, once the response team arrives, they must assess the patient, insert an intravenous line (i.e., an IV), and connect a prefilled syringe via luer lock to deliver the aqueous epinephrine. Further still, the location of a patient experiencing a cardiac event is not always ideal for treatment, requiring the patient to be loaded onto an emergency response vehicle before an IV is inserted for epinephrine delivery. Thus, epinephrine delivery is significantly delayed after the onset of a cardiac event because current epinephrine formulations are not readily available and require professional administration in response to cardiac events.

One study found that among adults with out-of-hospital cardiac arrest (OHCA), survival to hospital discharge decreased with delayed administration of epinephrine for patients with both shockable and nonshockable rhythms. Specifically, the risk ratio for receipt of epinephrine with survival to hospital discharge is highest 0-5 minutes after EMS arrival, and decreases anywhere from 4.4% to 5.5% per minute after EMS arrival. See, e.g., Okubo M, Komukai S, Callaway C W, Izawa J. Association of Timing of Epinephrine Administration With Outcomes in Adults With Out-of-Hospital Cardiac Arrest. JAMA Netw Open. 2021; 4(8):e2120176. doi:10.1001/jamanetworkopen.2021.20176, incorporated herein by reference in its entirety. Another study found that in comparison to the delivery of epinephrine within 1-3 minutes of the initiation of CPR, the delivery of epinephrine within 4-6 minutes of the initiation of CPR decreases probability of in-hospital survival by 12%. For delivery within 7-9 minutes, the probability of in-hospital survival is decreased by 27%, and for epinephrine delivery more than 9 minutes after the initiation of CPR, the likelihood of in-hospital survival is decreased by 49% in comparison to epinephrine delivery within 1-3 minutes. See, e.g., Donnino M W, Salciccioli J D, Howell M D, Cocchi M N, Giberson B, Berg K et al. Time to administration of epinephrine and outcome after in-hospital cardiac arrest with non-shockable rhythms: retrospective analysis of large in-hospital data registry BMJ 2014; 348:g3028 doi:10.1136/bmj.g3028. PMID: 24846323; PMCID: PMC4027796, incorporated herein by reference in its entirety. There is therefore a need for an intranasal epinephrine delivery method of a suitable dosage for use in treating sudden cardiac arrest (SCA) and other cardiac events immediately upon the onset of a confirmed cardiac event.

The aforementioned drawbacks of epinephrine auto-injectors have led to a search for new routes of delivering epinephrine including pulmonary, sublingual, and nasal delivery. Nasal delivery appears promising as it removes the needle-related concerns, provides a more portable device, and provides an easy-to-use delivery mechanism.

Nasal delivery of epinephrine, however, retains some of the drawbacks of injection if an aqueous formulation is employed. Aqueous formulations typically have shorter shelf lives than powders. Aqueous epinephrine formulations have preservatives, such as sodium bisulfite, which itself can cause an allergic reaction in many individuals. Additionally, when aqueous epinephrine formulations are delivered to the nasal passages, a significant portion of drug volume may be lost due to running down the back of the throat or back out the front of the nose when the device is removed. This may be exacerbated when a patient suffering an anaphylactic event is in a prone position. All of these factors lead to dose uncertainty for liquid nasal approaches. A particularly concerning drawback for aqueous formulations of epinephrine, such as that of U.S. Pat. No. 10,688,044 and US Patent Pub. No. 2008/0269347, is that they are subject to degradation when exposed to high temperatures. When exposed to high temperature, even for short durations, as in outdoor summertime activity or when left in an automobile, epinephrine can degrade and lose potency. See Lacwik, P., et. at., "Single, short-time exposure to heat in a car during sunny day can decrease epinephrine concentration in autoinjectors: a real-life pilot study," J. Allergy & Clin. Immunology, Apr. 1, 2019, 7(4): P1362-1364, published Nov. 28, 2018, doi.org/10.1016/j.jaip.2018.10.027, which is incorporated herein by reference in its entirety. Degradation of epinephrine and loss of potency is also a serious issue when traveling or living in areas where temperatures are elevated most of the year (e.g., the tropics). Also see, e.g., (1) Patil Armenian, Danielle Campagne, Geoff Stroh, Crystal Ives Tallman, William Z. D. Zeng, Thomas Lin & Roy R. Gerona (2017) Hot and Cold Drugs: National Park Service Medication Stability at the Extremes of Temperature, Prehospital Emergency Care, 21:3, 378-385, DOI: 10.1080/10903127.2016.1258098; (2) Rachid O, Simons F E, Rawas-Qalaji M, Lewis S, Simons K J. Epinephrine doses delivered from auto-injectors stored at excessively high temperatures. Drug Dev Ind Pharm. 2016 January; 42(1): 131-135. doi: 10.3109/03639045.2015.1035283. Epub 2015 May 22. PMID: 25997362; (3) Parish H G, Bowser C S, Morton J R, Brown J C. A systematic review of epinephrine degradation with exposure to excessive heat or cold. Ann Allergy Asthma Immunol. 2016 July; 117(1):79-87. doi: 10.1016/j.anai.2016.04.006. Epub 2016 May 21. PMID: 27221065; (4) Kassel L, Jones C, Mengesha A. Epinephrine drug degradation in autoinjector products. J Allergy Clin Immunol Pract. 2019 September-October; 7(7):2491-2493. doi: 10.1016/j.jaip.2019.04.028. Epub 2019 May 28. PMID: 31151888; (5) Rawas-Qalaji M, Simons F E, Collins D, Simons K J. Long-term stability of epinephrine dispensed in unsealed syringes for the first-aid treatment of anaphylaxis. Ann Allergy Asthma Immunol. 2009 June; 102(6):500-3. doi: 10.1016/51081-1206(10)60124-X. PMID: 19558009; and (6) Gill M A, Kislik A Z, Gore L, Chandna A. Stability of advanced life support drugs in the field. Am J Health Syst Pharm. 2004 Mar. 15; 61(6):597-602. doi: 10.1093/ajhp/61.6.597. PMID: 15061431, each of which is incorporated herein by reference in its entirety.

Patients are aware of this issue and many will not carry epinephrine at times or will not store epinephrine in locations where high temperatures are likely. This behavior is due to both the concern over loss of potency and the concern about the cost of replacing the device that has gone bad. As a result, epinephrine is often not available during emergencies, leading to greater morbidity.

Additionally, dry powder nasal sprays appear to be more readily absorbed during the initial minutes after delivery than aqueous nasal sprays. This may reflect the fact that a greater portion of the volume stays on the nasal mucosa. Further, aqueous nasal sprays frequently shown a biphasic peak blood plasma level. This is thought to reflect the gastrologic absorption of a portion of the spray that is swallowed (runs down the throat).

Nasal delivery of epinephrine in a dry powder eliminates the significant disadvantages of intramuscular or subcutaneous injection as well as the major drawbacks of aqueous formulations of the drug. The present invention describes dry powder formulations for delivery to the nasal passages by means of a nasal delivery device that are handheld.

Further, patients experience barriers to epinephrine usage, including, but not limited to, high cost of auto-injectors, lack of availability, lack of use even though a device is available (e.g., due to fear of using the device, due to an expired device), and incorrect technique. See, e.g., Prince B T, Mikhail I, Stukus D R. Underuse of epinephrine for the treatment of anaphylaxis: missed opportunities. J Asthma Allergy. 2018 Jun. 20; 11:143-151. doi: 10.2147/JAA.S159400. PMID: 29950873; PMCID: PMC6016581, which is incorporated herein by reference in its entirety. Both cost and supply are also factors that prevent epinephrine usage. See, e.g., Ponda P, Russell A F, Yu J E, Land M H, Crain M G, Patel K, Shroba J A, Sriaroon P. Access barriers to epinephrine autoinjectors for the treatment of anaphylaxis: A survey of practitioners. J Allergy Clin Immunol Pract. 2021 October; 9(10):3814-3815.e4. doi: 10.1016/j.jaip.2021.05.028. Epub 2021 Jun. 11. PMID: 34126272, which is incorporated herein by reference in its entirety. Further, low prescription rates of autoinjectors and lack of stock epinephrine in schools are barriers to use in pre-hospital settings. See, e.g., Ponda P, Russell A F, Yu J E, Land M H, Crain M G, Patel K, Shroba J A, Sriaroon P. Access barriers to epinephrine autoinjectors for the treatment of anaphylaxis: A survey of practitioners. J Allergy Clin Immunol Pract. 2021 October; 9(10):3814-3815.e4. doi: 10.1016/j.jaip.2021.05.028. Epub 2021 Jun. 11. PMID: 34126272, which is incorporated herein by reference in its entirety.

The present invention overcomes the drawbacks of earlier attempts to formulate epinephrine as a dry powder for nasal delivery. Such non-aqueous formulations reduce the susceptibility of the epinephrine product to heat-related degradation and extend product shelf life as previously discussed. This advantageously allows for the epinephrine formulation to be stored in emergency response kits used by emergency medical services or deployed for public access such as automated external defibrillator (AED) kits without the degradation experienced by aqueous epinephrine solutions.

There are a number of physiological changes that occur during anaphylaxis with the most important leading to significant drop in blood pressure (hypotension, cardiovascular collapse) and bronchoconstriction (respiratory collapse). According to a US FDA product review, "the mechanism of action of epinephrine for anaphylaxis is based on its mixed pharmacology including its ability to activate α1, α2, β1, and β2 receptors." See U.S. Food & Drug Administration. Multidisciplinary Review. NDA 201-739, S-008 and S-009. Auvi-Q (epinephrine injection, USP) Auto-Injector. September 2017, available at www.fda.gov/media/109468/download, which is incorporated herein by reference in its entirety. Epinephrine's ability to activate α1-receptors may decrease mucosal edema and membrane leakage, and most importantly increase vasoconstriction and vascular resistance, which may counteract the significant drop in blood pressure seen in anaphylaxis. Epinephrine's β2 effects importantly leads to bronchodilation and can help reverse the severe bronchoconstriction that can occur during anaphylaxis.

One formulation (Fleming—U.S. Pat. No. 9,789,071) described the potential for delivery of epinephrine in a powder form, but this formulation depended on the use of an alpha-adrenergic blocker as a vasodilator. One of the primary therapeutic goals of administering epinephrine during anaphylactic events is to counteract the drop in peripheral circulatory blood pressure, so the use of alpha-adrenergic antagonists as disclosed by Fleming is problematic because these agents act to widen blood vessels in smooth muscle and counteract the intended therapeutic action of epinephrine itself. Furthermore, unlike the currently available injectable epinephrine devices, this approach promotes the administration of two active adrenergic receptor agents (i.e., drugs) versus just one drug. Administering more than one drug at a time may pose additional risks. Advantageously, the present invention does not require administration of an additional vasodilator.

One prior art publication (Fleming—US Patent Pub. No. 2016/0220489) describes the potential for delivery of epinephrine in a powder form, but this formulation depends on the use of an alpha-adrenergic blocker as a vasodilator, which is disadvantageous for the reasons stated herein. Further, the '489 publication promotes the administration of two active adrenergic receptor agents (i.e., drugs) versus just one drug, unlike the currently available injectable epinephrine devices. Administering more than one drug at a time may introduce potentially harmful effects to a patient, and the specific inclusion of an alpha-adrenergic blocker counteracts the effect of the epinephrine delivered to the patient, thereby rendering the composition ineffective. Advantageously, the present invention does not require administration of an additional vasodilator where the '489 publication does.

There is a long-standing, unmet need for a formulation of epinephrine that is operable to be administered without a needle or syringe. Additionally, there is a long-standing, unmet need for a dry powder formulation of epinephrine that is operable to be successfully delivered by the nasal route and which does not contain vasodilating ingredients in the alpha blocker drug class. Further, there is a long-standing, unmet need for the formulation to maintain its integrity when exposed to high temperature conditions. Further still. there is also a long-standing, unmet need for a dry formulation of epinephrine with a consistent particle size that does not enter the lungs. There is also a long-standing, unmet need for a dry powder formulation of epinephrine that is readily available and easily deliverable in response to a cardiac event, such as sudden cardiac arrest (SCA). There is also a long-standing, unmet need for a dry powder formulation of epinephrine that is of a sufficient dosage and concentration so as to effectively counteract the physiological symptoms of cardiac events. Advantageously, the dry powder formulation of the present invention advances the ability to make epinephrine readily available in emergency situations for treatment of anaphylactic reactions, cardiac events, septic shock, and other indications.

Referring now to the drawings in general, the illustrations are for the purpose of describing one or more preferred embodiments of the invention and are not intended to limit the invention thereto.

Provided herein are pharmaceutical formulations comprising dry powder epinephrine and at least one dry powder enabling agent that have optimized systemic delivery of epinephrine through the nasal passages. The formulations preferably include at least one enabling agent, at least one carrier, and/or at least one flow agent that are combined in various ratios and employed to optimize the systemic delivery of epinephrine through the nasal passages. In some instances, the formulations include 0.1% to 75% w/w epinephrine. In one embodiment, the formulations include a salt of epinephrine. In one embodiment, the salt is epinephrine hydrochloride. Alternatively, the salt is epinephrine acetate, epinephrine tartrate, epinephrine bitartrate, epinephrine hydrogen tartrate, or epinephrine borate. In some instances, the formulations include 0.1% to 20% w/w of the at least one enabling agent. In some instances, the at least one enabling agent includes, but is not limited to, at least one mucoadhesive, at least one absorption enhancer, at least one permeability enhancer, at least one surfactant, at least one surface modifier, at least one sustained release agent, at least one vasodilator (e.g., a natural vasodilator, such as niacin), at least one anticaking agent, at least one stabilizing agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing during the manufacturing process to result in a dry powder formulation having the desired characteristics. In some embodiments, the at least one enabling agent includes chitosan, hyaluronic acid (e.g., sodium hyaluronate), sodium carboxymethyl cellulose (NaCMC), cyclodextrin, niacin (e.g., nicotinic acid), caffeine, sodium taurocholate, carnitine hydrochloride, dimethyl-beta-cyclodextrin, polysorbate (e.g., Polysorbate 80 (e.g., TWEEN® 80), sodium chloride (NaCl), potassium chloride (KCl), Poloxamer 188, L-leucine, histidine, glycine, arginine, crospovidone, a polyacrylic acid polymer (e.g., CARBOPOL® 934), magnesium stearate, ethylenediaminetetraacetic acid (EDTA), sodium starch glycolate, lactose (e.g., D-lactose), microcrystalline cellulose, mannitol, and/or a mixture of mannitol and hydroxypropyl methylcellulose (HPMC). In one embodiment, the intranasal dry powder formulations are spray-dried powder formulations.

In some embodiments, a single dose of epinephrine is about 0.01 mg to about 10 mg. In some embodiments, the amount of epinephrine is at least about: 0.01 mg, 0.05 mg, 1.0 mg, 2.0 mg, 5.0 mg, 10 mg, 12 mg, 15 mg, 18 mg, 20 mg, 25 mg, 30 mg, 35 mg, or 40 mg in the formulation. In some embodiments, the epinephrine present in the formulation is about: 0.01 mg to 0.05 mg, 0.05 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10.0 mg to 12.0 mg, 12.0 mg to 15.0 mg, 15.0 mg to 20.0 mg, 20.0 mg to 25.0 mg, or 25.0 mg to 30 mg. In some embodiments, the epinephrine present in the formulation is about: 1 mg to 20 mg, 3.0 mg to 30.0 mg, 3.0 mg to 25 mg, 10.0 mg to 40.0 mg, 10.0 mg to 25.0 mg, 14.0 mg to 40.0 mg, 15.0 mg to 25.0 mg, or 15.0 mg to 40.0 mg. In some embodiments, the amount of epinephrine is operable to be about: 0.15, 0.3, 0.5, 0.75, 1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mg in the formulation. In one instance, a single dose of epinephrine is about 0.75 mg. In one instance, a single dose of epinephrine is about 1.5 mg. In another instance, a single dose of epinephrine is about 3.0 mg. In another instance, a single dose of epinephrine is about 4.5 mg. In another instance, a single dose of epinephrine is about 15 mg. In another instance, a single dose of epinephrine is about 18 mg. In another instance, a single dose of epinephrine is about 20.0 mg. In another instance, a single dose of epinephrine is about 22 mg. In another instance, a single dose of epinephrine is about 25 mg. In another instance, a single dose of epinephrine is about 35 mg. In another instance, a single dose of epinephrine is about 40 mg. In some embodiments, the formulation, in the form of a single dose, contains about 0.1 mg to about 40 mg of epinephrine. In some embodiments, the formulation, in the form of a single dose, contains about 0.75 mg, 1.5 mg, or 3.0 mg of epinephrine. In some embodiments, based on a "standard" patient weight of 70 kg, the dose of epinephrine is operable to be adjusted according to an increased or decreased weight of the patient relative to the "standard" patient weight. In one embodiment, the dose of epinephrine is operable to be adjust according to the increased or decreased weight of the patient at an increased or decreased increment of at least 0.01 mg/kg, respectively.

In one embodiment, a unit dosage of epinephrine herein ranges from about 0.01 mg to about 1 mg, for example about: 0.1, 0.2, 0.3, 0.4, 0.5, 0.6, 0.7, 0.8, 0.9, or 1 mg in the formulation. In another embodiment, the unit dosage of epinephrine is also at least about: 0.01 0.1, 0.5, or 1 mg in the formulation. In one embodiment, a unit dosage of epinephrine herein ranges from about 1.0 mg to about 20 mg. In one embodiment, a unit dosage of epinephrine herein ranges from about 1.0 mg to about 30 mg, for example about: 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30 mg in the formulation In some embodiments, the epinephrine is about 0.25% to about 50% w/w of the weight of the formulation, for example about: 0.25%, 0.5%, 1%, 2%, 3%, 4%, 5%, 6%, 7%, 7.5%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 25%, 30%, 31%, 32%, 33%, 34%, 35%, 36%, 37%, 38%, 39%, 40%, 45%, or 50% w/w, based on the weight of the formulations and/or dosage units. For example, the epinephrine is about 4%, about 7.5%, or about 15% w/w of the weight of the formulation. In some embodiments, epinephrine is present in an amount of at least about: 0.25% w/w, 1% w/w, 5% w/w, 10% w/w, 20% w/w, 30% w/w, 40% w/w, or 50% w/w based on the weight of the formulations and and/or dosage units. In some embodiments, epinephrine is present in an amount of about: 0.25% to 1% w/w, 1% to 5% w/w, 5% to 10% w/w, 10% to 20% w/w, 20% to 30% w/w, 30% to 40% w/w, or 40% to 50% w/w based on the total weight of the formulations and/or dosage units. In one embodiment, epinephrine is present in an amount of about 1% w/w to about 10% w/w based on the total weight of the formulations and/or dosage units.

In some embodiments, the dry powder formulations provided herein, when administered to a patient, produce a maximal blood concentration (Cmax) of epinephrine that is at least about: 2- to 3-fold, 3- to 5-fold, 5- to 7-fold, or 7- to 10-fold more than the baseline level of epinephrine in the patient. In some embodiments, the dry powder formulations provided herein, when administered to a patient, produce a maximal blood concentration (Cmax) of epinephrine at least 2-, 3-, 4-, 5-, 6-, 7-, 8-, 9-, 10-, 11-, 12-, 13-, 14-, 15-, 16-, 17-, 18-, 19, or 20-fold more than the baseline level of epinephrine in the patient. In one embodiment, the dry powder formulations provided herein, when administered to a patient, produce a maximal blood concentration (Cmax) of epinephrine at least 2-fold more than the baseline level of the epinephrine in the patient. In one embodiment, the formulations provided herein, when administered to a patient, increase the blood concentration of epinephrine by about 0.01 to 0.1 ng/mL. In one embodiment, the formulations provided herein, when administered to a patient, increase the blood concentration of epinephrine by about 0.01, 0.02, 0.03, 0.04, 0.05, 0.06, 0.07, 0.08, 0.09, or 0.1 ng/mL. In one embodiment, the formulations provided herein, when administered to a patient, increase the blood concentration of epinephrine by about 50 to 1000 pg/mL. In one embodiment, the formulations provided herein, when administered to a patient, increase the blood concentration of epinephrine by about 200 to 4200 pg/mL. In one embodiment, the formulations provided herein, when administered to a patient, increase the blood concentration of epinephrine by about 800 to 4200 pg/mL. In one embodiment, the formulations provided herein, when administered to a patient, increase the blood concentration of epinephrine by about 50, 100, 200, 400, 600, 800, 1000, 1200, 1400, 1600, 1800, 2000, 2200, 2400, 2600, 2800, 3000, 3200, 3400, 3600, 3800, 4000, 4200 pg/mL.

In some embodiments, the dry powder formulations provided herein, when administered to a patient, reach a maximal blood concentration of epinephrine in less than about 60 minutes (Tmax) after administration. In some embodiments, the dry powder formulations provided herein, when administered to a patient, reach a maximal blood concentration of epinephrine in less than about 5 minutes (Tmax) after administration. In some embodiments, the dry powder formulations provided herein, when administered to a patient, reach a maximal blood concentration (Tmax) of epinephrine in less than about 60, 50, 40, 30, 20, 15, 10, 5, 3, or 1 minute(s) (Tmax) after administration.

In some embodiments, the dry powder formulations provided herein, when administered to a patient, reach a mean area under the curve (AUC) over a time period before administration to a time of a last detectable concentration of the delivered dose of the dry powder (0-t) (e.g., 0-40 minutes, 0-180 minutes) of epinephrine that is at least 20%, 30%, 40% 50%, 60%, 70%, 80%, 90%, 100%, 110%, 120%, 130%, 140%, or 150% of the mean AUC over the time period of an IV, IM, or SQ injected epinephrine. In some embodiments, the dry powder formulations provided herein, when administered to a patient, reach a mean area under the curve (AUC) over a time period (0-t) (e.g., 0-40 minutes, 0-180 minutes) of epinephrine that is at least about 80% to 120% of the mean AUC over the time period of an IV, IM, or SQ injected epinephrine. In some embodiments, the dry powder formulations provided herein, when administered to a patient, reach a mean AUC over a time period before administration extrapolated to infinity (0-∞) of epinephrine that is at least 20%, 30%, 40% 50%, 60%, 70%, 80%, 90%, 100%, 110%, 120%, 130%, 140% or 150% of the mean AUC over the time period of an IV, IM, or SQ injected epinephrine. In some embodiments, the dry powder formulations provided herein, when administered to a patient, reach a mean AUC over a time period (0-∞) of epinephrine that is at least about 80% to 120% of the mean AUC over the time period of an IV, IM, or SQ injected epinephrine. In some embodiments, the IV, IM, or SQ injected epinephrine contains 0.10 mg, 0.15 mg, 0.20 mg, 0.25 mg, 0.30 mg, 0.35 mg, 0.40 mg, 0.45 mg, 0.50 mg, 0.55 mg, 0.60 mg, 0.65 mg, 0.70 mg, 0.75 mg, 0.80 mg, 0.85 mg, 0.90 mg, 0.95 mg, or 1.0 mg, 1.10 mg, 1.20 mg, 1.25 mg, 1.30 mg, 1.40 mg, 1.50 mg, 1.60 mg, 1.70 mg, 1.75 mg, 1.80 mg, 1.90 mg, 2.0 mg, 2.10 mg, 2.20 mg, 2.25 mg, 2.30 mg, 2.40 mg, 2.50 mg, 2.60 mg, 2.70 mg, 2.75 mg, 2.80 mg, 2.90 mg, 3.0 mg, 3.10 mg, 3.20 mg, 3.25 mg, 3.30 mg, 3.40 mg, 3.50 mg, 3.60 mg, 3.70 mg, 3.75 mg, 3.80 mg, 3.90 mg, 4.0 mg, 4.10 mg, 4.20 mg, 4.25 mg, 4.30 mg, 4.40 mg, 4.50 mg, 4.60 mg, 4.70 mg, 4.75 mg, 4.80 mg, 4.90 mg, or 5.0 mg of epinephrine. For example, the dry powder formulations provided herein, when administered to a patient, reach a mean AUC over a time period (0-t) (e.g., 0-40 minutes, 0-180 minutes) of epinephrine that is at least 80% of the mean AUC over the time period of a 0.3 mg IM injected epinephrine. In one embodiment, the dry powder formulations provided herein, when administered to a patient, reach a mean AUC over a time period (e.g., 0-∞) of epinephrine that is at least 80% of the mean AUC over the time period of a 0.3 mg IM injected epinephrine. In one embodiment, the dry powder formulations provided herein, when administered to a patient, reach a mean AUC over a time period (0-t) (e.g., 0-40 minutes, 0-180 minutes) of epinephrine that is at least 80% of the mean AUC over the time period of 0.15-1 mg (e.g., 0.15 mg, 0.3 mg, 0.5 mg, or 1 mg) IV injected epinephrine. In one embodiment, the dry powder formulations provided herein, when administered to a patient, reach a mean AUC over a time period (e.g., 0-∞) of epinephrine that is at least 80% of the mean AUC over the time period of a 0.15-1 mg (e.g., 0.15 mg, 0.3 mg, 0.5 mg, or 1 mg) IV injected epinephrine. In one embodiment, the dry powder formulations provided herein, when administered to a patient, reach a mean AUC over a time period (0-t) (e.g., 0-40 minutes, 0-180 minutes) of epinephrine that is at least 80% of the mean AUC over the time period of 1 mg-10 mg (e.g., 1 mg, 2 mg, 3 mg, 4 mg, 5 mg, 6 mg, 7 mg, 8 mg, 9 mg, or 10 mg) IV injected epinephrine. In one embodiment, the dry powder formulations provided herein, when administered to a patient, reach a mean AUC over a time period (e.g., 0-∞) of epinephrine that is at least 80% of the mean AUC over the time period of 1 mg-10 mg (e.g., 1 mg, 2 mg, 3 mg, 4 mg, 5 mg, 6 mg, 7 mg, 8 mg, 9 mg, or 10 mg) IV injected epinephrine. In some embodiments, the IV, IM, or SQ injected epinephrine is injected by EPIPEN® auto-injector. In some embodiments, the IV, IM, or SQ injected epinephrine is injected by a manually actuated syringe (i.e., inserted parenterally via a pre-filled syringe with a Luer lock coupling system to an IV line). In some embodiments, the dry powder formulations provided herein, when administered to a patient, reach a mean AUC over a time period (e.g., 0-180 minutes) of epinephrine that is at least 10,000 pg·min/mL, 20,000 pg·min/mL, 40,000 pg·min/mL, 50,000 pg·min/mL, 100,000 pg·min/mL, 200,000 pg·min/mL, 300,000 pg·min/mL, 400,000 pg·min/mL, 500,000 pg·min/mL, 600,000 pg·min/mL, 700,000 pg·min/mL, 800,000 pg·min/mL, 900,000 pg·min/mL, 1,000,000 pg·min/mL, 1,200,000 pg·min/mL, 1,400,000 pg·min/mL, 1,600,000 pg·min/mL, 1,800,000 pg·min/mL, or 2,000,000 pg·min/mL. In some embodiments, the dry powder formulations provided herein, when administered to a patient, reach a mean AUC over a time period (e.g., 0-∞) of epinephrine that is at least 10,000 pg·min/mL, 20,000 pg·min/mL, 40,000 pg·min/mL, 50,000 pg·min/mL, 100,000 pg·min/mL, 200,000 pg·min/mL, 300,000 pg·min/mL, 400,000 pg·min/mL, 500,000 pg·min/mL, 600,000 pg·min/mL, 700,000 pg·min/mL, 800,000 pg·min/mL, 900,000 pg·min/mL, 1,000,000 pg·min/mL, 1,200,000 pg·min/mL, 1,400,000 pg·min/mL, 1,600,000 pg·min/mL, 1,800,000 pg·min/mL, or 2,000,000 pg·min/mL.

Pharmacokinetics of auto-injectors are discussed in Dreborg S, Kim H. The pharmacokinetics of epinephrine/adrenaline autoinjectors. Allergy Asthma Clin Immunol. 2021 Mar. 8; 17(1):25. doi: 10.1186/s13223-021-00511-y. PMID: 33685510; PMCID: PMC7938517, which is incorporated herein by reference in its entirety.

In certain embodiments, the dry powder formulations and/or unit doses provided herein is operable to raise the blood concentration of epinephrine in a subject to about 0.02 ng/mL within about less than 1 minute to about 60 minutes (e.g., about: 60, 50, 40, 30, 20, 15, 10, 5, 3, <1 minutes), or about 10 ng/mL within about less than 1 minute to 15 minutes (e.g., about: <1, 3, 5, 10, 11, 12, 13, 14, or 15 minutes) of intranasal administration. In one embodiment, the formulation provided herein increase the blood concentration of epinephrine by about 0.01 to 0.04 ng/mL, for example 0.02 or 0.03 ng/mL, in about less than 1 minute to about 15 minutes (e.g., about: <1, 10, 11, 12, 13, 14, or 15 minutes), or about 3 ng/mL within about less than 1 minute to about 60 minutes (e.g., about: 60, 50, 40, 30, 20, 15, 10, 5, 3, <1 minutes). In one embodiment, the formulation provided herein increases the blood concentration of epinephrine by about 0.2 to 2 ng/mL, for example 0.8 or 1.2 ng/mL, in about less than 1 minute to about 15 minutes (e.g., about: <1, 10, 11, 12, 13, 14, or 15 minutes), or about 5 ng/mL within about less than 1 minute to about 60 minutes (e.g., about: 60, 50, 40, 30, 20, 15, 10, 5, 3, <1 minutes).

In another embodiment, a single dose of epinephrine in the dry powder formulations and/or dosage units given intranasally is preferably bioequivalent (for example, in terms of peripheral blood levels, systemic exposure of epinephrine) to intravenously (IV), intramuscularly (IM), or subcutaneously (SQ) injected epinephrine (e.g., using EPIPEN® auto-injector of 0.3 mg for adult patients (e.g., anyone over 30 kg) or 1 mg IV epinephrine, using EPIPEN JR® auto-injector of 0.15 mg for pediatric patients or 0.01 mg/kg with a dilution of 0.1 mg/mL for IV epinephrine). In one example, bioequivalence includes a 90% confidence interval of a mean Tmax (e.g., the time to reach maximal blood concentration), a mean Cmax (e.g., maximal blood concentration), a mean AUC over a period of time (e.g., area under the plasma/serum/blood concentration-time curve from time zero to time t), and/or a mean AUC over a period of time from 0 to infinity (e.g., area under the plasma/serum/blood concentration-time curve from time zero to time infinity) are within 80.00% to 125.00% of a reference test. In one example, an 80% confidence interval of at least one of a mean Tmax (e.g., the time to reach maximal blood concentration), a mean Cmax (e.g., maximal blood concentration), a mean AUC over a period of time (e.g., area under the plasma/serum/blood concentration-time curve from time zero to time t), and a mean AUC over a period of time from 0 to infinity (e.g., area under the plasma/serum/blood concentration-time curve from time zero to time infinity) is within 80.00% to 125.00% of a reference test. In one embodiment, the reference test is an IV, IM, or SQ injected epinephrine composition. In one embodiment, bioequivalence is determined in a fasting state.

Vasodilators

In one embodiment, the dry powder formulation further includes a vasodilator; that is, a second vasodilator in addition to epinephrine. The vasodilator is preferably not an alpha-adrenergic blocker. The use of alpha-adrenergic antagonists is problematic because these agents act to widen blood vessels in smooth muscle and counteract the intended therapeutic action of epinephrine itself. Furthermore, unlike the currently available injectable epinephrine devices, this approach promotes the administration of two active adrenergic receptor agents (i.e., drugs) versus just one drug. In a preferred embodiment, the dry powder formulation does not include an additional vasodilator. Administering more than one drug at a time may pose additional risks.

In one embodiment, the vasodilator is caffeine or niacin. In some embodiments, a single dose of the formulation includes about 0.01 mg to about 10 mg of the vasodilator. In some embodiments, a vasodilator (e.g., niacin) herein is present in the formulation in an amount of about: 0.001 mg to 0.01 mg, 0.01 mg to 0.05 mg, 0.05 to 0.1 mg, 0.1 to 0.5 mg, 0.5 to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, or 9.0 to 10.0 mg. In some embodiments, a vasodilator (e.g., niacin) herein is operable to be at least about: 0.001 mg, 0.01 mg, 0.1 mg, 0.5 mg, 1.0 mg, 2.0 mg, 5.0 mg, or 10.0 mg in the formulation and/or unit doses. In some embodiments, a single dose of the formulation comprises about 0.5 mg or about 1.0 mg. In some embodiments, the formulation, in the form of a single dose, contains about 0.01 mg to about 10 mg of the vasodilator. In some embodiments, the formulation, in the form of a single dose, contains about 0.5 mg or about 1.0 mg of the vasodilator.

In some embodiments, the amount of the vasodilator is about 0.005% to about 50% w/w of the weight of the formulation, for example about: 0.005%, 0.01%, 0.05%, 0.1%, 0.5%, 1%, 2%, 2.5%, 3%, 4%, 5% 6%, 7%, 8%, 9%, 10%, 15%, 20%, 25%, 30%, 35%, 40%, 45% or 50% w/w of the weight of the formulation. In some embodiments, the amount of the vasodilator is about 2.5% w/w of the weight of the formulation.

Other vasodilators that are less preferred, but may be incorporated into the present invention, include ethanol. In one example, a powder form of ethanol is used as a vasodilator. However, some of the powder form of ethanol might be lost during the manufacturing process, so this embodiment is less preferred than other embodiments.

Enabling Agents

In one embodiment, the intranasal dry powder compositions and/or unit doses include at least one enabling agent. The at least one enabling agent includes, but is not limited to, at least one catechol-o-methyl transferase (COMT) inhibitor, at least one epinephrine potentiator, at least one atropine potentiator, at least one mucoadhesive, at least one absorption enhancer, at least one permeability enhancer, at least one surfactant, at least one surface modifier, at least one sustained release agent, at least one anticaking agent, at least one stabilizing agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, at least one pharmaceutically acceptable excipient, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

Additional details regarding nasal delivery of drugs, including information regarding enabling agents, are disclosed in (1) Bourganis V, Kammona O, Alexopoulos A, Kiparissides C. Recent advances in carrier mediated nose-to-brain delivery of pharmaceutics. Eur J Pharm Biopharm. 2018 July; 128:337-362. doi: 10.1016/j.ejpb.2018.05.009. Epub 2018 May 4. PMID: 29733950; (2) Davis S S, Illum L. Absorption enhancers for nasal drug delivery. Clin Pharmacokinet. 2003; 42(13):1107-28. doi: 10.2165/00003088-200342130-00003. PMID: 14531723; (3) Ganger S, Schindowski K. Tailoring Compositions for Intranasal Nose-to-Brain Delivery: A Review on Architecture, Physico-Chemical Characteristics and Mucociliary Clearance of the Nasal Olfactory Mucosa. Pharmaceutics. 2018 Aug. 3; 10(3):116. doi: 10.3390/pharmaceutics10030116. PMID: 30081536; PMCID: PMC6161189; and (4) Tiozzo Fasiolo L, Manniello M D, Tratta E, Buttini F, Rossi A, Sonvico F, Bortolotti F, Russo P, Colombo G. Opportunity and challenges of nasal powders: Drug composition and delivery. Eur J Pharm Sci. 2018 Feb. 15; 113:2-17. doi: 10.1016/j.ejps.2017.09.027. Epub 2017 Sep. 20. PMID: 28942007, each of which is incorporated herein by reference in its entirety.

In one embodiment, the intranasal dry powder compositions and/or unit doses include at least one COMT inhibitor. In some embodiments, the COMT inhibitor is a reversible COMT inhibitor. In one embodiment, the COMT inhibitor is entacapone or a pharmaceutically acceptable salt thereof. In some embodiments, a single dose of the COMT inhibitor is about 5 mg to about 800 mg. In one embodiment, a single dose of the COMT inhibitor is about 5 mg to about 200 mg. In some embodiments, the COMT inhibitor herein is present in the compositions in about: 0.05 mg to 0.1 mg, 0.1 mg to 0.5 mg, 0.5 mg to 0.75 mg, 0.75 mg to 1.5 mg, 1.5 mg to 3.0 mg, 3.0 mg to 4.5 mg, 4.5 mg to 6.0 mg, 6.0 mg to 7.5 mg, 7.5 mg to 9.0 mg, 9.0 mg to 10.0 mg, 10 mg to 25 mg, 25 mg to 50 mg, 50 mg to 100 mg, 100 mg to 150 mg, 150 mg to 200 mg, or 200 mg to 400 mg. In some embodiments, the COMT inhibitor herein is at least about: 0.001 mg, 0.01 mg, 0.1 mg, 0.5 mg, 1.0 mg, 2.0 mg, 5.0 mg, or 10.0 mg in the compositions and/or unit doses. In some embodiments, a single dose of the COMT inhibitor is about 0.5 mg, about 1.0 mg, about 5.0 mg, about 10.0 mg, about 25 mg, about 50 mg, about 75 mg, about 100 mg, about 150 mg, or about 200 mg. In some embodiments, the composition, in the form of a single dose, includes about 0.01 mg to about 25 mg of the COMT inhibitor. In some embodiments, the composition, in the form of a single dose, includes about 0.5 mg, about 1.0 mg, about 5.0 mg, about 10.0 mg, about 25 mg, about 50 mg, about 75 mg, about 100 mg, about 150 mg, or about 200 mg of the COMT inhibitor.

In one embodiment, the intranasal dry powder compositions and/or unit doses include at least one epinephrine potentiator. In one embodiment, the at least one epinephrine potentiator includes, but is not limited to, histidine, a flavonoid, a local anesthetic (e.g., benzocaine, lidocaine), a COMT inhibitor, levothyroxine sodium, at least one antihistamine, at least one tricyclic antidepressant, and/or a monoamine oxidase inhibitor (MAO) inhibitor. In one embodiment, the at least one tricyclic antidepressant includes amitriptyline, amoxapine, desipramine, doxepin, imipramine, nortriptyline, protriptyline, and/or trimipramine.

In one embodiment, the intranasal dry powder compositions and/or unit doses include at least one atropine potentiator. In one embodiment, the at least one atropine potentiator includes, but is not limited to, amantadine, at least one antihistamine, at least one tricyclic antidepressant, quinidine, and/or disopyramide. In one embodiment, the at least one tricyclic antidepressant includes amitriptyline, amoxapine, desipramine, doxepin, imipramine, nortriptyline, protriptyline, and/or trimipramine.

In one embodiment, the intranasal dry powder compositions and/or unit doses include at least one mucoadhesive. In one embodiment, the at least one mucoadhesive includes a starch, crystalline cellulose, a cellulose derivative, a polymer (e.g., chitosan, a carbopol (e.g., carbopol 943), carbophil, carbomer), a polyacrylic acid or polyacrylic acid derivative, a protein (e.g., mucin, lactoferrin, transferrin), and/or lecithin. See, e.g., (1) Takeuchi H, Thongborisute J, Matsui Y, Sugihara H, Yamamoto H, Kawashima Y. Novel mucoadhesion tests for polymers and polymer-coated particles to design optimal mucoadhesive drug delivery systems. Adv Drug Deliv Rev. 2005 Nov. 3; 57(11):1583-94. doi: 10.1016/j.addr.2005.07.008. Epub 2005 Sep. 16. PMID: 16169120; (2) D Tabor, Surface forces and surface interactions, J. Colloid Interface Sci., Volume 58, Issue 1, 1977, Pages 2-13, https://doi.org/10.1016/0021-9797(77)90366-6; and (3) Robert J Good, Surface free energy of solids and liquids: Thermodynamics, molecular forces, and structure, J. Colloid Interface Sci., Volume 59, Issue 3, 1977, Pages 398-419, https://doi.org/10.1016/0021-9797(77)90034-0.

In one embodiment, the intranasal dry powder compositions and/or unit doses include at least one absorption enhancer. In one embodiment, the at least one absorption enhancer includes a flavonoid (e.g., Vitamin P-like compound), vasopressin, methylphenidate, tropolone, desmethyl papaverine, pyrogallol, an amino acid (e.g., histidine), an antihistamine, an amphetamine, a local anesthetic, norepinephrine, isoproterenol, hydrocortisone, tripelennamine, bufotenine, harmine, methergine, a ganglionic blocker, guanethidine, mescaline, cocaine, lysergic acid diethylamide (LSD), or an enantiomer, diastereoisomer, racemate, prodrug, or salt of such compounds.

In one embodiment, the intranasal dry powder compositions and/or unit doses include at least one permeability enhancer and/or at least one mucosal permeation enhancer. In one embodiment, the at least one permeability enhancer and/or at least one mucosal permeation enhancer increases a fraction of the at least one active pharmaceutical ingredient that reaches circulation by at least about 10%, at least about 25%, preferably at least 50%, and most preferably at least 100%. In one embodiment, the at least one permeability enhancer includes a bile salt, an alkyl glycoside, a polymer, a tight junction modulation peptide, a lipid, a surfactant, a cyclodextrin, a chelator (e.g., EDTA), a Hsieh enhancer, a cyclic lactone, a cyclic diester, a cyclic ketone, a fatty acid, a salicylate, and/or an amphiphilic steroid (e.g., a fusidic acid derivative). In one embodiment, the alkyl glycoside includes an alkyl chain having between 8 and 20 carbons. In one embodiment, the alkyl glycoside is undecyl maltoside, dodecyl maltoside, tridecyl maltoside, tetradecyl maltoside, sucrose mono-dodecanoate, sucrose mono-tridecanoate, sucrose mono-tetradecanoate, and/or dodecyl-beta-D-maltoside. Tight junction modulating peptides are described in U.S. Patent Publication No. 20090220435, which is incorporated herein by reference in its entirety. In one embodiment, the cyclodextrin includes alpha-cyclodextrin, beta-cyclodextrin, gamma-cyclodextrin, hydroxypropyl-beta-cyclodextrin, and/or sulfobutylether beta-cyclodextrin. In one embodiment, the lipid includes 1,2-Dioleoyl-sn-Glycero-3 Ethylphosphocholine, 1,2-di-O-phytanyl-glycero-3-phosphocholine, 1-O-hexadecyl-2-acetoyl-sn-glycerol, 1-O-octadecyl-2-O-methyl-glycerol-3-phosphocholine, 16:0-09:0(ALDO)PC, 16:0-09:0(COOH)PC, 3-beta-hydroxy-5alpha-cholest-8(14)-en-15-one, C10 sucrose, C12 maltose, C12 sucrose, C14 maltose, C16-09:0, C6 glucose, C6 maltose, C7 glucose, C8 glucose, Cardiolipin (sodium salt), Ceramide (brain porcine), Ceramide C10:0, Ceramide C12:0, Ceramide C14:0, Ceramide C16:0, Ceramide C17:0, Ceramide C18:0, Ceramide C18:1, Ceramide C20:0, Ceramide C24:0, Ceramide C24:1, Ceramide C2:0, Ceramide C4:0, Ceramide C6:0, Ceramide C8:0, Cerebroside (brain porcine), Cerebroside Sulfatide (porcine), Dimethylsphingosine, Egg Ceramide, Galactosyl sphingosine, Glucosylsphingosine, Lactosyl(B) Sphingosine, Lyso-PAF, N-acetoyl ceramide-1-phosphate, N-octanoyl ceramide-1-phosphate, PGPC1, POVPC, Phosphatidylinositol (Soy), Phosphatidylinositol (bovine), Platelet-Activation Factor, Porcine brain ganglioside, Sphingomyelin (brain porcine), Sphingosine-1-phosphate, and trimethylsphingosine. The lipid is preferably a glycosylated sphingosine, an alkylglucoside, an oxidized lipid, and/or an ether lipid (PAF). In one embodiment, the fatty acid is sodium caprate, sodium laurate, sodium caprylate, capric acid, lauric acid, caprylic acid, and/or an acyl carnitine (e.g., palmitoyl carnitine, stearoyl carnitine, myristoyl carnitine, lauroyl carnitine). In one embodiment, the salicylate is sodium salicylate, 5-methoxy salicylate, and methyl salicylate. Hsieh enhancers are described in U.S. Pat. Nos. 5,023,252 and 5,731,303, each of which is incorporated herein by reference in its entirety. Cyclic lactones, cyclic diesters, and cyclic ketones are described in U.S. Pat. No. 8,481,043, which is incorporated herein by reference in its entirety. Amphiphilic steroids are discussed in U.S. Pat. Nos. 4,548,922 and 4,746,508, each of which is incorporated herein by reference in its entirety. In one preferred embodiment, the at least one permeability enhancer and/or the at least one mucosal permeation enhancer is a generally accepted as safe (GRAS) pharmaceutical excipient. Alternatively, the at least one permeability enhancer and/or the at least one mucosal permeation enhancer is a near-GRAS excipient and/or a non-GRAS excipient. In one embodiment, the at least one permeation enhancer and/or the at least one mucosal permeation enhancer is about 1% to about 30% w/w of the weight of the composition.

In one embodiment, the intranasal dry powder compositions and/or unit doses include at least one surfactant. The at least one surfactant is a non-ionic surfactant, an ionic surfactant, a cationic surfactant, an anionic surfactant, and/or a zwitterionic surfactant. Examples of the at least one surfactant compatible with the present invention include, but are not limited to, sodium glycocholate, sodium taurocholate, polyoxyethylene lauryl ether, polyacrylic acid gel, sodium lauryl sulfate, polysorbate, and/or sodium deoxycholate.

In one embodiment, the intranasal dry powder compositions and/or unit doses do not include a surfactant. Some liquid compositions of drugs require a surfactant to prevent aggregation of the active ingredient. Advantageously, dry powder compositions do not require a surfactant.

In one embodiment, the intranasal dry powder compositions and/or unit doses include at least one surface modifier. In one embodiment, the at least one surface modifier includes a lubricant (e.g., magnesium stearate), a fluidizing agent (e.g., talc, silicon dioxide), a nitric oxide (NO) stimulator, chitosan, and/or a chitosan derivative.

In one embodiment, the intranasal dry powder compositions and/or unit doses include at least one sustained release agent. In one embodiment, the at least one sustained release agent is achieved by manipulating one or more of the at least one active pharmaceutical ingredient to control its dissolution and/or the composition in which the at least one active pharmaceutical ingredient is suspended. In one embodiment, excipients with mucoadhesive and/or viscosity enhancing characteristics are incorporated. Additionally or alternatively, the composition is operable to reversibly diminish mucociliary clearance.

In one embodiment, the intranasal dry powder compositions and/or unit doses include at least one anticaking agent. The at least one anticaking agent includes, but is not limited to, tribasic calcium phosphate. In one embodiment, the at least one anticaking agent is about 0.5% to about 5% w/w of the weight of the composition. In some embodiments, the at least one anticaking agent has an average particle diameter of about 100 μm or less, for example about: 90 to 100 μm, 80 to 90 μm, 70 to 80 μm, 60 to 70 μm, 50 to 60 μm, 40 to 50 μm, 30 to 40 μm, 20 to 30 μm, or 10 to 20 μm. In some embodiments, the at least one anticaking agent has an average particle diameter of about 30 μm to 100 μm.

In one embodiment, the intranasal dry powder compositions and/or unit doses include at least one systemic vasodilator and/or at least one nasal mucosal vasodilator. In one embodiment, the at least one systemic vasodilator and/or the at least one nasal mucosal vasodilator includes an angiotensin-converting enzyme (ACE) inhibitor (e.g., Benazepril (Lotensin), Captopril (Capoten), Enalopril (Vasotec), Fosinopril (Monopril), Lisinopril (Prinivil, Zestril), Minoxidil (Loniten), Meoexipril (Univasc), Perindopril (Aceon), Quinapril (Accupril), Ramipril (Altace), Trandolaptril (Mavik)), an angiotensin II receptor antagonist (e.g., Losartan, Candesatran, Valsartan, Irbesartan, Telmisartan, Eprosartan, Olmesartan, Azilsartan), phentolamine, nitroglycerine, hydralazine, isosorbide mononitrate, isosorbide dinitrate, papaverine hydrochloride or mesylate, cocaine, ethyl nitrate, diltiazem, urapidil, nicorandil, sodium nitroprusside, glyceryl trinitrate-verapamil, phenoxybenzamine, dopexamine, chloropromazine, propiverine hydrochloride, or an enantiomer, diastereoisomer, racemate, prodrug, or salt of such compounds. In a preferred embodiment, the at least one systemic vasodilator and/or the at least one nasal mucosal vasodilator is phentolamine.

In one embodiment, the intranasal dry powder compositions and/or unit doses include at least one agent that reduces mucosal transit time. In one embodiment, the at least one agent that reduces mucosal transit time includes a polyacrylate mucoadhesive agent and/or a peptide. See, e.g., WIPO Publication No. WO2003037355, which is incorporated herein by reference in its entirety.

In one embodiment, the intranasal dry powder compositions and/or unit doses include at least one agent that increases mucosal absorption or adhesion or transport. In one embodiment, the at least one agent that increases mucosal absorption or adhesion or transport includes a surfactant, gelling microsphere, chitosan, sodium lauryl sulfate, sodium salicylate, oleic acid, lecithin, dehydrated alcohol, Tween, polyoxyl 40 stearate, polyoxyl ethylene 40 stearate, propylene glycol, hydroxyl fatty acid ester of polyethylene glycol, glycerol monooleate, fusieates, a bile salt, octoxynol, polysorbate 20, polysorbate 80, DDPC, DPPC, a chelator (e.g., EDTA, EGTA, citrate), and/or a surfactant. See, e.g., (1) Ilium L and Fisher A N (1997) Intranasal delivery of peptides and proteins, in Inhalation Delivery of Therapeutic Peptides and Proteins (Adjei A L and Gupta P K eds), Marcel Dekker, New York and (2) Costantino H R, Illum L, Brandt G, Johnson P H, Quay S C. Intranasal delivery: physicochemical and therapeutic aspects. Int J Pharm. 2007 Jun. 7; 337(1-2):1-24. doi: 10.1016/j.ijpharm.2007.03.025. Epub 2007 Mar. 25. PMID: 17475423, each of which is incorporated herein by reference in its entirety.

In one embodiment, the intranasal dry powder compositions and/or unit doses include at least one chelator. In one embodiment, the at least one chelator includes ethylenediaminetetraacetic acid (EDTA), ethylene glycol-bis(β-aminoethyl ether)-N,N,N',N'-tetraacetic acid (EGTA), and/or citrate.

In one embodiment, the intranasal dry powder compositions and/or unit doses include at least one steroid. In one embodiment, the at least one steroid includes at least one corticosteroid. In one embodiment, the at least one steroid is hydrocortisone, beclomethasone, fluticasone, triamcinolone, flunisolide, mometasone, ciclesonide, and/or budesonide.

In one embodiment, the intranasal dry powder compositions and/or unit doses include at least one stabilizing agent. One of ordinary skill in the art will appreciate that stabilizing agents (i.e., "stabilizers") are substances added to a product to maintain its physical and chemical properties over time. In the pharmaceutical industry, stabilizers are used to improve the stability and efficacy of drug compositions, protect against degradation, improve solubility and bioavailability, and control the release of pharmaceutical compositions over time. In one embodiment, the stabilizing agent of the present composition is an ingredient that includes both buffering (i.e., maintaining the pH of the composition) and antioxidizing (i.e., neutralizing the production of free radicals by inhibiting oxidation of the composition) characteristics. In one embodiment, the present invention utilizes trisodium citrate as stabilizing agent to raise the pH of the composition of the present invention, making it both more stable and more comfortable for patient use. The effect of trisodium citrate in buffering the pH of the present invention and thereby increasing the stability of the present composition was discovered after extensive experimentation as disclosed herein.

In one embodiment, the at least one stabilizing agent is a non-sulfite stabilizer (e.g., ascorbic acid, sodium citrate). In one embodiment, the at least one stabilizing agent is a buffering acid or a pharmaceutically acceptable salt derived therefrom. In one embodiment, the at least one stabilizing agent is ascorbic acid, sodium ascorbate, calcium ascorbate, potassium ascorbate, citric acid, sodium citrate (e.g., monosodium citrate, disodium citrate, trisodium citrate), potassium citrate (e.g., monopotassium citrate, tripotassium citrate), phosphoric acid, sodium phosphate (e.g., monosodium phosphate, disodium phosphate, trisodium phosphate), potassium phosphate (e.g., monopotassium phosphate, dipotassium phosphate, tripotassium phosphate), tartaric acid, sodium tartrate (e.g., monosodium tartrate, disodium tartrate), potassium tartrate (e.g., monopotassium tartrate, dipotassium tartrate), sodium potassium tartrate, acetic acid, sodium acetate, sodium diacetate, potassium acetate, potassium diacetate, alginic acid, sodium alginate, potassium alginate, succinic acid, sodium succinate, potassium succinate, malic acid, sodium malate (e.g., monosodium malate, disodium malate), benzoic acid, sodium benzoate, potassium benzoate, lactic acid, sodium lactate, potassium lactate, histidine, glycine, arginine, ammonium chloride, sodium chloride, potassium chloride, zinc chloride, calcium chloride, sodium acetate trihydrate, and/or triethanolamine. In one embodiment, the at least one stabilizing agent is about 1% to about 25% w/w of the weight of the composition, for example about: 1%, 5%, 7%, 8%, 9%, 10%, 11%, 12%, 13%, 14%, 15%, 16%, 17%, 18%, 19%, 20%, 21%, 22%, 23%, 24%, or 25% w/w based on the weight of the compositions and/or unit doses. In one embodiment, the at least one stabilizing agent is about 1% to 5%, 5% to 20%, 5% to 30%, 10% to 20%, or 10% to 30% w/w based on the weight of the compositions and/or unit doses.

In one embodiment, the intranasal dry powder compositions and/or unit doses include at least one preservative. The at least one preservative includes, but is not limited to a paraben, benzalkonium chloride, phenyl ethyl alcohol, ethylenediaminetetraacetic acid (EDTA), benzoyl alcohol, a thiol, glutathione, glutathione reductase, glutathione peroxidase, hydroquinone, amikasin sulfate, apomorphine hydrochloride, metaraminol, levobunonol, levobunonol hydrochloride, acamprosate calcium, fenoldopam, hydrocortisone/neomycin sulfate/polymyxin B, dexamethasone sodium phosphate, hydromorphone, dobutamine, epinephrine, etidicaine/epinephrine bitartrate, gentamycin, tinzaparin, isoproternerol, ketoconazole, sodium sulfacetamide, norepinephrine, bupivacaine/epinephrine bitartrate, morphine, tobramycin, rotigotine, orphenadrine, procaine, nalbuphine, oxytetracycline, nortriptyline, perphenazine, promethazine hydrochloride, prednisolone acetate, propofol, mesalamine, trimethoprim/sulfamethoxazole, carisoprodol/aspirin/codeine, streptomycin, mafenide acetate, tetracycline hydrochloride, pentazocine lactate, chlorpromazine, triethylperazine maleate, fluorinolone acetonide/hydroquinone/tretinoin, acetaminophen/codeine, doxycline calcium, and/or lidocaine/epinephrine. In one embodiment, the at least one preservative is about 0.01% to about 5% w/w of the weight of the composition, for example about: 0.01%, 0.05%, 0.1%, 0.2%, 0.5%, 1%, 2%, 3%, 4%, or 5% w/w based on the weight of the compositions and/or unit doses. In one embodiment, the at least one preservative is about 0.01% to 5%, 0.02% to 4%, or 0.05% to 2.5% w/w based on the weight of the compositions and/or unit doses. In a preferred embodiment, the at least one preservative is sulfite-free.

In a preferred embodiment, the intranasal dry powder compositions and/or unit doses do not include a preservative. Preservatives (e.g., sodium bisulfite, which is present in EpiPen® and other autoinjectors) can cause an allergic reaction in some individuals. Because aqueous compositions of drugs are often sensitive to light and heat, they generally include a preservative to improve stability. The intranasal dry powder compositions and/or unit doses of the present invention advantageously do not require a preservative. Additionally, not including a preservative in the intranasal dry powder compositions and/or unit doses reduces the risk of further allergic reaction(s) and/or sensitivities. "Despite documentation of sensitivity, sulfites should not be withheld from patients experiencing a life-threatening emergency. Non-sulfited alternatives are often available, and should be used preferentially." See, e.g., Roth J V, Shields A. A dilemma: How does one treat anaphylaxis in the sulfite allergic patient since epinephrine contains sodium metabisulfite? Anesth Analg. 2004 May; 98(5):1499; author reply 1500. doi: 10.1213/01.ane.0000120092.39021.f2. PMID: 15105239, which is incorporated herein by reference in its entirety. Also see, e.g., Susan C. Smolinske (1992) Review of Parenteral Sulfite Reactions, Journal of Toxicology: Clinical Toxicology, 30:4, 597-606, DOI: 10.3109/15563659209017945, which is incorporated herein by reference in its entirety. Drugs without sulfites are often available in a medical setting (e.g., hospital, clinic) because environmental conditions can be controlled. Aqueous preparations and auto-injectors generally contain preservatives because they are intended for ambient use. There is a long-standing, unmet need for epinephrine that does not contain a preservative.

In one embodiment, the intranasal dry powder compositions and/or unit doses include at least one thickening agent. In one embodiment, the at least one thickening agent includes microcrystalline cellulose and/or carboxymethylcellulose sodium.

In one embodiment, the intranasal dry powder compositions and/or unit doses include at least one humectant. The at least one humectant includes, but is not limited to, glycerine, glycerol, sorbitol, mannitol, and/or vegetable oil.

In one embodiment, the intranasal dry powder compositions and/or unit doses include at least one antihistamine. In one embodiment, the at least one antihistamine includes an $H_1$ receptor antagonist and/or an $H_2$ receptor antagonist. In one embodiment, the $H_1$ receptor antagonist includes an ethylenediamine, an ethanolamine, an alkylamine, a piperazine, a tricyclic, and/or a tetracyclic. In one embodiment, the at least one antihistamine includes loratadine, desloratadine, diphenhydramine, doxylamine, fexofenadine, chlorpheniramine, hydroxyzine, cetirizine, levocetrizine, brompheniramine, clemastine, carbinoxamine, azelastine, emadastine, mepyramine, promethazine, cyproheptadine, doxepin, mirtazapine, cimetidine, famotidine, nizatidine, roxatidine, lafutidine, and/or levocabastine. Additional information regarding antihistamines is disclosed in U.S. Patent Publication No. 20100055152 and U.S. Pat. No. 8,263,581, each of which is incorporated herein by reference in its entirety.

In one embodiment, the intranasal dry powder compositions and/or unit doses include at least one solubilizing agent. The at least one solubilizing agent includes, but is not limited to, a glycol, an alcohol, 2-(2-ethoxyethoxy)ethanol, a cyclodextrin, and/or a glyceride (e.g., a medium chain glyceride, LABRASOL®).

In one embodiment, the intranasal dry powder compositions and/or unit doses include at least one masking agent (e.g., taste, smell). In a preferred embodiment, the at least one masking agent includes, but is not limited to, at least one sweetener and/or at least one flavoring agent. The at least one sweetener includes, but is not limited to, saccharin (e.g., sodium salt, calcium salt), fructose, dextrose, aspartame, acesulfame potassium, glycerin, sucralose, maltodextrin, sucrose, glucose, maltose, xylitol, sorbitol, erythritol, and/or mannitol. In one embodiment, the at least one masking agent includes phenethyl alcohol, vanilla, cherry, cinnamon, lavender, lemon, menthol, orange, peppermint, spearmint, raspberry, strawberry, grape, ethyl vanillin, coriander, ginger, nutmeg, cardamom, butterscotch, cocoa, acacia syrup, anethole, anise oil, benzaldehyde, ethyl acetate, methyl salicylate, and/or tolu. In one embodiment, the at least one masking agent is about 0.001% to about 1% w/w of the weight of the composition, for example about: 0.001%, 0.005%, 0.01%, 0.02%, 0.05%, 0.1%, 0.2%, 0.3%, 0.4%, 0.5%, 0.6%, 0.7%, 0.8%, 0.9%, or 1% w/w based on the weight of the compositions and/or unit doses. In one embodiment, the at least one masking agent is about 0.01% to 0.5%, 0.02% to 0.2%, or 0.015% to 0.15% w/w based on the weight of the compositions and/or unit doses.

In one embodiment, the intranasal dry powder compositions and/or unit doses include at least one antioxidant. The at least one antioxidant includes, but is not limited to, sodium metabisulfite, sodium bisulfate, butylated hydroxytoluene, tocopherol, ascorbic acid (Vitamin C), glutathione, glutathione reductase, glutathione peroxidase, superoxide dismutase (CuZn-SOD), superoxide reductase, carnosine, ergothionene, ovothiol, lipoic acid, thioctic acid, thioredoxin peroxidase, monosodium citrate, disodium citrate, trisodium citrate and/or recombinant thermostable variants thereof. In one embodiment, the at least one antioxidant is about 0.0001% to about 10% w/w of the weight of the composition, for example about: 0.0001%, 0.0005%, 0.001%, 0.005%, 0.01%, 0.02%, 0.05%, 0.1%, 0.5%, 1%, 2%, 3%, 4%, 5%, 6%, 7% 8%, 9%, or 10% w/w based on the weight of the compositions and/or unit doses. In one embodiment, the at least one antioxidant is about 0.001% to 5%, 0.05% to 2%, or 0.1% to 1% w/w based on the weight of the compositions and/or unit doses. In one embodiment, the at least one antioxidant is about 10% to 20%, 12% to 18%, or 12% to 16% w/w based on the weight of the compositions and/or unit doses.

In one embodiment, the intranasal dry powder compositions and/or unit doses include at least one viscosity enhancing agent. The at least one viscosity enhancing agent includes, but is not limited to, a cellulose derivative (e.g., crystalline cellulose, amorphous cellulose, methylcellulose, carboxymethylcellulose, ethylcellulose, hypromellose, hydroxylpropyle cellulose, or a salt thereof), carrageenan, guar gum, an alginate, a carbomer, a polyethylene glycol, propylene glycol, a polyvinyl alcohol, xanthan gum, a polyvinylpyrrolidone (PVP), chitosan, a polysaccharide, a starch, and/or carbopol. In one embodiment, the at least one viscosity enhancing agent is about 0.1% to about 10% w/w of the weight of the composition, for example about: 0.1%, 0.5%, 1%, 2%, 3%, 4%, 5%, 6%, 7%, 7.5%, 8%, 9%, or 10% w/w based on the weight of the compositions and/or unit doses.

In one embodiment, the intranasal dry powder compositions and/or unit doses include at least one dispersing agent. In one embodiment, the at least one dispersing agent includes citric acid.

In one embodiment, the intranasal dry powder compositions and/or unit doses include at least one colorant. In a preferred embodiment, the at least one colorant is non-allergenic.

In one embodiment, the intranasal dry powder compositions and/or unit doses include at least one buffering agent. The at least one buffering agent includes, but is not limited to, a phosphate, a citrate (e.g., a sodium citrate), a succinate, histidine, glycine, arginine, malic acid, tartaric acid, acetic acid, benzoic acid, lactic acid, ascorbic acid, ammonium chloride, sodium chloride, potassium chloride, zinc chloride, calcium chloride, sodium acetate trihydrate, and/or triethanolamine. In one embodiment, the at least one buffering agent is about 0.10% to about 3% w/w of the weight of the composition, for example about: 0.01%, 0.05%, 0.1%, 0.2%, 0.3%, 0.4%, 0.5%, 0.6%, 0.7%, 0.8%, 0.9%, 1%, 1.5%, 2%, 2.5%, or 3% w/w based on the weight of the compositions and/or unit doses. In one embodiment, the at least one buffering agent is about 0.05% to 2.5% w/w based on the weight of the compositions and/or unit doses. In one embodiment, the at least one buffering agent is about 10% to 20%, 12% to 18%, or 12% to 16% w/w based on the weight of the compositions and/or unit doses.

In one embodiment, the compositions of the present invention do not include a pH buffer. For example, the most stable pH for liquid epinephrine is between 2.5 and 5. A pH buffer (e.g., hydrochloric acid) is often added to liquid formulations to reduce the pH. However, a low pH (e.g., between 2.5 and 5) may cause some discomfort for patients. Advantageously, in one embodiment, the compositions of the present invention do not require a pH buffer.

Carriers and Excipients

In some embodiments, the dry powder composition further includes at least one carrier and/or excipient (e.g., at least one pharmaceutically acceptable carrier and/or excipient). In one embodiment, the at least one carrier and/or excipient includes, but is not limited to, lactose (e.g., D-lactose, lactose monohydrate), sucrose, glucose, dextrose, trehalose, sodium carboxymethylcellulose (CMC), mannitol, sorbitol, malitol, xylitol, maltose, cellulose and derivatives, starch and derivatives, microcrystalline cellulose, hypromellose acetate succinate (HPMCAS), a cyclodextrin (e.g., dimethyl-beta-cyclodextrin), calcium carbonate, citric acid, tartaric acid, glycine, leucine, polyvinyl pyrrolidone (PVP), a polyethylene glycol, polysorbate (e.g., Polysorbate 80 (e.g., TWEEN® 80)), chitosan, hyaluronic acid (e.g., sodium hyaluronate), sodium carboxymethyl cellulose (NaCMC), magnesium stearate, calcium stearate, an alkyl saccharide (e.g., n-Dodecyl β-D-Maltoside (DDM)), niacin, ethanol (e.g., dried ethanol), caffeine, benzalkonium chloride, ubiquinone (i.e., coenzyme Q10), magnesium oxide, sodium chloride, dodecylphosphocholine (DPC), silicone, gelatin, a polyacrylic acid polymer (e.g., CARBOPOL® 934), sodium taurocholate, carnitine hydrochloride, Poloxamer 188, histidine, arginine, crospovidone, ethylenediaminetetraacetic acid (EDTA), sodium starch glycolate, and/or a mixture of mannitol and hydroxypropyl methylcellulose (HPMC). In one embodiment, the at least one carrier and/or excipient includes at least one carbohydrate. In one embodiment, the at least one carbohydrate includes at least one monosaccharide, at least one disaccharide, at least one cyclodextrin, at least one polysaccharide, at least one starch, and/or at least one cellulose. In one embodiment, the at least one carrier and/or excipient includes at least one alkyl saccharide. In one embodiment, the at least one alkyl saccharide includes a sucrose ester, a sugar ether, a lipid ester, and/or an alkyl glycoside. Alkyl saccharides, sucrose esters, sugar ethers, and/or alkyl glycosides are described in WIPO Publication Nos. WO2016016431, WO2015095389, and WO2018089709, U.S. Pat. Nos. 9,895,444 and 10,653,690, and U.S. Publication No. 20190269782, each of which is incorporated herein by reference in its entirety. In another embodiment, the at least one carrier and/or excipient does not include a sucrose ester, a sugar ether, and/or an alkyl glycoside. In one embodiment, the at least one carrier and/or excipient includes at least one salt. The at least one salt includes, but is not limited to, sodium chloride, potassium chloride, sodium phosphate, calcium phosphate, calcium sulfate, and/or magnesium sulfate.

In some embodiments, the at least one carrier and/or excipient includes a first cellulose and/or a second cellulose. In some embodiments, the first cellulose is a crystalline cellulose. In some embodiments, the first cellulose is a microcrystalline cellulose. In some embodiments, the first cellulose has an average particle diameter of about 100 μm or less, for example about: 90 to 100 μm, 80 to 90 μm, 70 to 80 μm, 60 to 70 μm, 50 to 60 μm, 40 to 50 μm, 30 to 40 μm, 20 to 30 μm, or 10 to 20 μm. In some embodiments, the first cellulose has an average particle diameter of less than about 100 μm, 90 μm, 80 μm, 70 μm, 60 μm, 50 μm, 40 μm, 30 μm, 20 μm, 10 μm, or 5 μm. In some embodiments, the first cellulose has an average particle diameter of about 30 μm or less. In some embodiments, the at least one carrier and/or excipient includes a second cellulose. In some embodiments, the second cellulose is a crystalline cellulose. In some embodiments, the second cellulose is a microcrystalline cellulose. In some embodiments, the at least one carrier and/or excipient further includes a starch. In some embodiments, the at least one carrier and/or excipient includes a second cellulose and starch. In some embodiments, the second cellulose and/or starch have an average particle diameter of about 30 to about 100 μm, for example about: 30-40 μm, 30-50 μm, 30-60 μm, 30-70 μm, 30-80 μm, or 30-90 μm. In some embodiments, the second cellulose and/or starch have an average particle diameter of less than about 100 μm, 90 μm, 80 μm, 70 μm, 60 μm, 50 μm, 40 μm, 30 μm, 20 μm, 10 μm, or 5 μm. In some embodiments, the second cellulose, the starch, or the second cellulose and starch each individually has an average particle diameter of about 30 to about 100 μm.

In one embodiment, the at least one carrier and/or excipient present in the intranasal dry powder compositions is a mixture of a first microcrystalline cellulose, a second microcrystalline cellulose, a starch, and/or tribasic calcium phosphate. In one embodiment, the at least one carrier and/or excipient includes: i) a first crystalline cellulose with an average particle diameter of about 30 μm or less, for example about: 30-10 μm, 30-15 μm, 30-20 μm, or 30-25 μm; ii) tribasic calcium phosphate; and iii) a second crystalline cellulose, or starch, with an average particle diameter of about 30 to about 100 μm, for example about: 30-40 μm, 30-50 μm, 30-60 μm, 30-70 μm, 30-80 μm, or 30-90 μm. See, e.g., U.S. Pat. No. 8,337,817, which is incorporated herein by reference in its entirety.

In one embodiment, the at least one carrier and/or excipient includes particles having an average diameter of 1 μm to 100 μm. This is applicable to unimodal or multimodal compositions. In a preferred embodiment, the at least one carrier and/or excipient includes particles having an average diameter of at least 15 μm. Advantageously, an average diameter greater than 15 μm prevents particles from entering the lungs. In a preferred embodiment, the at least one carrier and/or excipient includes particles having an average diameter of about 50 μm. In one embodiment, the at least one carrier and/or excipient includes particles having an average diameter of about 25 μm to about 75 μm.

In one embodiment, an average particle diameter of a dry powder composition is determined using a laser-diffraction particle size distribution analyzer. In some embodiments, an average particle diameter of a dry powder composition is determined using sieve sorting.

In one embodiment, the at least one carrier and/or excipient is about 40% to about 90% w/w of the weight of the composition, for example about: 40%, 43%, 45%, 48%, 51%, 53%, 55%, 57%, 60%, 63%, 66%, 69%, 75%, 80%, 85%, 88%, or 90% w/w based on the weight of the compositions and/or unit doses. In one embodiment, the carrier is about 20% to about 70% w/w of the weight of the composition, for example about: 20%, 25%, 30%, 35%, 40%, 45%, 48%, 49%, 50%, 51%, 52%, 55%, 60%, 65%, 70%, or % w/w based on the weight of the compositions and/or unit doses. In one embodiment, the at least one carrier and/or excipient is about 45% to 65% w/w based on the weight of the compositions and/or unit doses. In one embodiment, the at least one carrier and/or excipient is about 40% to 60%, 45% to 55%, or 48% to 53% w/w based on the weight of the compositions and/or unit doses.

The compositions of the present invention preferably do not include any liquid carriers (e.g., water, alcohol, and/or propylene glycol). Liquid carriers often require additional preservatives to improve stability. Advantageously, dry powder compositions do not require a preservative, which reduces the risk for allergic reactions.

Further, the formulations of the present invention preferably do not include a surfactant. Some liquid formulations of epinephrine require a surfactant to prevent aggregation of the active ingredient. Advantageously, dry powder formulations do not require a surfactant.

Active Ingredient Particle Characteristics

The epinephrine and other enabling agents are operable to be individually substantially amorphous or crystalline. In some embodiments, the formulations and/or unit doses provided herein are in the form of particles, and the shapes of the particles are operable to be individually, e.g., cylindrical, discoidal, spherical, tabular, ellipsoidal, angular, and/or irregular.

In some embodiments, the average particle diameter of the epinephrine, enabling agent, and/or carrier are, individually, up to 100 μm, up to 50 μm, or up to 30 μm. In a preferred embodiment, the average particle diameter of the epinephrine, enabling agent, and/or carrier are, individually, less than or equal to 50 μm. In one embodiment, the average particle diameter of the epinephrine, enabling agent, and/or carrier are, individually, about: 10-20, 20-30, 30-40, 40-50, 50-60, 60-70, 70-80, 80-90, or 90-100 μm. In another embodiment, the average particle diameter of the epinephrine, enabling agent, and/or carrier are, individually, about: 10, 15, 20, 25, 30, 35, 40, 45, 50, 55, 60, 65, 70, 75, 80, 85, 90, 95, or 100 μm.

In some embodiments, the median particle diameter of the epinephrine powder herein is about 30 μm (e.g., 28.7 μm). In some embodiments, the median particle diameter of the epinephrine powder herein is about: 10-50, 20-40, or 25-35 μm. In one embodiment, 90% of the epinephrine particles herein have a particle diameter under about 50 μm (e.g., about 45.5 μm). In another embodiment, 90% of the epinephrine particles herein have a particle diameter under about: 40, 45, 35, 30, 25, or 20 μm. In yet another embodiment, about 10% of the epinephrine particles herein have a particle diameter under about 20 μm (e.g., about 17.3 μm). In still another embodiment, about 10% of the epinephrine particles herein have a particle diameter under about: 19, 18, 17, 16, 15, 14, 13, 12, 11, or 10 μm.

In a preferred embodiment, the average particle size, and/or the mean particle size is greater than 15 μm. Advantageously, an average particle size and/or a mean particle size greater than 15 μm avoids any entry of the particles into the lungs. In a preferred embodiment, the average particle size and/or the mean particle size is about 50 μm. In one embodiment, the average particle size and/or the mean particle size is between about 25 μm and about 75 μm. In one embodiment, the composition undergoes an agglomeration step before being deposited into the reservoir of the device of the present invention. In one embodiment, the particle size of the epinephrine contained within the dispensing device is between about 100 m and about 1000 m. In one embodiment, the particle size of the epinephrine contained within a dispensing device is between about 100 m and about 500 m or between about 200 m and about 600 m. In one embodiment, the dispensation of the particles via the device mechanically breaks up the particles of the composition such that the particle delivered to the nasal passage has a median diameter (i.e., D50 for the particle) of about 25 m. In one embodiment, the dispensation of the particles via the device mechanically breaks up the particles of the composition such that the particle delivered to the nasal passage has a median diameter of at least 15 m. In one embodiment, the dispensation of the particles via the device mechanically breaks up the particles of the composition such that the particle delivered to the nasal passage has a median diameter of between about 15 m and about 75 m.

In one embodiment, the formulations or dosage units herein are not or do not include spray-dried particles. In some embodiments, the formulations herein do not possess a fine particle fraction of less than 5.6 microns of at least about 45 percent. In some embodiments, the formulations herein do not include particles including: (a) about 11 to about 21 weight percent epinephrine bitartrate; (b) about 62 to about 82 weight percent leucine; and/or (c) about 7 to about 17 weight percent sodium tartrate.

Spray Drying Formulation Preparation

Test formulations were prepared as stock solutions in a mixture of water and ethanol (EtOH). The ratio of water to ethanol for each test formulation is included in the figures. The spray-dried powder formulations were prepared using a Buchi B-290 Mini Spray Dryer. Each formulation was pumped into the heated inlet and then aspirated through a sonicated nozzle with compressed air into the heated spray cylinder where it dries, with the resultant powder collected through a cyclone and into a collection vessel. By controlling the concentration of the formulation within the feed solution, the spray dryer pump rate, inlet temperature, aspirator power and nozzle power, average particle size, and yield were manipulated. In one embodiment, the nozzle inlet temperature is between about 120° C. and about 140° C. In one embodiment, the nozzle inlet temperature is between about 115° C. and about 145° C. In one embodiment, the nozzle inlet temperature is between about 115° C. and about 185° C. In one embodiment, the nozzle inlet temperature is about 120° C. In one embodiment, the nozzle inlet temperature is about 125° C. In one embodiment, the nozzle inlet temperature does not exceed 155° C. in order to limit impurities which may be introduced at higher temperatures and in the presence of air. In one embodiment, the nozzle inlet temperature does not exceed 140° C.

Particle size distribution was determined for each formulation prepared with the following instrumentation and parameters to determine particle size. D-lactose (SIGMA-ALDRICH), sodium carboxymethylcellulose (Na-CMC) (SIGMA-ALDRICH), and trehalose (ACROS) were evaluated using a Malvern Mastersizer 2000 (MALVERN PANALYTICAL) with a propan-2-ol dispersant (refractive index 1.39) using a Mie scattering model. A measurement duration of 15 seconds and a measurement pause of 10 seconds was used. A total of six measurements were obtained. Three of the six measurements were performed with sonication and the other three were performed without sonication. Table 1 includes additional information for each additive.

TABLE 1

| | Lactose | Na-CMC | Trehalose |
|---|---|---|---|
| Particle refractive index | 1.347 (absorption 0.1) | 1.515 (absorption 0) | 1.652 (absorption 0) |
| Pump Speed (rpm) | 1800 | 1500 | 1800 (without sonication) 1500 (with sonication) |
| Sonication power (%) | 10 | 10 | 25 |

FIGS. 1-3 are summary tables for test formulations prepared, including composition, preparation parameters, and particle size distribution results. Batches of up to approximately 1 g of spray-dried product were made, with a yield of approximately 25%. The concentration of epinephrine was kept constant at 10% w/w throughout the formulation preparation process. No correction was made for salt to base for the drug substance. For the initial formulations, only active pharmaceutical ingredient (API) and backbone (or carrier) combinations were prepared. After instrument parameters were optimized, the other excipients under test were added into the formulation blends functioning as potential surface modifiers, vasodilators, surfactants, mucoadhesives, and/or controlled release modifiers. In a preferred embodiment, the formulation includes lactose and/or Na-CMC.

Leucine (added as a surface modifier) was added to the formulation at 10% w/w. In the lactose formulations, the introduction of leucine had a significant impact on particle size, which remained consistently and constantly below target despite changes made in nozzle power. Changes in nozzle power typically lead to corresponding changes in particle size. Acceptable particle size was achieved in a formulation including epinephrine, Na-CMC, and leucine.

Additional additives examined include sodium chloride (NaCl), niacin, polysorbate, caffeine, hyaluronate, chitosan, and Carbomer 934. Sodium chloride was introduced at a concentration of 2% w/w as another surface modifier. Formulations in both lactose and Na-CMC were successfully prepared with acceptable particle size distribution. Niacin (nicotinic acid) was successfully introduced into the formulation at a concentration of 2% w/w to function as a vasodilator. Polysorbate (TWEEN 80) was successfully introduced into the formulation at a concentration of 0.5% w/w to function as a surfactant. Caffeine was successfully introduced into the formulation at a concentration of 2% w/w to function as a controlled release additive. Hyaluronate was successfully introduced into the formulation at a concentration of 0.5% w/w to function as a mucoadhesive.

Chitosan, introduced into the formulation as a potential permeation enhancer at a concentration of 10%, was found only to be soluble at a low pH and also was too viscous to nebulize in the spray drier nozzle. Carbomer 934, introduced as another potential mucoadhesive, was assessed in the lactose carrier only.

The lactose-based feed solutions were clear and colorless in appearance and the spray-dried formulations are white powders. In contrast, the Na-CMC feed solutions had some color ranging from a clear pale straw color to a clear deep red solution. The Na-CMC spray-dried powders ranged in color from off-white to yellow powders.

Delivery Devices and Packaging

In one embodiment, provided herein is therapeutic product including: (a) a dose of an intranasal dry powder formulations disclosed herein; (b) a dry powder nasal delivery device; and/or (c) a secondary packaging for the device that provides protection against humidity, light, or oxygen or other gases that may reduce the stability or physical characteristics of the dry powder formulations disclosed herein. An example of such a delivery device is the UDS-P nasal delivery device manufactured by Aptar Pharma.

Nasal devices are disclosed in U.S. Pat. Nos. 10,814,079; 10,806,870; 10,668,228; 9,808,818; 9,156,048; 8,734,392; 8,016,209; 7,950,391; 7,946,455; 7,878,352; 7,389,946; 7,387,265; 7,353,971; 7,216,781; 7,011,234; 6,877,672; 6,725,857; 6,708,846; 6,679,248; 6,626,379; 6,484,715; 6,461,322; 6,450,216; 6,427,680; 6,425,499; 6,398,074; 6,367,473; 6,264,065; 6,234,366; 6,209,760; 6,179,164; 6,029,663; 5,901,883; 5,568,884; 5,328,099; and 5,240,149, U.S. Publication Nos. 20190358417, 20160318051, 20150299846, 20140103064, 20140034663, 20140000588, 20130312740, 20130171334, 20130171330, 20130149459, 20130081953, 20130022750, 20120318677, 20110233232, 20110194110, 20100078447, 20070272764, and 20040084554, and U.S. application Ser. Nos. 16/814,997 and 17/687,167, each of which is incorporated herein by reference in its entirety.

In one embodiment, the delivery device includes at least one nasal probe that is operable to be replaced between discharges, so that the device is operable to be used to treat two or more individuals. The packaging of the delivery device includes a plurality of replaceable nasal probes (e.g., corresponding to a number of doses in the device). In contrast to the existing injectors, wherein the needle comes in contact with tissue and blood of each individual, this embodiment of the delivery device advantageously enables the more rapid treatment of a plurality of patients. Additionally, this embodiment of the delivery device and the set of replaceable nasal probes reduces the physical space required for carriage or storage of the quantity of pharmaceutical agent needed to respond to a plurality of patients (e.g., on a battlefield, in an ambulance, etc.).

In one embodiment, the delivery device includes a reservoir that holds the dry powder composition. The delivery device preferably includes a reservoir and means for expelling a pharmaceutical dose in the form of a spray. The reservoir is operable to contain a plurality of pharmaceutical doses (e.g., at least 4 doses, at least 8 doses, at least 20 doses, at least 50 doses, etc.). In one embodiment, the reservoir has a fill weight of at least 10 mg. In another embodiment, the reservoir has a fill weight of between about 10 mg and about 80 mg (e.g., about 10 mg, 20 mg, 30 mg, 40 mg, 50 mg, 60 mg, 70 mg, or 80 mg). In yet another embodiment, the reservoir has a fill weight of between about 20 mg and about 60 mg. In one embodiment, the reservoir has a fill volume of at least 50 $mm^3$. In another embodiment, the reservoir has a fill volume of between about 50 $mm^3$ and about 300 $mm^3$ (e.g., about 50 $mm^3$, 80 $mm^3$, 100 $mm^3$, 130 $mm^3$, 150 $mm^3$, 175 $mm^3$, 200 $mm^3$, 225 $mm^3$, 250 $mm^3$, 275 $mm^3$, or 300 $mm^3$). In one embodiment, the delivery device includes a plurality of individual reservoirs, each containing a pharmaceutical dose (e.g., blisters). In some embodiments, the delivery device is disposable. In some embodiments, the delivery device is reusable. In some embodiments, the delivery device is recyclable. In some embodiments, the package further includes one intranasal delivery device.

In a preferred embodiment, the delivery device does not require priming or shaking. The delivery device is preferably operable to dispense a dose from any position (i.e., 360° functionality).

Figure 4:
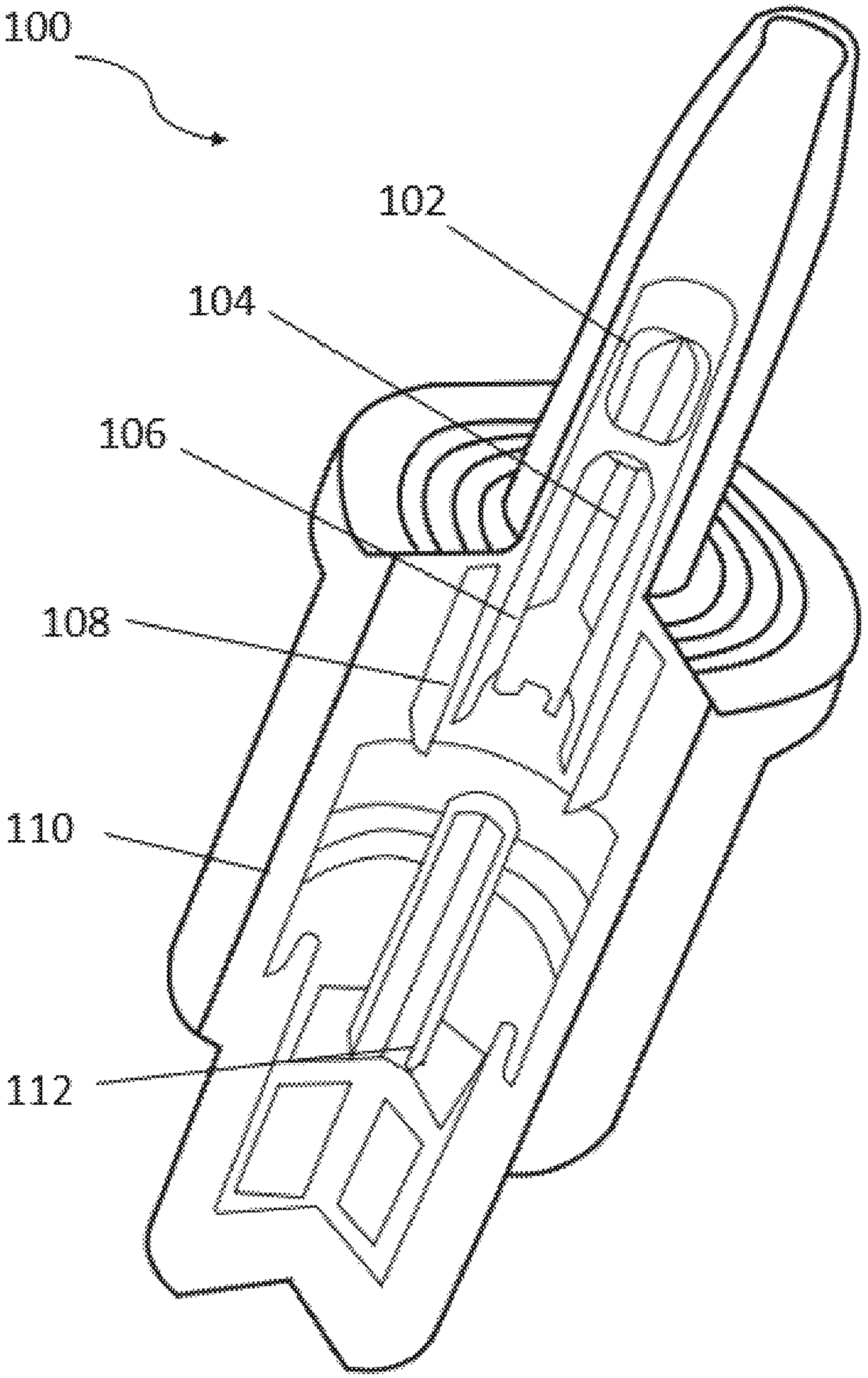
FIG. 4 illustrates one embodiment of a nasal delivery device according to the present invention.

FIG. 4 illustrates one embodiment of a nasal delivery device according to the present invention. The nasal delivery device 100 includes a plurality of components. In a preferred embodiment, the plurality of components includes a ball 102, a center piece 104, a container or reservoir 106, an actuator 108, a bottom 110, and a piston 112. In one embodiment, the plurality of components is formed of at least one plastic. The at least one plastic includes, but is not limited to, polypropylene (e.g., high density polypropylene (HDPE), linear low-density polyethylene (LLDPE)) and/or polyethylene. In one embodiment, one or more of the plurality of components further includes a dye or a colorant.

Figure 5D:
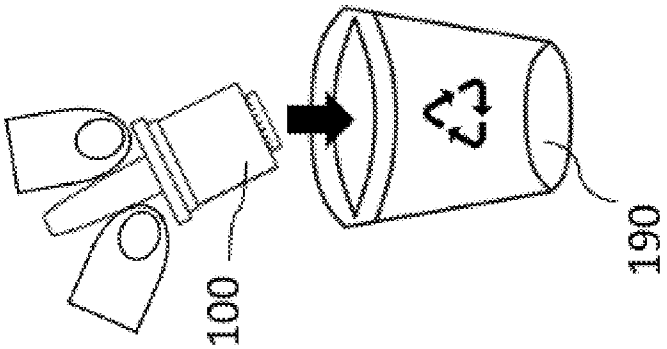
FIG. 5D illustrates disposal of the nasal delivery device following use according to one embodiment of the present invention.
Figure 5C:
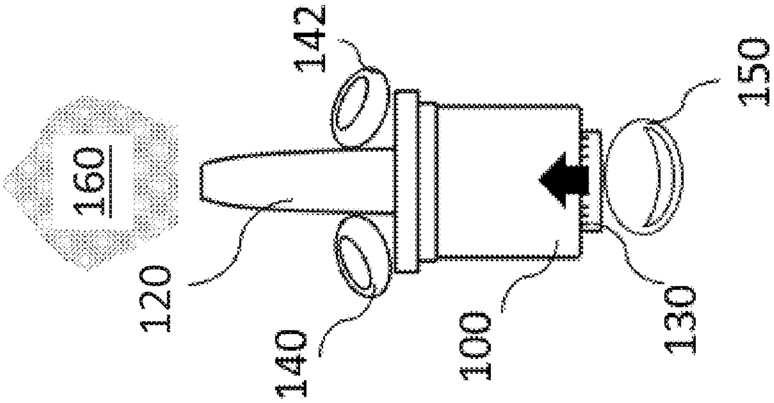
FIG. 5C illustrates discharge of the nasal delivery device according to one embodiment of the present invention.
Figure 5B:
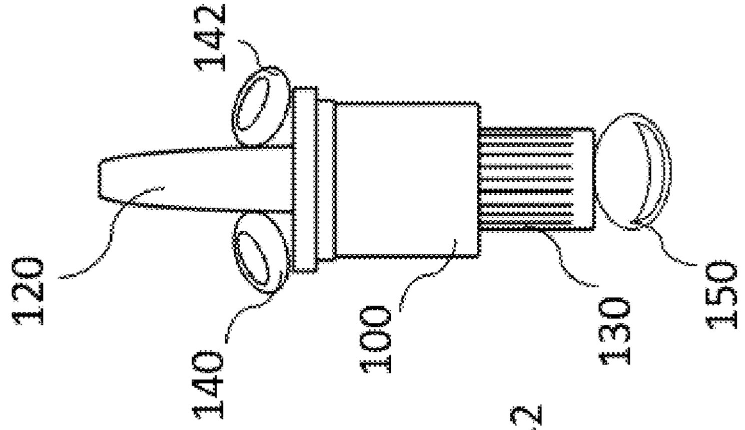
FIG. 5B illustrates positioning of fingers and a thumb on the nasal delivery device according to one embodiment of the present invention.
Figure 5A:
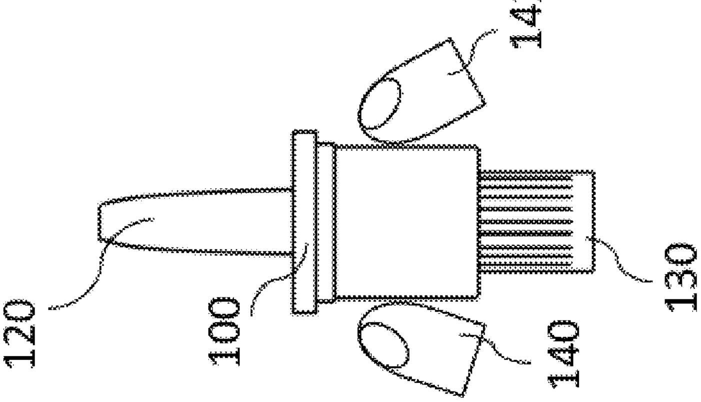
FIG. 5A illustrates a nasal delivery device at rest according to one embodiment of the present invention.

FIGS. 5A-5D illustrate one embodiment of a method of using a nasal delivery device according to the present invention. FIG. 5A illustrates one embodiment of the nasal delivery device 100 at rest. The nasal delivery device 100 includes a nasal probe 120 and a push button 130. FIG. 5B illustrates positioning of a first finger 140 and a second finger 142 on the nasal delivery device 130 according to one embodiment of the present invention. A thumb 150 is positioned on the push button 130 of the nasal delivery device 100. To discharge the nasal delivery device 100, the thumb 150 presses up on the push button 130 of the nasal delivery device 100 as shown in FIG. 5C. Discharge causes particles 160 to be expelled from the nasal delivery device 100 (e.g., into a nasal passage). The nasal delivery device 100 is preferably operable to be disposed of (e.g., in a recycling can 190) following use as shown in FIG. 5D.

Figure 6:
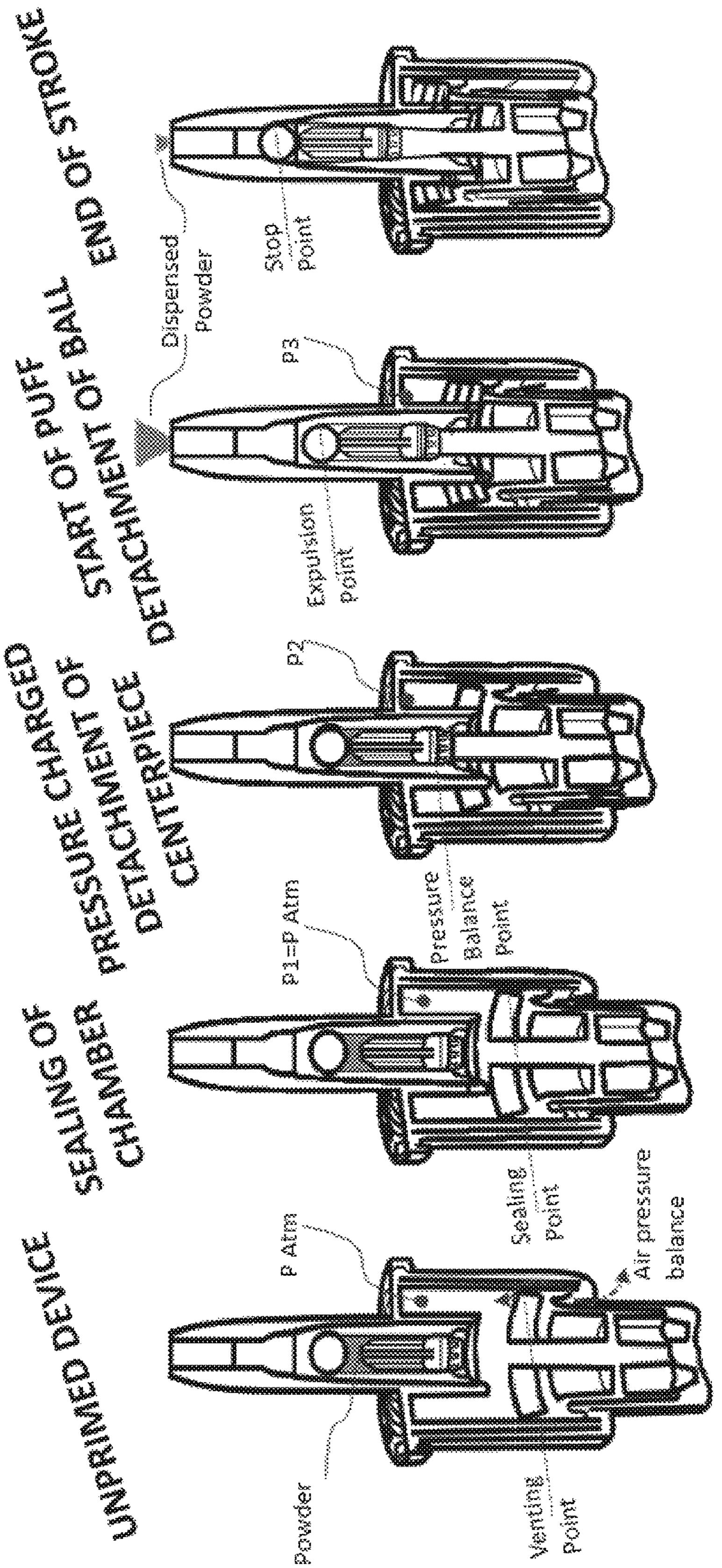
FIG. 6 illustrates the nasal delivery device in an unprimed state, with a sealed chamber, pressure charged detachment of a centerpiece, a start of a discharge, and an end of a stroke according to one embodiment of the present invention.

FIG. 6 illustrates the nasal delivery device in an unprimed state, with a sealed chamber, pressure charged detachment of a centerpiece, a start of a discharge, and an end of a stroke according to one embodiment of the present invention.

In one embodiment, the delivery device includes a counter or indicator. In one embodiment, the counter or the indicator is mechanical. Alternatively, the counter or indicator is electronic. In one embodiment, the electronic counter or indicator includes a sensor that is adapted to detect a displacement or a deformation of a portion of the delivery device (e.g., when the dry powder formulation is dispensed). In one embodiment, the electronic counter or indicator includes a display (e.g., LCD screen), a power supply (e.g., battery, rechargeable battery), a timer, a clock, at least one processor, at least one memory, a communication interface, and/or a printed circuit board (PCB). The sensor preferably transmits a signal to the PCB that causes the display to change when the delivery device is actuated. The at least one memory is operable to store information generated by the delivery device and/or the sensor. In one embodiment, the communications interface is operable to transmit data wirelessly (e.g., via BLUETOOTH®). In one embodiment, the data is transmitted wirelessly to at least one remote device (e.g., smartphone, tablet, etc.). The at least one remote device preferably includes a mobile application with a graphical user interface (GUI). In one embodiment, the mobile application tracks an expiration date of a delivery device, tracks use of the delivery device (e.g., remaining doses), and/or prompts ordering of another delivery device after use of the delivery device. In one embodiment, the at least one remote device is operable to provide messaging and/or notifications between a user and a third party (e.g., healthcare provider, parent, caregiver, emergency services, pharmacy). For example, the at least one remote device provides a notification to the third party when the delivery device dispenses a dose and/or provides a notification on a screen of the at least one remote device. In one embodiment, the delivery device displays a time of dose dispensation on the display (e.g., from the timer or the clock). Advantageously, this alerts the third party to the emergency situation (e.g., allergic reaction, anaphylaxis, cardiac arrest) and/or use of the device (e.g., to order a new delivery device). In the case of an anaphylactic reaction, conveying to the third party the time of dose dispensation is significant, as in many anaphylactic events a second dose is required. Thus, the knowledge of how much time has passed since the initial dosing is operable to guide the decision of whether to administer subsequent doses. In one embodiment, the at least one remote device is operable to transmit the data to at least one remote server. In another embodiment, the delivery device further includes an accelerometer and/or a gyroscope to detect movement of the delivery device. In one embodiment, the remote device is operable to transmit location data (e.g., to the third party) after the delivery device is discharged. In one embodiment, the location data is obtained from the remote device. Additionally, or alternatively, the device further includes a global positioning system (GPS) device or is coupled to a GPS device operable to provide location data. Advantageously, this alerts the third party to the emergency situation (e.g., allergic reaction, anaphylaxis, cardiac arrest). In one example, a third party (e.g., emergency services, a parent, and/or a healthcare provider) is alerted when the delivery device is discharged. In a preferred embodiment, the location of the delivery device is provided to the third party. Wireless communication in delivery devices is disclosed in U.S. Pat. Nos. 10,967,140; 7,861,943; and 6,886,556 and U.S. Patent Publication Nos. 20200164164, 20200246562, 20200155775, and 20190134322, each of which is incorporated herein by reference in its entirety.

The delivery device is preferably packaged in at least one secondary packaging. The at least one secondary packaging is operable to protect the delivery device from external elements (e.g., light, humidity, oxygen or other gases). The at least one secondary package includes, but is not limited to, a vial, a tube, a container, a bottle, a box, and/or a carton. In one embodiment, the at least one secondary package includes a desiccant or other agents that assist with stability of the epinephrine formulation (e.g., by preventing effects of temperature, light, humidity, oxygen or other gases). In one embodiment, the desiccant is included as a liner (e.g., a tube liner). In one embodiment, the at least one secondary package is formed of a plastic. In one embodiment, the plastic is a desiccant plastic. In one embodiment, the desiccant plastic includes a base polymer, a channeling agent, and a desiccant. Such materials are described in, for example U.S. Pat. Nos. 5,911,937; 6,080,350; 6,124,006; 6,130,263; 6,174,952; 6,194,079; 6,214,255; 6,221,446; 6,486,231; 7,005,459; and 9,902,788, each of which is incorporated herein by reference in its entirety. Advantageously, the desiccant removes moisture within the packaging and improves the stability of the API in the delivery device.

In one embodiment, the delivery device and/or one or more of the at least one secondary packaging includes a tamper resistant seal. In one embodiment, the one or more of the at least one secondary packaging and/or the delivery device includes a sensor to detect if the tamper resistant seal is removed. In one embodiment, a notification that the sensor detected the removal of the tamper resistant seal is transmitted to the mobile application and/or a third party. Advantageously, this provides notification that the delivery device is exposed to external elements (e.g., humidity). Additionally or alternatively, one or more of the at least one secondary packaging is child resistant.

In one embodiment, one or more of the at least one secondary packaging includes an authentication method to ensure that the delivery device enclosed in the at least one secondary packaging is from the manufacturer (e.g., and not counterfeit). In one embodiment, the authentication method includes, but is not limited to, at least one code (e.g., serial number, bar code), at least one image, at least one text, and/or at least one tracker (e.g., RFID chip). In one embodiment, the at least one authentication method is verifiable via the mobile application.

Figure 7:
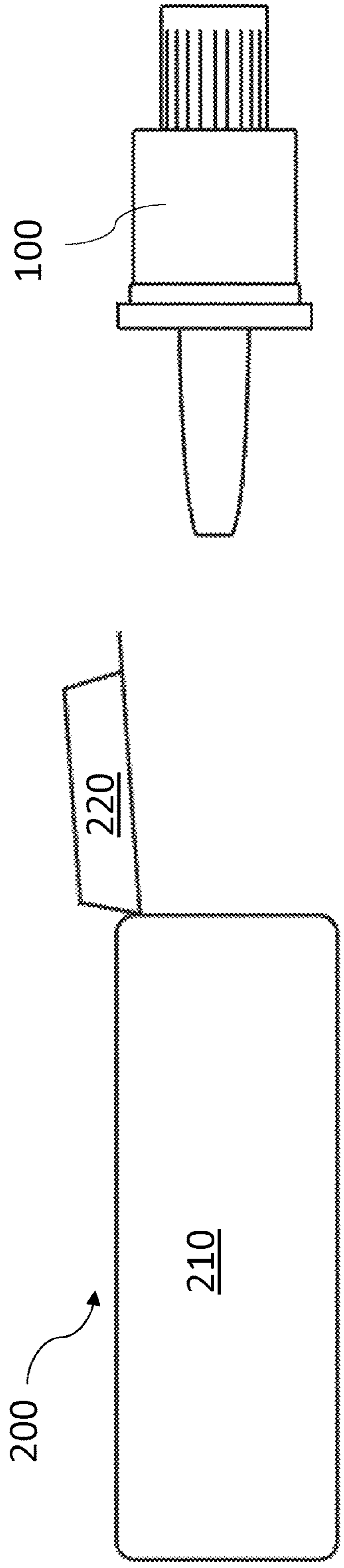
FIG. 7 illustrates a delivery device and a secondary packaging in the form of a container according to one embodiment of the present invention.

FIG. 7 illustrates one embodiment of a delivery device 100 and a secondary packaging in the form of a container 200. The delivery device 100 is operable to be stored in the container 200. The container 200 includes a base 210 and a lid 220. In one embodiment, the lid 220 is connected and/or attached to the base 210. Alternatively, the lid 220 is not connected and/or attached to the base 210 (e.g., screw on lid). Examples of a container compatible with the present invention include, but are not limited to, those disclosed in U.S. Pat. Nos. 9,834,341; 10,472,136; and 10,974,887, each of which is incorporated herein by reference in its entirety.

Figure 8:
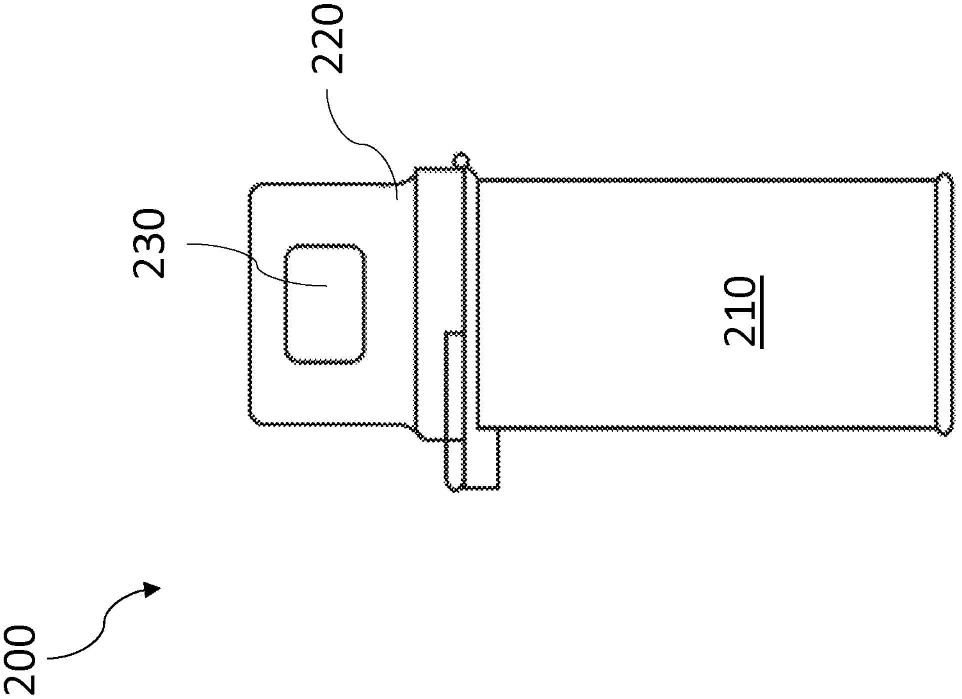
FIG. 8 illustrates a secondary packaging in the form of a container according to one embodiment of the present invention.

FIG. 8 illustrates one embodiment of a secondary packaging in the form of a container 200. The container 200 includes a base 210 and a lid 220. The container 200 is operable to store the delivery device (not shown). The lid 220 further includes a hole 230. The hole 230 is operable to attach the container 200 to a ring. The ring is further operable to attach the container 200 to a keychain or a set of keys, a backpack, a purse, or other personal item. Advantageously, this helps to ensure that the delivery device is conveniently located at all times.

In one embodiment, the at least one secondary package (e.g., carton) includes a first delivery device and a second delivery device. When providing epinephrine, the lowest effective dose is desired. If a patient does not adequately respond to delivery of a first dose from the first delivery device, the second delivery device is operable to provide a second dose. Advantageously, this also ensures that a second dose is available if the first delivery device is not used properly. However, unlike auto-injectors, the nasal delivery device is not subject to a syringe misfiring.

In one embodiment, the formulation of the present invention has a minimum shelf life of 24 months when stored within the nasal delivery device of the present invention. The shelf life of the dry powder formulation of the present invention is operable to be at least 24 months, 26 months 28 months, 32 months, 34 months, 36 months, 40 months, 42 months, 48 months, 54 months, or 60 months. The nasal delivery device in combination with the physiochemical properties of the composition as disclosed herein significantly reduce the degradation of an epinephrine composition in comparison to the prior art.

Training Device

In one embodiment, the present invention includes a training device. Advantageously, the training device educates a patient on proper use of the nasal delivery device, providing the patient with a greater level of confidence in the event of an emergency situation when the delivery device must be used. Patients with auto-injectors routinely receive training with a training device. Such as in a prescribing physician office or at a dispensing pharmacy. This creates familiarity with the device operation and is intended to reduce errors in usage and hesitancy to use the device in an emergency. Delay in administering epinephrine is associated with increased morbidity. However, many patients fear needles despite the training for auto-injectors. There is a long-standing, unmet need for a training device for epinephrine delivery that provides confidence in device operation while not invoking a fear of needles.

Methods of Treatment

Provided herein are methods of treating a patient by intranasally administrating the dry powder formulation provided herein. In some embodiments, the patient being treated is experiencing the symptoms of at least one of an anaphylactic reaction, an anaphylactoid reaction, cardiac arrest, exposure to a toxic synthetic organophosphorus compound, or exposure to cyanide or hydrogen sulfide. In some embodiments, the patient is experiencing one or more of bronchoconstriction (bronchospasm), hypotension (low blood pressure), hypotensive shock, and/or cardiac arrest (e.g., including minimal or no cardiac activity). In some instances, the patient in need of treatment is experiencing cardiac arrest and/or bronchospasm. In some embodiments, the patient is experiencing bronchoconstriction. In some embodiments, the patient is experiencing hemodynamic collapse. In some embodiments, the patient has hypotension. In some embodiments, the patient is experiencing hypotensive shock. In some embodiments, the patient is experiencing cardiac arrest. In some embodiments, the dry powder formulation is administered to a patient in a unit dose form as disclosed herein. In some embodiments, the dry powder formulation is administered to a patient by using a delivery device or product as disclosed herein. In some embodiments, as discussed above, the dry powder formulation provided herein provides a fast onset time.

In some embodiments, the patient is experiencing symptoms of an anaphylactic reaction. Anaphylaxis is a severe allergic reaction to venom, food, or medication. Most cases are caused by a bee sting or eating foods that are known to cause allergies (e.g., peanuts, tree nuts, shellfish). Anaphylaxis causes a series of symptoms known as anaphylactic shock, which include at least one of a skin reaction (e.g., hives, itching, flushed or pale skin), low blood pressure (hypotension), constriction of the airways, a swollen tongue or throat, a weak and rapid pulse, nausea, vomiting, diarrhea, dizziness, and/or fainting. In some embodiments, the patient is experiencing symptoms of an anaphylactoid reaction. Anaphylactoid reactions are defined as those reactions that produce the same clinical picture with anaphylaxis but are not IgE mediated, occur through a direct nonimmune-mediated release of mediators from mast cells and/or basophils, or result from direct complement activation. In some instances, the patient may be experiencing at least one of bronchoconstriction (bronchospasm), hypotension (low blood pressure), or hypotensive shock. In some instances, the patient may experience cardiac arrest if the patient's peripheral blood pressure drops sufficiently. The patient is provided with an effective dose of the intranasal epinephrine of the present invention. Emergency services often take up to 15 minutes (or longer) to arrive after a patient has an anaphylactic reaction. Advantageously, providing intranasal epinephrine before emergency services arrives reduces mortality.

In some embodiments, the patient is experiencing symptoms of cardiac arrest, including minimal or no cardiac activity. Such patients may also be experiencing hypotension and/or hypotensive shock. In some instances, the patient is in need of cardiopulmonary resuscitation (CPR) and/or basic or advanced cardiac life support (ACLS). The patient is provided with an effective dose of the intranasal epinephrine of the present invention. Emergency services often take up to 15 minutes (or longer) to arrive after a patient goes into cardiac arrest. Advantageously, providing intranasal epinephrine before emergency services arrives reduces mortality. See, e.g., Okubo M, Komukai S, Callaway C W, Izawa J. Association of Timing of Epinephrine Administration With Outcomes in Adults With Out-of-Hospital Cardiac Arrest. JAMA Netw Open. 2021 Aug. 2; 4(8):e2120176. Doi: 10.1001/jamanetworkopen.2021.20176. PMID: 34374770; PMCID: PMC8356068, which is incorporated herein by reference in its entirety. Further, it may be difficult to place an IV in a patient experiencing symptoms of cardiac arrest. The present invention advantageously is operable to be used without needing to place an IV. In one embodiment, at least one nasal delivery device of the present invention is included in a kit with a defibrillator (e.g., automated external defibrillator (AED)). Details regarding a formulation and delivery method directed to cardiac embodiments are included in U.S. patent application Ser. No. 18/514,634, which is incorporated herein by reference in its entirety.

In some embodiments, the patient is experiencing symptoms of exposure to a toxic synthetic organophosphorus compound. In one embodiment, the toxic synthetic organophosphorus compound includes, but is not limited to, nerve agents (e.g., sarin, soman, venomous agent X (VX)), a pesticide, and/or an insecticide. The patient is provided with an effective dose of the intranasal epinephrine of the present invention. Emergency services often take up to 15 minutes (or longer) to arrive after a patient is exposed to the toxic synthetic organophosphorus compound. Advantageously, providing intranasal epinephrine before emergency services arrives reduces mortality.

In some embodiments, the patient is experiencing symptoms of exposure to cyanide or hydrogen sulfide. The patient is provided with an effective dose of the intranasal epinephrine of the present invention. See, e.g., Judenherc-HaouzI A, Sonobe T, Bebarta V S, Haouzi P. On the Efficacy of Cardio-Pulmonary Resuscitation and Epinephrine Following Cyanide- and H2S Intoxication-Induced Cardiac Asystole. Cardiovasc Toxicol. 2018 October; 18(5):436-449. Doi: 10.1007/s12012-018-9454-2. PMID: 29644580; PMCID: PMC6126935, which is incorporated herein by reference in its entirety. See also, e.g., Bebarta V S, Pitotti R L, Dixon P S, Valtier S, Esquivel L, Bush A, Little C M. Hydroxocobalamin and epinephrine both improve survival in a swine model of cyanide-induced cardiac arrest. Ann Emerg Med. 2012 October; 60(4):415-22. Doi: 10.1016/j.annemergmed.2012.02.002. Epub 2012 Mar. 15. PMID: 22424656, which is incorporated herein by reference in its entirety.

In some embodiments, a single dose of the dry powder epinephrine formulation provided herein is administered to the patient. In some embodiments, more than one dose of the dry powder epinephrine formulation provided herein is administered to the patient. In some embodiments, the dry powder epinephrine formulation is administered more than once to the patient if a first administered dose of epinephrine does not increase the patient's arterial pressure to a normal range. In some instances, administration of the formulation is repeated (e.g., every 5-20 minutes) as necessary.

In some embodiments, intranasally administering the dry powder formulations provided herein results in application of the dry powder formulations to at least one mucosal surface of a nasal cavity or cavities of the patient (e.g., the mucosal surfaces of the anterior regions of the nose, the frontal sinus, the maxillary sinuses, and/or on each of the mucosal surfaces that overlie the turbinates covering the conchas).

In some embodiments, administration of the dry powder formulation intranasally to the patient is sufficient to increase an arterial pressure in the patient within 60 minutes, 50 minutes, 40 minutes, 30 minutes, 20 minutes, 10 minutes, 5 minutes, 3 minutes, 2 minutes, or less than 1 minute after administration. In some embodiments, the intranasal dry powder formulation is sufficient to increase a mean arterial pressure in the patient within 60 minutes, 50 minutes, 40 minutes, 30 minutes, 20 minutes, 10 minutes, 5 minutes, 3 minutes, 2 minutes, or less than 1 minute after administration. In some embodiments, the intranasal dry powder formulation is sufficient to increase a coronary perfusion pressure in the patient within 60 minutes, 50 minutes, 40 minutes, 30 minutes, 20 minutes, 10 minutes, 5 minutes, 3 minutes, 2 minutes, or less than 1 minute after administration. In some embodiments, the intranasal dry powder formulation is sufficient to resume a spontaneous circulation in the patient within 60 minutes, 50 minutes, 40 minutes, 30 minutes, 20 minutes, 10 minutes, 5 minutes, 3 minutes, 2 minutes, or less than 1 minute after administration. In some embodiments, the intranasal dry powder formulation is sufficient to relieve a bronchoconstriction in the patient within 60 minutes, 50 minutes, 40 minutes, 30 minutes, 20 minutes, 10 minutes, 5 minutes, 3 minutes, 2 minutes, or less than 1 minute after administration.

In some instances, the formulation is administered to the patient in the form of a unit dose as described above. In some embodiments, a single dose of the dry powder formulation includes about 0.01 mg to about 10 mg epinephrine. In some embodiments, a single dose of the dry powder formulation includes about 5 mg to about 40 mg epinephrine. In some embodiments, the amount of epinephrine in a single dose of the formulation is at least: 0.01 mg, 0.05 mg, 1.0 mg, 2.0 mg, 5.0 mg, 10 mg, 14 mg, 18 mg, 20 mg, 22 mg, 25 mg, 28 mg, or 30 mg. In some embodiments, a single dose of the formulation includes about: 0.01 mg to 0.05 mg, 0.05 mg to 0.75 mg, 0.75 mg to 1.5 mg, 1.5 mg to 3.0 mg, 3.0 to 4.5 mg, 4.5 to 6.0 mg, 6.0 to 7.5 mg, 7.5 to 9.0 mg, 9.0 to 10.0 mg, 10.0 mg to 12.0 mg, 12.0 mg to 15.0 mg, 15.0 mg to 20.0 mg, 20.0 mg to 25.0 mg, or 25.0 mg to 30 mg. In some embodiments, the epinephrine present in the formulation is about: 3.0 mg to 30.0 mg, 3.0 mg to 25 mg, 10.0 mg to 30.0 mg, 10.0 mg to 25.0 mg, 14.0 mg to 28.0 mg, 15.0 mg to 25.0 mg, 15.0 mg to 30.0 mg, or 15.0 mg to 40.0 mg. In some embodiments, a single dose of the formulation includes about: 0.15, 0.3, 0.5, 0.75, 1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mg epinephrine. In one instance, a single dose includes about 0.75 mg epinephrine. In one instance, a single dose includes about 1.5 mg epinephrine. In another instance, a single dose includes about 3.0 mg epinephrine. In another instance, a single dose includes about 10.0 mg epinephrine. In another instance, a single dose includes about 15.0 mg epinephrine. In another instance, a single dose includes about 18.0 mg epinephrine. In another instance, a single dose includes about 22.0 mg epinephrine. In another instance, a single dose includes about 25.0 mg epinephrine. In another instance, a single dose includes about 30.0 mg epinephrine. In another instance, a single dose includes about 40.0 mg of epinephrine. In some embodiments, a single dose includes about 0.01 mg to about 30 mg of epinephrine. In some embodiments, a single dose includes about: 0.75 mg, 1.5 mg, 3.0 mg, 4.5 mg, 10 mg, 14.5 mg, 15 mg, 18 mg, 20 mg, 22 mg, 25 mg, 30 mg, 35 mg, or 40 mg of epinephrine. In some embodiments, based on a "standard" patient weight of 70 kg, the dose of epinephrine is adjusted according to an increased or decreased weight of the patient relative to the "standard" patient weight. In one embodiment, the adjustment according to the increased or decreased weight of the patient is at an increased or decreased increment of at least 0.01 mg/kg, respectively. In some embodiments, the delivered dose of the dry powder formulation (i.e., the amount of the formulation delivered to the patient's nasal passages) when administered to the patient using the devices described herein is substantially similar to the unit dose of the formulation. In some embodiments, the dose administered to the patient results in the systemic blood bioequivalent of intravenously (IV), intramuscularly (IM) or subcutaneously (SQ) administered epinephrine (e.g., the systemic blood level achieved with administration of 1 mg epinephrine by IV or 0.3 mg epinephrine by EPIPEN® device for adults, 0.15 mg epinephrine by EPIPEN JR® device for pediatric patients or 0.01 mg/kg with a dilution of 0.1 mg/mL for IV epinephrine), referred to herein as "a nasal loading dose".

In some embodiments, the dry powder formulations provided herein, when administered to a patient, produce a maximal blood concentration (Cmax) of epinephrine that is at least about: 2- to 3-fold, 3- to 5-fold, 5- to 7-fold, 7- to 10-fold, 10- to 20-fold, 15- to 25-fold, 10- to 30-fold, or 15-40 fold more than the baseline level of epinephrine in the patient. In some embodiments, the dry powder formulations provided herein, when administered to a patient, produce a maximal blood concentration (Cmax) of epinephrine at least 2-, 3-, 4-, 5-, 6-, 7-, 8-, 9-, 10-, 11-, 12-, 13-, 14, -15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-fold more than the baseline level of epinephrine in the patient. In one embodiment, the dry powder formulations provided herein, when administered to a patient, produce a maximal blood concentration (Cmax) of epinephrine at least 2-fold more than the baseline level of the epinephrine in the patient. In one embodiment, the dry powder formulations provided herein, when administered to a patient, produce a maximal blood concentration (Cmax) of epinephrine at least 10-fold more than the baseline level of the epinephrine in the patient. In one embodiment, the dry powder formulations provided herein, when administered to a patient, produce a maximal blood concentration (Cmax) of epinephrine at least 15-fold more than the baseline level of the epinephrine in the patient.

In one embodiment, the formulations provided herein, when administered to a patient, increase the blood concentration of epinephrine by about 200 to 1000 pg/mL. In one embodiment, the formulations provided herein, when administered to a patient, increase the blood concentration of epinephrine by about 100, 200, 400, 600, 800, 1000, 1200, 1400, 1600, 1800, 2000, 2200, 2400, 2600, 2800, 3000, 3200, 3400, 3600, 3800, 4000 or 4200 pg/mL. pg/mL. In one embodiment, the formulations provided herein, when administered to a patient, increase the blood concentration of epinephrine by about 200 to 4200 pg/mL. In one embodiment, the formulations provided herein, when administered to a patient, increase the blood concentration of epinephrine by about 800 to 4200 pg/mL. In one embodiment, the formulations provided herein, when administered to a patient, increase the blood concentration of epinephrine by about 800 to 2000 pg/mL. In one embodiment, the formulations provided herein, when administered to a patient, increase the blood concentration of epinephrine by about 0.01 to 0.1 μg/mL. In one embodiment, the formulations provided herein, when administered to a patient, increase the blood concentration of epinephrine by about 0.01, 0.02, 0.03, 0.04, 0.05, 0.06, 0.07, 0.08, 0.09, or 0.1 μg/mL. In one embodiment, the formulations provided herein, when administered to a patient, increase the blood concentration of epinephrine by about 0.1 to 0.3 μg/mL. In one embodiment, the formulations provided herein, when administered to a patient, increase the blood concentration of epinephrine by about 0.1, 0.12, 0.14, 0.16, 0.18, 0.20, 0.22, 0.24, 0.26, 0.28, or 0.3 μg/mL.

In some embodiments, the dry powder formulations provided herein, when administered to a patient, reach a maximal blood concentration of epinephrine in less than about 60 minutes (Tmax) after administration. In some embodiments, the dry powder formulations provided herein, when administered to a patient, reach a maximal blood concentration (Tmax) of epinephrine in less than about: 60, 50, 40, 30, 20, 15, 10, 5, 3, or less than 1 minute (Tmax) after administration. In some embodiments, the dry powder formulations provided herein, when administered to a patient, reach a mean AUC in a time period (e.g., 0-180 minutes) of epinephrine that is at least 20%, 30%, 40% 50%, 60%, 70%, 80%, 90%, 100%, 110%, 120%, 130%, 140% or 150% of the mean AUC in the time period of an IV, IM, or SQ injected epinephrine. In some embodiments, the dry powder formulations provided herein, when administered to a patient, reaches a mean AUC in a time period (e.g., 0-∞) of epinephrine that is at least 20%, 30%, 40% 50%, 60%, 70%, 80%, 90%, 100%, 110%, 120%, 130%, 140% or 150% of the mean AUC in the time period of an IV, IM, or SQ injected epinephrine. In some embodiments, the IV, IM, or SQ injected epinephrine contains 0.10 mg, 0.15 mg, 0.20 mg, 0.25 mg, 0.30 mg, 0.35 mg, 0.40 mg, 0.45 mg, 0.50 mg, 0.55 mg, 0.60 mg, 0.65 mg, 0.70 mg, 0.75 mg, 0.80 mg, 0.85 mg, 0.90 mg, 0.95 mg, or 1.0 mg of epinephrine. For example, the dry powder formulations provided herein, when administered to a patient, reach a mean AUC in a time period (e.g., 0-180 minutes) of epinephrine that is at least 80% of the mean AUC in the time period of a 0.15 mg IV injected epinephrine. In another instance, the dry powder formulations provided herein, when administered to a patient, reach a mean AUC in a time period (e.g., 0-∞) of epinephrine that is at least 80% of the mean AUC in the time period of a 0.15-1 mg IV injected epinephrine. In some embodiments, the IV, IM, or SQ injected epinephrine is injected by EPIPEN® auto-injector (e.g., EPIPEN® 0.3 mg, EPIPEN JR® 0.15 mg). In some embodiments, the dry powder formulations provided herein, when administered to a patient, reach a mean AUC in a time period (e.g., 0-180 minutes) of epinephrine that is at least 50,000 pg·min/mL 100,000 pg·min/mL, 200,000 pg·min/mL, 300,000 pg·min/mL, 400,000 pg·min/mL, 500,000 pg·min/mL, 600,000 pg·min/mL, 700,000 pg·min/mL, 800,000 pg·min/mL, 900,000 pg·min/mL, or 1,000,000 pg·min/mL. In some embodiments, the dry powder formulations provided herein, when administered to a patient, reach a mean AUC in a time period (e.g., 0-∞) of epinephrine that is at least 50,000 pg·min/mL, 100,000 pg·min/mL, 200,000 pg·min/mL, 300,000 pg·min/mL, 400,000 pg·min/mL, 500,000 pg·min/mL, 600,000 pg·min/mL, 700,000 pg·min/mL, 800,000 pg·min/mL, 900,000 pg·min/mL, 1,000,000 pg·min/mL, 1,200,000 pg·min/mL, 1,400,000 pg·min/mL, 1,600,000 pg·min/mL, 1,800,000 pg·min/mL, or 2,000,000 pg·min/mL.

In certain embodiments, the dry powder formulations and/or unit doses provided herein are operable to raise the blood concentration of epinephrine in a subject to about 0.02 pg/mL within about less than 1 minute to about 60 minutes (e.g., about: 60, 50, 40, 30, 20, 15, 10, 5, 3, <1 minute). In one embodiment, the dry powder formulations and/or unit doses provided herein are operable to raise the blood concentration of epinephrine in a subject about 10 pg/mL within about less than 1 minute to about 15 minutes (e.g., about: <1, 3, 5, 10, 11, 12, 13, 14, or 15 minutes) of intranasal administration. In one embodiment, the formulations provided herein increase the blood concentration of epinephrine by about 0.01 to about 0.04 pg/mL (e.g., 0.02 or 0.03 pg/mL) in about less than 1 minute to about 15 minutes (e.g., about: <1, 10, 11, 12, 13, 14, or 15 minutes). In one embodiment, the formulations provided herein increase the blood concentration of epinephrine by about 3 pg/mL in about less than 1 minute to about 60 minutes (e.g., about: 60, 50, 40, 30, 20, 15, 10, 5, 3, <1 minute).

A single dose of epinephrine in the dry powder formulations and/or dosage units given intranasally is preferably bioequivalent (for example, in terms of peripheral blood levels, systemic exposure of epinephrine) to intravenously (IV), intramuscularly (IM), or subcutaneously (SQ) injected epinephrine (e.g., using EPIPEN® auto-injector of 0.3 mg for adult patients or 1 mg IV epinephrine, using EPIPEN® auto-injector of 0.15 mg for pediatric patients or 0.01 mg/kg with a dilution of 0.1 mg/mL for IV epinephrine). In one example, bioequivalence includes a 90% confidence interval of a mean Tmax (e.g., the time to reach maximal blood concentration), a mean Cmax (e.g., maximal blood concentration), a mean AUC over a period of time (e.g., area under the plasma/serum/blood concentration-time curve from time zero to time t), and/or a mean AUC over a period of time from 0 to infinity (e.g., area under the plasma/serum/blood concentration-time curve from time zero to time infinity) are within 80.00% to 125.00% of a reference test. In one embodiment, bioequivalence is determined in a fasting state.

In some instances, the patient in need of treatment is experiencing cardiac arrest and/or bronchospasm. In some embodiments, the method includes administering a nasal loading dose of a formulation as provided herein, wherein the nasal loading dose includes about 3 mg to about 40 mg of epinephrine (e.g., 3 to 10 mg, 10 to 30 mg, or 14.5, 22.5, or 28.0 mg) and at least one pharmaceutically acceptable carrier in an amount of about 1 mg to about 50 mg (e.g., 10 30 mg, 15 to 20 mg, or 18 mg). In some embodiments, the nasal loading dose about 15 mg to about 40 mg of epinephrine (e.g., 15 to 30 mg, 15 to 22.5 mg, or 15.0, 22.5, or 28.0 mg), about 1 pg to about 10 mg of a second vasodilator (a vasodilator other than epinephrine; e.g., niacin) (e.g., 0.1 to 5 mg, 0.1 to 1 mg, or 0.5 mg); and at least one pharmaceutically acceptable carrier in an amount of about 1 mg to about 50 mg (e.g., 10 30 mg, 15 to 20 mg, or 18 mg). In some instances, the dry powder formulation includes at least one agent that stabilizes the composition, at least one agent that reduces mucosal transit time, at least one agent that increases mucosal absorption and/or adhesion, and/or at least one agent that enhances mucosal transport, or the enantiomers, diastereoisomers, racemates, or salts of such compounds with pharmaceutically acceptable counterions. In one embodiment, an amount of the at least one agent that reduces mucosal transit time, the at least one agent that increases mucosal absorption and/or adhesion, and/or the at least one agent that enhances mucosal transport, or the enantiomers, diastereoisomers, racemates, or salts of such compounds with pharmaceutically acceptable counterions is synergistic for the treatment of bronchospasm and/or cardiac arrest. In some instances, the formulations provided herein include low doses that, when administered intranasally to a subject, result in a sufficiently high peak blood plasma concentration of epinephrine of at least: 2-fold, 3-5 fold, 5-7 fold, 7-10 fold, 10-20 fold, 10-30, or 15-40 fold more than baseline levels rapidly after administration (e.g., within 60, 50, 40, 30, 20, 15, 10, 5, 3, or <1 minute) so as to be effective in the treatment or reducing the symptoms of bronchospasm, and/or cardiac arrest.

In one embodiment, the invention provides a pharmaceutical formulation including dry powder epinephrine and chitosan (e.g., dry powder chitosan) as an enabling agent to optimize the systemic delivery of epinephrine through the nasal passages. In some embodiments, chitosan and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and hyaluronic acid (e.g., dry powder hyaluronic acid, dry powder sodium hyaluronate) as an enabling agent to optimize the systemic delivery of epinephrine through the nasal passages. In some embodiments, hyaluronic acid and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In a preferred embodiment, the invention provides a pharmaceutical formulation including dry powder epinephrine and sodium carboxymethyl cellulose (NaCMC) (e.g., dry powder NaCMC) as an enabling agent to optimize the systemic delivery of epinephrine through the nasal passages. In some embodiments, NaCMC and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation includes dry powder epinephrine and cyclodextrin (e.g., dry powder cyclodextrin) as an enabling agent to optimize the systemic delivery of epinephrine through the nasal passages. In some embodiments, cyclodextrin and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and niacin (e.g., dry powder niacin, dry powder nicotinic acid) as an enabling agent to optimize the systemic delivery of epinephrine through the nasal passages. In some embodiments, niacin and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and caffeine (e.g., dry powder caffeine) as an enabling agent to optimize the systemic delivery of epinephrine through the nasal passages. In some embodiments, caffeine and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and sodium taurocholate (e.g., dry powder sodium taurocholate) as an enabling agent to optimize the systemic delivery of epinephrine through the nasal passages. In some embodiments, sodium taurocholate and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and carnitine hydrochloride (e.g., dry powder carnitine hydrochloride) as an enabling agent to optimize the systemic delivery of epinephrine through the nasal passages. In some embodiments, carnitine hydrochloride and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and dimethyl-beta-cyclodextrin (e.g., dry powder dimethyl-beta-cyclodextrin) as an enabling agent to optimize the systemic delivery of epinephrine through the nasal passages. In some embodiments, dimethyl-beta-cyclodextrin and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and polysorbate (e.g., dry powder polysorbate) as an enabling agent to optimize the systemic delivery of epinephrine through the nasal passages. In some embodiments, polysorbate and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and sodium chloride (NaCl) (e.g., dry powder NaCl) as an enabling agent to optimize the systemic delivery of epinephrine through the nasal passages. In some embodiments, NaCl and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation comprising dry powder epinephrine and potassium chloride (KCl) (e.g., dry powder KCl) as an enabling agent to optimize the systemic delivery of epinephrine through the nasal passages. In some embodiments, KCl and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and 2-(2-propoxypropoxy)ethanol (also known as Poloxamer 188) (e.g., dry powder Poloxamer 188) as an enabling agent to optimize the systemic delivery of epinephrine through the nasal passages. In some embodiments, Poloxamer 188 and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and leucine (e.g., dry powder leucine, dry powder L-leucine) as an enabling agent to optimize the systemic delivery of epinephrine through the nasal passages. In some embodiments, leucine and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and histidine (e.g., dry powder histidine) as an enabling agent to optimize the systemic delivery of epinephrine through the nasal passages. In some embodiments, histidine and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and glycine (e.g., dry powder glycine) as an enabling agent to optimize the systemic delivery of epinephrine through the nasal passages. In some embodiments, glycine and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and arginine (e.g., dry powder arginine) as an enabling agent to optimize the systemic delivery of epinephrine through the nasal passages. In some embodiments, arginine and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and crospovidone (e.g., dry powder crospovidone) as an enabling agent to optimize the systemic delivery of epinephrine through the nasal passages. In some embodiments, crospovidone and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and a polyacrylic acid polymer (e.g., CARBOPOL® 934) (e.g., a dry powder polyacrylic acid polymer) as an enabling agent to optimize the systemic delivery of epinephrine through the nasal passages. In some embodiments, the polyacrylic acid polymer and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and magnesium stearate (e.g., dry powder magnesium stearate) as an enabling agent to optimize the systemic delivery of epinephrine through the nasal passages. In some embodiments, magnesium stearate and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

Alternatively, in a preferred embodiment, the present invention does not include magnesium stearate. Magnesium stearate may cause allergic reactions in some individuals. See, e.g., Tammaro A, Abruzzese C, Narcisi A, Cortesi G, Persechino F, Parisella F R, Persechino S. Magnesium stearate: an underestimated allergen. J Biol Regul Homeost Agents. 2012 October-December; 26(4):783-4. PMID: 23241129, which is incorporated herein by reference in its entirety. Advantageously, sodium chloride is safer to use than magnesium stearate.

In one embodiment, the invention provides a pharmaceutical formulation including dry powder epinephrine and ethylenediaminetetraacetic acid (EDTA) (e.g., dry powder EDTA) as an enabling agent to optimize the systemic delivery of epinephrine through the nasal passages. In some embodiments, EDTA and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and sodium starch glycolate (e.g., dry powder sodium starch glycolate) as an enabling agent to optimize the systemic delivery of epinephrine through the nasal passages. In some embodiments, sodium starch glycolate and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In a preferred embodiment, the invention provides a pharmaceutical formulation including dry powder epinephrine and lactose (e.g., dry powder lactose, dry powder D-lactose) as an enabling agent to optimize the systemic delivery of epinephrine through the nasal passages. In some embodiments, lactose and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and microcrystalline cellulose (e.g., dry powder microcrystalline cellulose) as an enabling agent to optimize the systemic delivery of epinephrine through the nasal passages. In some embodiments, microcrystalline cellulose and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and mannitol (e.g., dry powder mannitol) as an enabling agent to optimize the systemic delivery of epinephrine through the nasal passages. In some embodiments, mannitol and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

In one embodiment, the invention provides a pharmaceutical formulation including dry powder epinephrine and a mixture of mannitol and hydroxypropyl methylcellulose (HPMC) (e.g., a mixture of dry powder mannitol and HPMC) as an enabling agent to optimize the systemic delivery of epinephrine through the nasal passages. In some embodiments, a mixture of mannitol and HPMC and at least one excipient (e.g., at least one enabling agent, at least one carrier, and/or at least one flow agent) are combined in various ratios and employed to optimize the systemic delivery of epinephrine through the nasal passages. In some embodiments, the concentration of the at least one enabling agent ranges from 0% and 20% w/w. The at least one enabling agent includes, but is not limited to, at least one mucoadhesive, at least one absorption enhancer, at least one permeability enhancer, at least one surfactant, at least one surface modifier, at least one sustained release agent, at least one vasodilator, at least one anticaking agent, and at least one disintegrant. In some embodiments, the formulation includes at least one excipient that impacts the characteristics of the dry powder formulation that directly or indirectly affect the transport of epinephrine across the nasal mucosa. In some embodiments, the formulation includes at least one excipient that facilitates solubilization or processing so as to provide a spray-dried powder having the desired characteristics.

It will be appreciated that, while the categories of pharmaceutical ingredients cited herein (that accompany the primary active ingredient of epinephrine) are used as a means of describing the inventive formulations, some of the ingredients will have multiple mechanisms of action that fall under more than one category. These categories of ingredients, including absorption enhancers, mucoadhesives, vasodilators, surfactants, sustainer release agents, carriers, and manufacturing process enablers, are therefore indicative while not being mutually exclusive. For example, an ingredient may serve as a carrier but also have a mucoadhesive action in the context of nasal delivery of epinephrine, or an ingredient may have actions as both a surfactant and absorption enhancer.

In some embodiments, the devised formulation(s) for delivery to the nasal passages and nasal mucosa are of a particle size having a range of about 3 μm to about 100 μm for epinephrine. In some embodiments, the devised formulation(s) for delivery to the nasal passages and nasal mucosa are of a particle size having a range of about 3 μm to about 50 μm for epinephrine. In another embodiment, the formulation(s) for delivery of epinephrine to the nasal passages and nasal mucosa are a nanoformulation with a particle size having a range of about 30 nm to about 100 nm.

In some embodiments, the devised formulation (s) for delivery of epinephrine to the nasal passages and nasal mucosa have a particle size for the at least one enabling agent, the at least one carrier, the at least one flow agent, and/or other generally accepted as safe (GRAS) pharmaceutical excipients having a range of about 3 μm to about 200 μm. In one embodiment, the formulation(s) for delivery of epinephrine to the nasal passages and nasal mucosa are a nanoformulation with a particle size having a range of about 30 nm to about 100 nm for the at least one enabling agent, the at least one carrier, the at least one flow agent, and/or other generally accepted as safe (GRAS) pharmaceutical excipients.

In another embodiment, provided herein is a product including a nasal delivery device containing the pharmaceutical formulations described herein. The nasal delivery device contains in a body, a cavity, or a reservoir of the device the required quantity of the pharmaceutical preparation to deliver the appropriate amount of epinephrine to the nasal passages and nasal mucosa for systemic delivery. The nasal delivery device preferably includes a pump spray device, a metered dose spray, or a mechanical spray device. In one embodiment, the nasal delivery device is a single dose device. Alternatively, the nasal delivery device is a multiple dose device.

In another embodiment, provided herein is a method of treating anaphylaxis, the method including delivering a dry powder formulation as provided herein intranasally to a subject in need thereof. In some instances, the dry powder formulation is administered using a nasal delivery device as described herein.

Additional information about epinephrine, nasal delivery, bioequivalence, and/or conditions treated by epinephrine are in the following references: (1) Clutter W E, Bier D M, Shah S D, Cryer P E. Epinephrine plasma metabolic clearance rates and physiologic thresholds for metabolic and hemodynamic actions in man. J Clin Invest. 1980 July; 66(1):94-101. Doi: 10.1172/JCI109840. PMID: 6995479; PMCID: PMC371510; (2) Duvauchelle T, Robert P, Donazzolo Y, Loyau S, Orlandini B, Lehert P, Lecomte J M, Schwartz J C. Bioavailability and Cardiovascular Effects of Adrenaline Administered by Anapen Autoinjector in Healthy Volunteers. J Allergy Clin Immunol Pract. 2018 July-August; 6(4):1257-1263. Doi: 10.1016/j.jaip.2017.09.021. Epub 2017 Nov. 3. PMID: 29109047; (3) Hill R L, Wilmot J G, Belluscio B A, Cleary K, Lindisch D, Tucker R, Wilson E, Shukla R B. Comparison of drug delivery with autoinjector versus manual prefilled syringe and between three different autoinjector devices administered in pig thigh. Med Devices (Auckl). 2016 Aug. 2; 9:257-66. Doi: 10.2147/MDER.S83406. PMID: 27536164; PMCID: PMC4976900; (4) Dodd A, Hughes A, Turner P J, 2021, Anaphylaxis management Why are guidelines inconsistent?: A rapid review of advanced life support guidelines for cardiac arrest associated with anaphylaxis., Resuscitation, Vol:159, Pages: 165-167; (5) Turner P, Patel N, 2021, Using data from food challenges to inform management of food-allergic consumers: a systematic review with individual participant data meta-analysis, Journal of Allergy and Clinical Immunology, ISSN:0091-6749; (6) Turner P, 2021, A Cost-effectiveness Analysis of Epinephrine Autoinjector Risk Stratification for Patients with Food Allergy-One Epinephrine Autoinjector or Two?, Journal of Allergy and Clinical Immunology: in Practice, ISSN:2213-2201; (7) Lam C, Turner P, Hemming D, et al., 2021, Seasonality of food related anaphylaxis admissions and associations with temperature and pollen levels, Journal of Allergy and Clinical Immunology: in Practice, Vol:9, ISSN:2213-2198, Pages:518-520; (8) Turner P, Boyle R, Durham S, 2021, Limited effect of intramuscular epinephrine on cardiovascular parameters during peanut-induced anaphylaxis: an observational cohort study, Journal of Allergy and Clinical Immunology: in Practice, Vol:9, ISSN:2213-2198, Pages:527-530; (9) Johnstone J, Hobbins S, Parekh D, O'Hickey S. Excess subcutaneous tissue may preclude intramuscular delivery when using adrenaline auto-injectors in patients with anaphylaxis. Allergy. 2015 June; 70(6):703-6. Doi: 10.1111/all.12595. Epub 2015 Mar. 29. PMID: 25676800; (10) Moss, J, Jani, Y, Edwards, B, Tomlin, S, Rashed, AN. Pharmacokinetic and pharmacodynamic evidence of adrenaline administered via auto-injector for anaphylactic reactions: A review of literature. *Br J Clin Pharmacol.* 2021: 87: 816-824. https://doi.org/10.1111/bcp.14438; (11) Simons F E, Roberts J R, Gu X, Simons K J. Epinephrine absorption in children with a history of anaphylaxis. J Allergy Clin Immunol. 1998 January; 101(1 Pt 1):33-7. Doi: 10.1016/50091-6749(98)70190-3. PMID: 9449498; (12) Paul Turner, Imperial College London. Pharmacokinetics of Intramuscular Adrenaline in Food—Allergic Teenagers: Does Dose Matter? The PIMAT Study. Version 1.2, 29 Sep. 2017; (13) Turner P J, Ruiz-Garcia M, Durham S R, Boyle R J. Limited effect of intramuscular epinephrine on cardiovascular parameters during peanut-induced anaphylaxis: An observational cohort study. J Allergy Clin Immunol Pract. 2021 January; 9(1):527-530. Doi: 10.1016/j.jaip.2020.08.041. Epub 2020 Sep. 2. PMID: 32889224; PMCID: PMC7794658; (14) Worm, M., Nguyen, D., Rackley, R. et al. Epinephrine delivery via EpiPen® Auto-Injector or manual syringe across participants with a wide range of skin-to-muscle distances. Clin Transl Allergy 10, 21 (2020). https://doi.org/10.1186/s13601-020-00326-x; (15) Kuehl P J, Barrett E G, Cox J, Hammond B, Rudolph K, Suman J D, Williams G, Vermillion M., Nasal Sumatriptan: Deposition and Pharmacokinetic Effect of an Absorption Enhancer in Non-Human Primates, Respiratory Drug Delivery 2020. Volume 1, 2020: 165-174; (16) US FDA, FY2018 Regulatory Science Report: Physiologically-Based Absorption and Pharmacokinetic Models for Non-Oral Routes, https://www.fda.gov/media/130623/download (last accessed Jun. 10, 2021); (17) Rygg A, Hindle M, Longest P W. Linking Suspension Nasal Spray Drug Deposition Patterns to Pharmacokinetic Profiles: A Proof-of-Concept Study Using Computational Fluid Dynamics. J Pharm Sci. 2016 June; 105(6):1995-2004. Doi: 10.1016/j.xphs.2016.03.033. PMID: 27238495; PMCID: PMC4886237; (18) Satish Balakrishna Bhise, Adhikrao Vyankatrao Yadav, Amelia Makrand Avachat, Rajkumar Malayandi, Bioavailability of intranasal drug delivery system, Biopharmaceutical Research Group, Department of Biopharmaceutics, Government College of Pharmacy, Karad, India, Asian Journal of Pharmaceutics, Vol. 2, No. 4 (2008); (19) Simons F E, Gu X, Simons K J. Epinephrine absorption in adults: intramuscular versus subcutaneous injection. J Allergy Clin Immunol. 2001 November; 108(5):871-3. Doi: 10.1067/mai.2001.119409. PMID: 11692118; (20) Song T T, Nelson M R, Chang J H, Engler R J, Chowdhury B A. Adequacy of the epinephrine autoinjector needle length in delivering epinephrine to the intramuscular tissues. Ann Allergy Asthma Immunol. 2005 May; 94(5):539-42. Doi: 10.1016/S1081-1206(10)61130-1. PMID: 15945556; (21) Chowdhury B A, Meyer R J. Intramuscular versus subcutaneous injection of epinephrine in the treatment of anaphylaxis. J Allergy Clin Immunol. 2002 April; 109(4):720; author reply 720-1. Doi: 10.1067/mai.2002.123252. PMID: 11941328; (22) Kemp S F, Lockey R F, Simons F E; World Allergy Organization ad hoc Committee on Epinephrine in Anaphylaxis. Epinephrine: the drug of choice for anaphylaxis. A statement of the World Allergy Organization. Allergy. 2008 August; 63(8):1061-70. Doi: 10.1111/j.1398-9995.2008.01733.x. PMID: 18691308; (23) Sclar D A. Bioequivalence evaluation of epinephrine autoinjectors with attention to rapid delivery. Ther Clin Risk Manag. 2013; 9:149-51. Doi: 10.2147/TCRM.S43774. Epub 2013 Apr. 12. PMID: 23610523; PMCID: PMC3629870; (24) Haidar S H, Makhlouf F, Schuirmann D J, Hyslop T, Davit B, Conner D, Yu L X. Evaluation of a scaling approach for the bioequivalence of highly variable drugs. AAPS J. 2008 September; 10(3):450-4. Doi: 10.1208/s12248-008-9053-4. Epub 2008 Aug. 26. Erratum in: AAPS J. 2008 September; 10(3):480. PMID: 18726698; PMCID: PMC2761698; (25) Karalis V, Symillides M, Macheras P. Comparison of the reference scaled bioequivalence semi-replicate method with other approaches: focus on human exposure to drugs. Eur J Pharm Sci. 2009 Aug. 12; 38(1):55-63. Doi: 10.1016/j.ejps.2009.05.013. Epub 2009 Jun. 11. PMID: 19524039; and (26) Muraro A, Worm M, Alviani C, Cardona V, DunnGalvin A, Garvey L H, Riggioni C, de Silva D, Angier E, Arasi S, Bellou A, Beyer K, Bijlhout D, Bilb M B, Bindslev-Jensen C, Brockow K, Fernandez-Rivas M, Halken S, Jensen B, Khaleva E, Michaelis L J, Oude Elberink H N G, Regent L, Sanchez A, Vlieg-Boerstra B J, Roberts G; European Academy of Allergy and Clinical Immunology, Food Allergy, Anaphylaxis Guidelines Group. EAACI guidelines: Anaphylaxis (2021 update). Allergy. 2022 February; 77(2):357-377. Doi: 10.1111/all.15032. Epub 2021 Sep. 1. PMID: 34343358. Each of the above listed references is incorporated herein by reference in its entirety.

Rat Studies

The plasma pharmacokinetics (PK) following intranasal (IN) delivery of a plurality of dry powder formulations of epinephrine administered at different doses in Sprague Dawley rats was determined. Epinephrine administered by the intramuscular (IM) route was used as a comparator. The dose formulations were one of seven combinations of epinephrine with either lactose or sodium carboxymethylcellulose (CMC) as the carrier. The excipients included sodium chloride, polysorbate (TWEEN 80), niacin, caffeine, hyaluronate, and leucine. Blood was collected at 7 timepoints after dose administration using jugular catheterized animals. The nominal dose for the epinephrine IN formulations was 0.5 mg of epinephrine free base. The dose of the reference IM formulation was 0.7 mg/kg.

Each formulation was administered via intranasal instillation once using a nasal device (APTAR) with 5 mg of the formulation per unit, except for group 15 controls via intramuscular injection. Each nasal device was weighed before and after injection.

Blood (250 μL) was collected from each animal prior to dosing and at 1, 3, 5, 10, 15, 30, and 60 minutes after dosing via a jugular catheter and placed into a $K_2$EDTA tube. Samples were centrifuged within 30 minutes of collection at 1500 g for 15 min at 4° C. and the plasma removed. For each sample, 5 μL of SMBS (sodium metabisulfite) was added to each 100 μL of plasma, and the sample was vortexed. Plasma samples were stored frozen at or below −70° C. in cryotubes for bioanalysis.

FIG. 10 is a table of epinephrine concentration-time data in rats for epinephrine with a lactose carrier. FIG. 11 is a table of epinephrine concentration-time data in rats for epinephrine with a sodium CMC carrier.

FIG. 12 is a table of epinephrine concentration-time data in rats for epinephrine and caffeine (5% w/w) with a lactose carrier. FIG. 13 is a table of epinephrine concentration-time data in rats for epinephrine and caffeine (5% w/w) with a sodium CMC carrier.

FIG. 14 is a table of epinephrine concentration-time data in rats for epinephrine and hyaluronate (0.5% w/w) with a lactose carrier. FIG. 15 is a table of epinephrine concentration-time data in rats for epinephrine and hyaluronate (0.5% w/w) with a sodium CMC carrier.

FIG. 16 is a table of epinephrine concentration-time data in rats for epinephrine and leucine (10% w/w) with a lactose carrier. FIG. 17 is a table of epinephrine concentration-time data in rats for epinephrine and leucine (10% w/w) with a sodium CMC carrier.

FIG. 18 is a table of epinephrine concentration-time data in rats for epinephrine and sodium chloride (2% w/w) with a lactose carrier. FIG. 19 is a table of epinephrine concentration-time data in rats for epinephrine and sodium chloride (2% w/w) with a sodium CMC carrier.

FIG. 20 is a table of epinephrine concentration-time data in rats for epinephrine and niacin (2% w/w) with a lactose carrier. FIG. 21 is a table of epinephrine concentration-time data in rats for epinephrine and niacin (2% w/w) with a sodium CMC carrier.

FIG. 22 is a table of epinephrine concentration-time data in rats for epinephrine and polysorbate (0.5% w/w) with a lactose carrier. FIG. 23 is a table of epinephrine concentration-time data in rats for epinephrine and polysorbate (0.5% w/w) with a sodium CMC carrier.

FIG. 24 is a table of epinephrine concentration-time data in rats for epinephrine intramuscular injection at 0.7 mg/kg.

FIG. 25 is a table of epinephrine pharmacokinetic parameters in rats for epinephrine with a lactose carrier including Cmax (i.e., maximum observed plasma concentration), Tmax (i.e., time of maximum concentration, obtained directly from the observed concentration versus time data), AUClast (i.e., area under the concentration-time curve from time 0 to the last measurable concentration calculated by the linear up-log down trapezoidal method), t½ (i.e., terminal phase half-life, estimated as ln(2)/λz, where λz is the elimination rate constant estimated by linear regression of the log-transformed concentration versus time data), and AUCinf (i.e., the area under the concentration-time curved from time 0 extrapolated to infinity, calculated as AUClast+Clast/λz). FIG. 26 is a table of epinephrine pharmacokinetic parameters in rats for epinephrine with a sodium CMC carrier including Cmax, Tmax, AUClast, t½, and AUCinf.

FIG. 27 is a table of epinephrine pharmacokinetic parameters in rats for epinephrine and caffeine (5% w/w) with a lactose carrier including Cmax, Tmax, AUClast, t½, and AUCinf. FIG. 28 is a table of epinephrine pharmacokinetic parameters in rats for epinephrine and caffeine (5% w/w) with a sodium CMC carrier including Cmax, Tmax, AUClast, t½, and AUCinf.

FIG. 29 is a table of epinephrine pharmacokinetic parameters in rats for epinephrine and hyaluronate (0.5% w/w) with a lactose carrier including Cmax, Tmax, AUClast, t½, and AUCinf. FIG. 30 is a table of epinephrine pharmacokinetic parameters in rats for epinephrine and hyaluronate (0.5% w/w) with a sodium CMC carrier including Cmax, Tmax, AUClast, t½, and AUCinf.

FIG. 31 is a table of epinephrine pharmacokinetic parameters in rats for epinephrine and leucine (10% w/w) with a lactose carrier including Cmax, Tmax, AUClast, t½, and AUCinf. FIG. 32 is a table of epinephrine pharmacokinetic parameters in rats for epinephrine and leucine (10% w/w) with a sodium CMC carrier including Cmax, Tmax, AUClast, t½, and AUCinf.

FIG. 33 is a table of epinephrine pharmacokinetic parameters in rats for epinephrine and sodium chloride (2% w/w) with a lactose carrier including Cmax, Tmax, AUClast, t½, and AUCinf. FIG. 34 is a table of epinephrine pharmacokinetic parameters in rats for epinephrine and sodium chloride (2% w/w) with a sodium CMC carrier including Cmax, Tmax, AUClast, t½, and AUCinf.

FIG. 35 is a table of epinephrine pharmacokinetic parameters in rats for epinephrine and niacin (2% w/w) with a lactose carrier including Cmax, Tmax, AUClast, t½, and AUCinf. FIG. 36 is a table of epinephrine pharmacokinetic parameters in rats for epinephrine and niacin (2% w/w) with a sodium CMC carrier including Cmax, Tmax, AUClast, t½, and AUCinf.

FIG. 37 is a table of epinephrine pharmacokinetic parameters in rats for epinephrine and polysorbate (0.5% w/w) with a lactose carrier including Cmax, Tmax, AUClast, t½, and AUCinf. FIG. 38 is a table of epinephrine pharmacokinetic parameters in rats for epinephrine and polysorbate (0.5% w/w) with a sodium CMC carrier including Cmax, Tmax, AUClast, t½, and AUCinf.

FIG. 39 is a table of epinephrine pharmacokinetic parameters in rats for epinephrine intramuscular injection at 0.7 mg/kg including Cmax, Tmax, AUClast, t½, and AUCinf.

Figure 40:
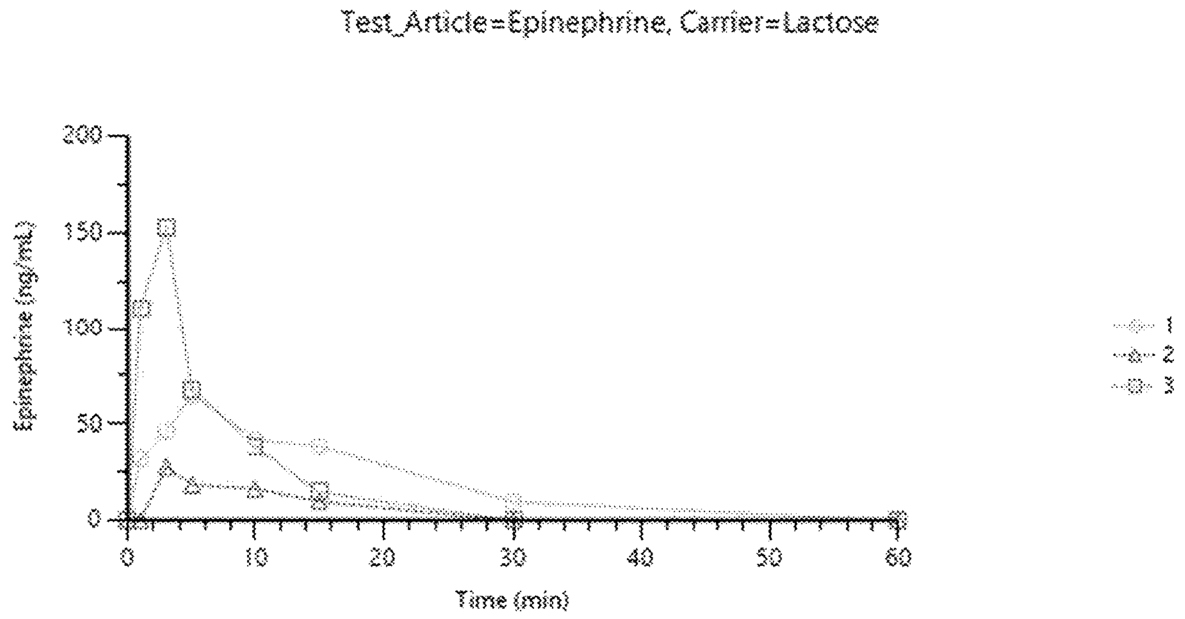
FIG. 40 is a linear graph of epinephrine concentration-time profiles in rats for epinephrine with a lactose carrier.
Figure 41:
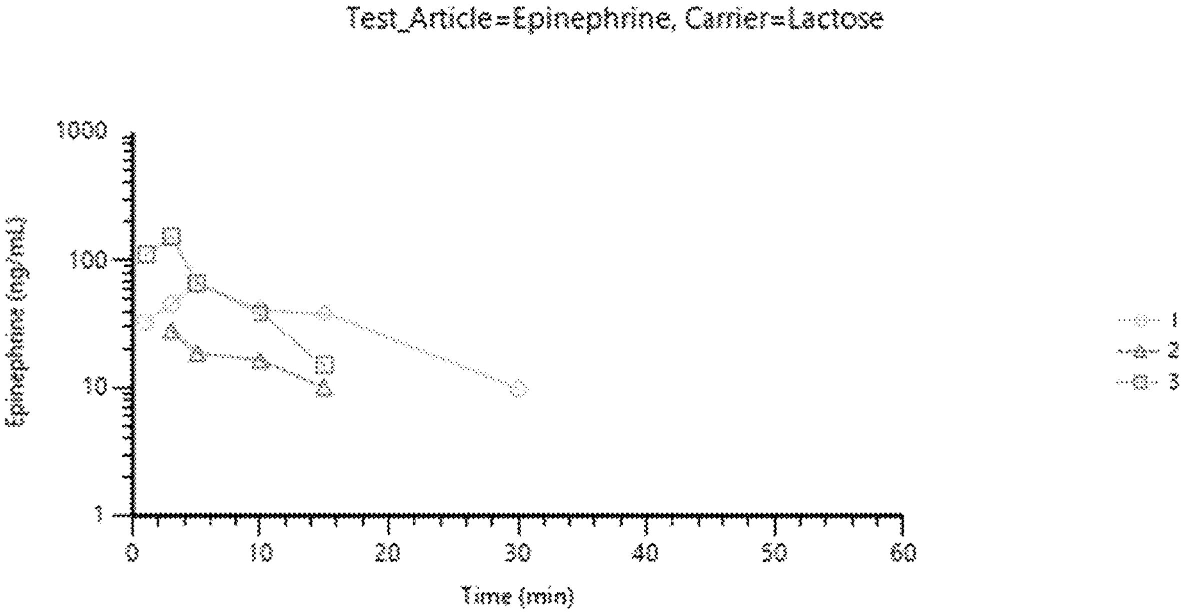
FIG. 41 is a log-linear graph of epinephrine concentration-time profiles in rats for epinephrine with a lactose carrier.

FIG. 40 is a linear graph of epinephrine concentration-time profiles in rats for epinephrine with a lactose carrier. FIG. 41 is a log-linear graph of epinephrine concentration-time profiles in rats for epinephrine with a lactose carrier.

Figure 42:
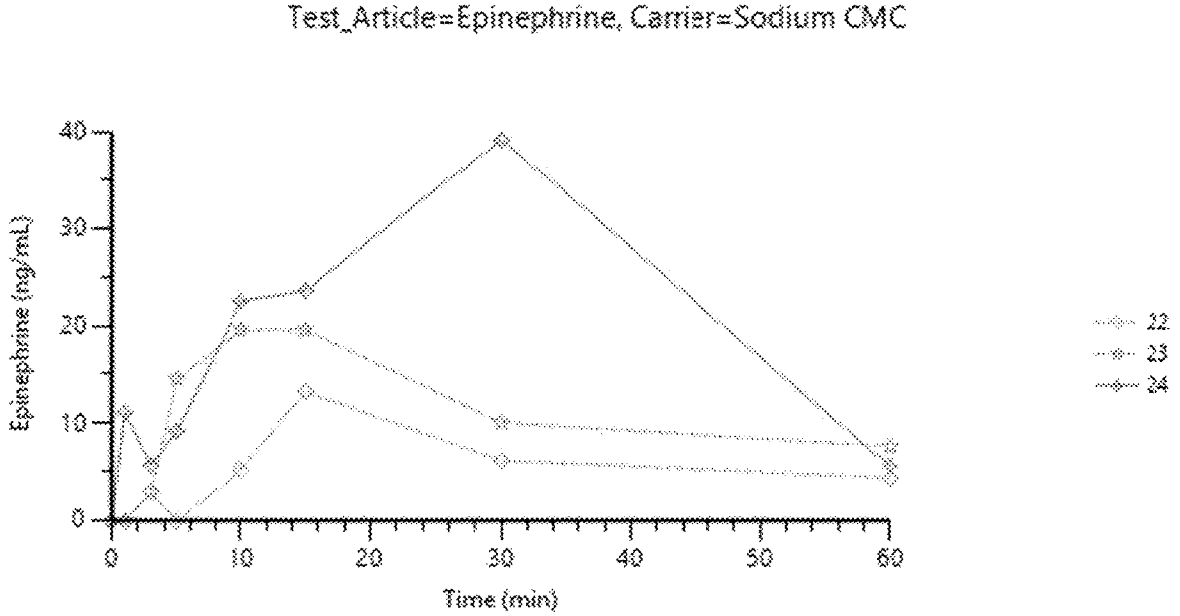
FIG. 42 is a linear graph of epinephrine concentration-time profiles in rats for epinephrine with a sodium CMC carrier.
Figure 43:
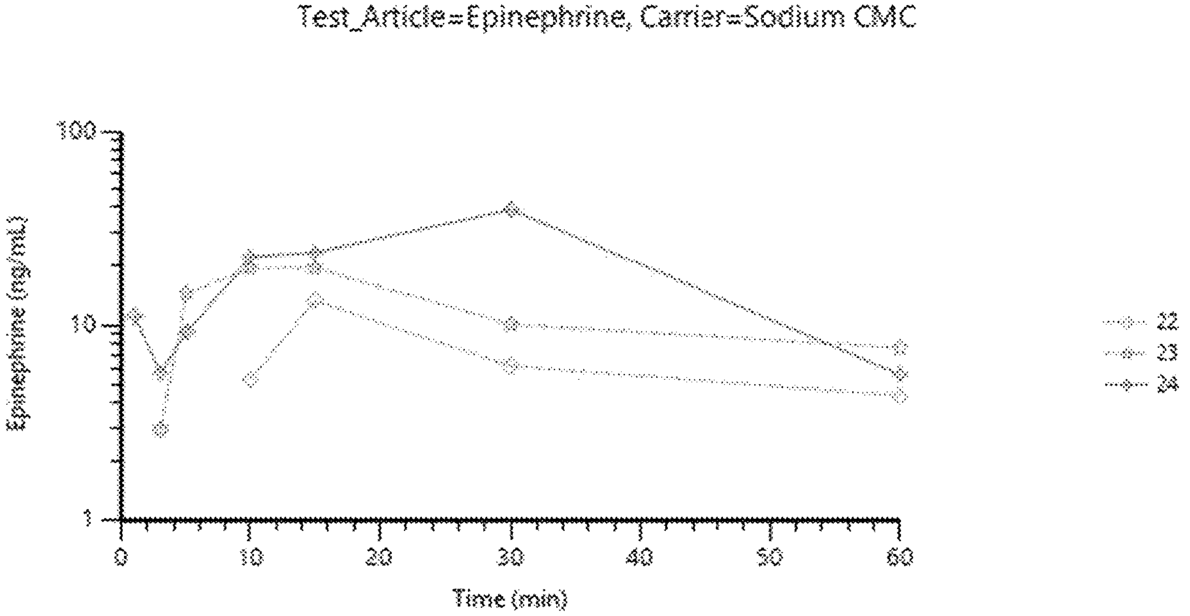
FIG. 43 is a log-linear graph of epinephrine concentration-time profiles in rats for epinephrine with a sodium CMC carrier.

FIG. 42 is a linear graph of epinephrine concentration-time profiles in rats for epinephrine with a sodium CMC carrier. FIG. 43 is a log-linear graph of epinephrine concentration-time profiles in rats for epinephrine with a sodium CMC carrier.

Figure 44:
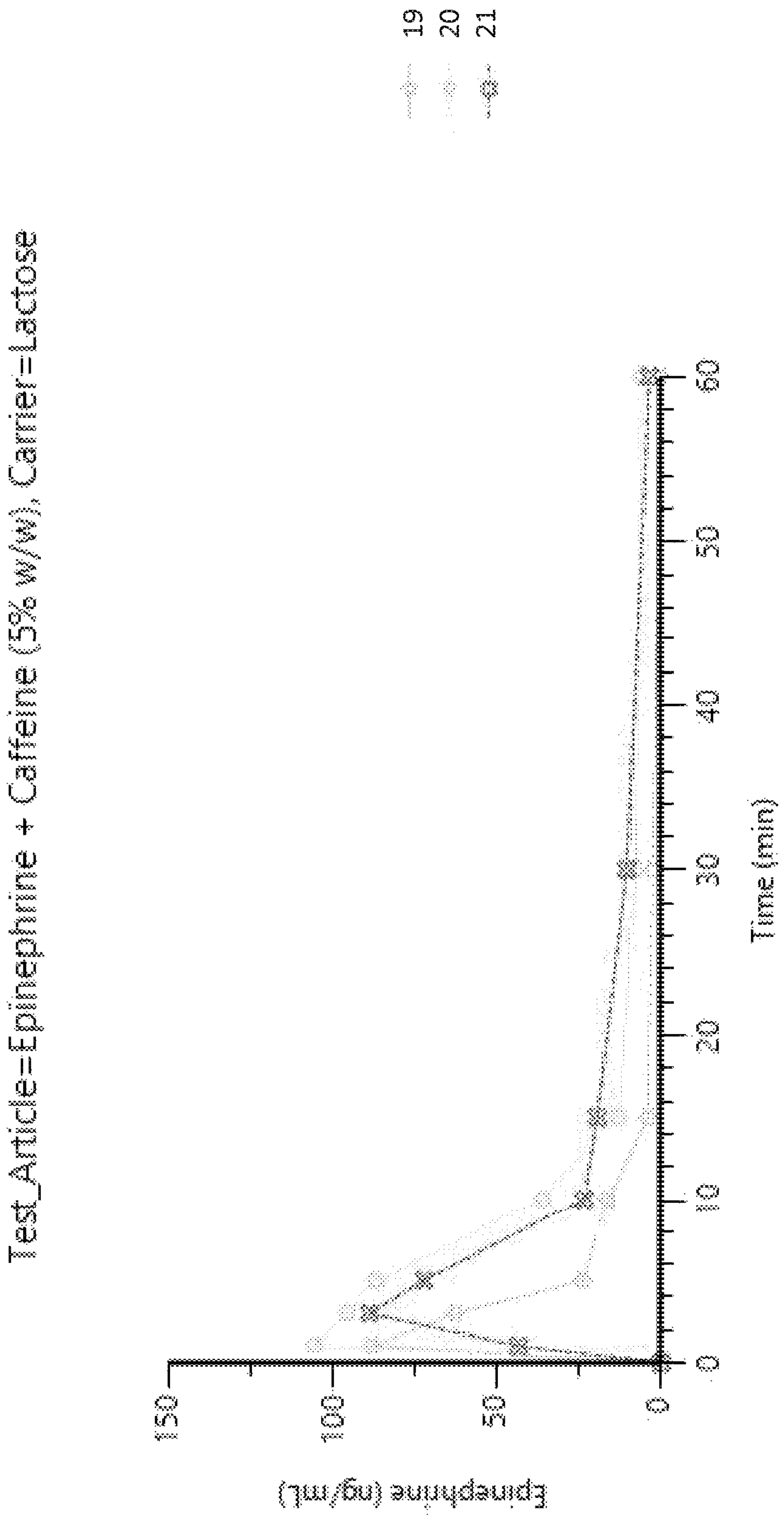
FIG. 44 is a linear graph of epinephrine concentration-time profiles in rats for epinephrine and caffeine (5% w/w) with a lactose carrier.
Figure 45:
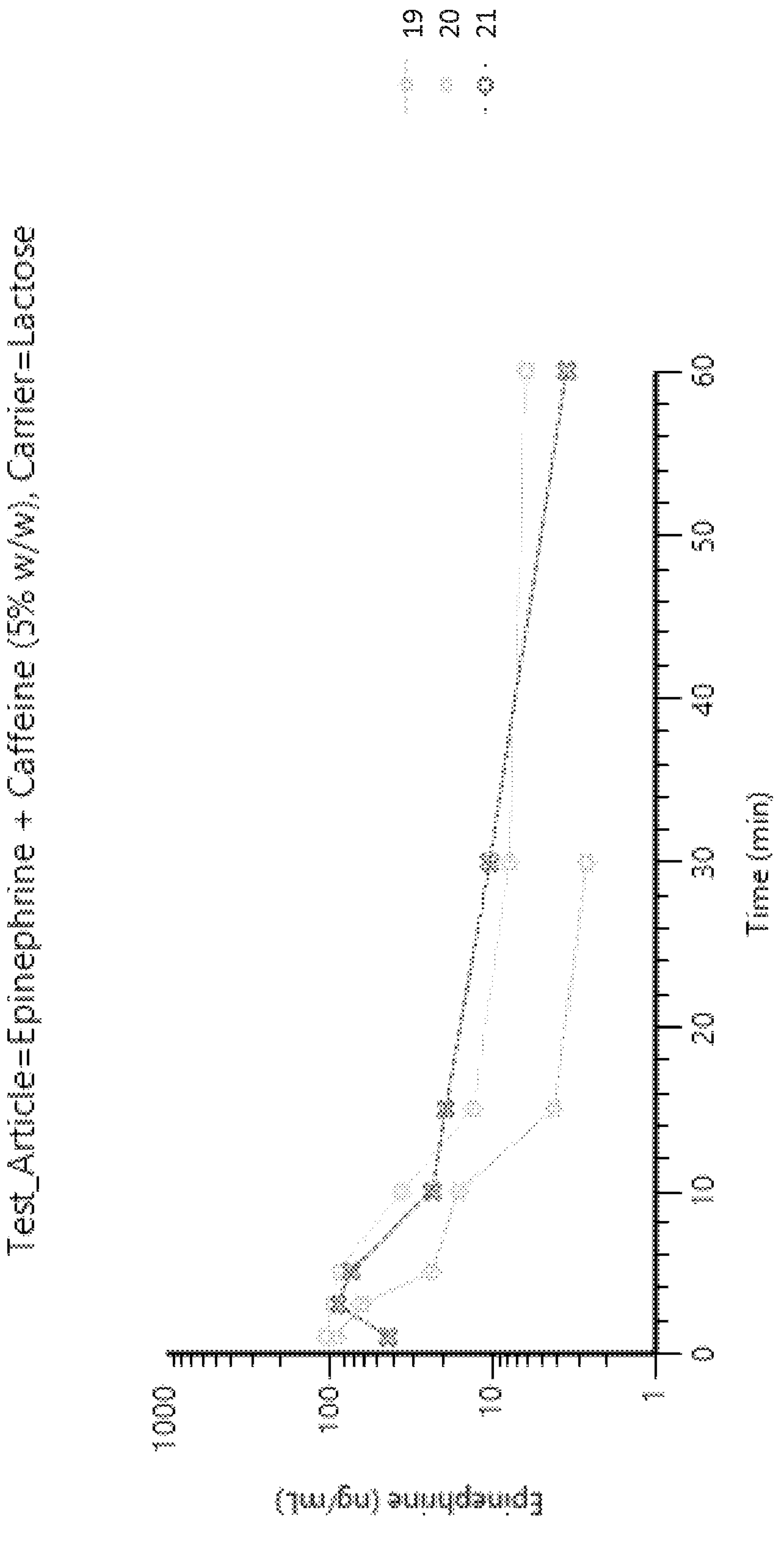
FIG. 45 is a log-linear graph of epinephrine concentration-time profiles in rats for epinephrine and caffeine (5% w/w) with a lactose carrier.

FIG. 44 is a linear graph of epinephrine concentration-time profiles in rats for epinephrine and caffeine (5% w/w) with a lactose carrier. FIG. 45 is a log-linear graph of epinephrine concentration-time profiles in rats for epinephrine and caffeine (5% w/w) with a lactose carrier.

Figure 46:
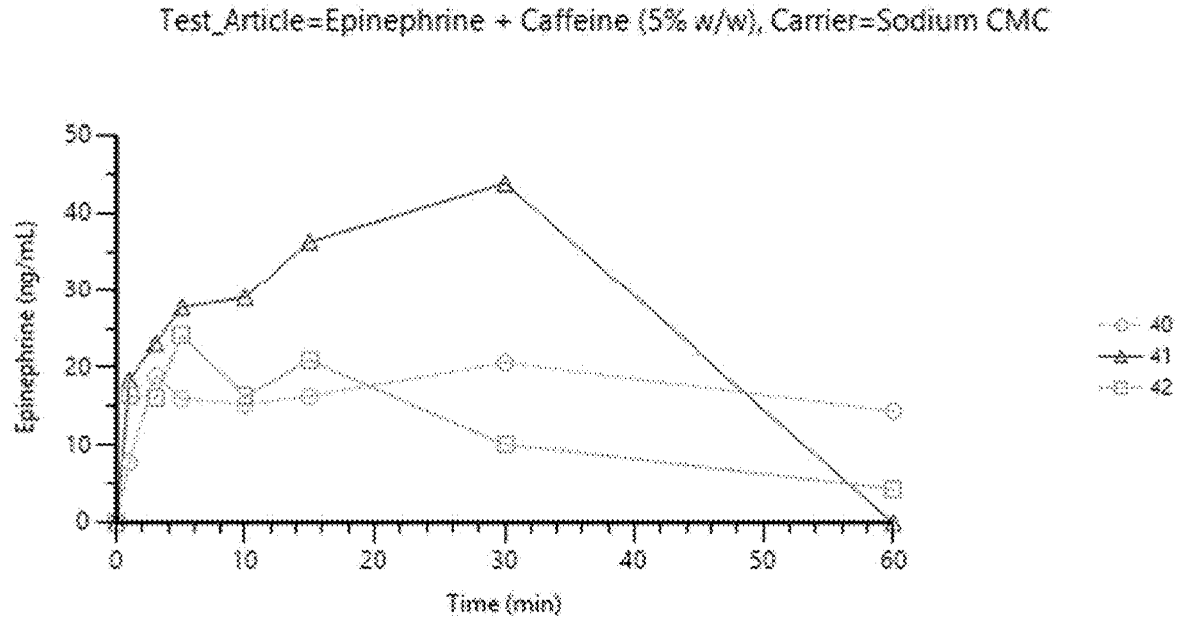
FIG. 46 is a linear graph of epinephrine concentration-time profiles in rats for epinephrine and caffeine (5% w/w) with a sodium CMC carrier.
Figure 47:
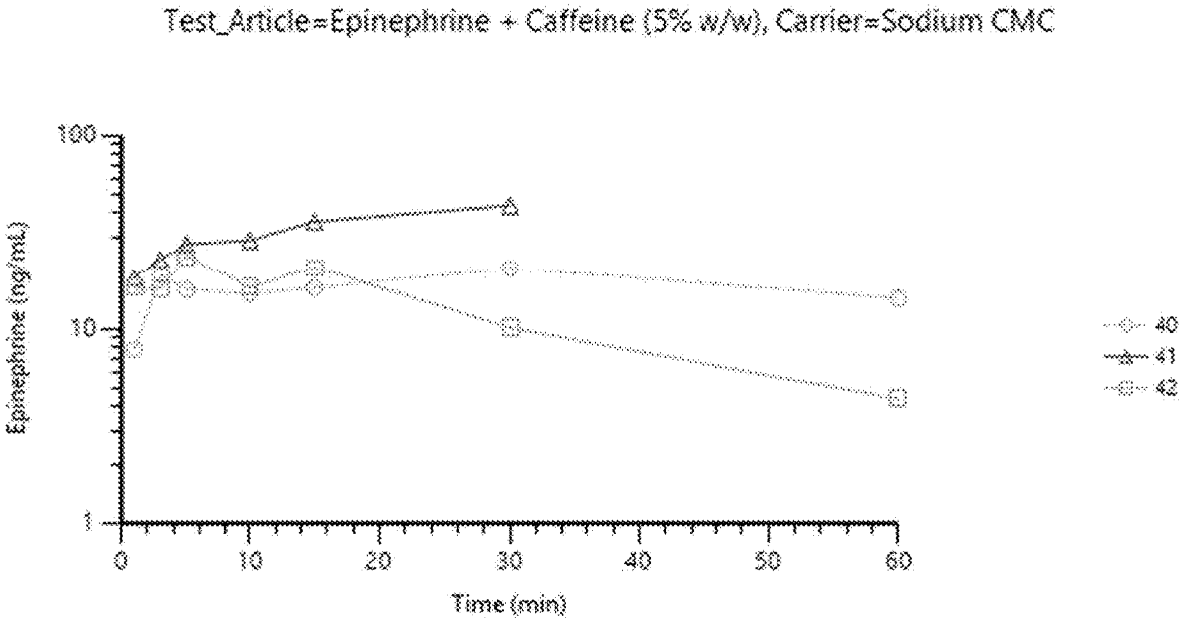
FIG. 47 is a log-linear graph of epinephrine concentration-time profiles in rats for epinephrine and caffeine (5% w/w) with a sodium CMC carrier.

FIG. 46 is a linear graph of epinephrine concentration-time profiles in rats for epinephrine and caffeine (5% w/w) with a sodium CMC carrier. FIG. 47 is a log-linear graph of epinephrine concentration-time profiles in rats for epinephrine and caffeine (5% w/w) with a sodium CMC carrier.

Figure 48:
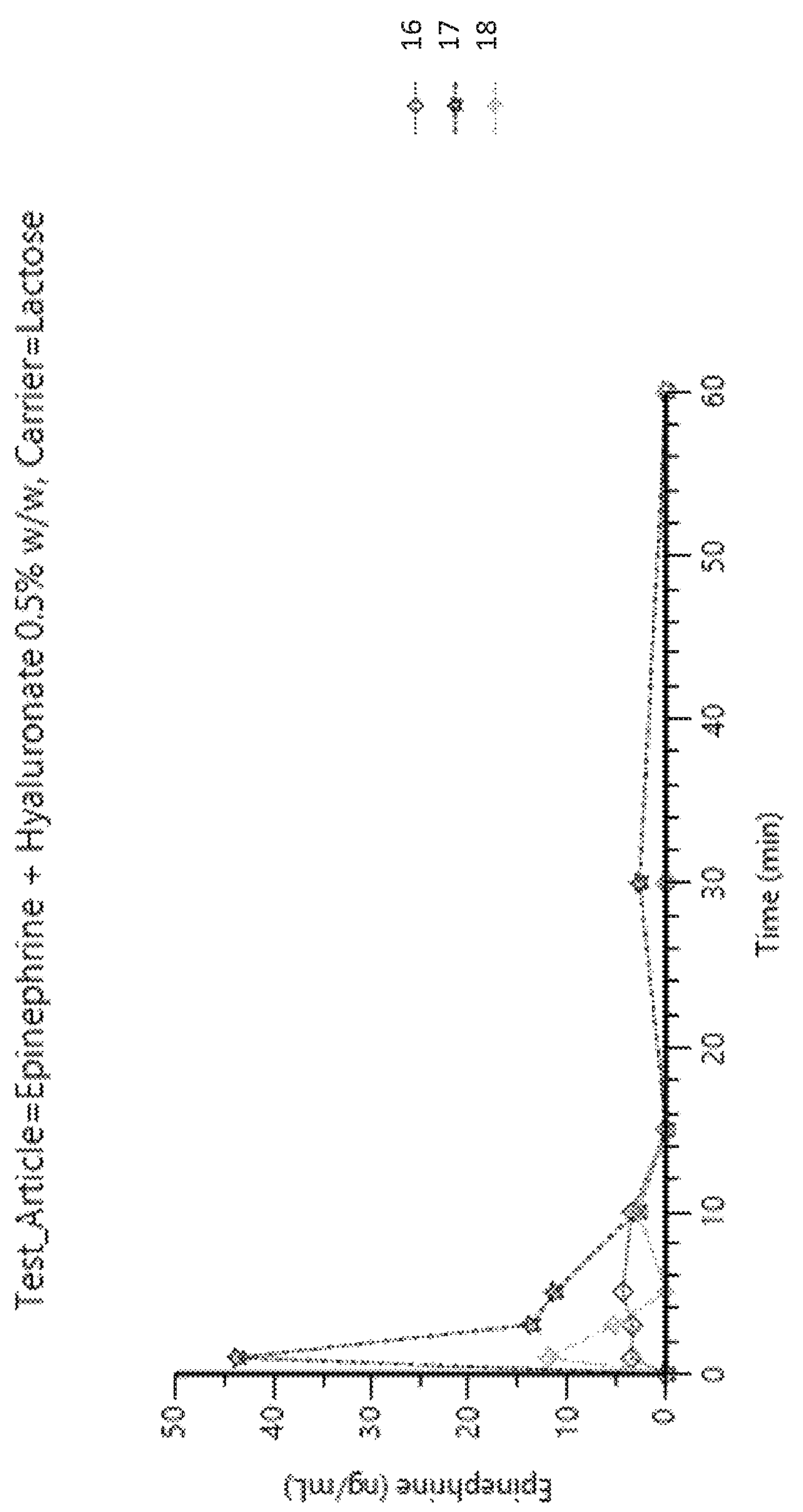
FIG. 48 is a linear graph of epinephrine concentration-time profiles in rats for epinephrine and hyaluronate (0.5% w/w) with a lactose carrier.
Figure 49:
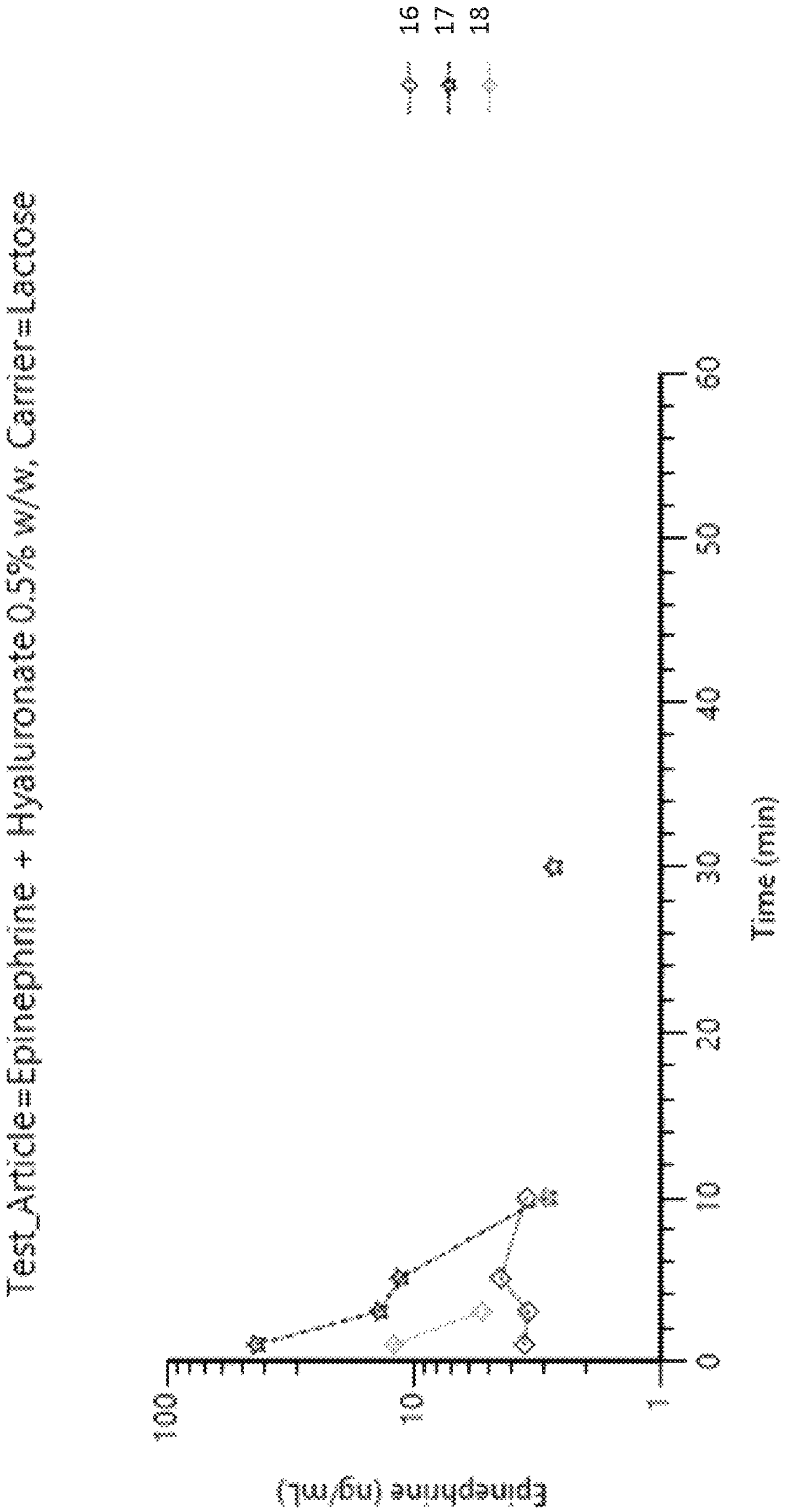
FIG. 49 is a log-linear graph of epinephrine concentration-time profiles in rats for epinephrine and hyaluronate (0.5% w/w) with a lactose carrier.

FIG. 48 is a linear graph of epinephrine concentration-time profiles in rats for epinephrine and hyaluronate (0.5% w/w) with a lactose carrier. FIG. 49 is a log-linear graph of epinephrine concentration-time profiles in rats for epinephrine and hyaluronate (0.5% w/w) with a lactose carrier.

Figure 50:
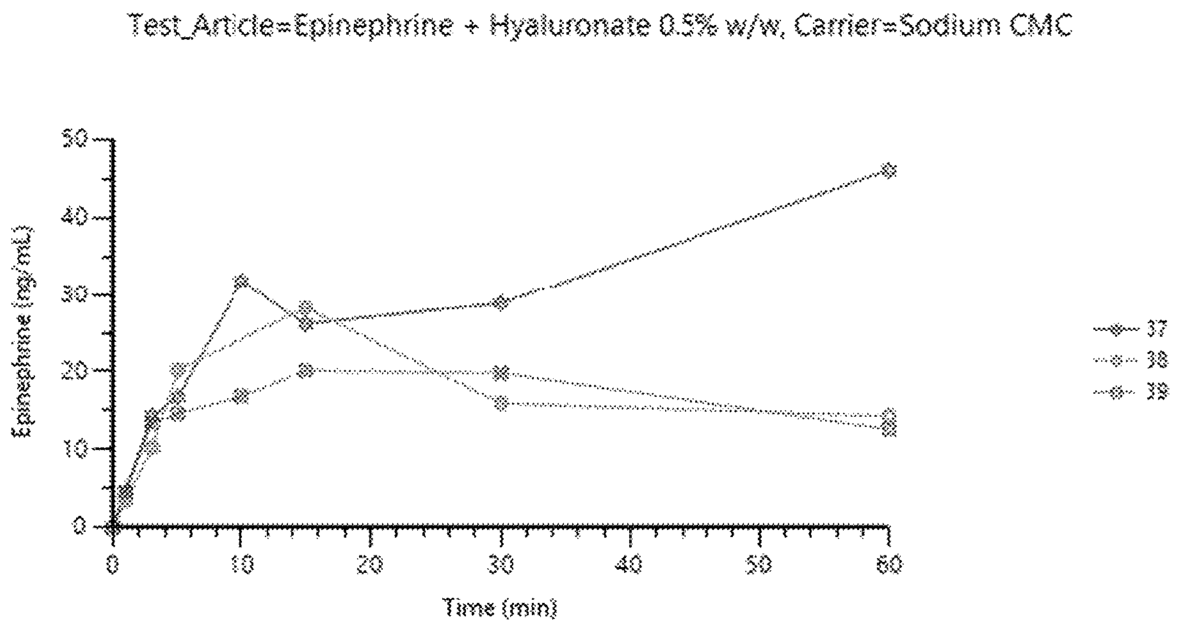
FIG. 50 is a linear graph of epinephrine concentration-time profiles in rats for epinephrine and hyaluronate (0.5% w/w) with a sodium CMC carrier.
Figure 51:
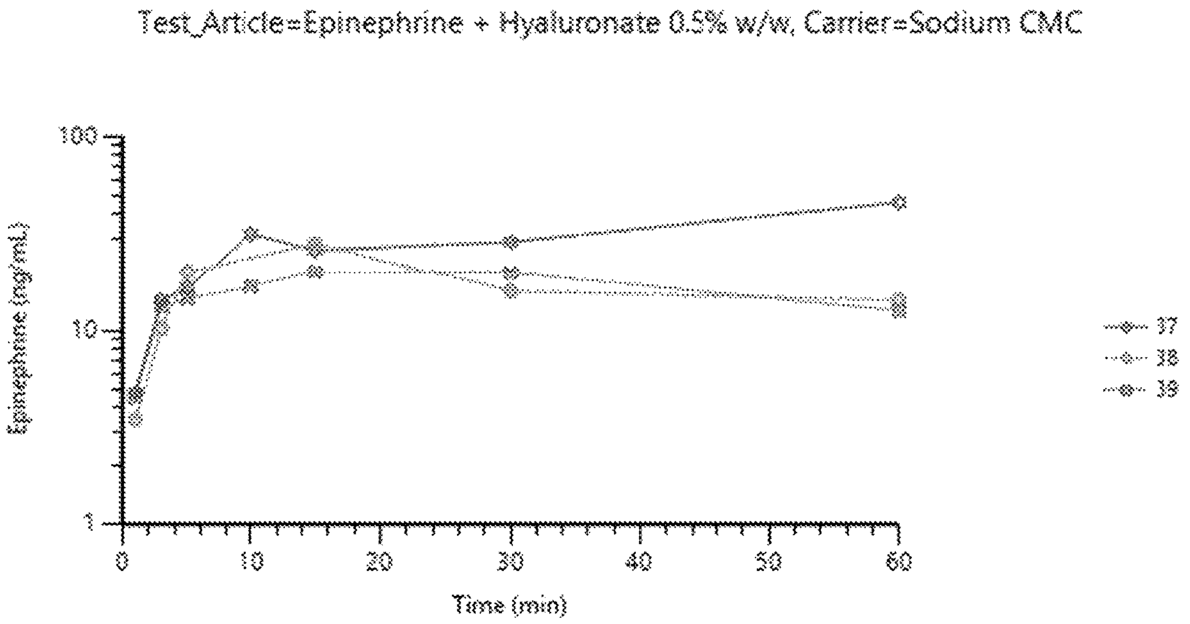
FIG. 51 is a log-linear graph of epinephrine concentration-time profiles in rats for epinephrine and hyaluronate (0.5% w/w) with a sodium CMC carrier.

FIG. 50 is a linear graph of epinephrine concentration-time profiles in rats for epinephrine and hyaluronate (0.5% w/w) with a sodium CMC carrier. FIG. 51 is a log-linear graph of epinephrine concentration-time profiles in rats for epinephrine and hyaluronate (0.5% w/w) with a sodium CMC carrier.

Figure 52:
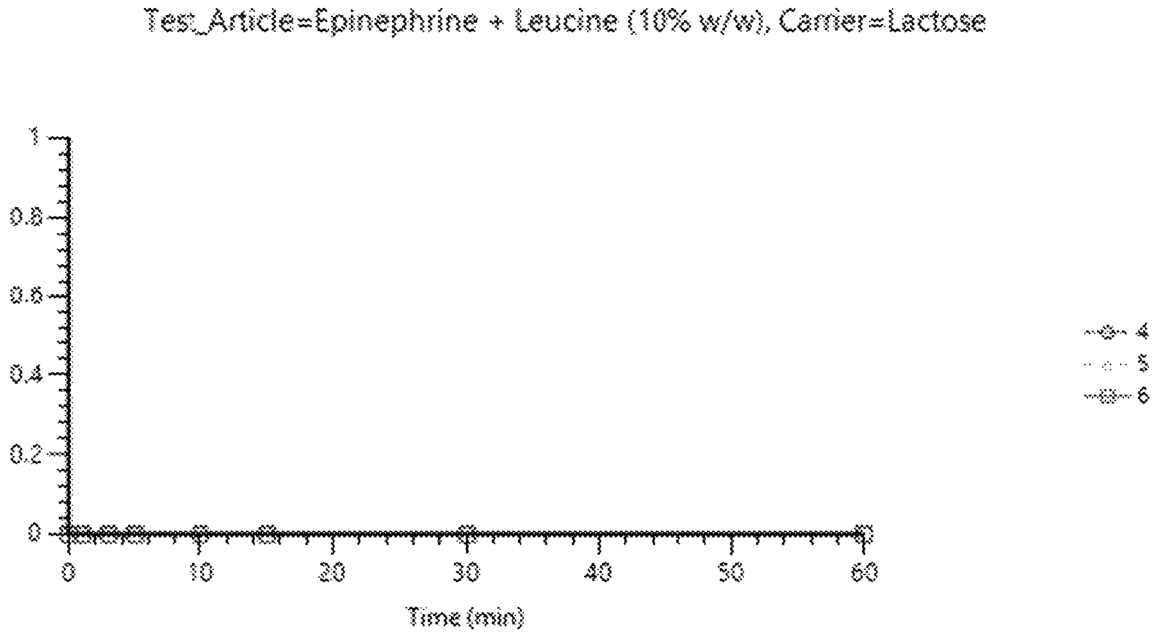
FIG. 52 is a linear graph of epinephrine concentration-time profiles in rats for epinephrine and leucine (10% w/w) with a lactose carrier.
Figure 53:
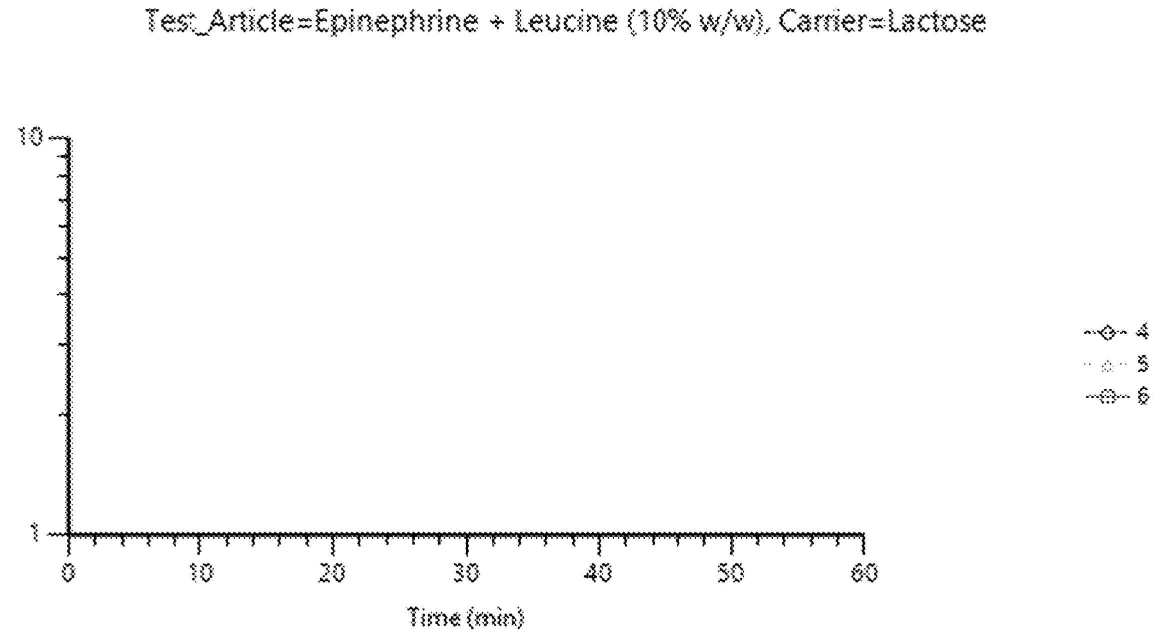
FIG. 53 is a log-linear graph of epinephrine concentration-time profiles in rats for epinephrine and leucine (10% w/w) with a lactose carrier.

FIG. 52 is a linear graph of epinephrine concentration-time profiles in rats for epinephrine and leucine (10% w/w) with a lactose carrier. FIG. 53 is a log-linear graph of epinephrine concentration-time profiles in rats for epinephrine and leucine (10% w/w) with a lactose carrier.

Figure 54:
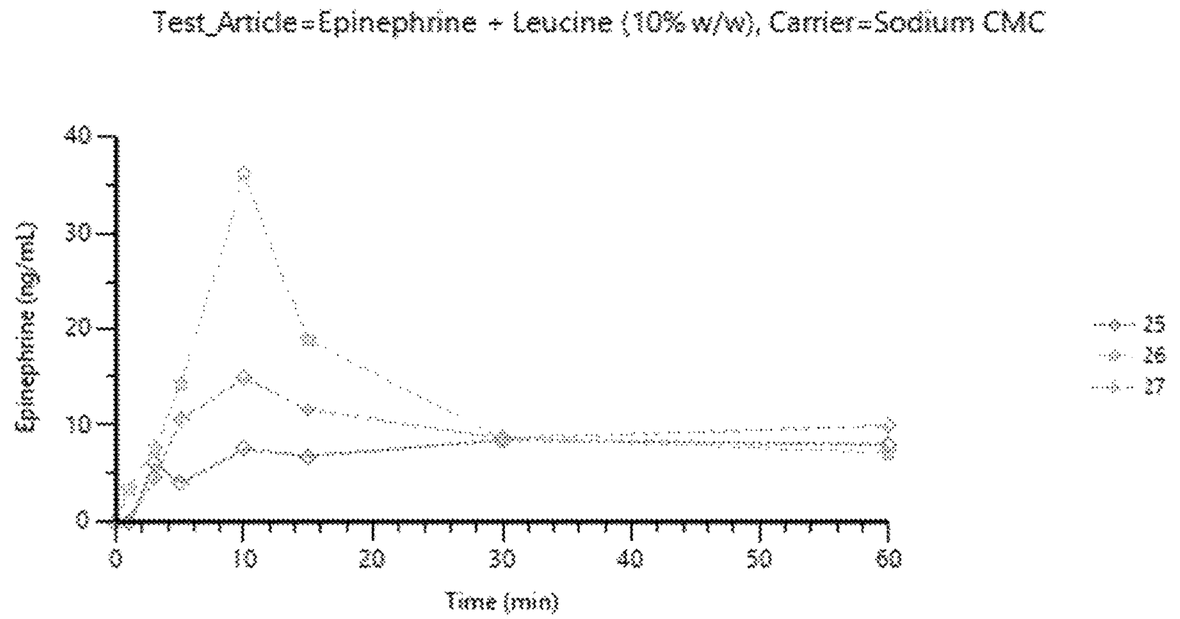
FIG. 54 is a linear graph of epinephrine concentration-time profiles in rats for epinephrine and leucine (10% w/w) with a sodium CMC carrier.
Figure 55:
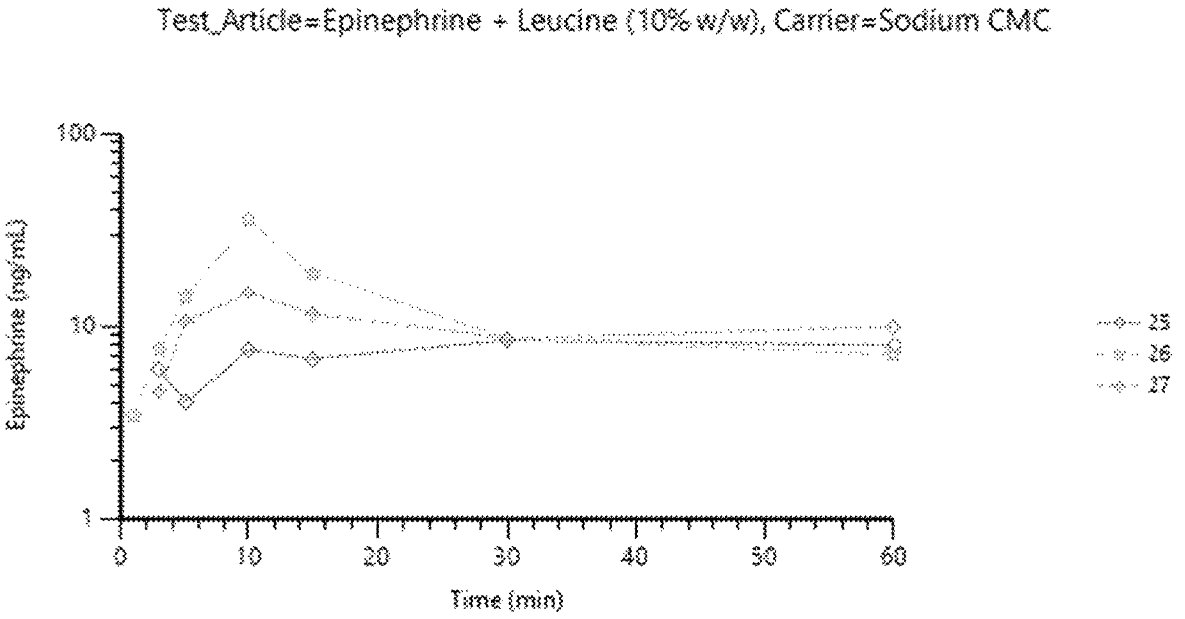
FIG. 55 is a log-linear graph of epinephrine concentration-time profiles in rats for epinephrine and leucine (10% w/w) with a sodium CMC carrier.

FIG. 54 is a linear graph of epinephrine concentration-time profiles in rats for epinephrine and leucine (10% w/w) with a sodium CMC carrier. FIG. 55 is a log-linear graph of epinephrine concentration-time profiles in rats for epinephrine and leucine (10% w/w) with a sodium CMC carrier.

Figure 56:
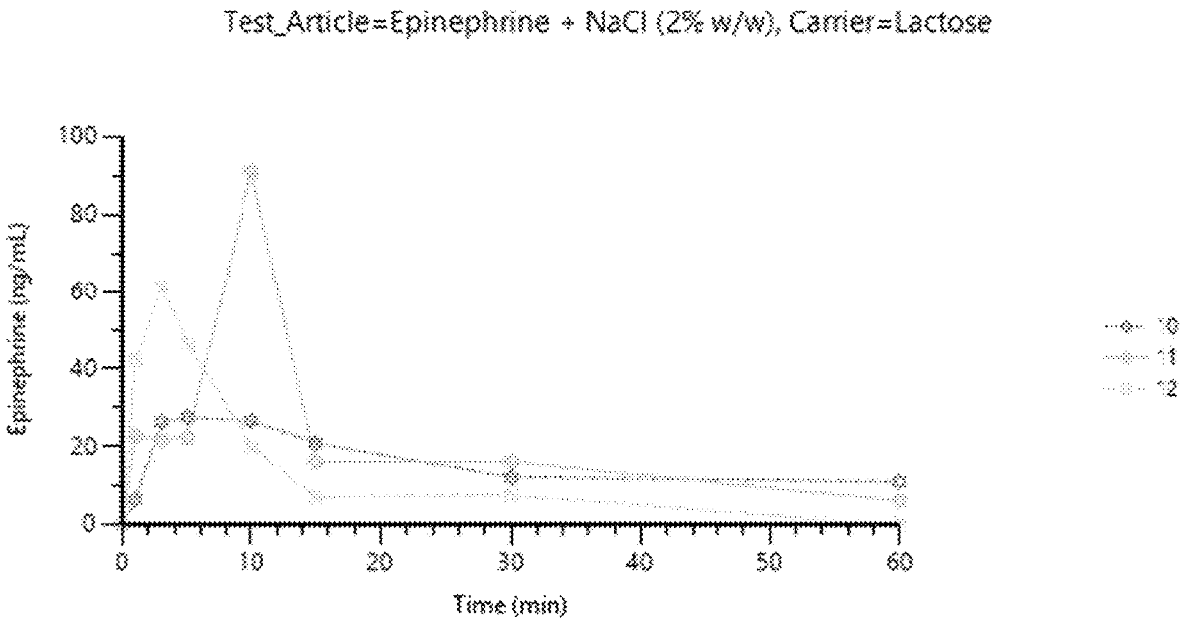
FIG. 56 is a linear graph of epinephrine concentration-time profiles in rats for epinephrine and sodium chloride (2% w/w) with a lactose carrier.
Figure 57:
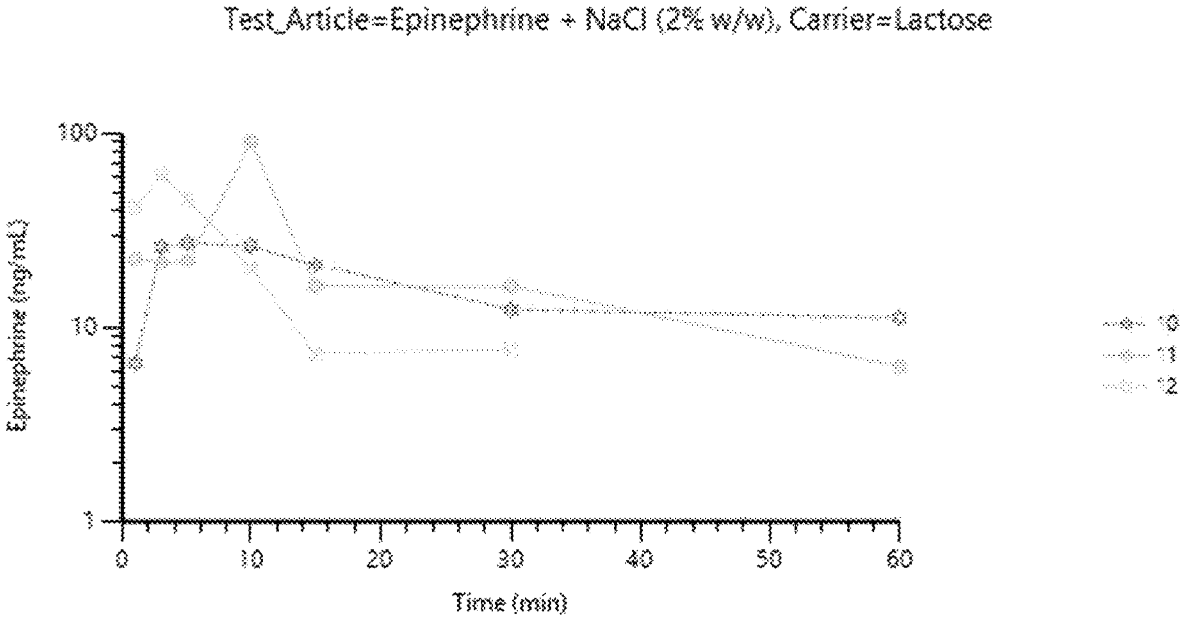
FIG. 57 is a log-linear graph of epinephrine concentration-time profiles in rats for epinephrine and sodium chloride (2% w/w) with a lactose carrier.

FIG. 56 is a linear graph of epinephrine concentration-time profiles in rats for epinephrine and sodium chloride (2% w/w) with a lactose carrier. FIG. 57 is a log-linear graph of epinephrine concentration-time profiles in rats for epinephrine and sodium chloride (2% w/w) with a lactose carrier.

Figure 58:
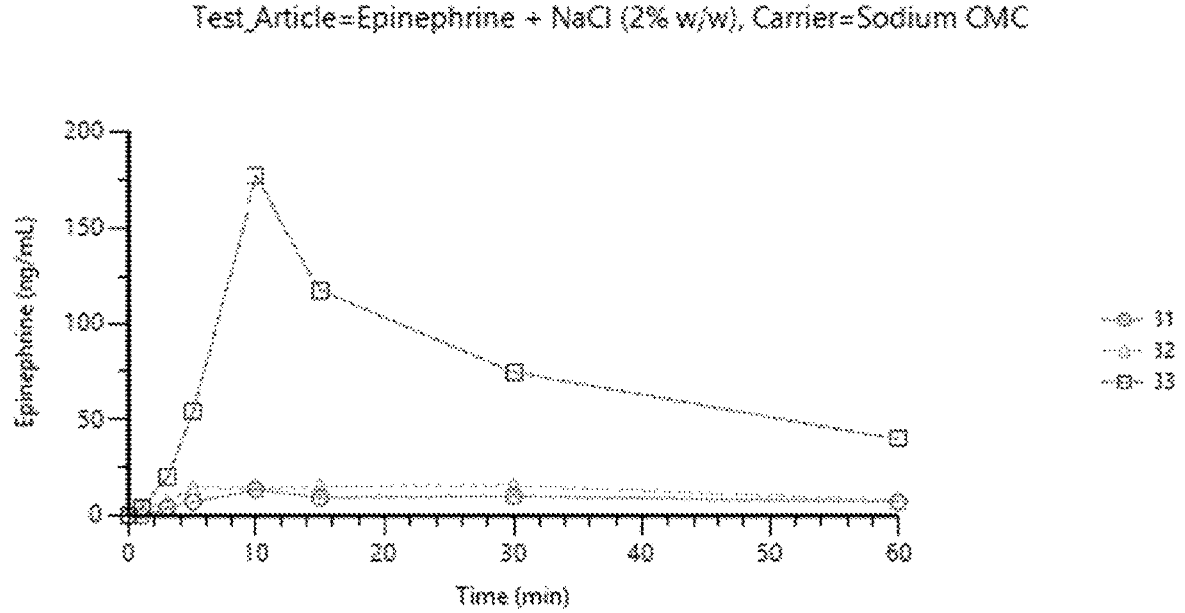
FIG. 58 is a linear graph of epinephrine concentration-time profiles in rats for epinephrine and sodium chloride (2% w/w) with a sodium CMC carrier.
Figure 59:
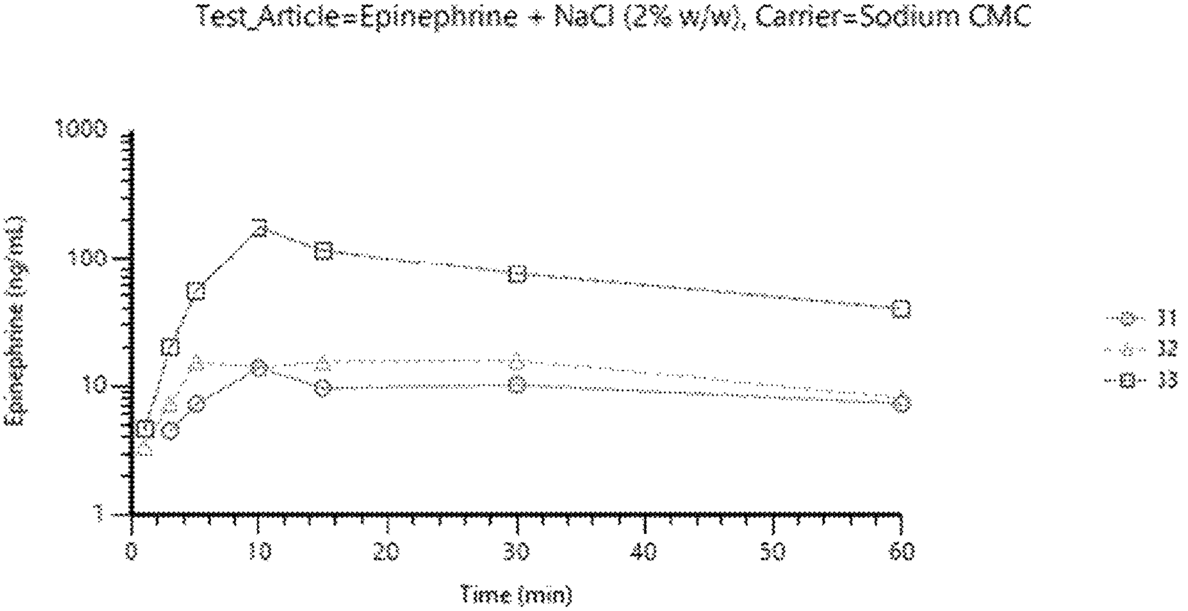
FIG. 59 is a log-linear graph of epinephrine concentration-time profiles in rats for epinephrine and sodium chloride (2% w/w) with a sodium CMC carrier.

FIG. 58 is a linear graph of epinephrine concentration-time profiles in rats for epinephrine and sodium chloride (2% w/w) with a sodium CMC carrier. FIG. 59 is a log-linear graph of epinephrine concentration-time profiles in rats for epinephrine and sodium chloride (2% w/w) with a sodium CMC carrier.

Figure 60:
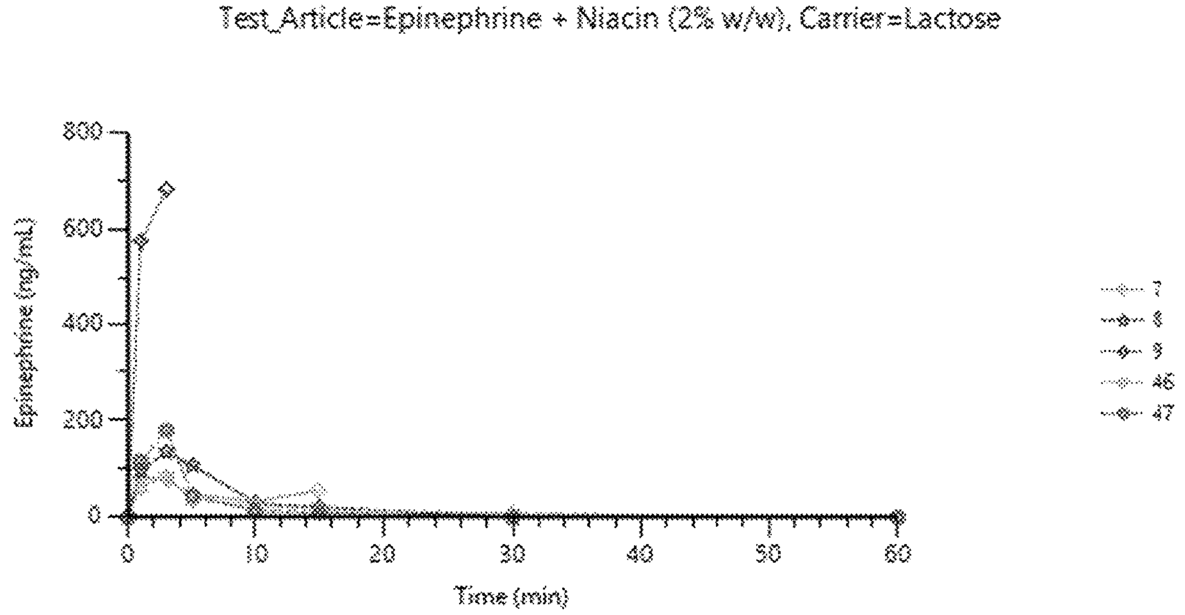
FIG. 60 is a linear graph of epinephrine concentration-time profiles in rats for epinephrine and niacin (2% w/w) with a lactose carrier.
Figure 61:
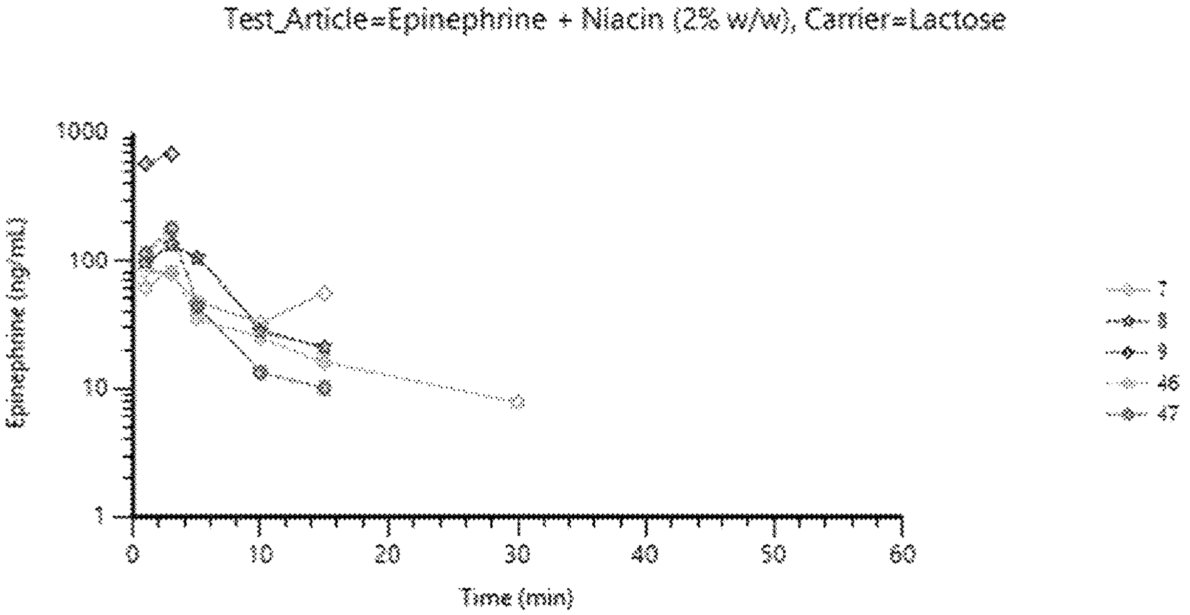
FIG. 61 is a log-linear graph of epinephrine concentration-time profiles in rats for epinephrine and niacin (2% w/w) with a lactose carrier.

FIG. 60 is a linear graph of epinephrine concentration-time profiles in rats for epinephrine and niacin (2% w/w) with a lactose carrier. FIG. 61 is a log-linear graph of epinephrine concentration-time profiles in rats for epinephrine and niacin (2% w/w) with a lactose carrier.

Figure 62:
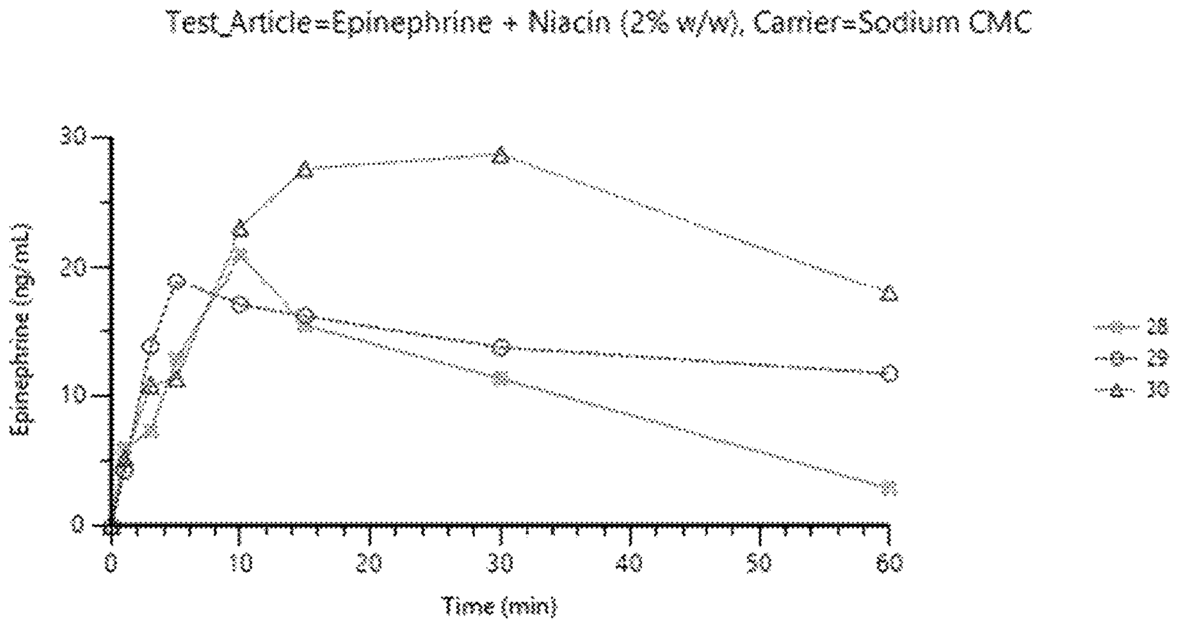
FIG. 62 is a linear graph of epinephrine concentration-time profiles in rats for epinephrine and niacin (2% w/w) with a sodium CMC carrier.
Figure 63:
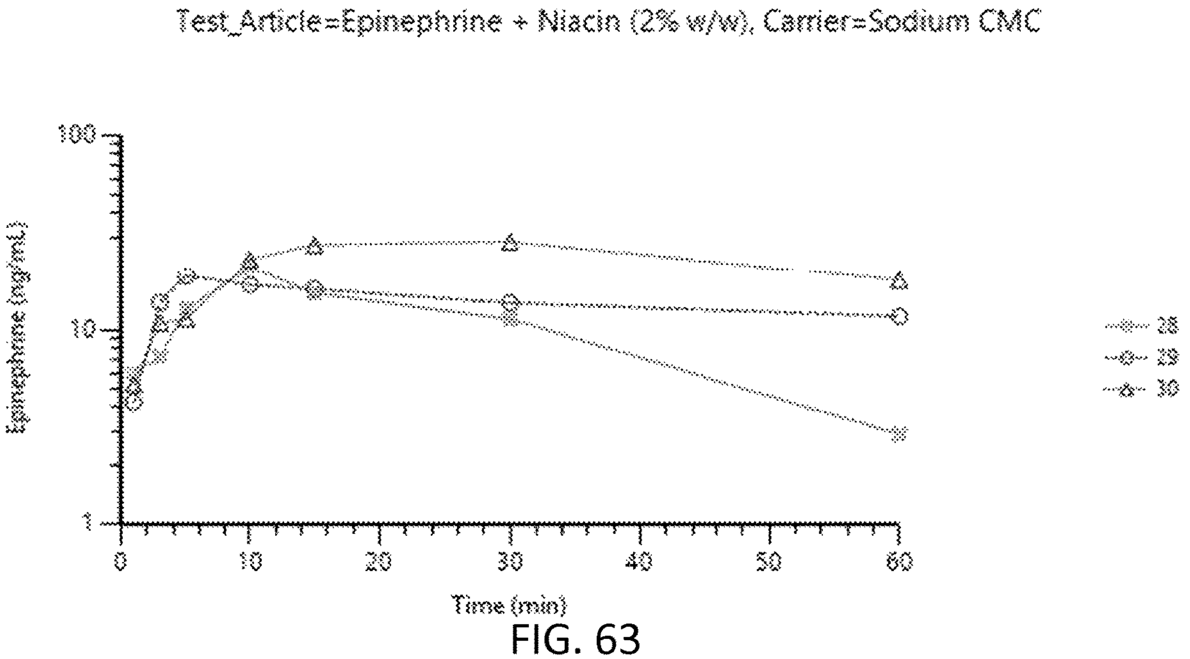
FIG. 63 is a log-linear graph of epinephrine concentration-time profiles in rats for epinephrine and niacin (2% w/w) with a sodium CMC carrier.

FIG. 62 is a linear graph of epinephrine concentration-time profiles in rats for epinephrine and niacin (2% w/w) with a sodium CMC carrier. FIG. 63 is a log-linear graph of epinephrine concentration-time profiles in rats for epinephrine and niacin (2% w/w) with a sodium CMC carrier.

Figure 64:
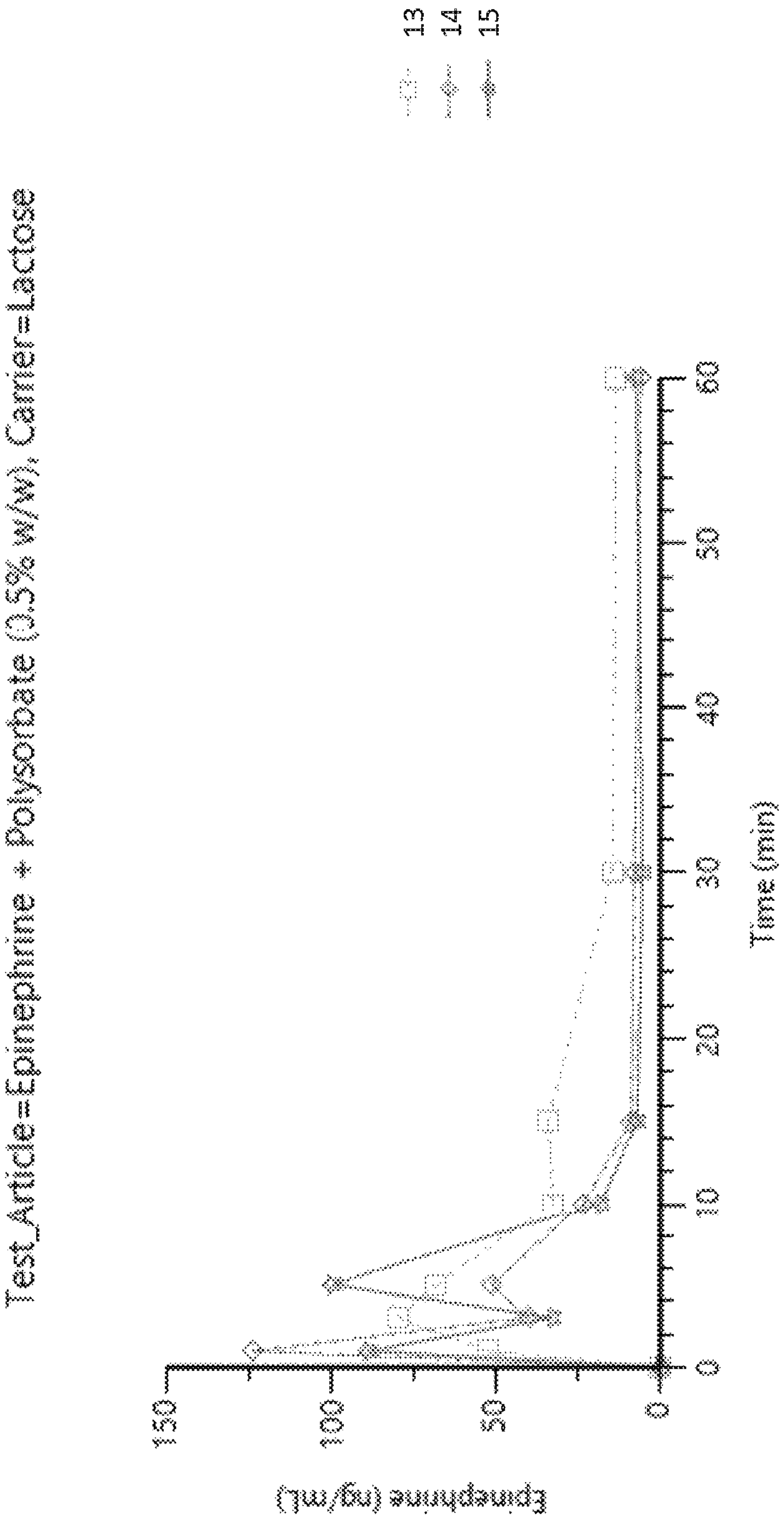
FIG. 64 is a linear graph of epinephrine concentration-time profiles in rats for epinephrine and polysorbate (0.5% w/w) with a lactose carrier.
Figure 65:
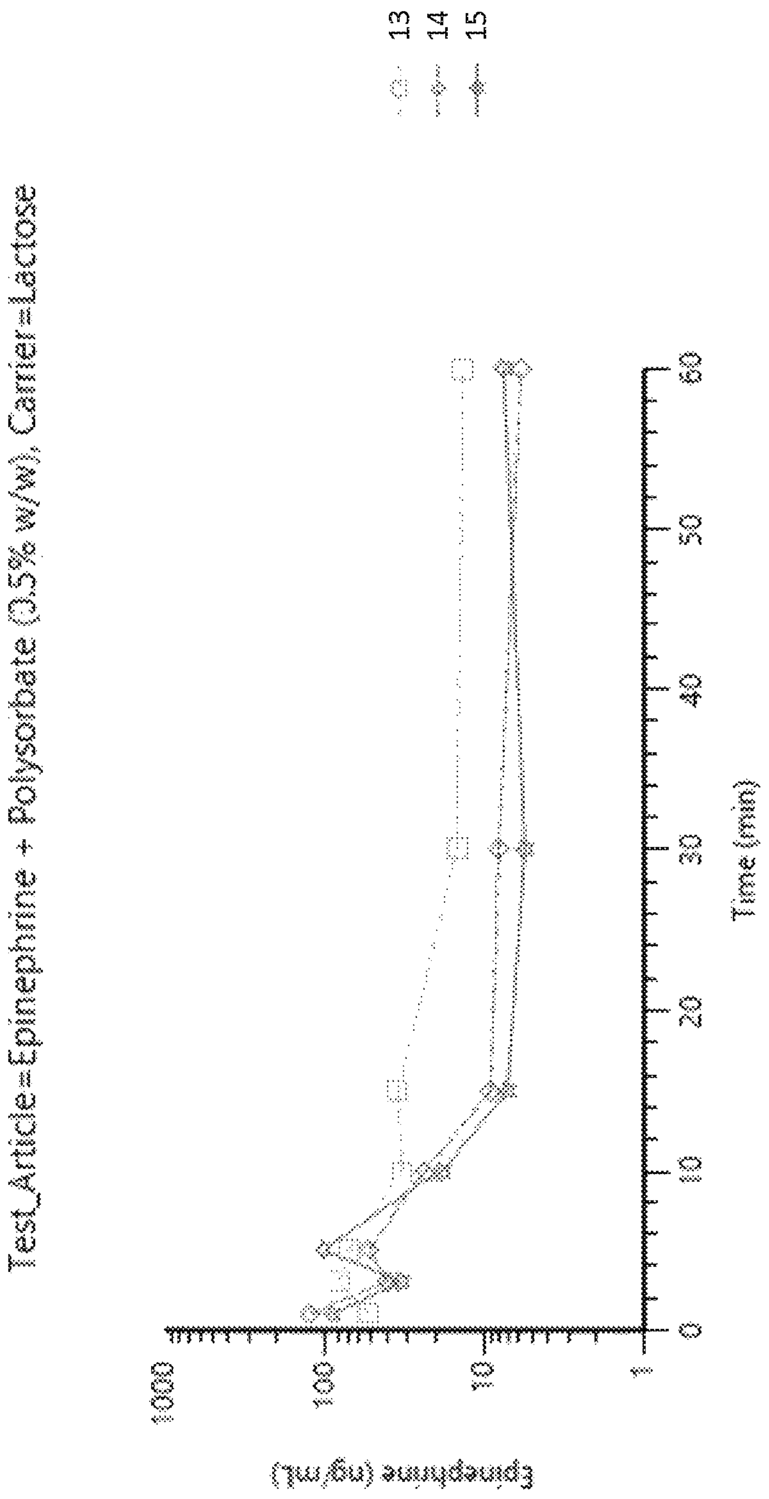
FIG. 65 is a log-linear graph of epinephrine concentration-time profiles in rats for epinephrine and polysorbate (0.5% w/w) with a lactose carrier.

FIG. 64 is a linear graph of epinephrine concentration-time profiles in rats for epinephrine and polysorbate (0.5% w/w) with a lactose carrier. FIG. 65 is a log-linear graph of epinephrine concentration-time profiles in rats for epinephrine and polysorbate (0.5% w/w) with a lactose carrier.

Figure 66:
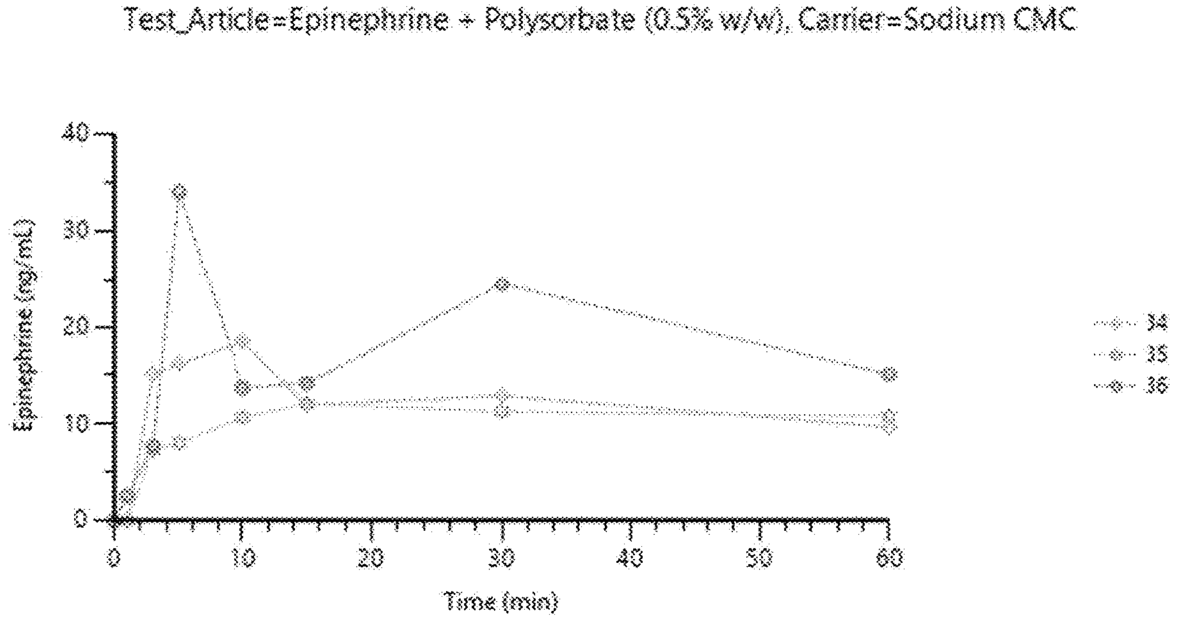
FIG. 66 is a linear graph of epinephrine concentration-time profiles in rats for epinephrine and polysorbate (0.5% w/w) with a sodium CMC carrier.
Figure 67:
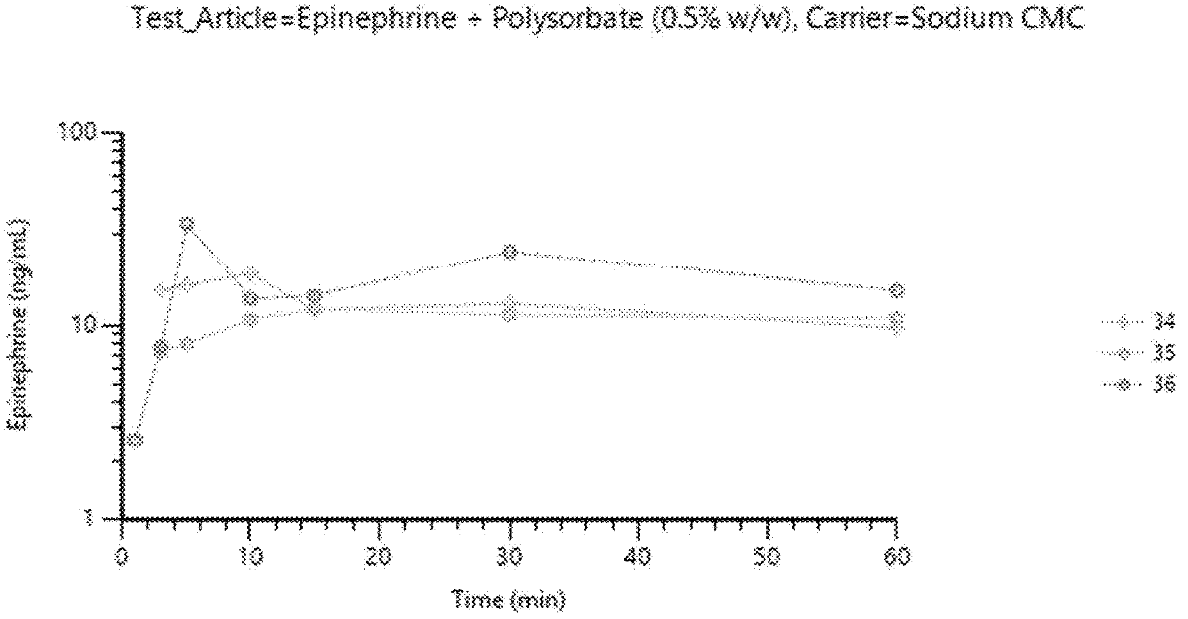
FIG. 67 is a log-linear graph of epinephrine concentration-time profiles in rats for epinephrine and polysorbate (0.5% w/w) with a sodium CMC carrier.

FIG. 66 is a linear graph of epinephrine concentration-time profiles in rats for epinephrine and polysorbate (0.5% w/w) with a sodium CMC carrier. FIG. 67 is a log-linear graph of epinephrine concentration-time profiles in rats for epinephrine and polysorbate (0.5% w/w) with a sodium CMC carrier.

Figure 68:
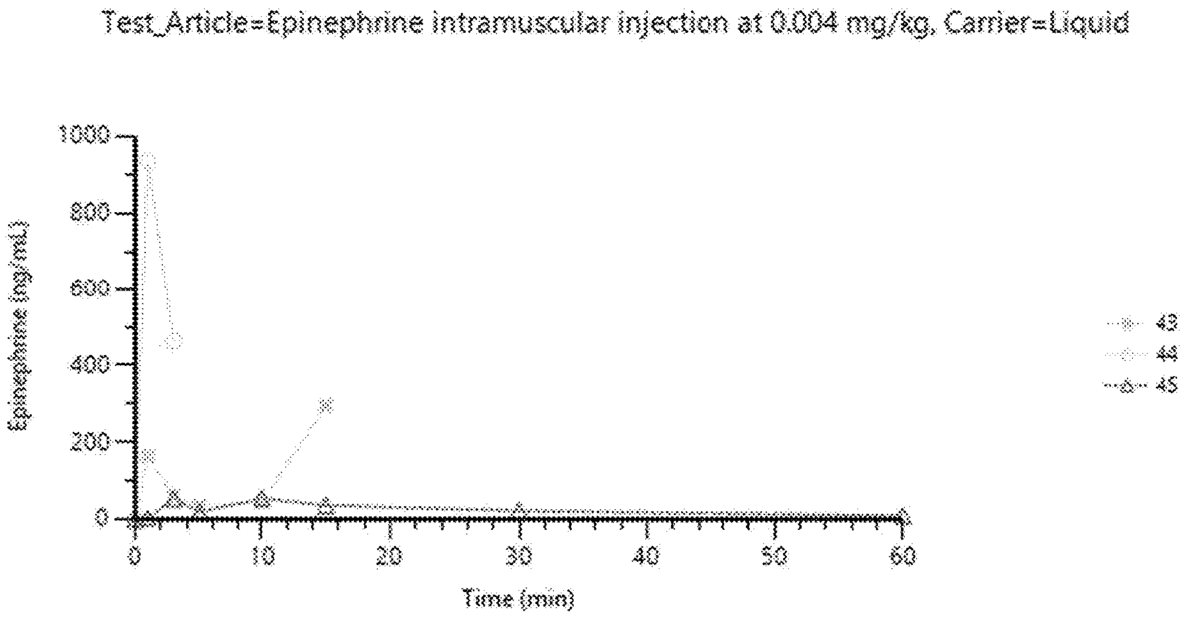
FIG. 68 is a linear graph of epinephrine concentration-time profiles in rats for epinephrine intramuscular injection at 0.7 mg/kg.
Figure 69:
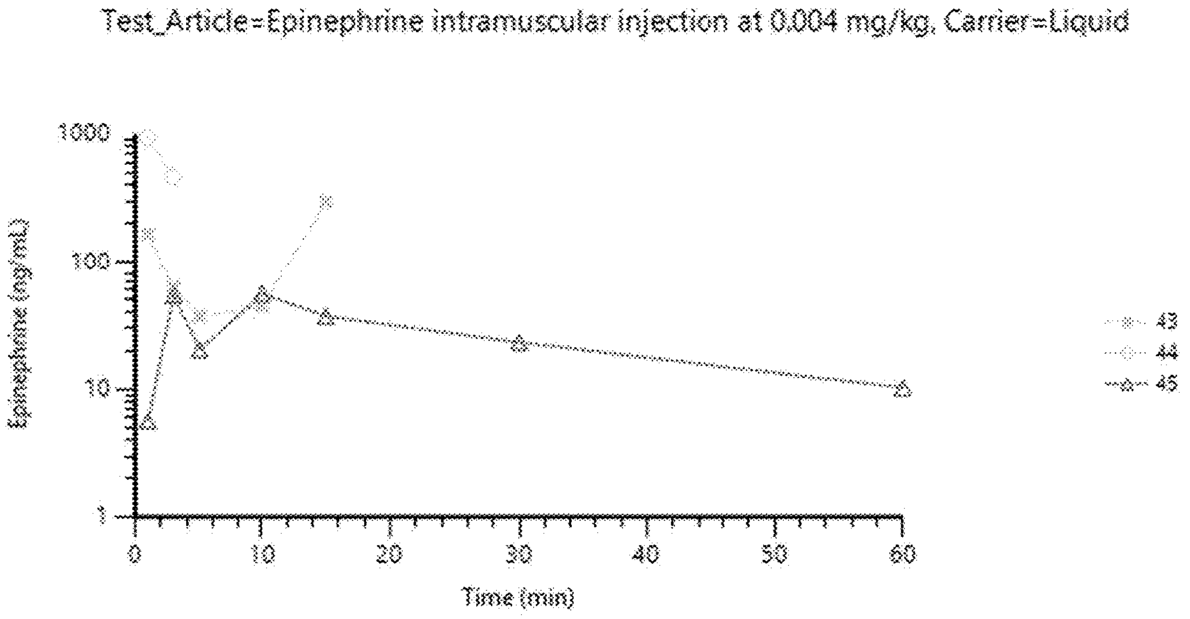
FIG. 69 is a log-linear graph of epinephrine concentration-time profiles in rats for epinephrine intramuscular injection at 0.7 mg/kg.

FIG. 68 is a linear graph of epinephrine concentration-time profiles in rats for epinephrine intramuscular injection at 0.7 mg/kg. FIG. 69 is a log-linear graph of epinephrine concentration-time profiles in rats for epinephrine intramuscular injection at 0.7 mg/kg.

Figure 70:
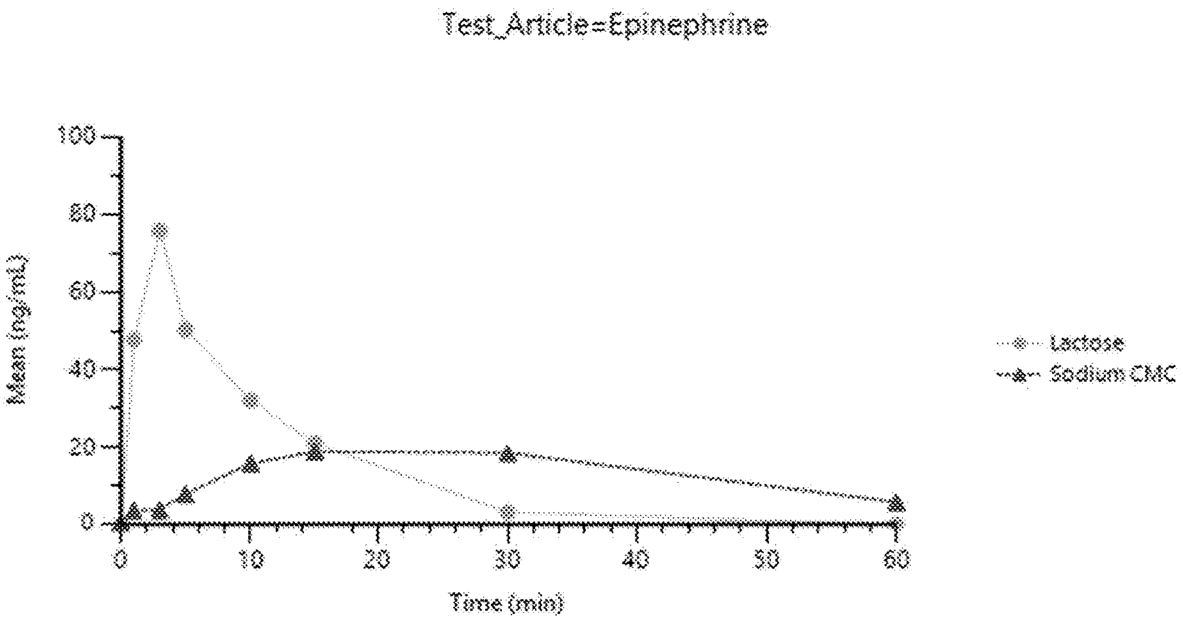
FIG. 70 is a graph of mean epinephrine concentration-time profiles following IN administration in rats for epinephrine with a lactose carrier and epinephrine with a sodium CMC carrier.

FIG. 70 is a graph of mean epinephrine concentration-time profiles following IN administration in rats for epinephrine with a lactose carrier and epinephrine with a sodium CMC carrier.

Figure 71:
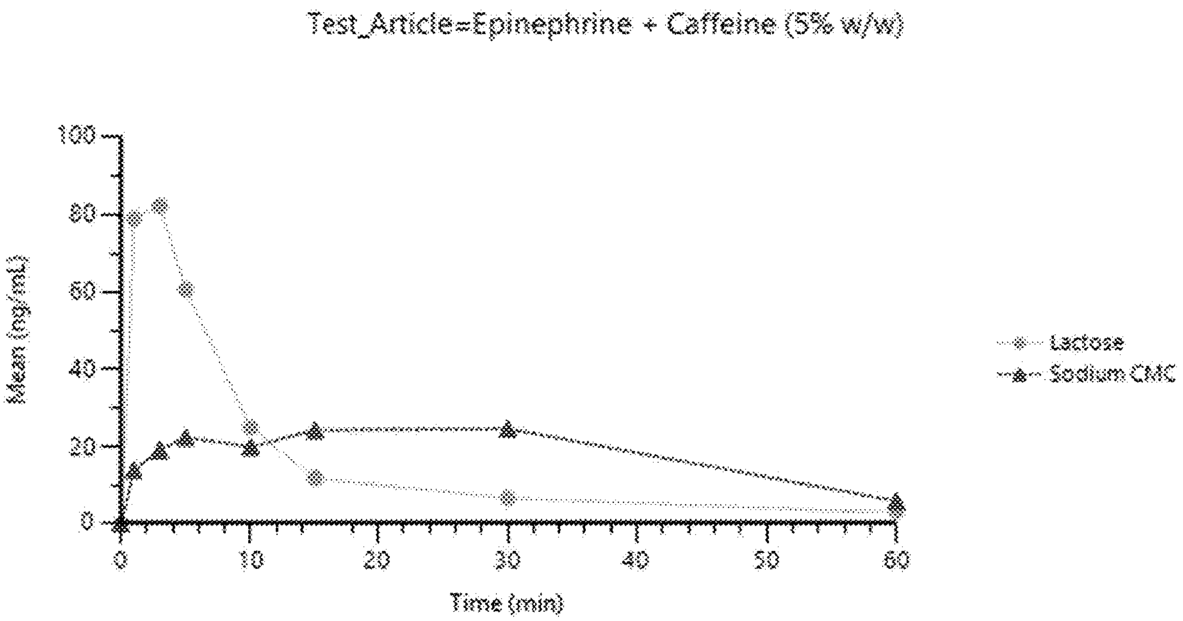
FIG. 71 is a graph of mean epinephrine concentration-time profiles following IN administration in rats for epinephrine and caffeine (5% w/w) with a lactose carrier and epinephrine and caffeine (5% w/w) with a sodium CMC carrier.

FIG. 71 is a graph of mean epinephrine concentration-time profiles following IN administration in rats for epinephrine and caffeine (5% w/w) with a lactose carrier and epinephrine and caffeine (5% w/w) with a sodium CMC carrier.

Figure 72:
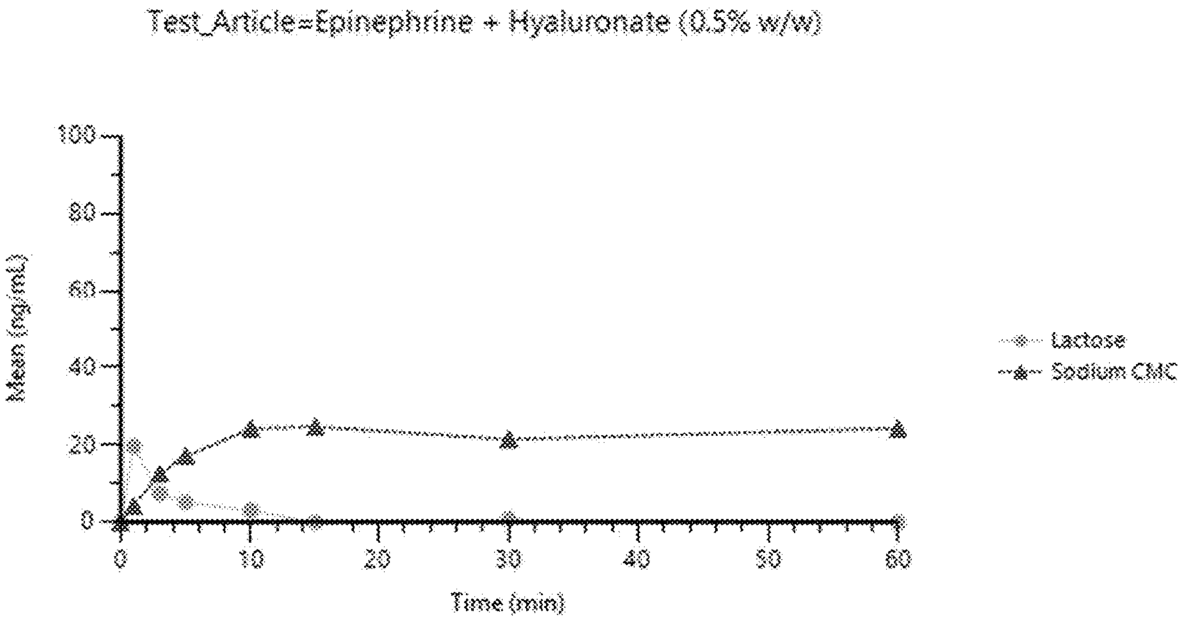
FIG. 72 is a graph of mean epinephrine concentration-time profiles following IN administration in rats for epinephrine and hyaluronate (0.5% w/w) with a lactose carrier and epinephrine and hyaluronate (0.5% w/w) with a sodium CMC carrier.

FIG. 72 is a graph of mean epinephrine concentration-time profiles following IN administration in rats for epinephrine and hyaluronate (0.5% w/w) with a lactose carrier and epinephrine and hyaluronate (0.5% w/w) with a sodium CMC carrier.

Figure 73:
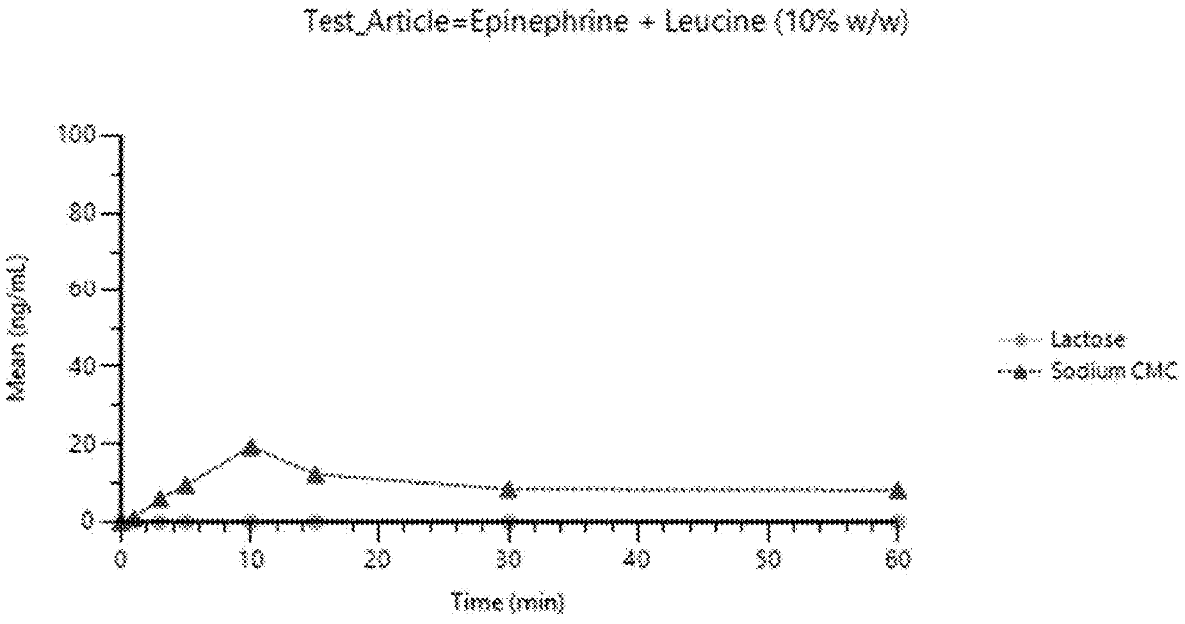
FIG. 73 is a graph of mean epinephrine concentration-time profiles following IN administration in rats for epinephrine and leucine (10% w/w) with a lactose carrier and epinephrine and leucine (10% w/w) with a sodium CMC carrier.

FIG. 73 is a graph of mean epinephrine concentration-time profiles following IN administration in rats for epinephrine and leucine (10% w/w) with a lactose carrier and epinephrine and leucine (10% w/w) with a sodium CMC carrier.

Figure 74:
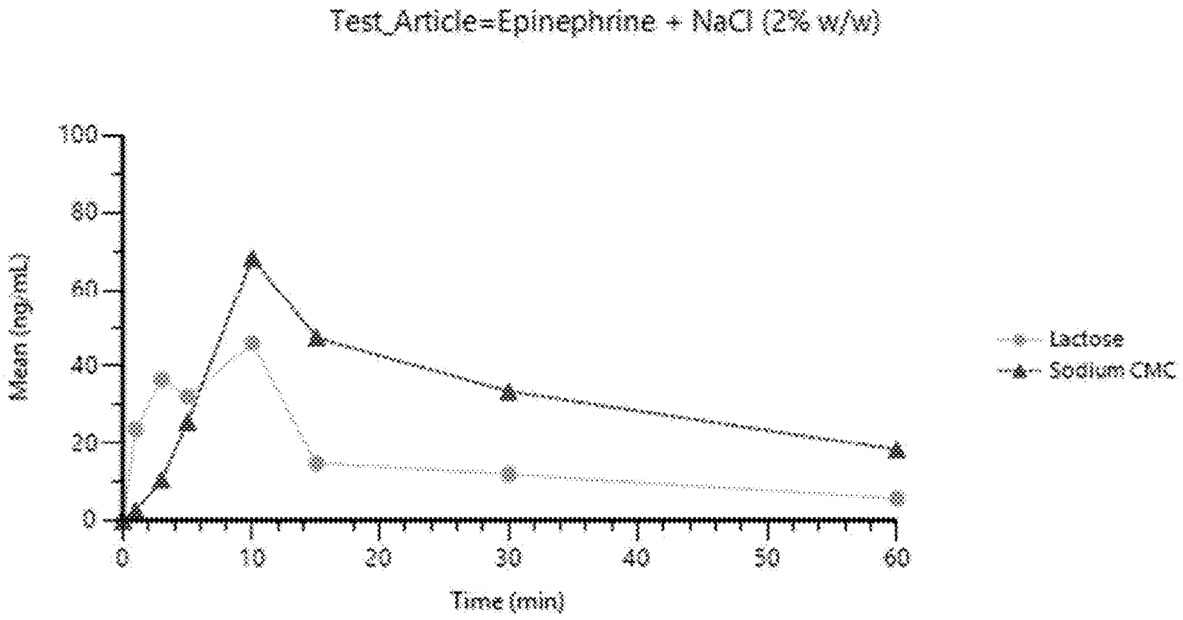
FIG. 74 is a graph of mean epinephrine concentration-time profiles following IN administration in rats for epinephrine and sodium chloride (2% w/w) with a lactose carrier and epinephrine and sodium chloride (2% w/w) with a sodium CMC carrier.

FIG. 74 is a graph of mean epinephrine concentration-time profiles following IN administration in rats for epinephrine and sodium chloride (2% w/w) with a lactose carrier and epinephrine and sodium chloride (2% w/w) with a sodium CMC carrier.

Figure 75:
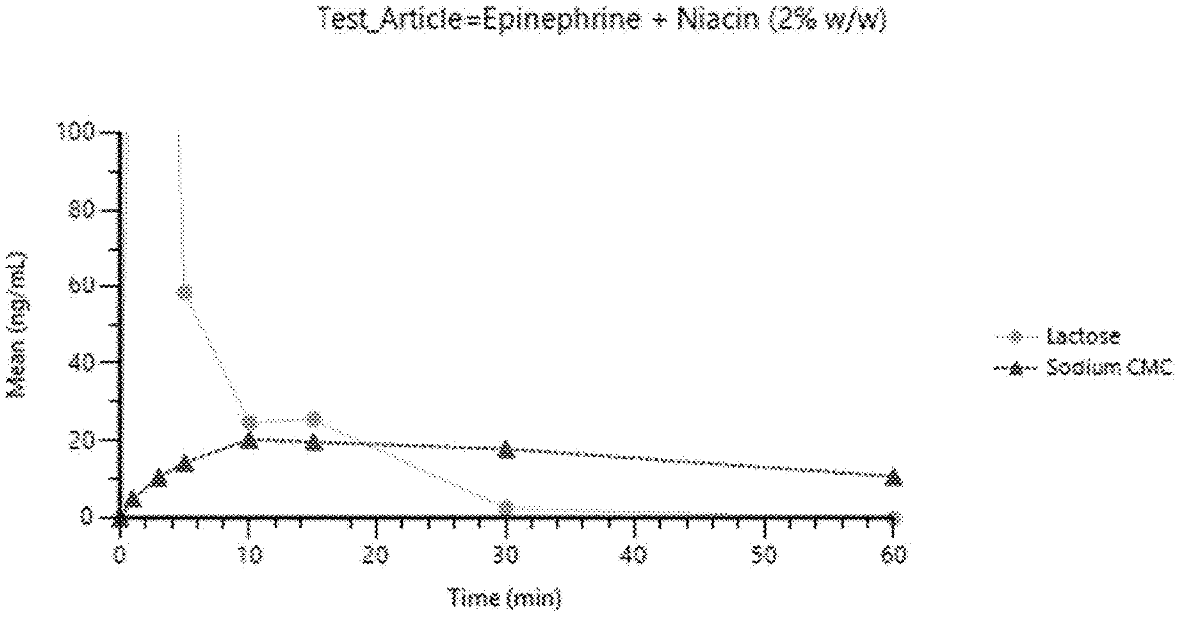
FIG. 75 is a graph of mean epinephrine concentration-time profiles following IN administration in rats for epinephrine and niacin (2% w/w) with a lactose carrier and epinephrine and niacin (2% w/w) with a sodium CMC carrier.

FIG. 75 is a graph of mean epinephrine concentration-time profiles following IN administration in rats for epinephrine and niacin (2% w/w) with a lactose carrier and epinephrine and niacin (2% w/w) with a sodium CMC carrier.

Figure 76:
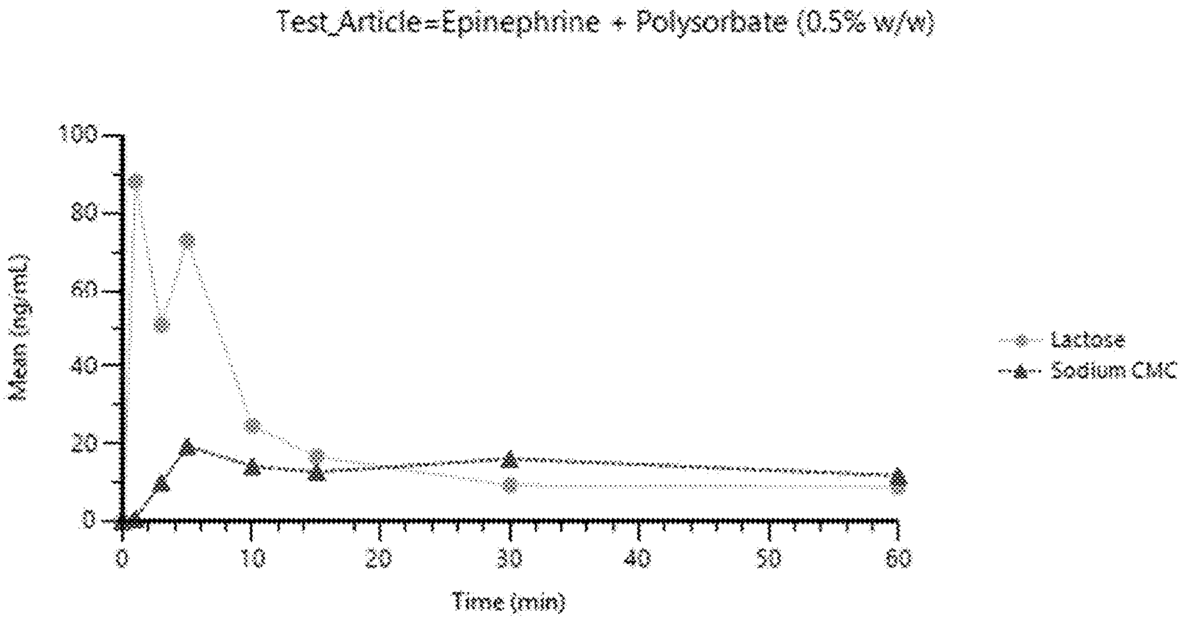
FIG. 76 is a graph of mean epinephrine concentration-time profiles following IN administration in rats for epinephrine and polysorbate (0.5% w/w) with a lactose carrier and epinephrine and polysorbate (0.5% w/w) with a sodium CMC carrier.

FIG. 76 is a graph of mean epinephrine concentration-time profiles following IN administration in rats for epinephrine and polysorbate (0.5% w/w) with a lactose carrier and epinephrine and polysorbate (0.5% w/w) with a sodium CMC carrier.

Figure 77:
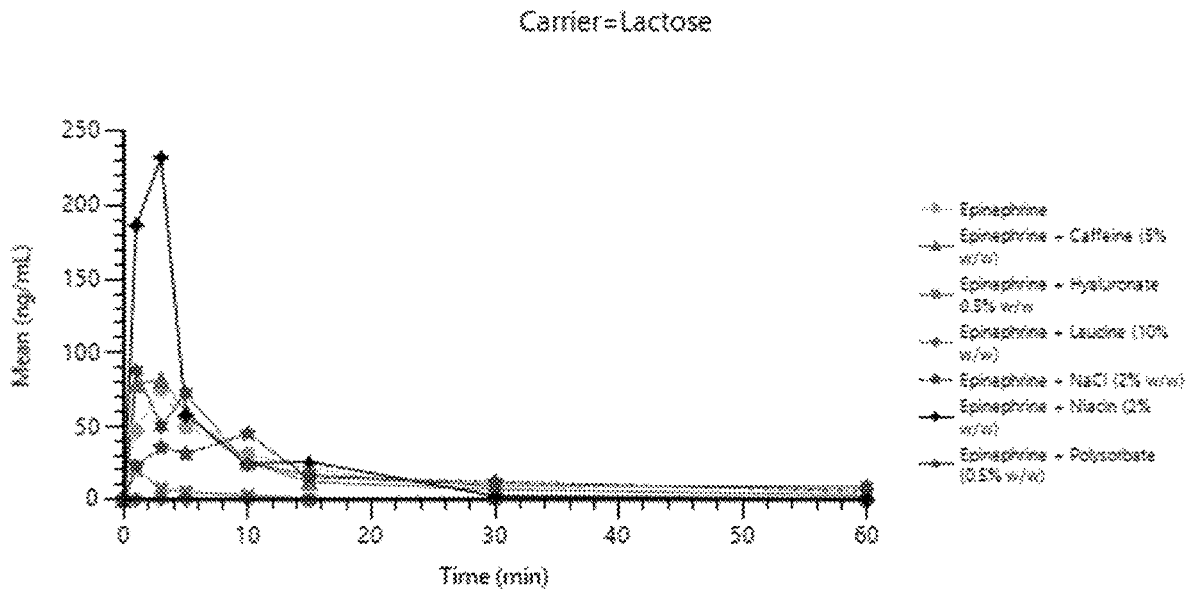
FIG. 77 is a graph of mean epinephrine concentration-time profiles following IN administration in rats grouped by lactose carrier including epinephrine, epinephrine and caffeine (5% w/w), epinephrine and hyaluronate (0.5% w/w), epinephrine and leucine (10% w/w), epinephrine and sodium chloride (2% w/w), epinephrine and niacin (2% w/w), and epinephrine and polysorbate (0.5% w/w).

FIG. 77 is a graph of mean epinephrine concentration-time profiles following IN administration in rats grouped by lactose carrier including epinephrine, epinephrine and caffeine (5% w/w), epinephrine and hyaluronate (0.5% w/w), epinephrine and leucine (10% w/w), epinephrine and sodium chloride (2% w/w), epinephrine and niacin (2% w/w), and epinephrine and polysorbate (0.5% w/w).

Figure 78:
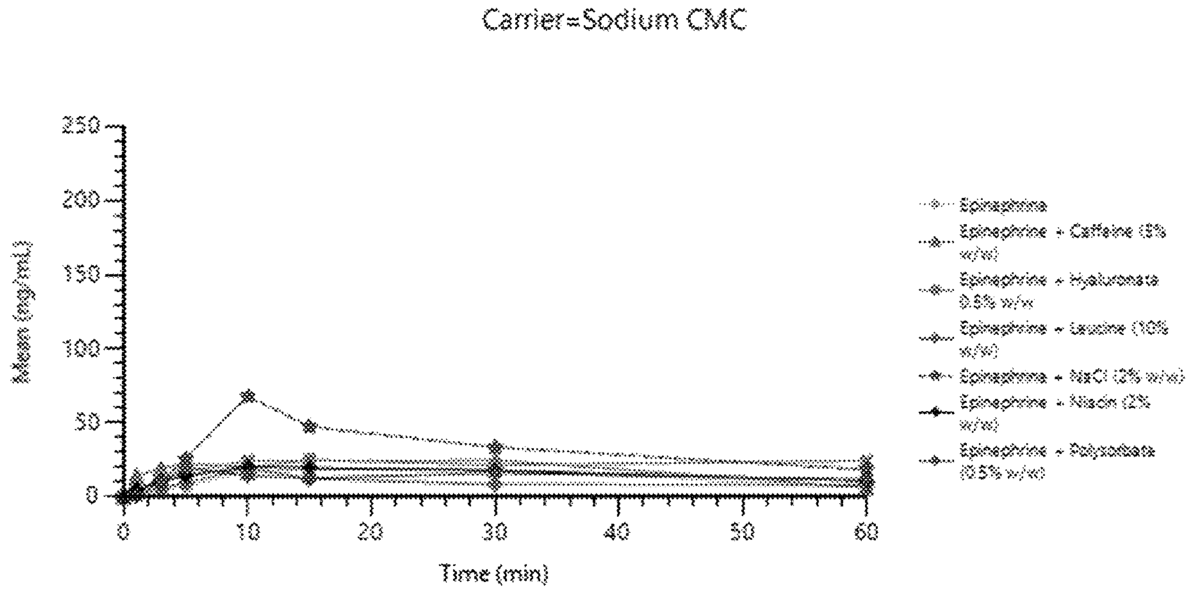
FIG. 78 is a graph of mean epinephrine concentration-time profiles following IN administration in rats grouped by sodium CMC carrier including epinephrine, epinephrine and caffeine (5% w/w), epinephrine and hyaluronate (0.5% w/w), epinephrine and leucine (10% w/w), epinephrine and sodium chloride (2% w/w), epinephrine and niacin (2% w/w), and epinephrine and polysorbate (0.5% w/w).

FIG. 78 is a graph of mean epinephrine concentration-time profiles following IN administration in rats grouped by sodium CMC carrier including epinephrine, epinephrine and caffeine (5% w/w), epinephrine and hyaluronate (0.5% w/w), epinephrine and leucine (10% w/w), epinephrine and sodium chloride (2% w/w), epinephrine and niacin (2% w/w), and epinephrine and polysorbate (0.5% w/w).

FIG. 79 is a table of calibration curve data for epinephrine in rat potassium EDTA plasma.

FIG. 80 is a table of quality control evaluation data for epinephrine in rat potassium EDTA plasma.

For epinephrine alone, Cmax ranged from 28.0 to 153 ng/mL, Tmax ranged from 3 to 5 hours, and half-life averaged 8.38 minutes for lactose. Cmax ranged from 13.3 to 39.2 ng/mL, Tmax ranged from 10 to 30 minutes, and a half-life average was unable to be reliably estimated due to slow absorption for sodium CMC. AUClast values were similar, averaging 707 min*ng/mL for lactose and 755 min*ng/mL for sodium CMC.

For epinephrine with 5% caffeine, Cmax averaged 93.9 ng/mL with low variability, Tmax ranged from 3 to 5 minutes, and half-life averaged of 23.3 minutes for lactose. Cmax ranged from 29.5 ng/mL, Tmax ranged from 5 to 30 minutes, and a half-life average was unable to be reliably estimated due to slow absorption for sodium CMC. AUClast values were similar, averaging 902 min*ng/mL for lactose and 909 min*ng/mL for sodium CMC.

For epinephrine with 0.5% hyaluronate, Cmax averaged 20.0 ng/mL and Tmax ranged from 1 to 5 minutes for lactose. Cmax averaged 31.5 ng/mL and Tmax ranged from 15 to 60 minutes for sodium CMC. Half-life values could not be reliably estimated for either formulation. AUClast values averaged 76.1 min*ng/mL for lactose and much higher, 1300 min*ng/mL, for sodium CMC due to protracted absorption throughout the sampling interval.

For epinephrine with 10% leucine, no quantifiable concentrations of epinephrine were observed in any animal. Cmax averaged 19.8 ng/mL and Tmax ranged from 10 to 30 minutes. AUClast values averaged 582 min*ng/mL for sodium CMC due to protracted absorption throughout the sampling interval. Half-life and AUCinf estimates do not appear to be reliable.

For epinephrine with 2% sodium chloride, Cmax averaged 60.1 ng/mL with low variability, Tmax ranged from 3 to 10 minutes, and a half-life average was 27.9 minutes for lactose. Cmax averaged 68.9 ng/mL, Tmax ranged from 1 to 30 minutes, and a half-life average was 65.4 minutes for sodium CMC. AUClast values averaged 889 min*ng/mL for lactose and 1930 min*ng/mL for sodium CMC.

For epinephrine with 2% niacin, Cmax averaged 233 ng/mL, Tmax ranged from 1 to 3 minutes, and a half-life average was 11.9 minutes for lactose. Cmax was much lower, averaging 22.9 ng/mL, Tmax ranged from 5 to 30 minutes, and a half-life average was 56.1 minutes for sodium CMC. AUClast values averaged 934 min*ng/mL for lactose and 929 min*ng/mL for sodium CMC.

For epinephrine with 0.5% polysorbate, Cmax averaged 101 ng/mL, Tmax ranged from 1 to 5 minutes, and an AUClast value was 824 min*ng/mL for lactose. Cmax averaged 21.5 ng/mL, Tmax ranged from 1 to 15 minutes, and an AUClast value was 1580 min*ng/mL for sodium CMC. Half-life values could not be reliably estimated for either formulation.

Variability was high in plasma epinephrine concentrations following IM administration of epinephrine at a dose level of 0.7 mg/kg, precluding the calculation of relative bioavailability values.

Based on the studies, it was determined that rats are not a good species for pharmacokinetic studies for intranasal epinephrine because the amount loaded in the device (APTAR) is lower than the optimal performance range of the device, which resulted in high variability. Further, administration to the animal required an adapter due to the small size of the rat nostril, which also may have created high variability in dose delivery and concentration-time data.

As shown in FIGS. 70-78, the fastest absorption of epinephrine occurs with lactose formulations (e.g., epinephrine alone, epinephrine with caffeine, niacin, or polysorbate). In contrast, formulations with sodium CMC typically displayed much slower absorption based on later observed Tmax values. The excipients leucine and hyaluronic acid resulted in the lowest absorption of epinephrine. The excipients caffeine and niacin resulted in the highest bioavailability; however, there are safety concerns with use due to animal deaths. Sodium chloride and polysorbate 80 were determined to be the excipients used in future canine pharmacokinetic studies.

Canine Studies

The plasma pharmacokinetics (PK) following intranasal (IN) delivery of four dry powder formulations of epinephrine administered at different doses in four anesthetized Beagle dogs was determined. Epinephrine administered by the intramuscular (IM) route was used as a comparator.

The formulations used in the study include a 40 mg dosage of 10% w/w epinephrine, 2% NaCl, 0.1% w/v polysorbate (TWEEN 80), and lactose as a dry powder pre-loaded into a nasal device (APTAR) for intranasal dosing; a 60 mg dosage of 10% w/w epinephrine, 2% NaCl, and lactose as a dry powder pre-loaded into a nasal device (APTAR) for intranasal dosing; a 60 mg dosage of 10% w/w epinephrine, 2% NaCl, 0.1% w/v polysorbate (TWEEN 80), and lactose as a dry powder pre-loaded into a nasal device (APTAR) for intranasal dosing; a 30 mg dosage of 20% w/w epinephrine, 2% NaCl, and lactose as a dry powder pre-loaded into a nasal device (APTAR) for intranasal dosing; a 30 mg dosage of 20% w/w epinephrine, 2% NaCl, 0.1% w/v polysorbate (TWEEN 80), and lactose as a dry powder pre-loaded into a nasal device (APTAR) for intranasal dosing; and a 0.3 mg IM dosage of epinephrine using an EPIPEN as shown in Table 2.

TABLE 2

| Treatment | Route | Formulation Amount (mg) | Epinephrine Dose (mg) | No. of dogs dosed |
|---|---|---|---|---|
| Lactose + 2% NaCl + 0.1% w/v Tween 80 with 10% w/w Epinephrine | IN | 40 | 4 | 4 |
| Lactose + 2% NaCl w/10% w/w Epinephrine | IN | 60 | 6 | 3 |
| Lactose + 2% NaCl + 0.1% w/v Tween 80 w/ 10% w/w Epinephrine | IN | 60 | 6 | 2 |
| Lactose + 2% NaCl w/20% w/w Epinephrine | IN | 30 | 6 | 4 |
| Lactose + 2% NaCl + 0.1% w/v Tween 80 w/ 20% w/w Epinephrine | IN | 30 | 6 | 3 |
| EPIPEN IM | IM | — | 0.3 | 4 |

For the studies, the animals received a single treatment of the comparator (EPIPEN) intramuscularly. For the studies, formulations in various amounts were administered intranasally in one nostril, with one spray representing one dose. Variations in target dose were controlled by formulation and/or amount of powder loaded into the nasal device. At least two days of washout were present between Studies. Blood was collected at a plurality of time points before and after treatment: two samples were collected before dosing, at 10 minutes post anesthesia and at 20 minutes post anesthesia. Post-dose samples were obtained at 2 or 3 minutes, and at 5, 7, 10, 15, 20, 30, 60, 90, and 120 minutes after dosing.

30.0 mL of 200 mg/mL sodium metabisulfite (Na2S2O5, CAS #7681-57-4), pH 3.0 was prepared by adding 6.00 g Na2S2O5 to 24.0 mL of water. The pH was adjusted to 3.0 with hydrochloric acid and the solution was brought to a final volume of 30.0 mL. The 200 mg/mL solution of sodium metabisulfite, pH 3.0 is operable to be stored at 2-8° C. for up to 30 days.

Blood collection tubes containing potassium EDTA (ethylenediaminetetraacetic acid) were pre-spiked with 10 μL of the 200 mg/mL solution of sodium metabisulfite, pH 3.0 for the collection of 1 mL of whole blood. Tubes are operable to be kept on wet ice immediately prior to use. The blood samples collected in the pre-spiked tubes were centrifuged at 1300 g for a minimum of 10 minutes at 2° C. to 8° C. within 30 minutes of collection. The resulting plasma was removed, placed into a cryovial, and frozen at −90° C. to −70° C. until bioanalysis.

Filled devices were weighed prior to dosing and after dosing. The tip of the device was wiped free of obvious secretions prior to weighing the device after dosing.

To dose the animal, the nose was wiped free of any obvious secretions. One spray was delivered intranasally to one nostril per animal for each study. Animals were anesthetized with inhaled isoflurane for dosing and through all blood collection timepoints.

Plasma samples were analyzed for epinephrine concentration using a qualified LC-MS/MS method. The assay was verified with respect to standard bioanalytical methodology including acceptable accuracy and precision based upon quality control sample analysis and results. The quantifiable range of the method is 200 to 10,000 pg/mL.

Pharmacokinetic parameters were derived using noncompartmental methods employing PHOENIX WINNONLIN version 8.3 (Pharsight Corp, St. Louis, MO).

FIG. 81 illustrates a table of plasma epinephrine concentration-time data in dogs following a 40 mg dosage of 10% w/w epinephrine, 2% NaCl, 0.1% w/v polysorbate (TWEEN 80), and lactose. FIG. 82 illustrates a table of plasma epinephrine concentration-time data in dogs following a 60 mg dosage of 10% w/w epinephrine, 2% NaCl, and lactose. FIG. 83 illustrates a table of plasma epinephrine concentration-time data in dogs following a 60 mg dosage of 10% w/w epinephrine, 2% NaCl, 0.1% w/v polysorbate (TWEEN 80), and lactose. FIG. 84 illustrates a table of plasma epinephrine concentration-time data in dogs following a 30 mg dosage of 20% w/w epinephrine, 2% NaCl, and lactose. FIG. 85 illustrates a table of plasma epinephrine concentration-time data in dogs following a 30 mg dosage of 20% w/w epinephrine, 2% NaCl, 0.1% w/v polysorbate (TWEEN 80), and lactose. FIG. 86 illustrates a table of plasma epinephrine concentration-time data in dogs following a 0.3 mg IM dosage of epinephrine using an EPIPEN.

FIG. 87 illustrates a table of epinephrine pharmacokinetic parameters in dogs following a 40 mg dosage of 10% w/w epinephrine, 2% NaCl, 0.1% w/v polysorbate (TWEEN 80), and lactose. The pharmacokinetic parameters include Cmax (pg/mL), Tmax (min), and AUClast (min*pg/mL). FIG. 88 illustrates a table of epinephrine pharmacokinetic parameters in dogs following a 60 mg dosage of 10% w/w epinephrine, 2% NaCl, and lactose. FIG. 89 illustrates a table of epinephrine pharmacokinetic parameters in dogs following a 60 mg dosage of 10% w/w epinephrine, 2% NaCl, 0.1% w/v polysorbate (TWEEN 80), and lactose. FIG. 90 illustrates a table of epinephrine pharmacokinetic parameters in dogs following a 30 mg dosage of 20% w/w epinephrine, 2% NaCl, and lactose. FIG. 91 illustrates a table of epinephrine pharmacokinetic parameters in dogs following a 30 mg dosage of 20% w/w epinephrine, 2% NaCl, 0.1% w/v polysorbate (TWEEN 80), and lactose. FIG. 92 illustrates a table of epinephrine pharmacokinetic in dogs following a 0.3 mg IM dosage of epinephrine using an EPIPEN.

FIG. 93 illustrates a summary of epinephrine AUClast results for a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

FIG. 94 illustrates relative bioavailability calculations (AUClast) for a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

FIG. 95 illustrates comparative bioavailability calculations (AUClast) for a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 96:
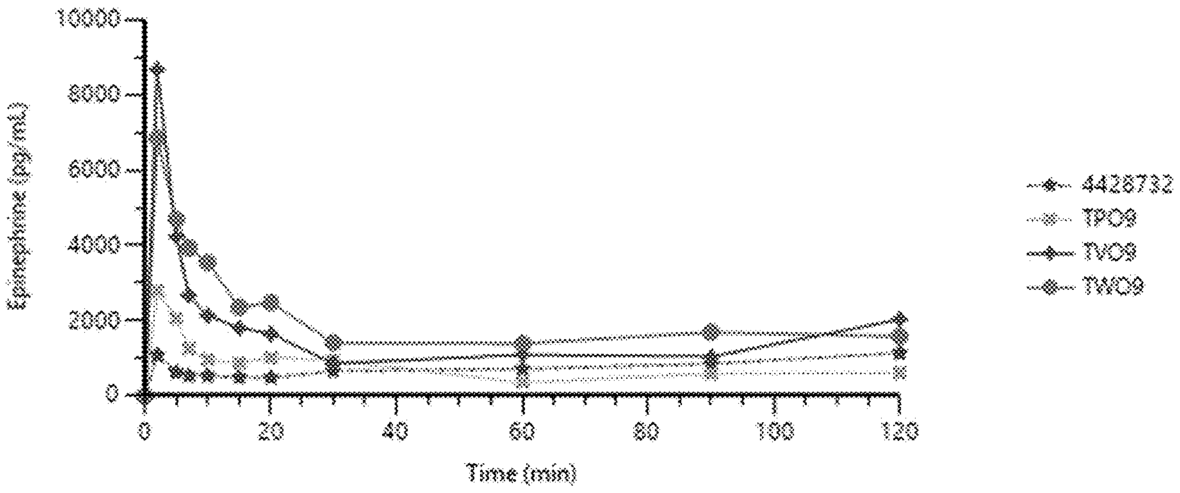
FIG. 96 illustrates a linear graph of individual epinephrine concentration-time profiles for a 40 mg dosage of 10% w/w epinephrine, 2% NaCl, 0.1% w/v polysorbate (TWEEN 80), and lactose.
Figure 97:
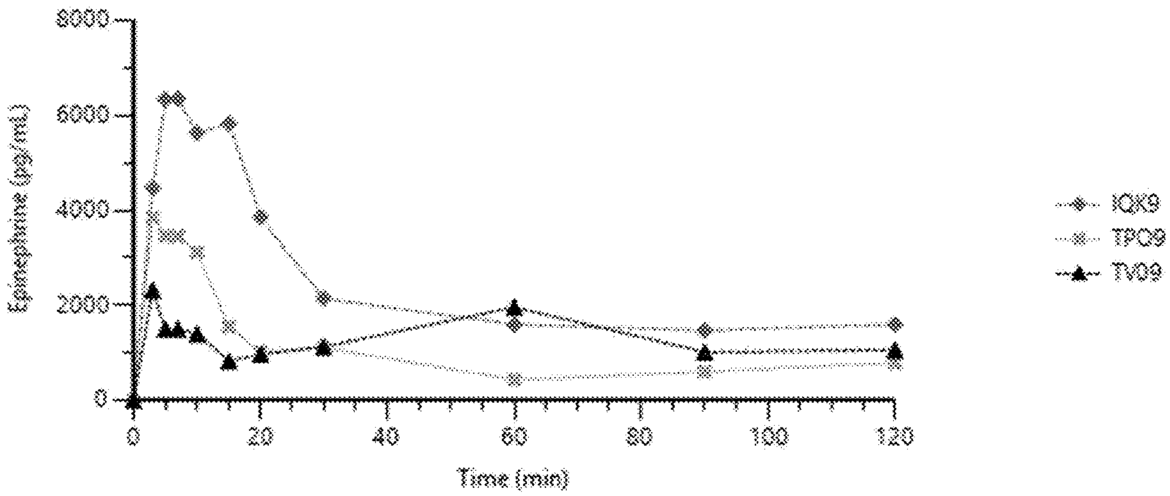
FIG. 97 illustrates a linear graph of individual epinephrine concentration-time profiles for a 60 mg dosage of 10% w/w epinephrine, 2% NaCl, and lactose.
Figure 98:
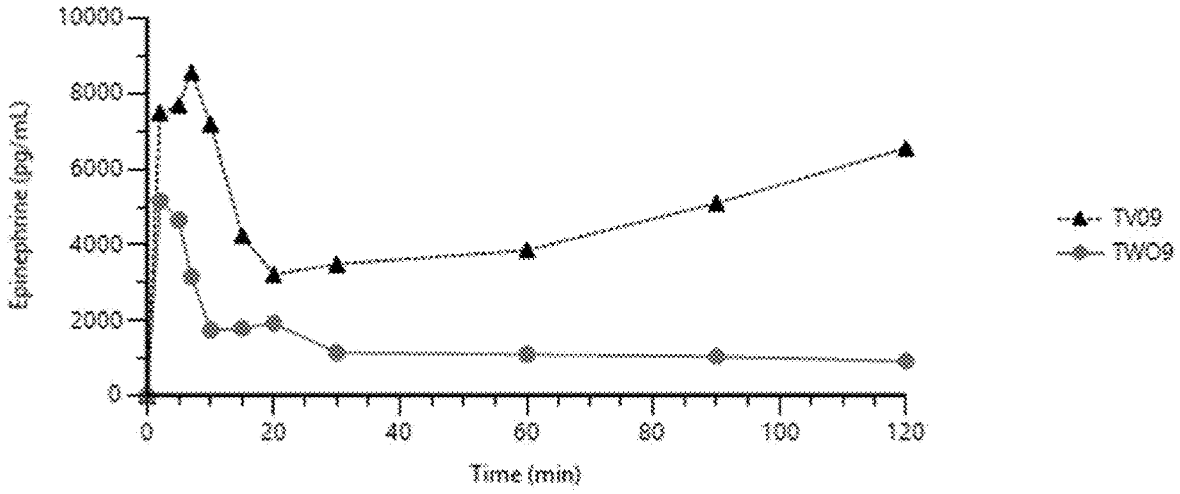
FIG. 98 illustrates a linear graph of individual epinephrine concentration-time profiles for a 60 mg dosage of 10% w/w epinephrine, 2% NaCl, 0.1% w/v polysorbate (TWEEN 80), and lactose.
Figure 99:
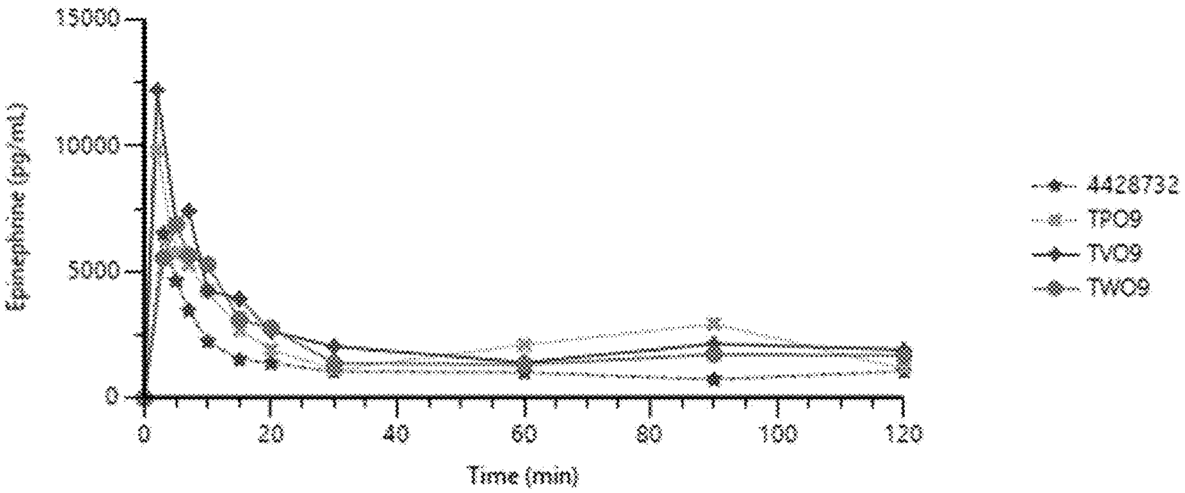
FIG. 99 illustrates a linear graph of individual epinephrine concentration-time profiles for a 30 mg dosage of 20% w/w epinephrine, 2% NaCl, and lactose.
Figure 100:
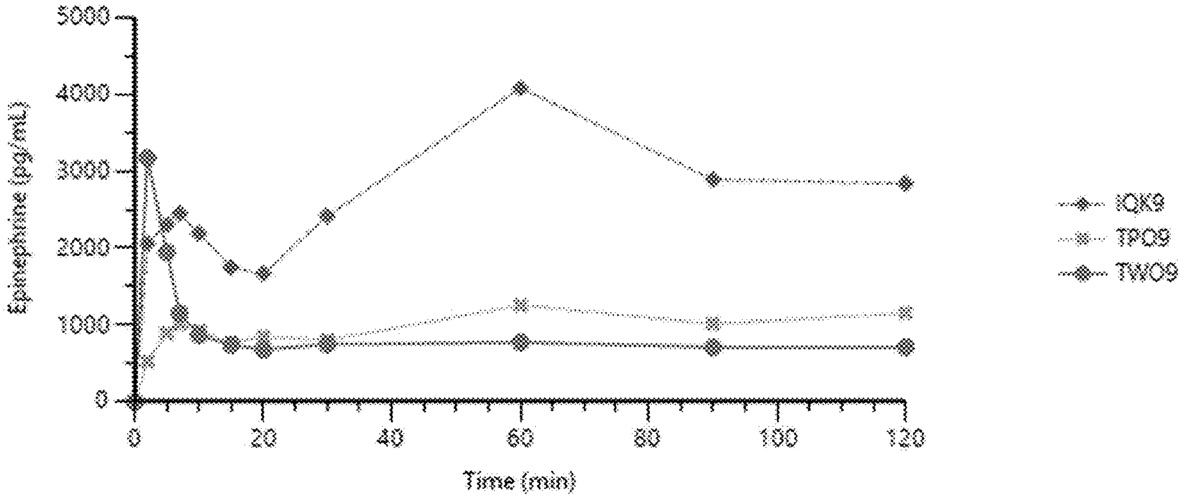
FIG. 100 illustrates a linear graph of individual epinephrine concentration-time profiles for a 30 mg dosage of 20% w/w epinephrine, 2% NaCl, 0.1% w/v polysorbate (TWEEN 80), and lactose.
Figure 101:
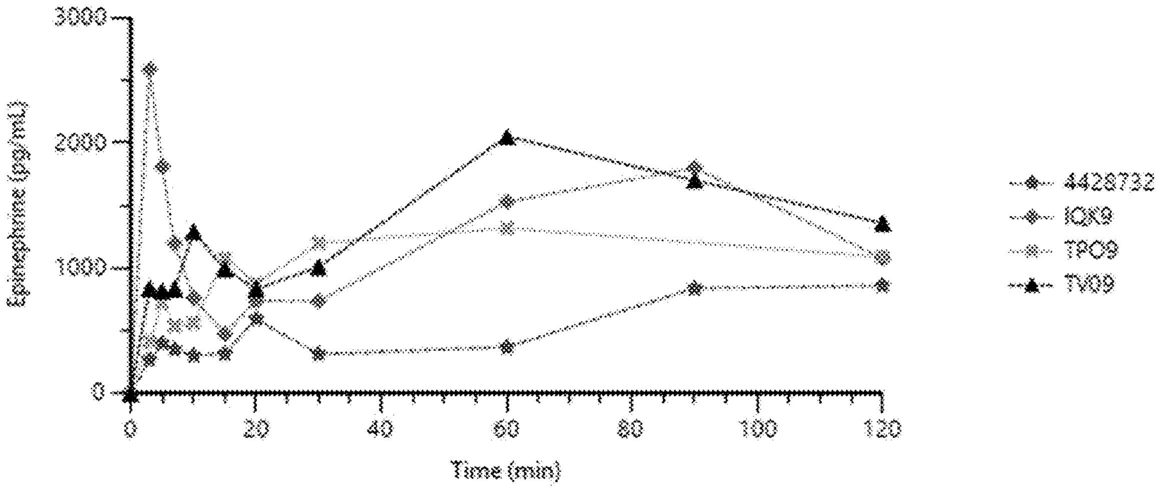
FIG. 101 illustrates a linear graph of individual epinephrine concentration-time profiles for a 0.3 mg IM dosage of epinephrine using an EPIPEN.

FIG. 96 illustrates a linear graph of individual epinephrine concentration-time profiles for a 40 mg dosage of 10% w/w epinephrine, 2% NaCl, 0.1% w/v polysorbate (TWEEN 80), and lactose. FIG. 97 illustrates a linear graph of individual epinephrine concentration-time profiles for a 60 mg dosage of 10% w/w epinephrine, 2% NaCl, and lactose. FIG. 98 illustrates a linear graph of individual epinephrine concentration-time profiles for a 60 mg dosage of 10% w/w epinephrine, 2% NaCl, 0.1% w/v polysorbate (TWEEN 80), and lactose. FIG. 99 illustrates a linear graph of individual epinephrine concentration-time profiles for a 30 mg dosage of 20% w/w epinephrine, 2% NaCl, and lactose. FIG. 100 illustrates a linear graph of individual epinephrine concentration-time profiles for a 30 mg dosage of 20% w/w epinephrine, 2% NaCl, 0.1% w/v polysorbate (TWEEN 80), and lactose. FIG. 101 illustrates a linear graph of individual epinephrine concentration-time profiles for a 0.3 mg IM dosage of epinephrine using an EPIPEN.

Figure 102:
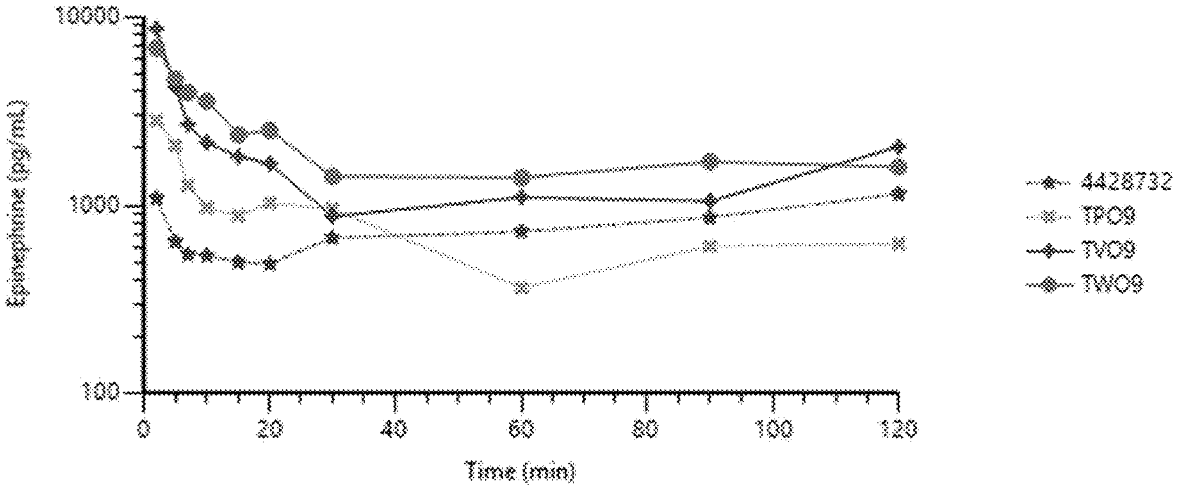
FIG. 102 illustrates a log-linear graph of individual epinephrine concentration-time profiles for a 40 mg dosage of 10% w/w epinephrine, 2% NaCl, 0.1% w/v polysorbate (TWEEN 80), and lactose.
Figure 103:
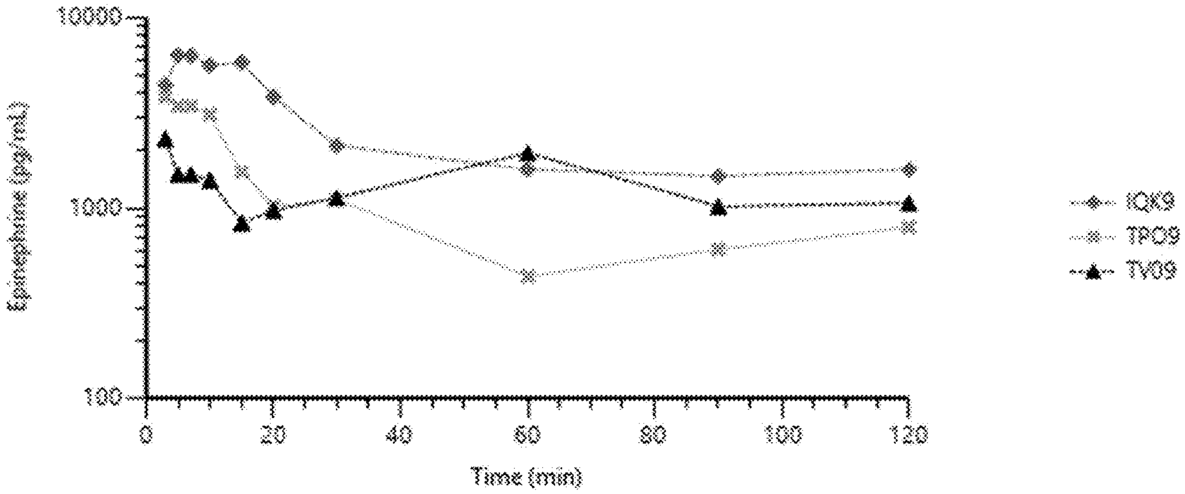
FIG. 103 illustrates a log-linear graph of individual epinephrine concentration-time profiles for a 60 mg dosage of 10% w/w epinephrine, 2% NaCl, and lactose.
Figure 104:
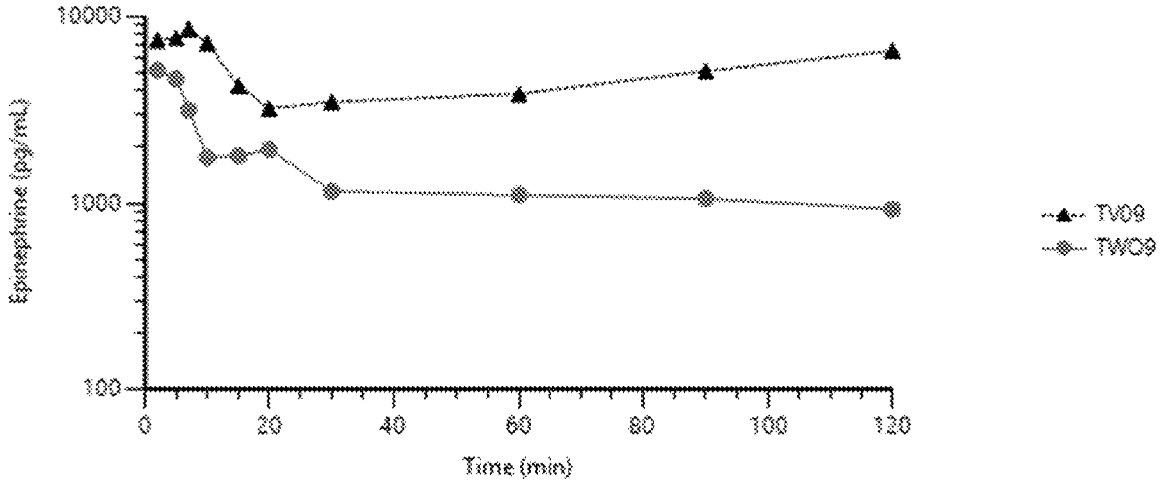
FIG. 104 illustrates a log-linear graph of individual epinephrine concentration-time profiles for a 60 mg dosage of 10% w/w epinephrine, 2% NaCl, 0.1% w/v polysorbate (TWEEN 80), and lactose.
Figure 105:
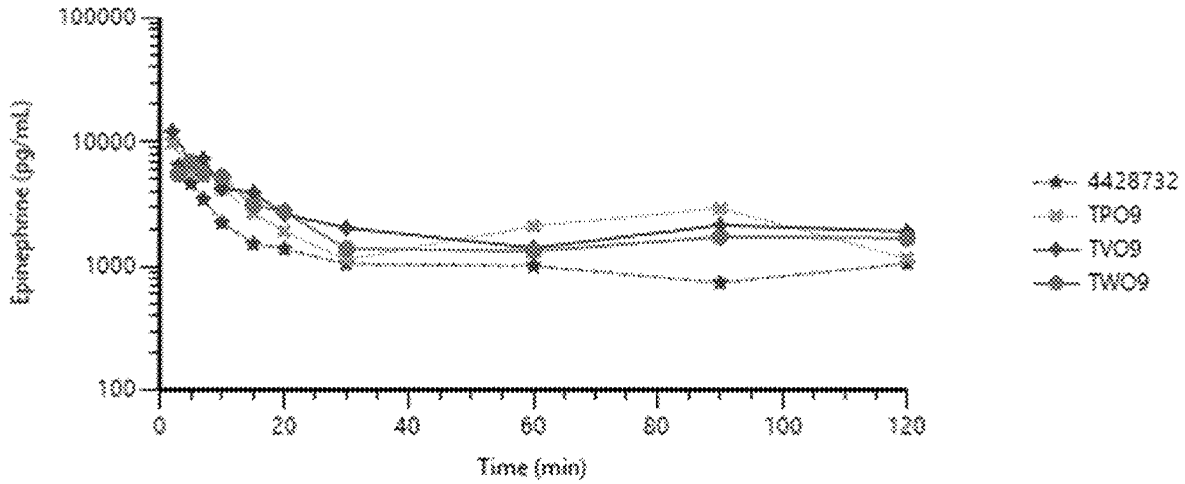
FIG. 105 illustrates a log-linear graph of individual epinephrine concentration-time profiles for a 30 mg dosage of 20% w/w epinephrine, 2% NaCl, and lactose.
Figure 106:
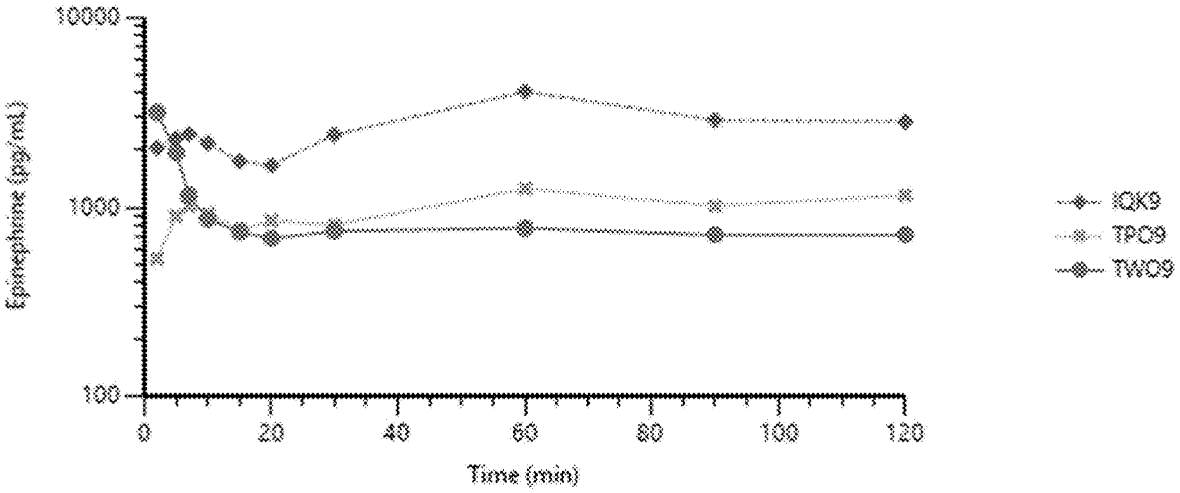
FIG. 106 illustrates a log-linear graph of individual epinephrine concentration-time profiles for a 30 mg dosage of 20% w/w epinephrine, 2% NaCl, 0.1% w/v polysorbate (TWEEN 80), and lactose.
Figure 107:
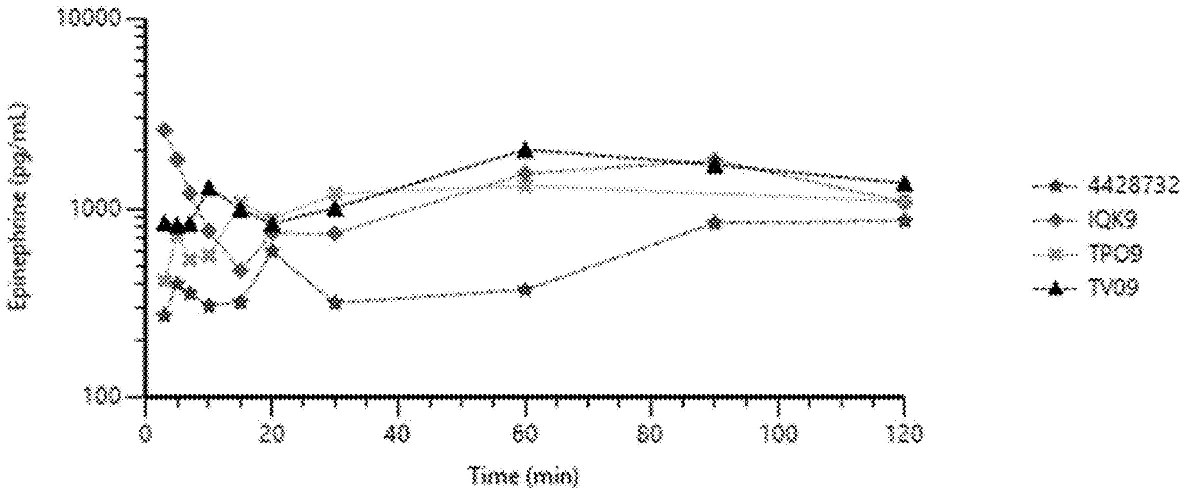
FIG. 107 illustrates a log-linear graph of individual epinephrine concentration-time profiles for a 0.3 mg IM dosage of epinephrine using an EPIPEN.

FIG. 102 illustrates a log-linear graph of individual epinephrine concentration-time profiles for a 40 mg dosage of 10% w/w epinephrine, 2% NaCl, 0.1% w/v polysorbate (TWEEN 80), and lactose. FIG. 103 illustrates a log-linear graph of individual epinephrine concentration-time profiles for a 60 mg dosage of 10% w/w epinephrine, 2% NaCl, and lactose. FIG. 104 illustrates a log-linear graph of individual epinephrine concentration-time profiles for a 60 mg dosage of 10% w/w epinephrine, 2% NaCl, 0.1% w/v polysorbate (TWEEN 80), and lactose. FIG. 105 illustrates a log-linear graph of individual epinephrine concentration-time profiles for a 30 mg dosage of 20% w/w epinephrine, 2% NaCl, and lactose. FIG. 106 illustrates a log-linear graph of individual epinephrine concentration-time profiles for a 30 mg dosage of 20% w/w epinephrine, 2% NaCl, 0.1% w/v polysorbate (TWEEN 80), and lactose. FIG. 107 illustrates a log-linear graph of individual epinephrine concentration-time profiles for a 0.3 mg IM dosage of epinephrine using an EPIPEN.

Figure 108:
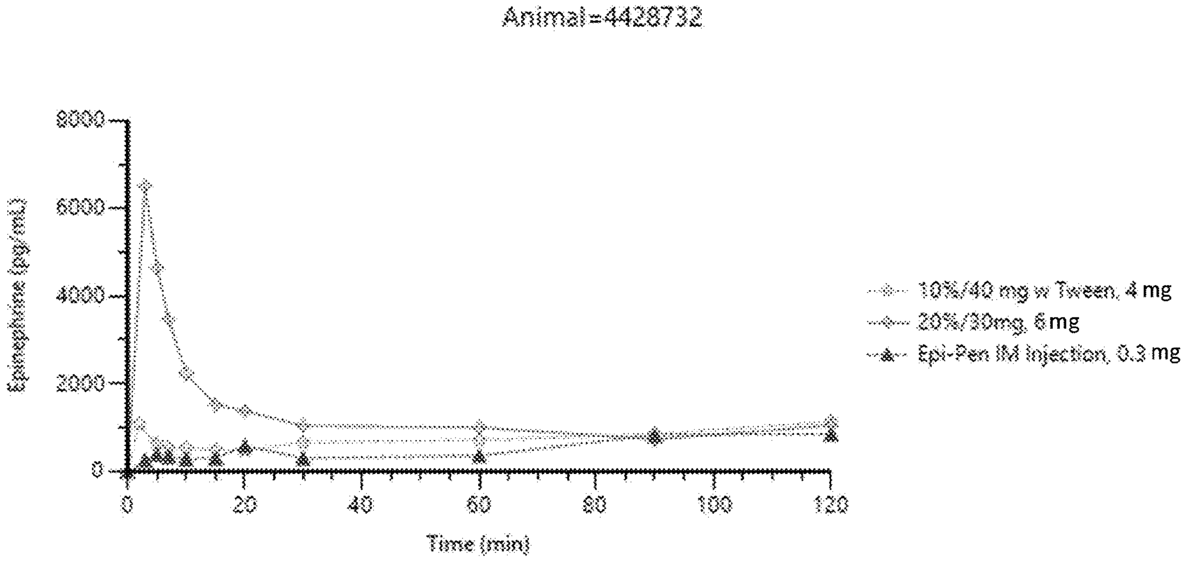
FIG. 108 illustrates a graph of epinephrine concentration-time profiles for a first dog.

FIG. 108 illustrates a graph of epinephrine concentration-time profiles for animal 4428732 for a 40 mg dosage of 10% w/w epinephrine, 2% NaCl, 0.1% w/v polysorbate (TWEEN 80), and lactose; a 30 mg dosage of 20% w/w epinephrine, 2% NaCl, and lactose; and a 0.3 mg IM dosage of epinephrine using an EPIPEN.

Figure 109:
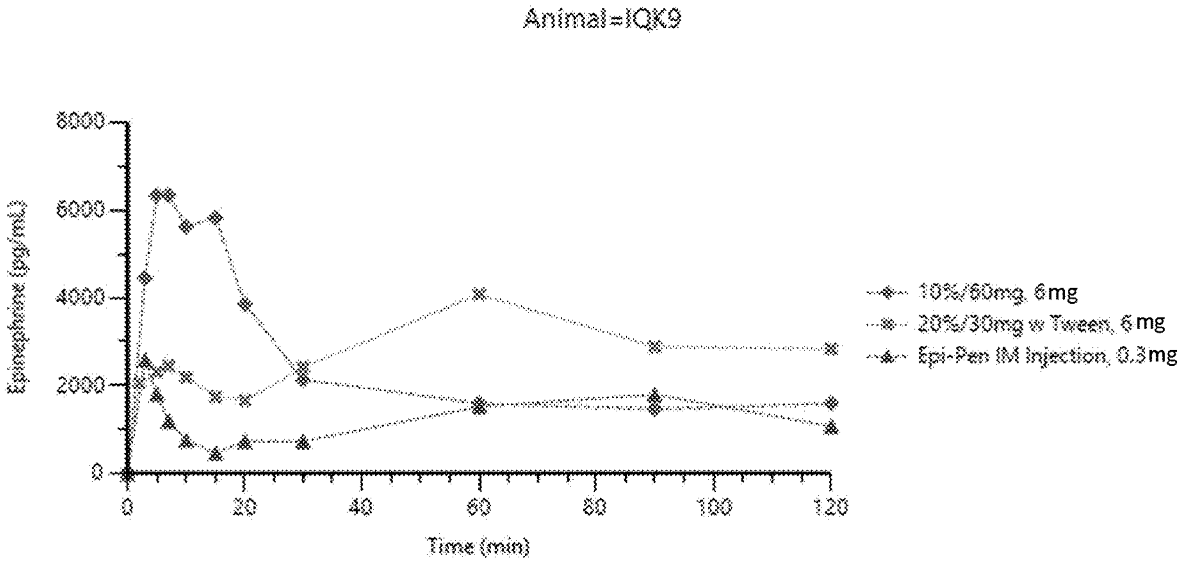
FIG. 109 illustrates a graph of epinephrine concentration-time profiles for a second dog.

FIG. 109 illustrates a graph of epinephrine concentration-time profiles for animal IQK9 for a 60 mg dosage of 10% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 110:
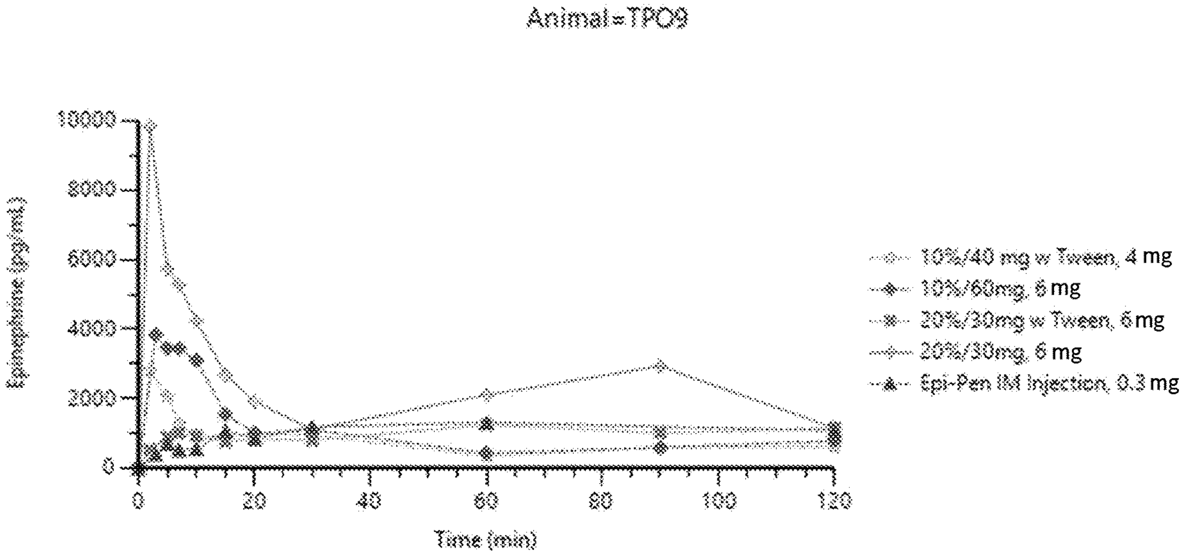
FIG. 110 illustrates a graph of epinephrine concentration-time profiles for a third dog.

FIG. 110 illustrates a graph of epinephrine concentration-time profiles for animal TPO9 for a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 111:
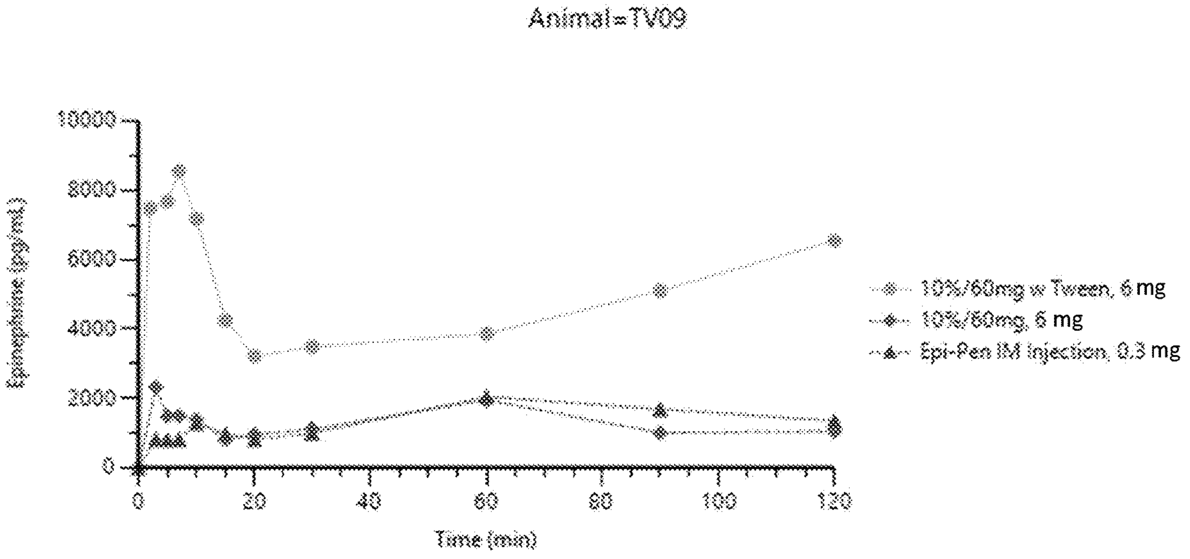
FIG. 111 illustrates a graph of epinephrine concentration-time profiles for a fourth dog.

FIG. 111 illustrates a graph of epinephrine concentration-time profiles for animal TV09 for a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; and a 0.3 mg IM dosage of epinephrine using an EPIPEN.

Figure 112:
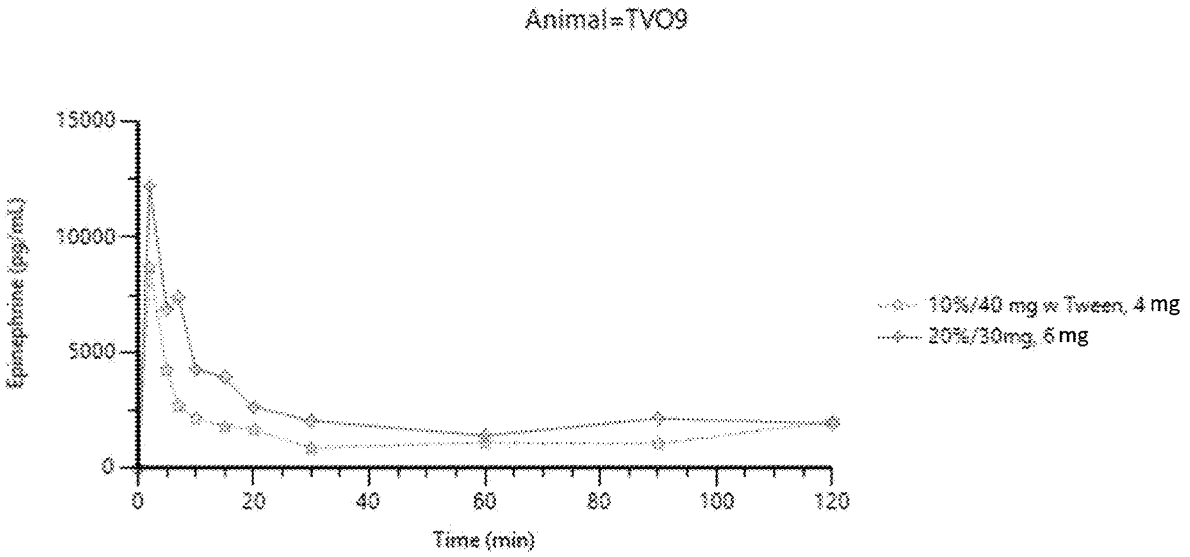
FIG. 112 illustrates a graph of epinephrine concentration-time profiles for a fifth dog.

FIG. 112 illustrates a graph of epinephrine concentration-time profiles for animal TVO9 for a 40 mg dosage of 10% w/w epinephrine, 2% NaCl, 0.1% w/v polysorbate (TWEEN 80), and lactose; and a 30 mg dosage of 20% w/w epinephrine, 2% NaCl, and lactose.

Figure 113:
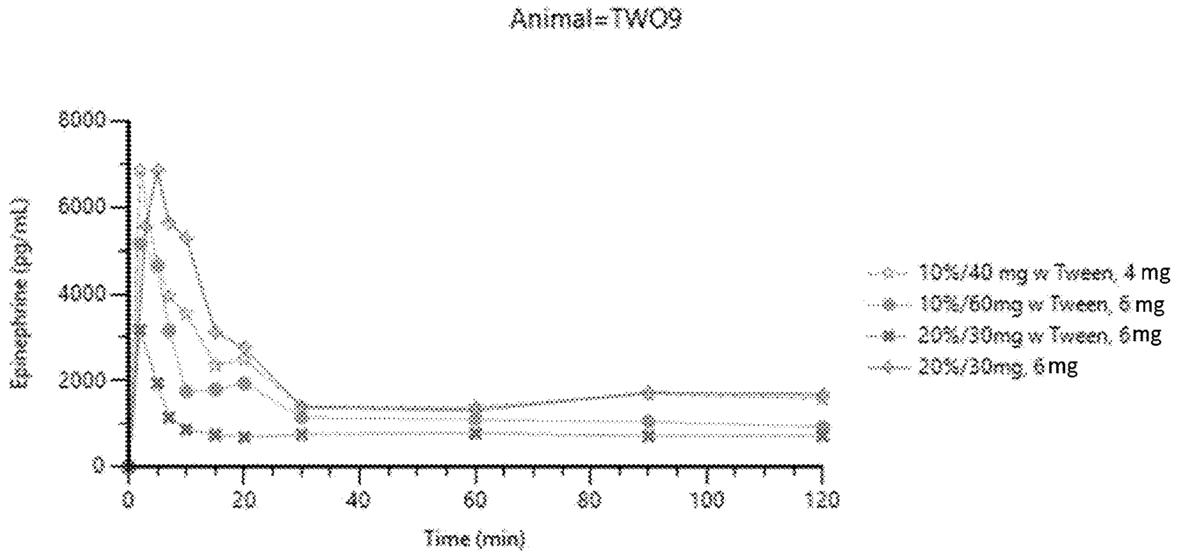
FIG. 113 illustrates a graph of epinephrine concentration-time profiles for a sixth dog.

FIG. 113 illustrates a graph of epinephrine concentration-time profiles for animal TWO9 for a 40 mg dosage of 10% w/w epinephrine, 2% NaCl, 0.1% w/v polysorbate (TWEEN 80), and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; and a 30 mg dosage of 20% w/w epinephrine, 2% NaCl, 0.1% w/v polysorbate (TWEEN 80), and lactose.

Figure 114:
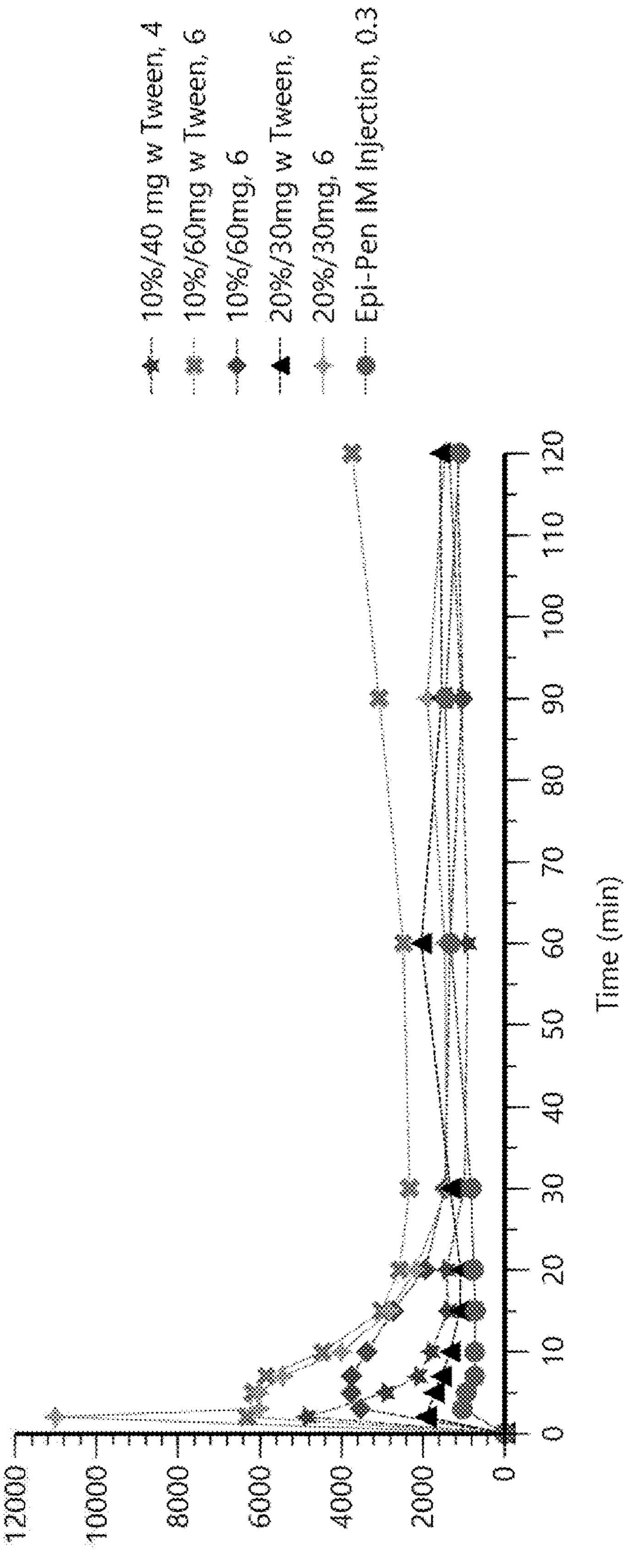
FIG. 114 illustrates a graph of mean plasma epinephrine concentration-time profiles by treatment.

FIG. 114 illustrates a graph of mean plasma epinephrine concentration-time profiles by treatment. The treatments shown include a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 115:
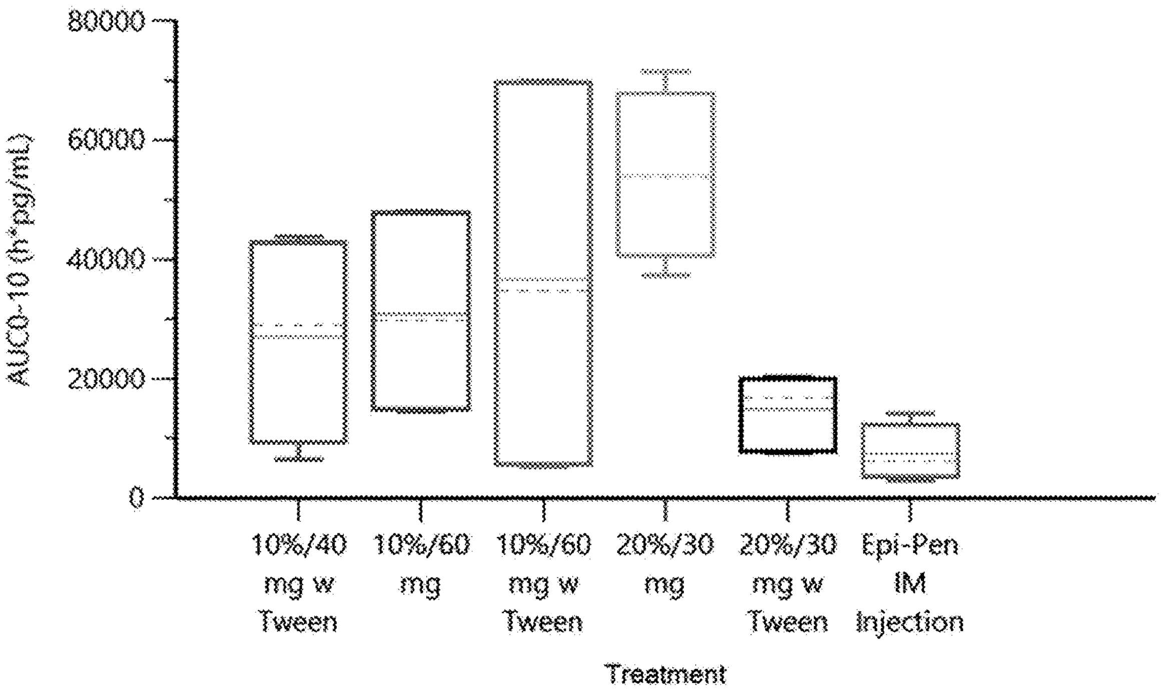
FIG. 115 illustrates a graph of partial AUC for 0-10 minutes by treatment.

FIG. 115 illustrates a graph of partial AUC for 0-10 minutes by treatment. The treatments shown include a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 116:
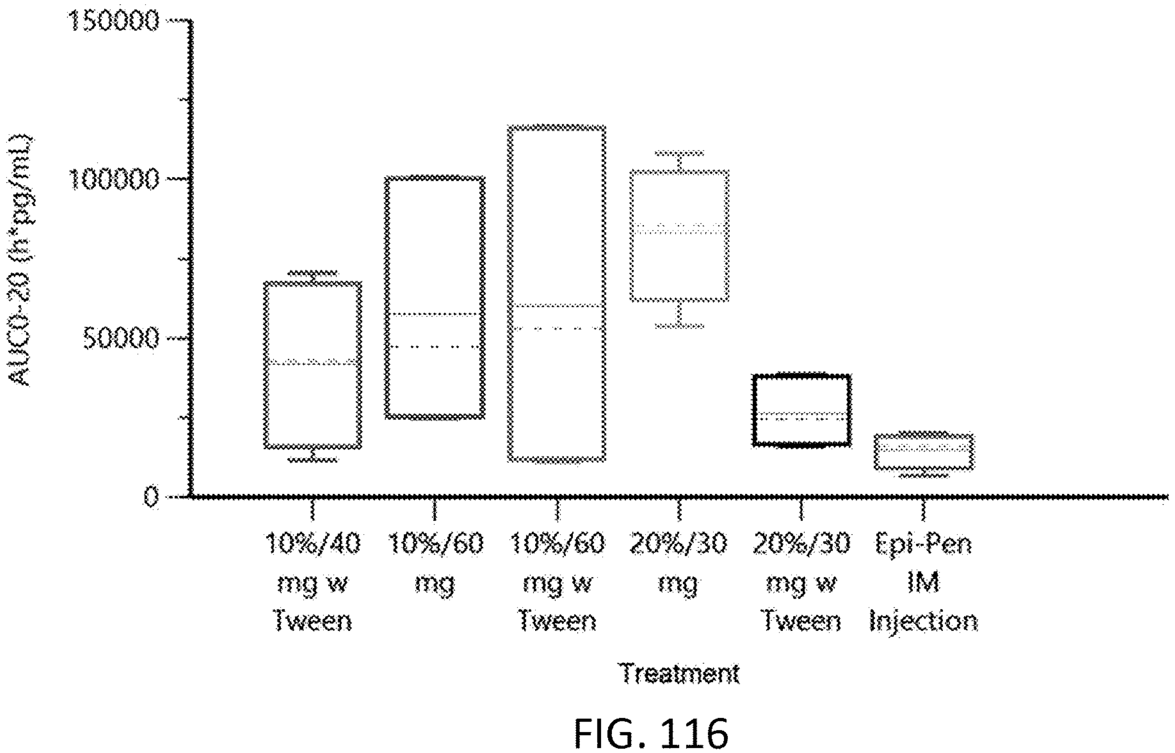
FIG. 116 illustrates a graph of partial AUC for 0-20 minutes by treatment.

FIG. 116 illustrates a graph of partial AUC for 0-20 minutes by treatment. The treatments shown include a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 117:
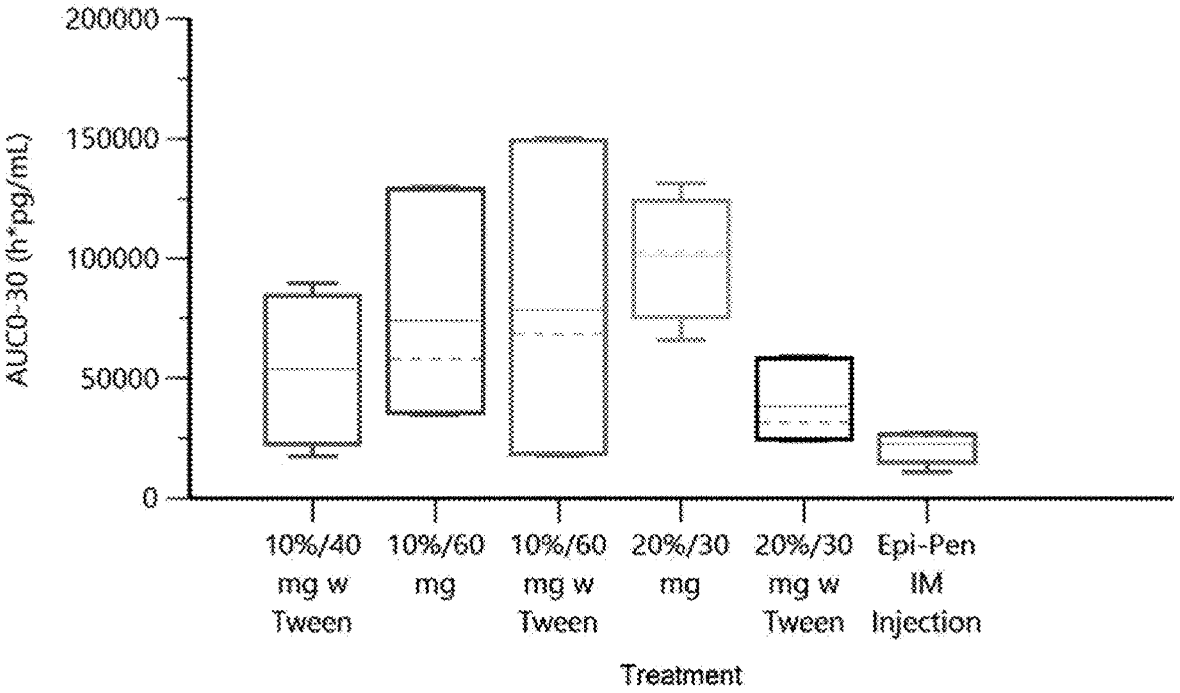

FIG. 117 illustrates a graph of partial AUC for 0-30 minutes by treatment. The treatments shown include a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 118:
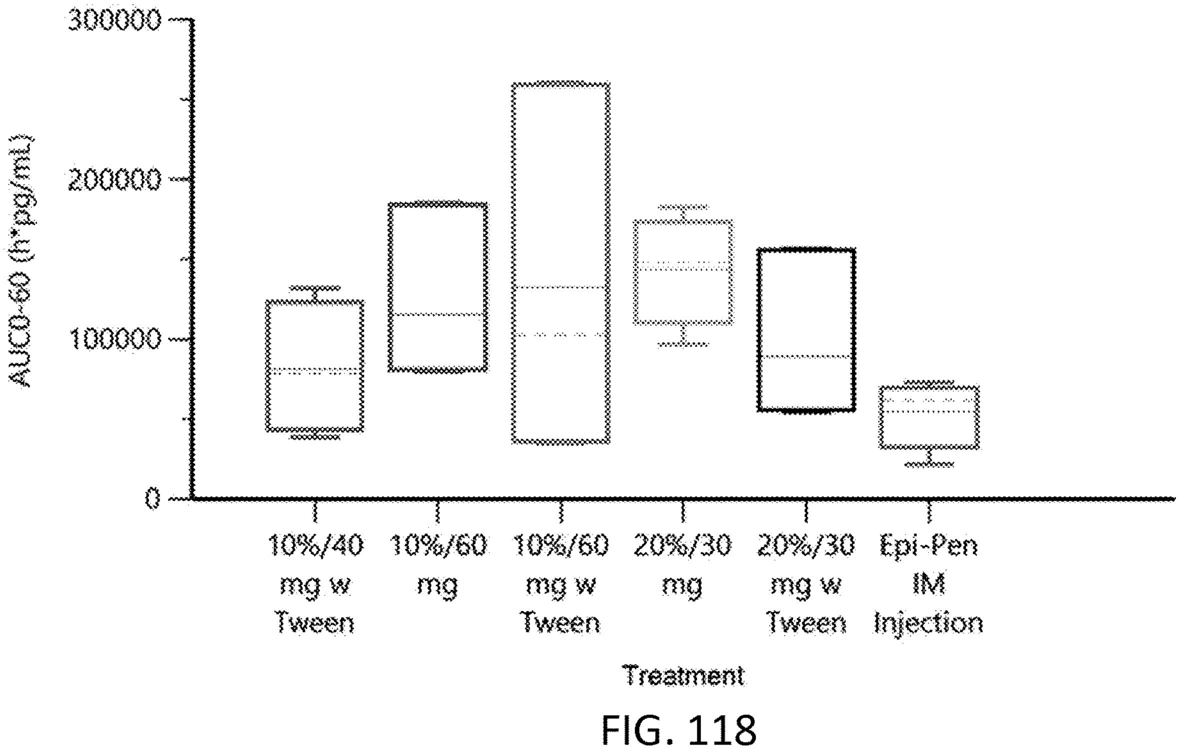

FIG. 118 illustrates a graph of partial AUC for 0-60 minutes by treatment. The treatments shown include a 40 mg dosage of 10% w/w epinephrine, 2% NaCl, 0.1% w/v polysorbate (TWEEN 80), and lactose; a 60 mg dosage of 10% w/w epinephrine, 2% NaCl, and lactose; a 60 mg dosage of 10% w/w epinephrine, 2% NaCl, 0.1% w/v polysorbate (TWEEN 80), and lactose; a 30 mg dosage of 20% w/w epinephrine, 2% NaCl, and lactose; a 30 mg dosage of 20% w/w epinephrine, 2% NaCl, 0.1% w/v polysorbate (TWEEN 80), and lactose; and a 0.3 mg IM dosage of epinephrine using an EPIPEN.

Figure 119:
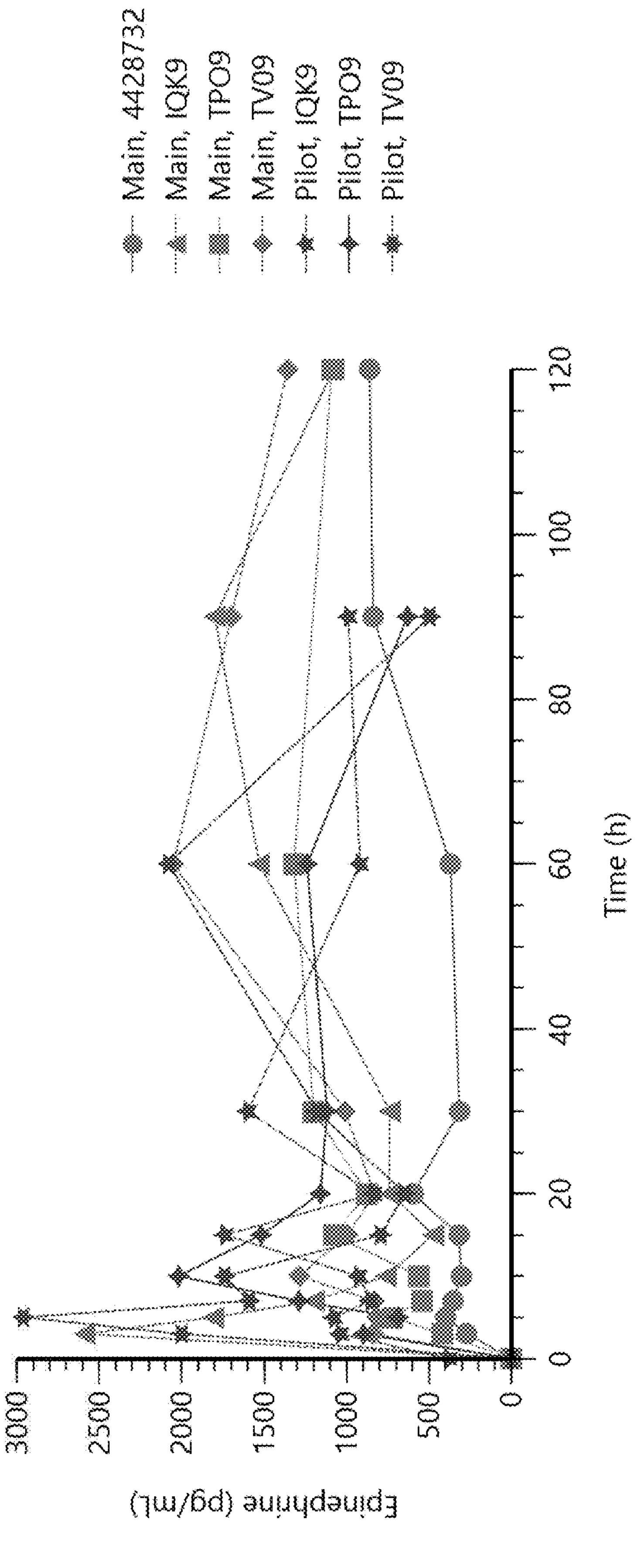

FIG. 119 illustrates a graph of individual animal plasma epinephrine concentration-time profiles for 0.3 mg IM administration for a pilot study and a main study.

Figure 120:
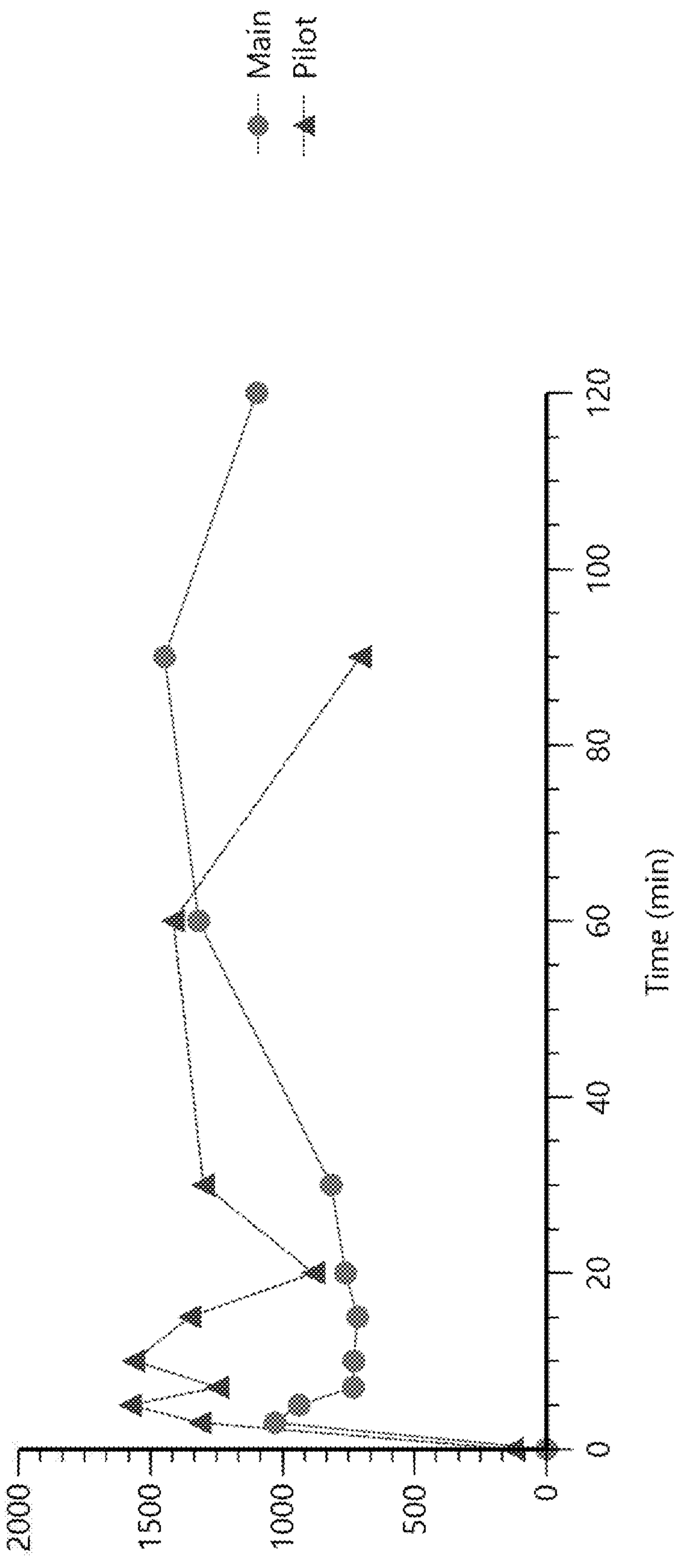

FIG. 120 illustrates a graph of mean plasma epinephrine concentration-time profiles for 0.3 mg IM administration for a pilot study and a main study.

Tabular results with summary statistics are displayed in FIGS. 81-85 for the IN formulations and in FIG. 86 for IM administered EPIPEN. The concentration-time data are plotted for individual animals within each treatment group in linear (FIGS. 96-101) and log-linear (FIGS. 102-107). FIGS. 108-113 contain plots of the data for each treatment received by each individual animal.

Measurable epinephrine concentrations were observed in all dosed animals for all formulations treatments at the first sampling time (e.g., 2 or 3 minutes after dosing). All dosed animals also had measurable concentrations at 120 minutes after dosing. All pre-dose concentrations were below the lower limit of quantification (LLOQ) of the method of 200 pg/mL. Following IN administration, most dogs displayed an initial peak followed by a decay phase that lasted until about 30 minutes after dosing. Concentrations were then relatively flat through to the 120-minute sample. However, for the EPIPEN, all dogs displayed an initial peak followed by a later peak that, in 3 out of 4 dogs was higher than the initial one. Between-dog variability was high for all IN treatments and the EPIPEN formulation. For the IN formulations, the percent coefficient of variation (% CV) values ranged from 36% to 98.6% for all formulations except the 20%/30 mg formulation where the % CV values were typically <30%. The EPIPEN formulation also displayed high variability with most of % CV values >50%.

Pharmacokinetic parameters for epinephrine following IN formulation administration are summarized in FIGS. 87-91. There was insufficient terminal phase data to permit reliable estimation of half-lives so the noncompartmental pharmacokinetic analysis was restricted to Cmax, Tmax, and AUClast. Epinephrine was rapidly absorbed following IN administration as evidenced by Tmax occurring at either 2 or 3 minutes for the majority of dogs. There were a limited number of Tmax values that occurred at 5 to 7 minutes. A single dog had a Tmax at 120 minutes after dosing. Mean Cmax values ranged from 2840 to 8850 ng/mL with considerable variability between formulation and between-dog variability. Mean AUClast values ranged from 147,000 to 367,000 min*pg/mL, also with high variability.

Pharmacokinetic parameters after EPIPEN dosing are summarized in FIG. 92. Tmax values tended to occur at later times than those observed following IN dosing. One dog displayed a Tmax of 3 minutes, but 2 dogs had Tmax values of 60 minutes and for 1 dog the Tmax occurred at the last sampling time at 120 minutes. Mean Cmax was 1710 pg/mL and AUClast averaged 132,000 min*pg/mL. Both were quite variable with % CV of 45% and 36%, respectively.

Partial AUC values were calculated, and box plots of the results are displayed in FIGS. 115-118. The data indicated that much of the AUC following administration of the IN formulations occurs early in the concentration-time profile, whereas the opposite is true for the EPIPEN and the 20%/30 mg formulation with polysorbate.

AUClast values for all dogs and the treatments they received are presented in FIG. 93. These values were used to calculate the relative and comparative bioavailability for the IN formulations in comparison to EPIPEN and the results are summarized in FIG. 94 and FIG. 95, respectively. This study used a crossover design to reduce variability, but since a replacement dog was required, and the results from 3 dogs were excluded from the analysis, all dogs did not receive all treatments as shown in FIG. 93. For dogs who did receive both a IN formulation and an EPIPEN dose, the relative bioavailability ranged from 4.3 to 16.3%. The combination of the IN doses of 4 or 6 mg epinephrine and the relative bioavailability of those formulations resulted in comparative bioavailability values ranging from 65.2 to 325%.

Surprisingly, while polysorbate is a surfactant, formulations with polysorbate are more available than formulations without the polysorbate, which is illustrated in the figures above. See, e.g., FIG. 111. In one example, the presence of polysorbate elevated the whole curve, increasing the AUC, but not affecting the kinetics (e.g., Tmax, elimination rate). In another example, the presence of polysorbate shifted the Tmax towards the y-axis (i.e., earlier) and changed the clearance rate (i.e., tail on the right) by making the epinephrine more readily available, thereby shutting down the vasculature (vasoconstriction).

Analytical Test Data

Four batches of epinephrine were studied for shot weight, actuation force, particle distribution, and moisture content.

TABLE 3

| | Batch 1 | Batch 2 | Batch 3 | Batch 4 |
|---|---|---|---|---|
| Lactose (% w/w) | 88 | 88 | 78 | 78 |
| Epinephrine (% w/w) | 10 | 10 | 20 | 20 |
| NaCl (% w/w) | 2 | 2 | 2 | 2 |
| Tween 80 (% w/v) | N/A | 0.1 | N/A | 0.1 |

Figure 121:
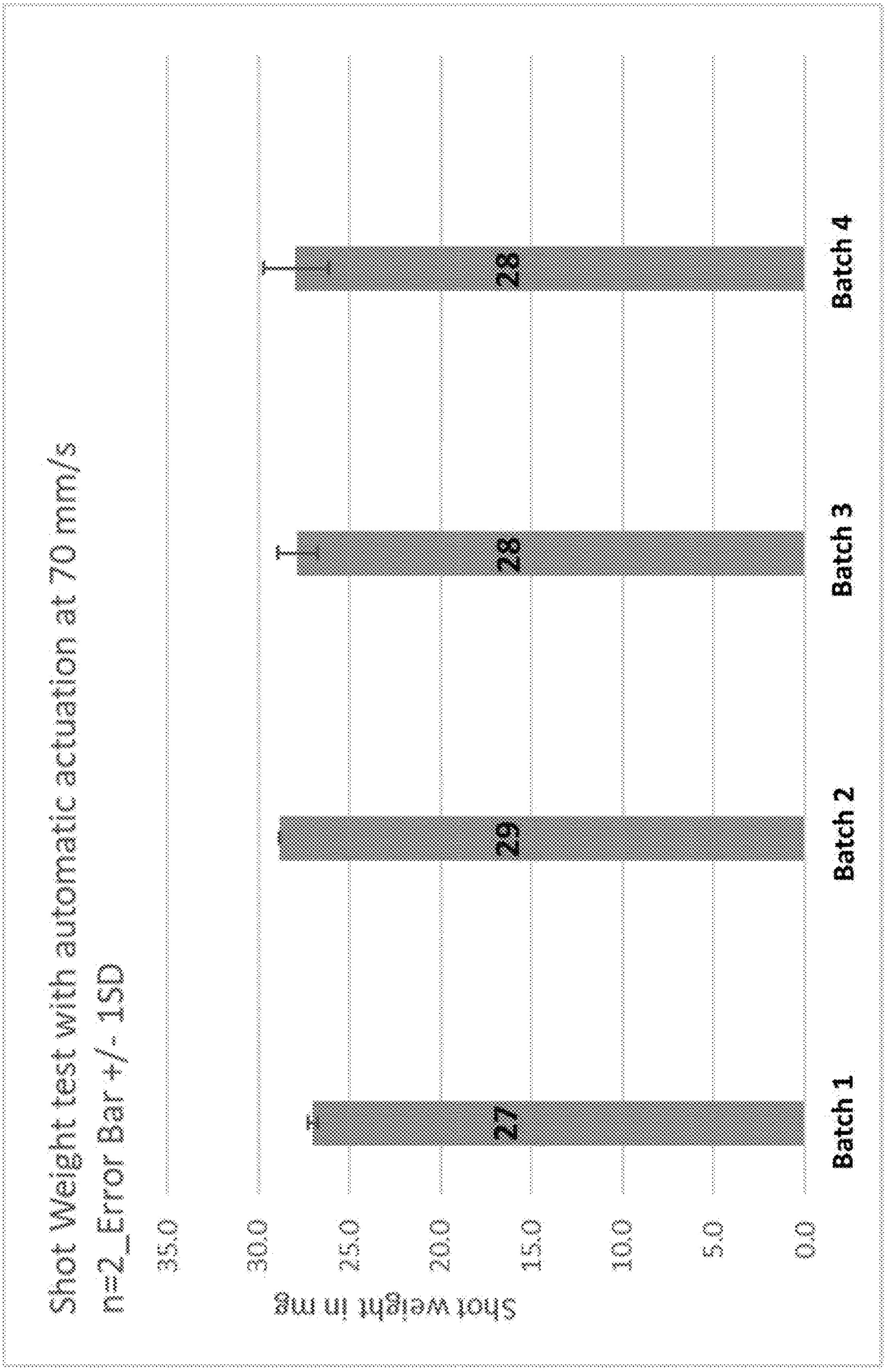

Each sample included a fill weight of 30 mg. The shot weight (i.e., the weight of composition metered with actuation) was assessed using a Proveris Actuator (Hudson, MA) with an actuation velocity of 70 mm/s, an actuation acceleration of 5000 m/s2, a contact force of 0.3 kg, an end of stroke force of 8 kg, and a hold time of 300 ms. In each case, the shot weight was found to be reproducible, indicating no adverse clogging or blocking of the valve mechanism. As shown in FIG. 121, the results indicate that at least 90% of the filled dose is delivered.

Figure 122:
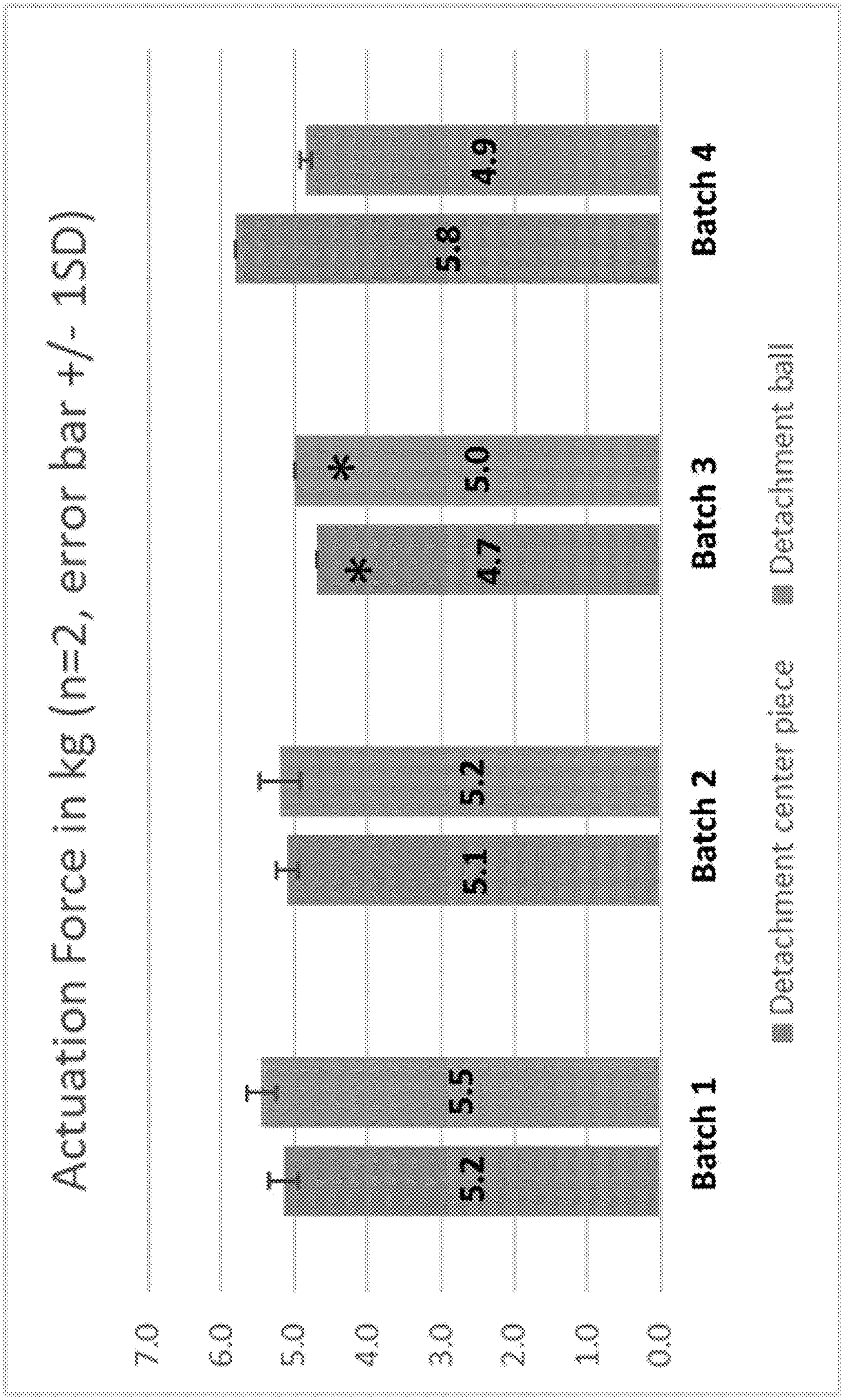
Figure 123:
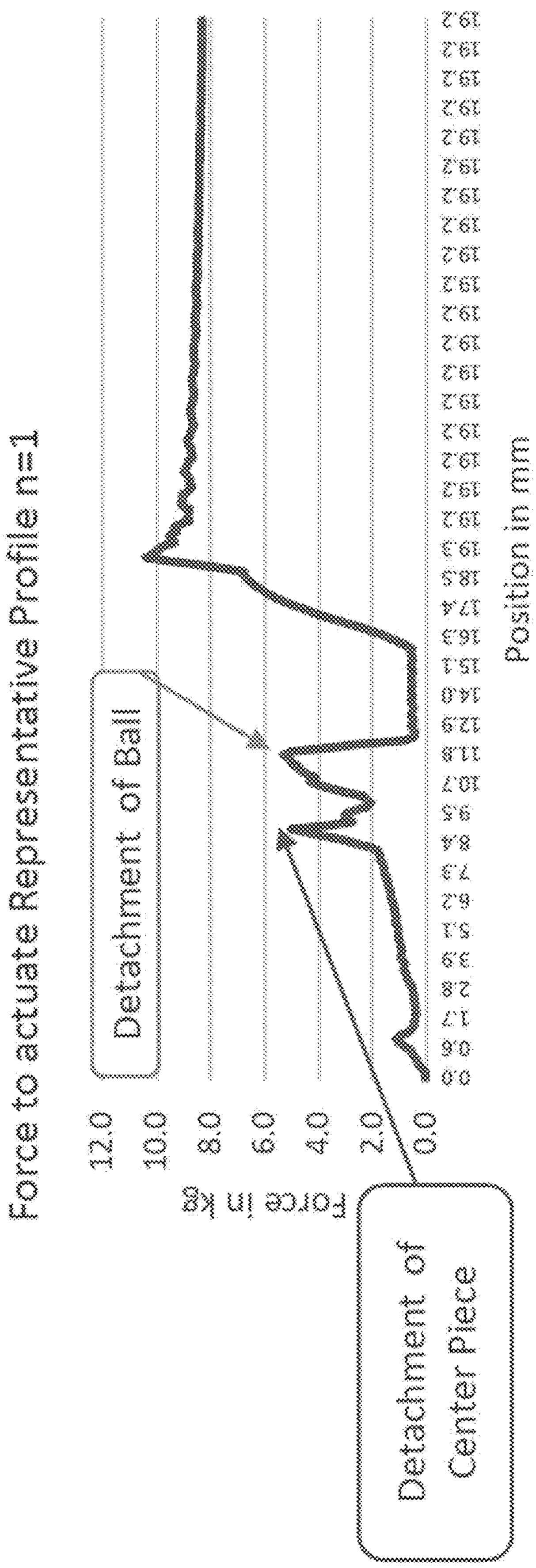

The actuation force was assessed using an actuation velocity of 70 mm/s, an actuation acceleration of 5000 m/s2, a contact force of 0.3 kg, an end of stroke force of 8 kg, and a hold time of 300 ms. Two samples were tested for Batch 1, Batch 2, and Batch 4. In each case, the actuation force was found to be reproducible. One sample was tested for Batch 3. FIG. 122 illustrates the actuation force for the detachment center piece and the detachment ball. A force to actuate representative profile is shown in FIG. 123.

Figure 124:
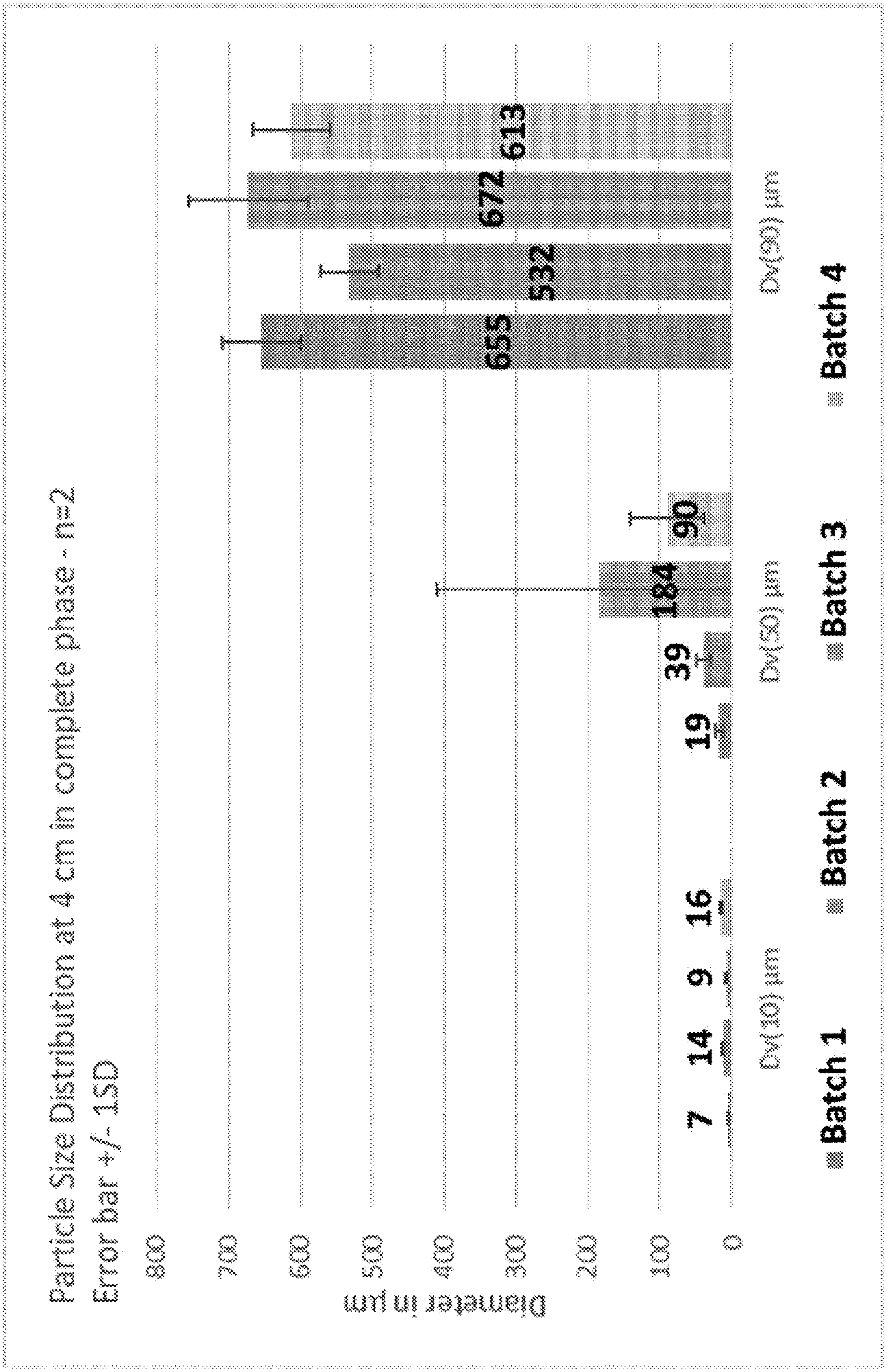
Figure 125:
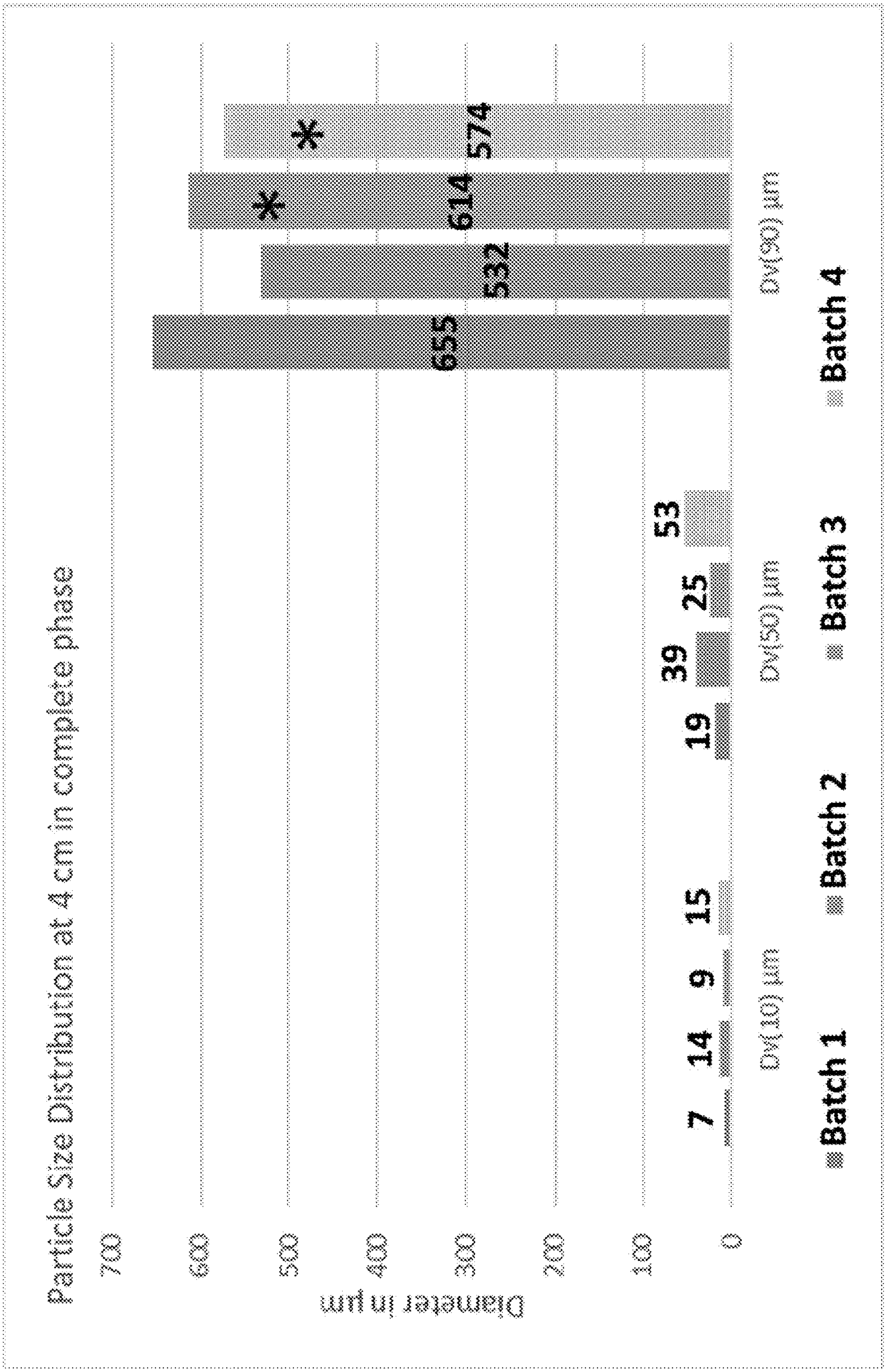

Particle size distribution was assessed using an actuation velocity of 70 mm/s, an actuation acceleration of 5000 m/s2, a contact force of 0.3 kg, an end of stroke force of 8 kg, and a hold time of 300 ms. FIG. 124 illustrates particle size distribution at 4 cm in complete phase. FIG. 125 illustrates particle distribution at 4 cm in complete phase without outliers. As shown in FIGS. 124-125, the results indicate a large variability for Batch 3 and Batch 4. Additionally, a higher percentage of fine particles are present for Batch 1 and Batch 3.

Figure 126:
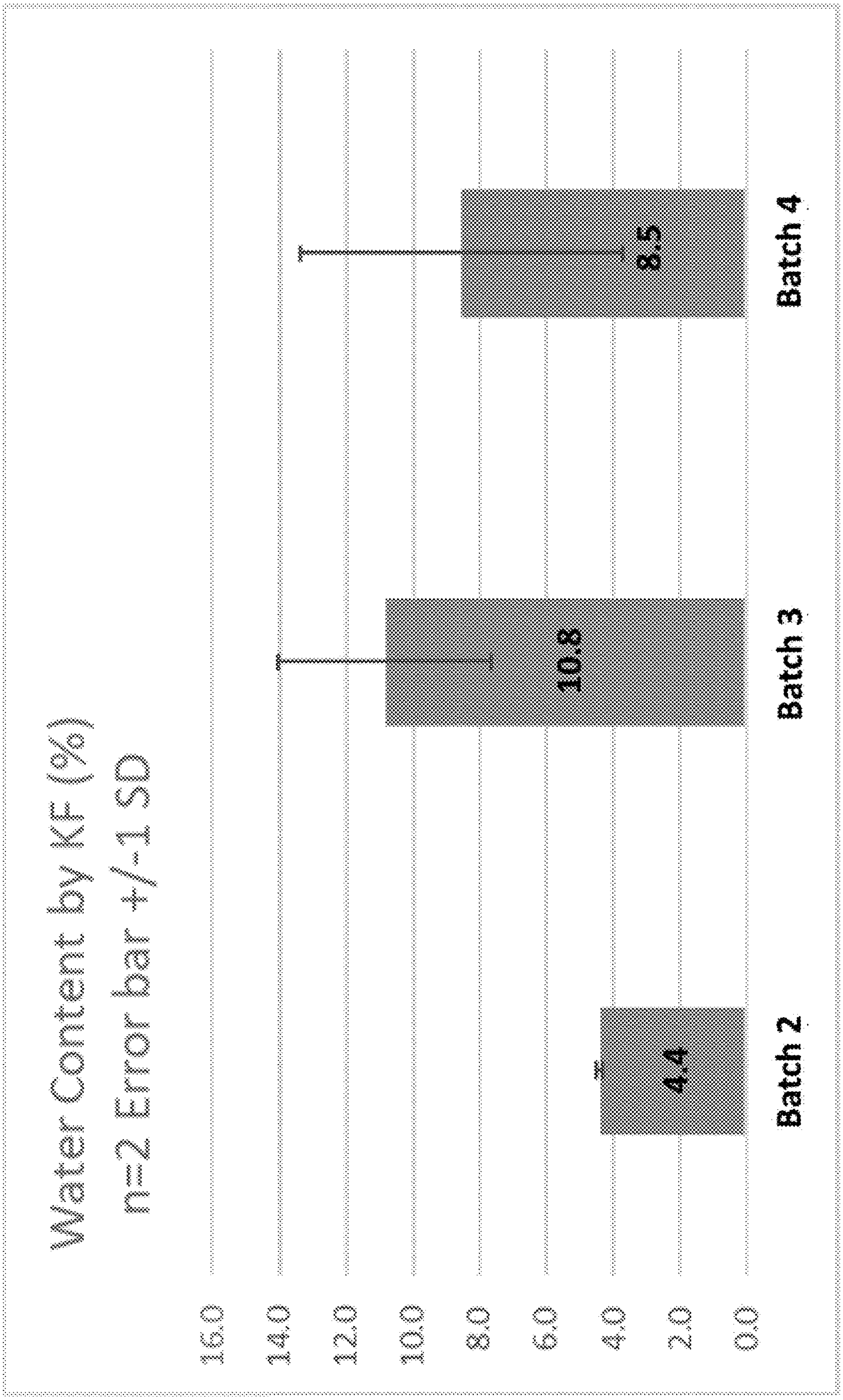

Moisture content was determined using Karl Fischer as shown in FIG. 126. No moisture content was performed on Batch 1 because the formulation was too sticky. Results for Batches 2-4, which were performed in duplicate, are shown in Table 4 below. The second repetition for Batches 3 and 4 has a higher water content, suggesting a high hygroscopicity of the material, which was visually confirmed. The formulation becomes stickier and more transparent in less than 10 minutes.

TABLE 4

| Sample Name | Water Content (%) |
|---|---|
| Batch 2-1 | 4.34 |
| Batch 2-2 | 4.47 |
| Batch 3-1 | 8.58 |
| Batch 3-2 | 13.09 |
| Batch 4-1 | 5.13 |
| Batch 4-2 | 11.93 |

Visual appearance of all four batches was noted immediately after opening and after exposure to laboratory conditions as shown in Table 5.

TABLE 5

| | Immediately After Opening | After Exposure to Laboratory Conditions |
|---|---|---|
| Batch 1 | White, agglomerated, and "sticky" | Becomes translucid and "sticky" |
| Batch 2 | White powder, electrostatic | Stays white, but becomes slightly "sticky" |
| Batch 3 | White, agglomerated, and "sticky" | Becomes slightly translucid and "sticky" |
| Batch 4 | White powder, electrostatic | Stays white, but becomes slightly "sticky" |

Impact of device orientation was determined for the UDS-P nasal delivery device. Delivery angle and insertion have an impact on regional deposition. Lower angles (e.g., 30° and 45°) result in higher posterior deposition. Higher insertion depth results in higher olfactory region deposition.

Figure 128:
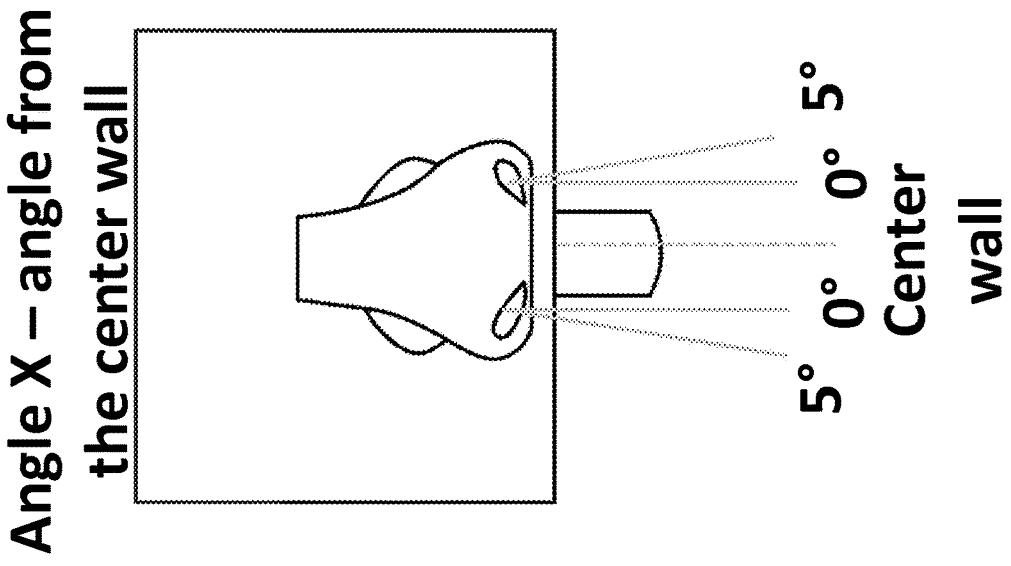
Figure 127:
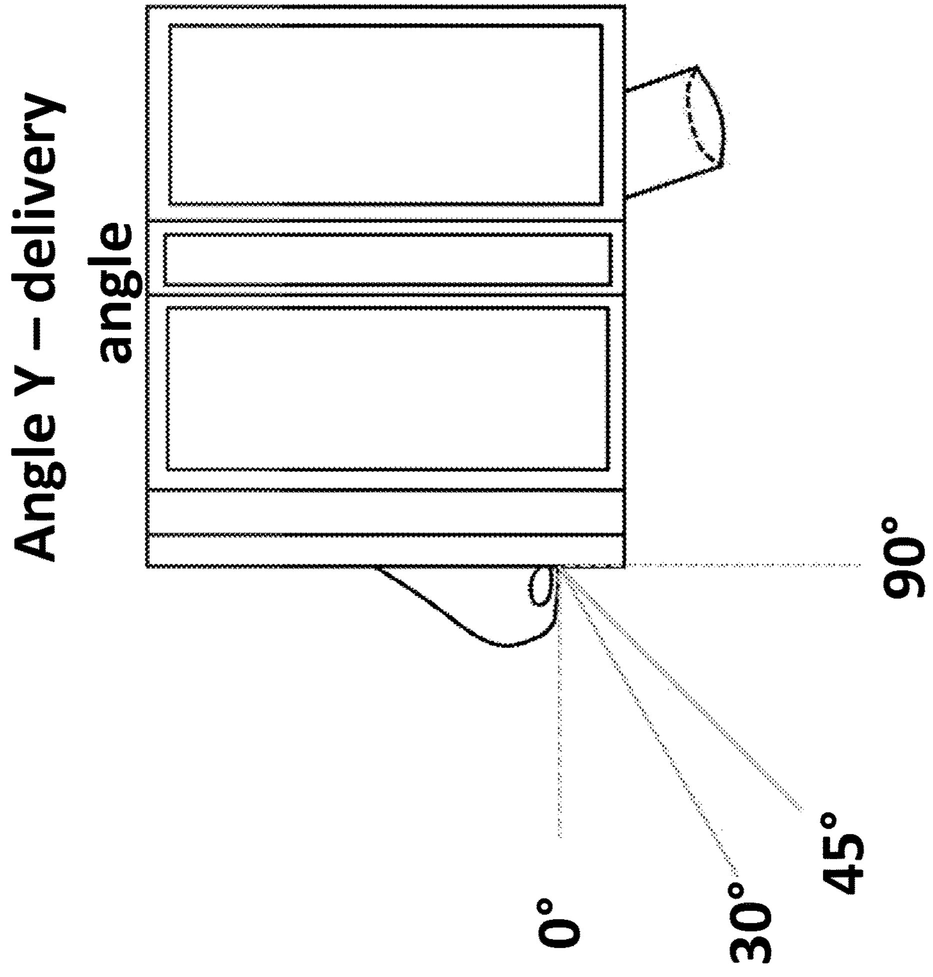

FIG. 127 illustrates a delivery angle. FIG. 128 illustrates an angle from the center wall of the nose.

FIG. 129 illustrates a graph of impact of insertion depth and angle using a 5° angle from the center wall. Samples (shown left to right) include a 60° delivery angle, 5° angle from the center wall, and 0.5 cm insertion depth; a 60° delivery angle, 5° angle from the center wall, and 1 cm insertion depth; a 60° delivery angle, 5° angle from the center wall, and 1.5 cm insertion depth; a 45° delivery angle, 5° angle from the center wall, and 0.5 cm insertion depth; a 45° delivery angle, 5° angle from the center wall, and 1 cm insertion depth; a 45° delivery angle, 5° angle from the center wall, and 1.5 cm insertion depth; a 30° delivery angle, 5° angle from the center wall, and 0.5 cm insertion depth; a 30° delivery angle, 5° angle from the center wall, and 1 cm insertion depth; and a 30° delivery angle, 5° angle from the center wall, and 1.5 cm insertion depth. The graph includes % deposition for the nose, nasal valve, floor, turbinates, ethmoids, rhino-pharynx, and lungs.

In one embodiment, the composition of the present invention is a bulk drug intermediate. In one embodiment, the composition of the present invention has an epinephrine content of about 10%. In one embodiment, the composition of the present invention is an amorphous, white to off-white powder free of visible particulates with a 90-110% nominal assay, a related substance report of unspecified impurities >0.1%, no individual unspecified impurity ≥0.5%, total impurities ≤3.0%, and contains ≤3.0% of the S-enantiomer. In one embodiment, the particle size distribution of the composition is about 5-100 μm with a moisture content of less than about 5%. In one embodiment, the residual solvent is no more than 5000 ppm of ethanol. In one embodiment, the microbial burden is no more than 100 cfu/g for TAMC (total aerobic microbial count), no more than 10 cfu/g TYMC (total yeast and mold count), and contains no objectional organisms. In one embodiment, the composition of the present invention has a shelf life of at least 12 months. In one embodiment, the composition of the present invention has a shelf life of at least 24 months. In one embodiment, the composition of the present invention has a shelf-life between about 24 months to about 36 months, about 24 months to about 48 months, about 24 months to about 60 months, about 24 months to about 72 months, about 12 months to about 36 months, about 12 months to about 48 months, about 12 months to about 60 months, or about 12 months to about 72 months. In one embodiment, the shelf life of the composition is improved by one or more physical and/or chemical characteristics of the delivery device used to store and administer the device. In one embodiment, the composition of the present invention does not degrade. Aqueous solutions of epinephrine, as disclosed herein, degrade when exposed to significant heat. The present invention advantageously maintains compositional integrity, even when exposed to significant heat.

A number of analytical methods were performed during development of the formulation of the present invention to ensure purity, potency, uniformity, and the desired physicochemical characteristics were obtained for performance and regulatory adherence. Table 6 is included herein as an exemplary list of analytical methods. The analytical methods used to determine the physiochemical characteristics of the composition of the present invention are determined by the United States Pharmacopeial Convention (USP), ensuring the resulting composition is compliant with the standard of quality determined by USP. However, it should be noted that not every test performed during the development of the drug substance was determined to be required in validation or commercial manufacturing of the composition of the present invention. The required analytical methods were identified after extensive experimentation and observation of the experimental compositions, requiring reformulation and careful analysis, which was not only expensive but also time consuming.

TABLE 6

| Test | Note |
|---|---|
| Appearance | Visual of the solid |
| Foreign particulate matter | Visual of a solution or microscopy of the solid |
| Identity | USP HPLC method |
| Assay | USP HPLC method |
| Related substances | USP HPLC method |
| Enantiomeric purity | USP HPLC method |
| Moisture content | Karl Fischer |
| Particle size distribution | Laser diffraction |
| D90 | |
| D50 | |
| D10 | |
| XRPD | X-ray diffraction |
| Residual solvents | GC |
| Ethanol | |
| Microbial limits | USP<61> |
| TAMC | |
| TYMC | |
| Objectionable organisms | USP<62> |

The analytical methods were used to determine the ideal specifications of the present formulation, specifically the release profile of the composition. The ideal specifications which should be identified as a result of each analytical method are listed herein in Table 7. High Pressure Liquid Chromatography (HPLC), X-Ray Powered Diffraction (XRPD), and Gas Chromatography (GC) are included in the methods for analysis. Additionally, the total aerobic microbial count (TAMC) and total yeast and mold count (TYMC) are determined using the USP <61> test, commonly referred to as a microbial limits test, while the test for specified microorganisms according to USP <62> is performed to identify objectionable organisms.

TABLE 7

| Test | Specification | Method |
|---|---|---|
| Appearance | White to off-white powder | Visual, Solid |
| Foreign particulate matter | No visible particulates | Visual, Solid |
| Identity | Aligns with reference standard | HPLC |
| Assay | 100 + 2 wt % epinephrine | HPLC |
| Related substances | | HPLC |
| Adrenolone | NMT 0.2% | |
| Epinephrine sulfonate | NMT 0.2% | |
| Norepinephrine | NMT 0.2% | |
| Individual unspecified impurities | NMT 0.1% | |
| Total impurities | NMT 0.5% | |
| Enantiomeric purity | NMT 3.0% (+)-epinephrine | HPLC |
| Moisture content | NMT 5% | Karl Fischer |
| Particle size distribution | | Laser diffraction |
| D90 | NLT 40 μm | |
| D50 | NLT 15 μm | |
| D10 | NLT 3 μm | |
| XRPD | Amorphous | XRPD |
| Residual solvents | | GC |
| Ethanol | NMT 5000 ppm | |
| Microbial limits | | USP<61> |
| TAMC | NMT 100 cfu/g | |
| TYMC | NMT 10 cfu/g | |
| Objectionable organisms | Absent | USP<62> |

In one embodiment, the composition of the present invention is 10% epinephrine (USP) by weight, 88% purified lactose (i.e., lactose NF), and 2% NaCl, wherein the NaCl and the epinephrine adhere to the Unites States Pharmacopeia (USP) standard. In this composition, the epinephrine is the active ingredient while the lactose NF functions as a carrier and the NaCl USP acts as a dispersing agent. In one embodiment, the composition of the present invention is 9.9% epinephrine by weight, 88% purified lactose (i.e., lactose NF), 2% NaCl USP, and 0.1% TWEEN80. In one embodiment, the composition of the present invention is 10% epinephrine by weight, 87.9% purified lactose (i.e., lactose NF), 2% NaCl USP, and 0.1% TWEEN80. In one embodiment, the composition of the present invention is 10% epinephrine by weight, 88% purified lactose (i.e., lactose NF), 1.9% NaCl USP, and 0.1% TWEEN80. It was suggested an acidic environment be used to acidify the solution and improve the solubility of the API (i.e., epinephrine.) Thus, in order to solubilize the epinephrine base in the selected solvent system (i.e., water and ethanol), HCl was added to the feed solution.

Table 8 is an exemplary composition of the bulk solution, also referred to herein as a feed solution, for spray drying according to one embodiment of the present invention. For trials including TWEEN80 (e.g., Trial 13), the bulk solution includes 0.0025% TWEEN80, about 0.015 mg/600 g. One of more than ordinary skill in the art will appreciate the minute differences between a feed solution and a bulk solution. However, both terms are used herein to describe a solution prepared in advance of experimentation from which a solid powder will be extracted. In one embodiment, this bulk solution has a pH of 3.3. In one embodiment, the bulk solution is operable to be altered to obtain a specific pH value. The bulk solution pH is directly associated with epinephrine dissolution, as an acidic solution is required to solubilize the epinephrine. In one embodiment, the bulk solution is stored in an environment with variable temperature to prevent degradation. In one embodiment, the bulk solution is stored in an anaerobic environment to prevent degradation. In one embodiment, the bulk solution is stored in an environment that is significantly free of luminous pollution (e.g., lighting is reduced between 75%-100% in comparison to a standard lighting environment) to prevent degradation.

TABLE 8

| Material | % w/w | mg/600 g |
|---|---|---|
| Epinephrine (API) | 0.250 | 1.500 |
| Lactose monohydrate | 2.200 | 13.200 |
| Sodium chloride | 0.050 | 0.300 |
| Ethanol | 19.480 | 116.91 |
| Sterile water for irrigation | 77.700 | 466.200 |
| 5M Hydrochloric acid | 0.315 | 1.89 |
| Total | 100.0 | 600 g |

The stock solution of Table 8 produces a solution with about 2.5% solid content levels. In order to increase the amount of solid content within the formulation (while keeping the API to lactose monohydrate ratio constant), an additional amount of HCl is required to obtain a clear solution, which leads to a decrease in the pH of the solution. Qualitatively, lower pH values indicate increased stability of the solution by lowering the oxidative potential. Stock solutions prepared at a lower pH of 2.2 were more stable compared to the solutions prepared at pH 3.9. At pH 3.9, some related substances peaks, albeit small, appeared in the chromatograms of samples not purged with $N_2$ after 24 hours. These increased when measured after 72 hours. However, while the overall stability of the stock solution may increase as pH decreases, low pH is suspected to contribute to the decomposition of the resultant powder as disclosed herein.

FIGS. 130A-130C illustrate the technical batches used in one round of experimentation to identify the drug substance of the present invention. The batches utilize the formulation of Table 8 as a feed solution batch, with the exceptions of Trial 12, Trial 13, and Trial 14. In Trial 12, the target pH was 2.2 rather than 3.3 and only HCl was used for pH adjustment. In Trial 13, TWEEN80 was added to the stock solution. In Trial 14, lactose was replaced with mannitol. Trial 10 produced a spray dried powder of acceptable purity, though with low yield. Trial 11 was a 66% scale-up of Trial 10 in which the spray drying time was increased from 270 to 440 min. The assays between the trials were comparable; however, the percentage of related substances increased from 0.1 in Trial 10 to 2.1 in Trial 11, as depicted in FIG. 130B. Further, one of ordinary skill in the art will appreciate that Trial 9 is not depicted in FIGS. 130A-130C as it was a placebo formulation manufactured to confirm that the impurities in the trials were related to the API rather than the excipients. Lactose was used in Trial 9 to compensate for the absence of the API.

In order to reduce the possibility of oxidative degradation, Trials 5 through 9 were conducted using $N_2$ as both atomization gas and processing gas, saturating the equipment chamber with $N_2$. Trial 5 was conducted using the same process parameters as Trial 3. Trial 6 was also produced keeping the process parameters as Trials 3 and 5, expect that the stock solution was manufactured at 2400 g scale rather than the previous 600 g scale used for Trials 1 through 5. Trial 7 and Trial 8 were also manufactured at a large scale, 2400 g and 2000 g respectively.

The analytical testing methods described herein were applied to the trials. Testing for Trials 5, 7, 8, and 9 showed a single glass transition temperature for the spray-dried powder. Two glass transitions were observed in Trial 6. Assays for Trials 5 through 8 ranged from approximately 94% label claim for Trial 7 to 98% for Trial 5. The level of related substances for Trial 6 were comparable to Trial 5. The impurity level of Trial 7 was 2.7%, slightly higher compared to Trials 5 and 6, displayed impurities of 2.2%. This slight increase in impurity is attributed in part to the increased batch size of Trial 7, as larger batch sizes require increased processing time, thus prolonging the exposure of the composition to elevated temperature. However, Trial 8 showed relatively low total impurities of 1.6% when compared to Trial 5, despite being manufactured at higher batch size. After 4 weeks stored at room conditions (i.e., 25° C. and 60% relative humidity (RH)), the impurities of Trial 8 increased to 7.8%. This increased significantly to 52.9% after storage for 4 weeks. Trial 9 did not show any related substances. Values of residual solvent (i.e., combination of water and ethanol) are above 5% for all trials. Increased amounts of residual solvent (14.27%) were observed for Trial 9 when tested with simultaneous thermogravimetric analysis (STA). Trials 5 through 8 showed about 6-8% of total moisture content. The water content of Trial 9 was 6.2% when tested with KF.

Trials 10 through 13 were conducted at a reduced nozzle inlet temperature in order to reduce impurities. A secondary drying step was added in an attempt to reduce the moisture content of the powder. Drying was performed at 40° C. in a vacuum oven for 24 hours. However, increasing impurity levels were observed for trials in which secondary drying at 40° C. was used. Trial 10 was processed at a lower temperature and showed a lower initial percentage of impurities of 0.1% in comparison to other trials. However, this percentage increased to 0.3% after 9 days stored at room conditions and increased again to 2% after overnight storage (i.e., 12 hours) in the oven at 40° C. Additionally, an increase in water content was observed after storage of Trial 10, which may be attributed to a Maillard reaction between the API and lactose. A higher initial percentage of impurities, 2.1%, was observed for Trial 11. This increased to 5.2% after 12 hours and increased again to 6.2% after storage in the oven at 40° C. for 24 hours. Trial 13 showed higher impurities at 2.7% than both Trial 11 and Trial 10. Trial 12 showed 15.8% total related substances. The impurity results for Trial 12 and Trial 13 indicate that either Tween 80 or lower pH contribute to increase the impurity levels within the sample. Around 3 to 5% of water content was observed for Trials 10 through 13, and a single glass transition temperature was observed for these trials.

Trial 14 was also conducted at a reduced nozzle inlet temperature in order to reduce impurities. Additionally, lactose monohydrate was replaced with 2.45% w/w of mannitol (7.7 g/batch) to prevent any possible Maillard reaction. Trial 14 showed 16.6% initial impurities, which further increased to 46.1% after storage overnight at 40° C. and increased to 61.1% after 24 hours at 40° C. The water content of Trial 14 was between 1.1 to 1.2%. A larger D-Epinephrine peak was initially observed, which increased over time. No glass transition temperature was observed for Trial 14.

FIGS. 131-139 depict the results of HPLC chromatography conducted for selected trials. In all trials, related impurities increased over time. FIG. 131 depicts the initial chromatogram of Trial 10, including related substances. FIG. 132 depicts the initial chromatogram of Trial 8. FIG. 133 depicts the chromatogram, including related substances, of Trial 8 after the trial was maintained at ambient temperature for four weeks. FIG. 134 depicts the initial chromatogram of Trial 11, including related substances. FIG. 135 depicts the chromatogram of Trial 11, including related substances, after the trial was maintained at 40° C. for 24 hours. FIG. 136 depicts the chromatogram of Trial 11 at a pH of 3.1, including related substances.

FIG. 137 depicts the chromatogram of Trial 12 at a pH of 2.3, including related substances. It was suggested that a bulk solution with a lower pH would protect the epinephrine from oxidation. The Trial 12 bulk solution was prepared at pH 2.27 (i.e., about pH 2.3), comparatively lower than the average pH of about 3.1 for the other trials.

FIG. 138 depicts the chromatogram of Trial 14, including related substances. Amines and reducing sugars, such as lactose, are known to react via the Maillard Reaction. Though the reaction is more common with primary amines, the reaction has been observed with secondary amines such as epinephrine. Thus, Trial 14 was conducted using the same bulk solution composition while substituting mannitol for lactose in order to eliminate the possibility of a Maillard reaction and determine if mannitol is a desirable substitution for lactose in the composition of the present invention. The spray drying parameters for Trial 14 were the same as for Trials 10-13. The trials disclosed herein conducted with lactose have similar impurities as those conducted with mannitol, based on the relevant retention time of the impurities in HPLC chromatography. In one embodiment, the composition of the present invention eliminates the risk of a Maillard Reaction between epinephrine and lactose by utilizing a non-reducing sugar or sugar alcohol (e.g., mannitol). Alternative non-reducing sugars include but are not limited to stachyose, sucrose, verbascose, trehalose, raffinose, and sugar alcohols made therefrom.

FIG. 139 depicts the initial chromatogram of Trial 11, including related substances overlaid with the chromatogram of Trial 14, including related substances.

The variables of particular interest for these trials were acidity (i.e., pH and pKa), time (i.e., the number of impurities observed over time), and the excipient (i.e., lactose and non-reducing sugars such as mannitol). From observing these trials, it was determined that low pH as well as nozzle inlet temperature, extended processing times, and extended storage times of the drug substance at ambient temperature or above may contribute to impurities in the drug substance.

Trials 1-14 using a spray dried solution of (−)-epinephrine free base, aqueous HCl to pH 3.5, NaCl, and lactose dissolved in ethanol and water failed to produce a stable powder. It is suspected that pH and the strength of the acid used in combination with time and temperature contributes to decomposition. As a result, in one embodiment, the feed solution of the present invention uses a weaker acid (e.g., citric acid) with a higher pH (i.e., a pH of 4 or greater) in place of HCl. In one embodiment, the bulk formulation utilizes trisodium citrate to adjust the pH of the solution. In one embodiment, the bulk formulation utilizes epinephrine bitartrate (e.g., (−)-epinephrine bitartrate) in order to eliminate the use of an acid altogether. In one embodiment, the composition of the present invention comprises epinephrine bitartrate, trisodium citrate to pH 4.0-4.5, and lactose dissolved in ethanol and water.

Epinephrine bitartrate is the bitartrate salt form of epinephrine. The use of epinephrine bitartrate eliminates the need to acidify an aqueous solution to solubilize epinephrine. Epinephrine free base is insoluble in water, thus requiring the use of an acidic aqueous solution to dissolve the epinephrine free base. The addition of epinephrine free base to a non-acidic solution necessitates the use of HCl or a similar acid to acidify the solution and thereby dissolve the epinephrine into the solution. Epinephrine bitartrate, however, is an acid salt formed from the neutralization of epinephrine free base. The bitartrate anion is ionically bound to the epinephrine free base in the neutralization reaction, forming epinephrine bitartrate. This bond is disassociated in water, causing the acidification of a solution of epinephrine bitartrate in water. The $pH_{CA}$ of an epinephrine bitartrate solution in water is about 3.5, which is significantly acidic so as to cause the dissolution of the epinephrine. Thus, there is no need to add an acid (e.g., HCl) to a solution including epinephrine bitartrate in order to solubilize the epinephrine. One of ordinary skill in the art will appreciate that epinephrine bitartrate is operable to be substituted for epinephrine at a ratio of 1:1 on a molar basis (i.e., the number of moles of the epinephrine divided by the number of liters of solution). However, epinephrine free base is replaced by epinephrine bitartrate at a ratio of 1:1.82 (i.e., 1.82 grams of epinephrine bitartrate is used as a substitute for 1 gram of epinephrine free base).

Trisodium citrate, also referred to as sodium citrate, is useful as a pH buffering agent in the composition of the present invention. Trisodium citrate also acts as an antioxidant and chelating agent, inhibiting oxidation of the composition of the present invention and thereby inhibiting the degradation of the composition of the present invention.

In one embodiment, the composition of the present invention is about 35% w/w epinephrine bitartrate (20% epinephrine as the free base), about 51% w/w purified lactose, and about 14% w/w trisodium citrate. In this composition, the epinephrine is the active ingredient while the lactose functions as a carrier and the trisodium citrate acts as both a buffering agent and an antioxidant. In one embodiment, the epinephrine bitartrate of the present invention comprises about 20% free base. The weight percentage of epinephrine bitartrate used in an epinephrine bitartrate composition of the present invention is higher than the weight percentage of compositions comprising epinephrine free base as disclosed herein. A weight percentage of about 35% of epinephrine bitartrate in the composition of the present invention is equivalent to about 20% w/w epinephrine free base. Thus, in one embodiment, the present invention comprises about 20% w/w epinephrine free base, about 14% w/w to 29% w/w trisodium citrate, 51% w/w to about 66% w/w purified lactose.

FIGS. 140A-140C illustrate the technical batches used in Trial SD12, Trial SD13, Trial SD15.1, Trial SD15.2, Trial SD15.3, Trial SD16, and Trial SD17. A variety of analytical tests were performed for each trial, the results of which are included in FIGS. 140A-142. Trial SD12, Trial SD13, Trial SD15.1, Trial SD15.2, and Trial SD15.3 were performed with a target of 10% epinephrine (free base) content. This was increased to 20% for Trial SD16 and subsequent trials when bulk densities of greater than 0.200 g/mL were viewed as not achievable.

Table 9 lists the analytical methods and ideal specifications which should be identified as a result of each analytical method for a second round of experimentation to identify the drug substance of the present invention. These trials include Trial SD12, Trial SD13, Trial SD15.1, Trial SD15.2, Trial SD15.3, Trial SD16, and Trial SD17. High Pressure Liquid Chromatography (HPLC), Fourier-Transform Infrared Spectroscopy (FT-IR), X-Ray Powered Diffraction (XRPD), and Gas Chromatography (GC) are included in the methods for analysis. Additionally, the total aerobic microbial count (TAMC) and total yeast and mold count (TYMC) are determined using the USP <61> test, commonly referred to as a microbial limits test. The presence or absence of specified objectionable microorganisms is identified using the USP <62> test, commonly referred to as the test for specified microorganisms.

TABLE 9

| Test | Specification | Method |
| --- | --- | --- |
| Appearance | White to off-white powder, for information | Visual/ Microscopy |
| Identity | Aligns with reference standard | HPLC |
| Identity | Compares to reference standard | FT-IR |
| Assay | 20 + 1 wt % epinephrine | HPLC |
| Related substances | | HPLC |
| Adrenalone | NMT 0.2% | |
| Epinephrine sulfonate | NMT 0.2% | |
| Norepinephrine | NMT 0.2% | |
| Individual unspecified impurities | NMT 0.5% (Report >0.1%) | |
| Total impurities | NMT 3.0% | |
| Enantiomeric purity | NMT 3.0% (+)-epinephrine | HPLC |
| Moisture content | NMT 5% | Karl Fischer |
| pH of bulk solution | 4-4.5 | Titration of solution |
| Particle size distribution | | Laser diffraction |
| D90 | Report | |
| D50 | $D_{50}$ 30-50 μm | |
| D10 | $D_{10}$ > 10 μm | |
| XRPD | amorphous | XRPD |
| Residual solvents | | GC |
| TBD | Ethanol NMT 5000 ppm | |
| Microbial limits | | USP<61-62> |
| TAMC | NMT 100 cfu/g | |
| TYMC | NMT 10 cfu/g | |
| Objectionable organisms | Absent | |

FIG. 141 illustrates the results of Scanning Electron Microscopy (SEM) of a homogenous powder composition with acceptable particle size and dispersion according to one embodiment of the present invention. The SEM is an observation of the formulation of Trial 15.1, wherein the nozzle inlet temperature was 125° C.

FIG. 142 illustrates the results of Scanning Electron Microscopy (SEM) of a powder composition which has agglomerated. The SEM is an observation of the formulation of Trial 15.2, wherein the nozzle inlet temperature was 135° C. The spray drier utilized a two-fluid nozzle with nitrogen gas and a peristaltic liquid pump. The results of Trial SD12, Trial SD13, Trial SD15.1, Trial SD15.2, Trial SD15.3, Trial SD16, and Trial SD17 where the inlet temperature of the spray drier was greater than 125° C. led to the formation of glass-like agglomerates, indicating that an inlet temperature greater than 125° C. exceeds the glass transition temperature of lactose and leads to the formation of impurities. It should be noted that Trial SD17 was the first trial with an inlet temperature equal to 125° C. where glass-like agglomerates were observed. However, one of ordinary skill in the art will appreciate the variety of confounding variables that may attribute to unexpected results for a singular test. However, the lack of agglomeration in multiple trials wherein the nozzle inlet temperature was about 125° C. with repeatable results suggest that such a confounding variable may have been present for Trial 17.

In one embodiment, the formulation of the present invention is operable to have a particle size of $D_{10}$>10 μm and $D_{50}$ of 30-50 μm while increasing the bulk density to greater than 500 mg/mL. In one embodiment of the present invention, a scaled formulation is operable to produce about 5 kilograms of the spray-dried composition of the present invention.

Example Combinations

The following are examples of embodiments used in combination. However, the present disclosure is not limited to the example embodiments provided below. The intranasal dry powder compositions and/or unit doses are operable to include any combination of the at least one active pharmaceutical ingredient, the at least one enabling agent, and/or the at least one carrier and/or excipient.

Example Composition 1

In one embodiment, the intranasal dry powder compositions and/or unit doses include a vasoactive agent (e.g., epinephrine). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 2

In one embodiment, the intranasal dry powder compositions and/or unit doses include a vasoactive agent (e.g., epinephrine) and at least one antihistamine. In one embodiment, the at least one antihistamine includes, but is not limited to, diphenhydramine, doxylamine, loratadine, desloratadine, cetirizine, levocetirizine, fexofenadine, famotidine, cimetidine, and/or nizatidine. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 3

In one embodiment, the intranasal dry powder compositions and/or unit doses include a vasoactive agent (e.g., epinephrine) and at least one steroid (e.g., hydrocortisone). In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 5% w/v.

Example Composition 4

In one embodiment, the intranasal dry powder compositions and/or unit doses include a vasoactive agent (e.g., epinephrine) and a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 5

In one embodiment, the intranasal dry powder compositions and/or unit doses include a vasoactive agent (e.g., epinephrine) and sodium chloride. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 6

In one embodiment, the intranasal dry powder compositions and/or unit doses include a vasoactive agent (e.g., epinephrine) and polysorbate. In one embodiment, the polysorbate is polysorbate 80. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 7

In one embodiment, the intranasal dry powder compositions and/or unit doses include a vasoactive agent (e.g., epinephrine), sodium chloride, and polysorbate. In one embodiment, the polysorbate is polysorbate 80. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 8

In one embodiment, the intranasal dry powder compositions and/or unit doses include a vasoactive agent (e.g., epinephrine), a salt, and a surfactant. In one embodiment, the surfactant is a polysorbate, a fatty acid, a phospholipid, sodium glycocholate, sodium taurocholate, polyoxyethylene lauryl ether, polyacrylic acid gel, sodium lauryl sulfate, and/or sodium deoxycholate. In one embodiment, the salt includes sodium chloride, potassium chloride, sodium phosphate, calcium phosphate, calcium sulfate, and/or magnesium sulfate. In one embodiment, the polysorbate is polysorbate 80. In one embodiment, the salt is present in a range between 0.01% w/w and 5% w/w. In one embodiment, the surfactant is present in a range between 0.01% w/v and 5% w/v. In another embodiment, the surfactant is present in a range between 0.01% w/v and 1% w/v. In one embodiment, the intranasal dry powder compositions and/or unit doses further include a vasodilator (e.g., phentolamine). In one embodiment, the intranasal dry powder compositions and/or unit doses further include a COMT inhibitor (e.g., entacapone). In one embodiment, the intranasal dry powder compositions and/or unit doses further include at least one enabling agent and/or at least one carrier and/or excipient.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one non-sulfite stabilizer, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes magnesium stearate. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Example Composition 9

In one embodiment, the intranasal dry powder compositions and/or unit doses include a vasoactive agent (e.g., epinephrine). In one embodiment, the intranasal dry powder compositions and/or unit doses further include at least one enabling agent. In one embodiment, the intranasal dry powder compositions and/or unit doses further include at least one carrier.

The at least one enabling agent includes, but is not limited to, at least one epinephrine potentiator, at least one stabilizing agent, at least one mucoadhesive, at least one absorption enhancer, at least one permeability enhancer, at least one surfactant, at least one surface modifier, at least one sustained release agent, at least one anticaking agent, at least one stabilizing agent, at least one systemic vasodilator, at least one nasal mucosal vasodilator, at least one mucosal permeation enhancer, at least one agent that reduces mucosal transit time, at least one agent that increases mucosal absorption or adhesion or transport, at least one chelator, at least one steroid, at least one preservative, at least one thickening agent, at least one humectant, at least one antihistamine, at least one solubilizing agent, at least one masking agent (e.g., taste, smell), at least one antioxidant, at least one viscosity enhancing agent, at least one dispersing agent, and/or at least one colorant. In some instances, the enabling agent includes at least one agent that reduces mucosal transit time, at least one agent that increases mucosal absorption and/or adhesion, at least one agent that enhances mucosal transport, or the enantiomers, diastereoisomers, racemates, or salts of such compounds with pharmaceutically acceptable counterions.

In one embodiment, the at least one enabling agent includes, but is not limited to, vasopressin, caffeine, at least one antihistamine (e.g., diphenhydramine, doxylamine, loratadine, desloratadine, cetirizine, levocetirizine, fexofenadine, famotidine, cimetidine, nizatidine), hydrocortisone, EDTA, magnesium stearate, tribasic calcium phosphate, citrate, sodium citrate, disodium citrate, trisodium citrate, citric acid, and/or ascorbic acid. In one embodiment, the at least one enabling agent includes vasopressin. In one embodiment, the at least one enabling agent includes caffeine. In one embodiment, the at least one enabling agent includes diphenhydramine. In one embodiment, the at least one enabling agent includes doxylamine. In one embodiment, the at least one enabling agent includes loratadine. In one embodiment, the at least one enabling agent includes desloratadine. In one embodiment, the at least one enabling agent includes cetirizine. In one embodiment, the at least one enabling agent includes levocetirizine. In one embodiment, the at least one enabling agent includes fexofenadine. In one embodiment, the at least one enabling agent includes famotidine. In one embodiment, the at least one enabling agent includes cimetidine. In one embodiment, the at least one enabling agent includes nizatidine. In one embodiment, the at least one enabling agent includes hydrocortisone. In one embodiment, the at least one enabling agent includes EDTA. In one embodiment, the at least one enabling agent includes tribasic calcium phosphate. In one embodiment, the at least one enabling agent includes citrate. In one embodiment, the at least one enabling agent includes sodium citrate, disodium citrate, or trisodium citrate. In one embodiment, the at least one enabling agent includes citric acid. In one embodiment, the at least one enabling agent includes ascorbic acid.

In one embodiment, the at least one carrier and/or excipient includes at least one cellulose derivative and/or starch. In one embodiment, the at least one carrier and/or excipient includes lactose. In one embodiment, the at least one carrier and/or excipient includes sodium carboxymethylcellulose. In one embodiment, the at least one carrier and/or excipient includes chitosan. In one embodiment, the at least one carrier and/or excipient includes a cyclodextrin (e.g., dimethyl-beta-cyclodextrin). In one embodiment, the at least one carrier and/or excipient includes mannitol. In one embodiment, the at least one carrier and/or excipient includes dodecylphosphocholine. In one embodiment, the at least one carrier and/or excipient includes an alkyl saccharide. In one embodiment, the at least one carrier and/or excipient includes ethanol (e.g., dried ethanol). In one embodiment, the at least one carrier and/or excipient includes lactose and hyaluronic acid (e.g., sodium hyaluronate). In one embodiment, the at least one carrier and/or excipient includes lactose and leucine. In one embodiment, the at least one carrier and/or excipient includes lactose and sodium chloride. In one embodiment, the at least one carrier and/or excipient includes lactose and niacin. In one embodiment, the at least one carrier and/or excipient includes lactose and polysorbate. In one embodiment, the at least one carrier and/or excipient includes sodium carboxymethylcellulose and hyaluronic acid (e.g., sodium hyaluronate). In one embodiment, the at least one carrier and/or excipient includes sodium carboxymethylcellulose and leucine. In one embodiment, the at least one carrier and/or excipient includes sodium carboxymethylcellulose and sodium chloride. In one embodiment, the at least one carrier and/or excipient includes sodium carboxymethylcellulose and niacin. In one embodiment, the at least one carrier and/or excipient includes sodium carboxymethylcellulose and/or polysorbate. In one embodiment, the at least one carrier and/or excipient includes sodium carboxymethylcellulose, lactose, sodium chloride, and/or polysorbate. In one embodiment, the polysorbate is polysorbate 80. In one embodiment, the sodium chloride is present in a range between 0.01% w/w and 5% w/w. In one embodiment, the polysorbate is present in a range between 0.01% w/v and 5% w/v. In another embodiment, the polysorbate is present in a range between 0.01% w/v and 1% w/v.

Kits

As previously described, in one embodiment, the present invention includes at least one kit. In one embodiment, the kit includes: (a) a dose of an intranasal dry powder composition disclosed herein and (b) instructions reciting when the dry powder composition in (a) is to be administered to a subject. In some embodiments, the kit further includes at least one intranasal delivery apparatus for dispensing the dry powder composition. In some embodiments, each of the at least one intranasal delivery apparatus is operable to deliver a therapeutically acceptable amount of the dry powder composition. In some embodiments, the apparatus is operable to intranasally deliver a therapeutically acceptable amount of the dry powder composition. In a preferred embodiment, the dry powder composition is delivered intranasally.

In another preferred embodiment, the kit includes a plurality of nasal devices. For example, and not limitation, the plurality of nasal devices includes a first nasal device, a second nasal delivery device, a third nasal delivery device, and/or a fourth nasal delivery device. In one embodiment, the plurality of nasal devices includes at least two nasal delivery devices including the same dry powder composition. For example, and not limitation, the plurality of nasal devices includes a dry powder composition including epinephrine. A second dose of epinephrine is often needed when anaphylaxis occurs. See, e.g., Patel N, Chong K W, Yip A Y G, Ierodiakonou D, Bartra J, Boyle R J, Turner P J. Use of multiple epinephrine doses in anaphylaxis: A systematic review and meta-analysis. J Allergy Clin Immunol. 2021 November; 148(5):1307-1315. doi: 10.1016/j.jaci.2021.03.042. Epub 2021 Apr. 20. PMID: 33862009;

PMCID: PMC8588837, which is incorporated herein by reference in its entirety. Advantageously, the kits of the present invention meet the long-standing, unmet need of delivering nasal epinephrine with a plurality of nasal devices.

In one embodiment, the plurality of nasal devices includes a first nasal device having a first dry powder composition and a second nasal device having a second dry powder composition. For example, and not limitation, the first nasal device includes a first dry powder composition (e.g., epinephrine, lactose, polysorbate, and/or sodium chloride), and the second nasal device includes a second dry powder composition (e.g., epinephrine, sodium carboxymethylcellulose, polysorbate, and/or sodium chloride).

In one embodiment, the plurality of nasal devices includes a first nasal device having a first dry powder composition, a second nasal device having a second dry powder composition, and/or a third nasal device having a third dry powder composition. For example, and not limitation, the first nasal device includes a first dry powder composition (e.g., epinephrine, lactose, polysorbate, and/or sodium chloride), the second nasal device includes a second dry powder composition (e.g., epinephrine, sodium carboxymethylcellulose, polysorbate, and/or sodium chloride); and the third nasal device includes a third dry powder composition (e.g., epinephrine, lactose, sodium carboxymethylcellulose, polysorbate, sodium chloride, at least one antihistamine, and/or at least one steroid (e.g., hydrocortisone)).

In yet another embodiment, the kit includes at least one nasal device and at least one beta-2 agonist. In one embodiment, the at least one beta-2 agonist is included in an inhaler (e.g., a meter-dose inhaler). In one embodiment, the at least one beta-2 agonist includes, but is not limited to, salbutamol or albuterol. In one embodiment, the kit further includes a spacer. In another embodiment, the at least one beta-2 agonist is in liquid form. In one embodiment, the kit further includes a nebulizer.

In one embodiment, the kit is included in a pouch. In one embodiment, the pouch includes at least one closeable opening. In one embodiment, the at least one closeable opening is operable to open and/or close via at least one securing mechanism. The at least one securing mechanism includes, but is not limited to, at least one zipper, a hook and loop system (e.g., VELCRO®), at least one button, at least one snap, at least one hook, at least one tie, at least one clip, and/or at least one buckle. The pouch is preferable waterproof or water resistant. In one embodiment, the pouch includes a desiccant. In one embodiment, the desiccant is a plastic desiccant.

In another embodiment, the kit is included in a hard case. In one embodiment, the hard case is formed of polypropylene or acrylonitrile butadiene styrene (ABS). The hard case is preferably waterproof or water resistant. In one embodiment, the hard case includes at least one handle (e.g., for carrying the hard case) and/or at least one loop. In one embodiment, the at least one handle and/or at least one loop is operable to attach a carabiner or other hook. In one embodiment, the hard case includes a desiccant. In one embodiment, the desiccant is a plastic desiccant.

In one embodiment, the pouch and/or the hard case is MOLLE-compatible. In one embodiment, the pouch incorporates a pouch attachment ladder system (PALS), which is a grid of webbing used to attach smaller equipment onto load-bearing platforms, such as vests and backpacks. For example, the PALS grid consists of horizontal rows of 1-inch (2.5 cm) webbing, spaced about one inch apart, and reattached to the backing at 1.5-inch (3.8 cm) intervals. In one embodiment, the webbing is formed of nylon (e.g., cordura nylon webbing, MIL-W-43668 Type III nylon webbing).

In one embodiment, an exterior finish of the pouch and/or the hard case is operable to be any color including, but not limited to, white, brown, green, orange (e.g., international orange), yellow, black, red, or blue, or any pattern (e.g., camouflage). In one embodiment, the exterior of the pouch and/or the hard case includes a reflective tape, fabric, or material. Advantageously, the reflective tape, fabric, or material improves visibility of the user in low-light conditions.

Methods of Treatment

Provided herein are methods of treating a patient by intranasally administrating the dry powder composition disclosed herein. Also provided herein are methods of treating a patient by using the delivery devices and/or kits disclosed herein.

In one embodiment, the patient has been exposed to at least one organophosphate compound. The at least one organophosphate compound includes, but is not limited to, sarin (GB), tabun (GA), soman (GD), cyclosarin (GF), VX, VR (Russian VX), diisopropyl-fluorophosphate, azinphos-methyl, chlorpyrifos, diazinon, dichlorvos, dimethoate, ethephon, malathion, methamidophos, naled, oxydemeton-methyl, parathion, fenthion, ethion, echothiophate, isoflurophate, trichlorfon, and/or tribufos.

Also provided herein are methods for treating patients exposed to nerve agents including applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or unit doses herein.

The methods, kits, compositions, doses, or products herein are useful for treating patients. In some instances, the patient has minimal to severe respiratory distress including bronchorrhea and bronchospasms. In some instances, the patient has excess sweating and salivation, seizures, and paralysis. In some embodiments, the composition provides a fast onset time and is suitable for intranasal use.

In some embodiments, the intranasal dry powder composition is sufficient to improve respiratory function and breathing in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to reduce bronchorrhea and bronchospasms in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to decrease excess sweating and salivation, seizures, and paralysis in the patient within 60 minutes, 50 minutes, 40 minutes, 30 minutes, 20 minutes, 10 minutes, 5 minutes, 3 minutes, 2 minutes, or 1 minute after administration. In one embodiment, the intranasal administration of the dry powder composition is used to treat a patient with asthma.

In some embodiments, the method of dilating a bronchus in a subject includes the intranasal administration of the dry powder composition disclosed herein. In some embodiments, the dilation occurs without substantial pulmonary inhalation. In some embodiments, the method of delivering epinephrine in a subject at least one of alpha-adrenergic receptors, beta-adrenergic receptors, or any combination thereof, include the intranasal administration of the dry powder composition disclosed herein. In some embodiments, the alpha-adrenergic receptors consist of the group including alpha-1 and alpha-2 adrenergic receptors. In some embodiments, the beta-adrenergic receptors consist of the group including beta-1, beta-2, and beta-3 adrenergic receptors. In some embodiments, delivery of epinephrine is localized. In some embodiments, delivery of epinephrine is systemic. In some embodiments, the method of treating a subject with asthma includes the intranasal administration of the dry powder composition disclosed herein. In some embodiments, the method of treating a subject with croup includes the intranasal administration of the dry powder composition disclosed herein. In some embodiments, the method of treating a subject by increasing the heart rate of the subject includes the intranasal administration of the dry powder composition disclosed herein. In some embodiments, the method of treating a subject by increasing the respiratory rate of the subject includes the intranasal administration of the dry powder composition disclosed herein. In some embodiments, the method of increasing the blood concentration of epinephrine in a subject includes the intranasal administration of the dry powder composition disclosed herein. In some embodiments, the method of treating pulmonary edema in a subject includes the intranasal administration of the dry powder composition disclosed herein. In some embodiments, the method of treating serum sickness in a subject in a subject includes the intranasal administration of the dry powder composition disclosed herein. In some embodiments, the method of counteracting bronchoconstriction effects in a subject following certain chemical exposures includes the intranasal administration of the dry powder composition disclosed herein.

The methods, kits, compositions, doses, or products herein are useful for treating patients. In some embodiments, the patient has bronchoconstriction, hypotension, and/or minimal or no cardiac activity. In some embodiments, the patient has low blood pressure. In some embodiments, the patient has hypotension. In some embodiments, the patient is experiencing hypotensive shock. In some embodiments, the composition also provides a fast onset time and is suitable for intranasal use.

In some embodiments, the intranasal dry powder composition is sufficient to increase arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to increase a mean arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to increase coronary perfusion pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to resume a spontaneous circulation in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is sufficient to relieve the bronchoconstriction in the patient within 60 minutes, 50 minutes, 40 minutes, 30 minutes, 20 minutes, 10 minutes, 5 minutes, 3 minutes, 2 minutes, or 1 minute after administration.

Also provided herein are methods for treating bronchospasm, cardiac arrest, hypotensive shock, or other situations requiring the need to implement cardiopulmonary resuscitation (CPR) and/or basic or advanced cardiac life support (ACLS) in an individual, including, applying to a mucosal surface(s) of the nasal cavity or cavities of an individual (e.g., the mucosal surfaces of the anterior regions of the nose, the frontal sinus, the maxillary sinuses, and/or on each of the mucosal surfaces which overlie the turbinates covering the conchas) any of the pharmaceutical compositions or unit doses herein by administering a vasoactive agent (e.g., epinephrine). In one embodiment, a nasal loading dose is an amount of epinephrine administered nasally that results in the systemic blood bioequivalent of intravenously (IV), intramuscularly (IM), or subcutaneously (SQ) administered epinephrine (e.g., 1 mg IV or 0.3 mg doses of EPIPEN®). In a related aspect, the method of treating a patient with cardiac arrest and/or bronchospasm in need of treatment with a composition including the nasal loading dose of about 0.05 mg to about 10 mg of a vasoactive agent (e.g., epinephrine), for example, about 0.5 mg to about 5 mg. In one embodiment, the composition includes about 0.75, 1.5, or 3.0 mg of the vasoactive agent (e.g., epinephrine) and optionally includes about 0.001 mg (or 1 pg) to 10 mg of a vasodilator (e.g., phentolamine), for example, about 0.1 mg to about 5 mg. In one embodiment, the composition includes about 0.1 to about 1 mg, or about 0.5 mg of the vasodilator (e.g., phentolamine). In one embodiment, the composition includes a pharmaceutically acceptable carrier mixture of about 1 to about 50 mg, for example about 10 to about 30 mg, about 15 to about 20 mg, or about 18 mg, and optionally, an agent that stabilizes the composition, an agent that reduces mucosal transit time, an agent that increases mucosal absorption and/or adhesion, an agent that enhances mucosal transport, (or the enantiomers, diastereoisomers, racemates, and the salts of such compounds with pharmaceutically acceptable counterions), wherein the amounts are operable to be synergistic for the treatment of bronchospasm and/or cardiac arrest. When used in such low doses, compositions herein are operable to provide a sufficiently high peak blood plasma concentration of the vasoactive agent (e.g., epinephrine) of at least about: 2-fold, 3-5 fold, 5-7 fold, 7-10, 10-30 fold, or 15-40 fold more than baseline levels rapidly after administration, within about: 60, 50, 40, 30, 20, 15, 10, 5, or 3 minutes to be effective in the treatment or reducing the symptoms of bronchospasm and/or cardiac arrest.

In some embodiments, the method herein further includes (a) initiating cardiopulmonary resuscitation (CPR), (b) using an automated external defibrillator (AED), or both (a) and (b). In some embodiments, the intranasal dry powder composition is administered if (a), (b), or both fail to increase the arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to increase the mean arterial pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to increase coronary perfusion pressure in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to resume a spontaneous circulation in the patient within 60 minutes, 50 minutes, 40 minutes, 30 minutes, 20 minutes, 10 minutes, 5 minutes, 3 minutes, 2 minutes, or 1 minute after administration. In some embodiments, the intranasal dry powder composition is administered if (a), (b), or both fail to relieve the allergic reaction in the patient within 60 minutes, 50 minutes, 40 minutes, 30 minutes, 20 minutes, 10 minutes, 5 minutes, 3 minutes, 2 minutes, or 1 minute after administration.

In another aspect, the methods, kits, compositions, doses, or products herein are useful for treating patients in a hospital. In some embodiments, the patient is not in a hospital. In some embodiments, the patient is in a hospital. In some embodiments, the patient is in a combat setting. In some embodiments, the patient is in a civil emergency setting. In some embodiments, the patient has a wound.

Location data is created in the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Figure 9:
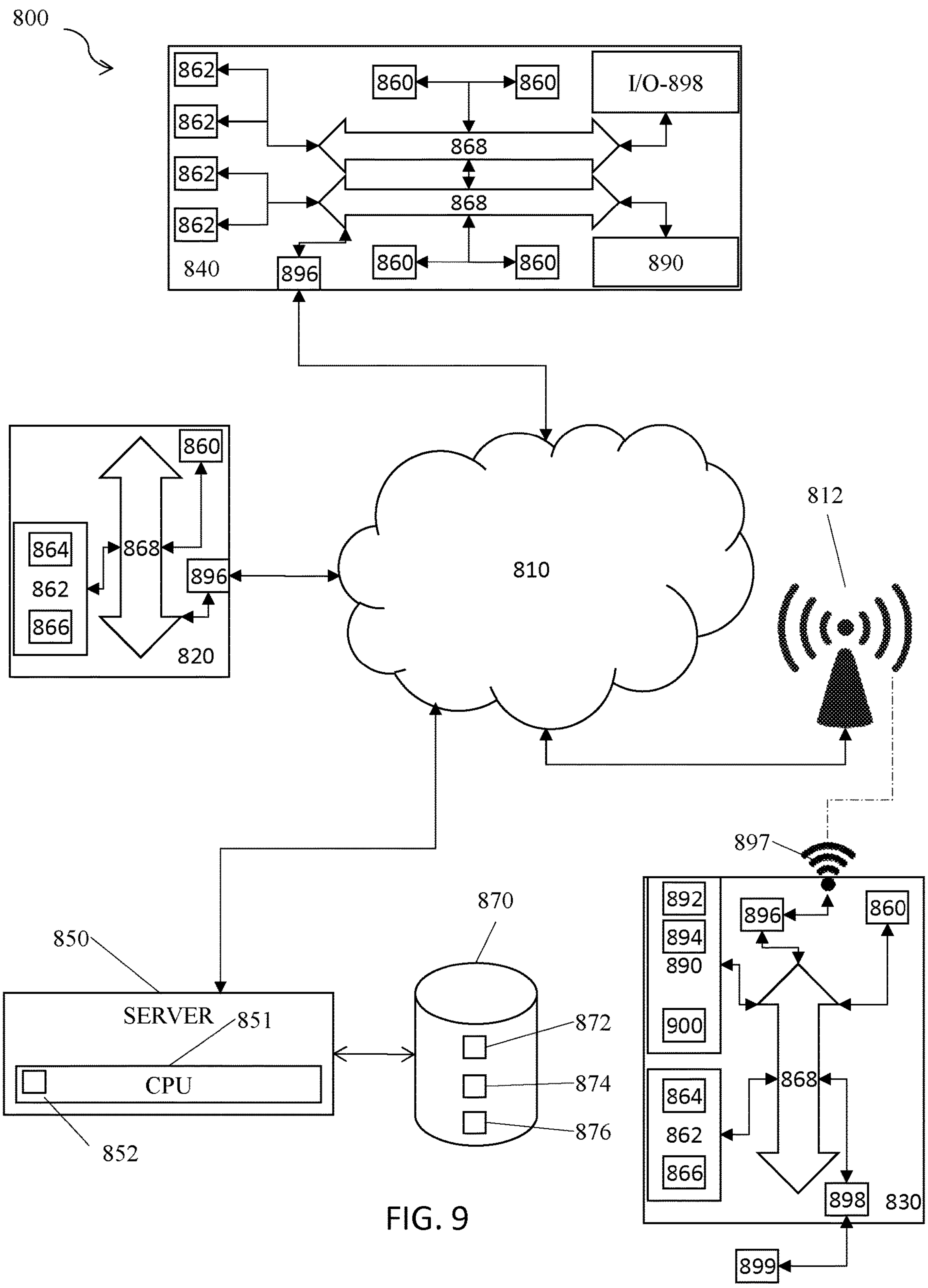
FIG. 9 is a schematic diagram of a system of the present invention.

FIG. 9 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 9, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 9, is operable to include other components that are not explicitly shown in FIG. 9, or is operable to utilize an architecture completely different than that shown in FIG. 9. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. An intranasal device for administration of a pharmaceutical composition comprising:

a reservoir and a means for discharging one or more doses of the pharmaceutical composition, wherein the reservoir contains a quantity of the pharmaceutical composition;

wherein the pharmaceutical composition is a dry powder comprising:

epinephrine or a pharmaceutically acceptable salt thereof, wherein the pharmaceutical composition provides a dose of about 0.01 mg to about 10 mg of the epinephrine or the pharmaceutically acceptable salt thereof;

citric acid or a pharmaceutically acceptable salt thereof; and a carrier.

2. The intranasal device of claim 1, wherein a median particle diameter of the epinephrine or the pharmaceutically acceptable salt thereof is about 20 μm to about 75 μm.

3. The intranasal device of claim 1, wherein the pharmaceutical composition further comprises an anticaking agent.

4. The intranasal device of claim 1, wherein the pharmaceutical composition further comprises at least one antihistamine.

5. The intranasal device of claim 1, wherein the pharmaceutical composition further comprises at least one steroid.

6. The intranasal device of claim 1, wherein the pharmaceutical composition further comprises a catechol-o-methyl transferase (COMT) inhibitor.

7. The intranasal device of claim 1, wherein the pharmaceutical composition further comprises one or more agents selected from a group consisting of a mucosal permeation or penetration enhancer, a mucoadhesive, a mucosal transit slowing agent, a mucosal transport enhancer, or any combination thereof.

8. The intranasal device of claim 1, wherein the intranasal device has 360° functionality and is constructed and configured to dispense a dose from any position.

9. The intranasal device of claim 1, wherein the intranasal device further includes an intranasal device global positioning system (GPS) device or is coupled to a GPS device, wherein the intranasal device GPS or the GPS device is constructed and configured to provide location data.

10. The intranasal device of claim 1, wherein the intranasal device further includes a communications interface, wherein the communications interface is constructed and configured to transmit data wirelessly to at least one remote device.

11. The intranasal device of claim 1, wherein the carrier includes mannitol, a cyclodextrin, citric acid, lactose, and/or sodium carboxymethylcellulose.

12. The intranasal device of claim 1, wherein the quantity of the pharmaceutical composition is between about 5 mg and about 75 mg.

13. The intranasal device of claim 1, wherein the intranasal device further includes a sensor that is adapted to detect a displacement or a deformation of a portion of the intranasal device when the dry powder is dispensed from the reservoir.

14. The intranasal device of claim 13, wherein the intranasal device further includes a display and a power supply, a timer, a clock, and a printed circuit board, wherein the display is constructed and configured to display a time of dose dispensation.

15. A kit for intranasal administration of a pharmaceutical composition comprising:

at least one intranasal device, wherein each of the at least one intranasal device includes a reservoir and a means for discharging one or more doses of the pharmaceutical composition, wherein the reservoir contains a quantity of the pharmaceutical composition; and a pouch and/or a hard case, wherein the at least one intranasal device is enclosed in the pouch and/or the hard case;

wherein the pharmaceutical composition is a dry powder comprising:

epinephrine or a pharmaceutically acceptable salt thereof, wherein the pharmaceutical composition provides a dose of about 0.01 mg to about 10 mg of the epinephrine or the pharmaceutically acceptable salt thereof;

citric acid or a pharmaceutically acceptable salt thereof; and a carrier.

16. The kit of claim 15, wherein the hard case includes a desiccant plastic.

17. The kit of claim 15, wherein the pouch and/or the hard case is water resistant or waterproof.

18. The kit of claim 15, wherein the pouch and/or the hard case is Modular Lightweight Load-carrying Equipment (MOLLE)-compatible.

19. An intranasal device for administration of a pharmaceutical composition comprising:

a reservoir and a means for discharging one or more doses of the pharmaceutical composition, wherein the reservoir contains a quantity of the pharmaceutical composition;

wherein the pharmaceutical composition is a spray-dried powder comprising:

epinephrine or a pharmaceutically acceptable salt thereof, wherein the pharmaceutical composition provides a dose of about 0.01 mg to about 10 mg of the epinephrine or the pharmaceutically acceptable salt thereof;

a pharmaceutically acceptable citrate salt; and a carrier;

wherein the pharmaceutical composition does not include an additional vasodilator; and wherein the intranasal device further includes a nasal probe and an actuator.

20. The intranasal device of claim 19, wherein the pharmaceutically acceptable citrate salt is trisodium citrate.

* * * * *